(12) United States Patent
Egawa et al.

(10) Patent No.: US 8,193,701 B2
(45) Date of Patent: *Jun. 5, 2012

(54) STILBENE DERIVATIVES, LIGHT-EMITTING ELEMENT AND LIGHT-EMITTING DEVICE

(75) Inventors: Masakazu Egawa, Kanagawa (JP); Harue Nakashima, Kanagawa (JP); Sachiko Kawakami, Kanagawa (JP); Nobuharu Ohsawa, Kanagawa (JP); Satoshi Seo, Kanagawa (JP); Ryoji Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/036,234

(22) Filed: Feb. 28, 2011

(65) Prior Publication Data

US 2011/0147729 A1    Jun. 23, 2011

Related U.S. Application Data

(60) Continuation of application No. 12/351,138, filed on Jan. 9, 2009, now Pat. No. 7,898,171, which is a division of application No. 11/542,157, filed on Oct. 2, 2006, now Pat. No. 7,476,745.

(30) Foreign Application Priority Data

Oct. 5, 2005 (JP) ................................ 2005-292366
Nov. 29, 2005 (JP) ................................ 2005-343674

(51) Int. Cl.
*H01J 1/62* (2006.01)
(52) U.S. Cl. ...................................... 313/504; 548/440
(58) Field of Classification Search .................. None
See application file for complete search history.

(56) References Cited

U.S. PATENT DOCUMENTS

| | | | |
|---|---|---|---|
| 4,666,810 A | 5/1987 | Umehara et al. | |
| 4,859,556 A | 8/1989 | Sasaki | |
| 4,892,949 A | 1/1990 | Sasaki | |
| 6,468,675 B1 | 10/2002 | Ishikawa et al. | |
| 2005/0214565 A1 | 9/2005 | Ikeda et al. | |
| 2008/0091030 A1 | 4/2008 | Egawa et al. | |

FOREIGN PATENT DOCUMENTS

| | | |
|---|---|---|
| JP | 62-18565 | 1/1987 |
| JP | 5-295359 | 11/1993 |
| JP | 2001-126873 | 5/2001 |
| JP | 2004-35447 | 2/2004 |
| JP | 2004-75580 | 3/2004 |
| WO | WO 02/20694 A1 | 3/2002 |

OTHER PUBLICATIONS

Thelakkat, M. et al, "Novel Functional Materials Based on Triarylamines—Synthesis and Application in Electroluminescent Devices and Photorefractive Systems," Phys. Chem. Chem. Phys., vol. 1, No. 8, Apr. 15, 1999, pp. 1693-1698.
Cha, S.W. et al., "Electroluminescence of LEDs Consisting Two Layers of $Alq_3$ and High $T_g$, Blue-Light Emitting Branched Compounds," Synthetic Metals, vol. 143, 2004, pp. 97-101.
International Search Report, re Application No. PCT/JP2006/319653, dated Dec. 26, 2006.
Written Opinion, re Application No. PCT/JP2006/319653, dated Dec. 26, 2006.
European Search Report re application No. EP 06798494.8, dated May 7, 2010.

*Primary Examiner* — Yong Chu
(74) *Attorney, Agent, or Firm* — Husch Blackwell LLP

(57) ABSTRACT

The present invention provides a novel substance having an excellent color purity of blue, a light-emitting element and a light-emitting device using the novel substance. A stilbene derivative has a structure shown by the general formula (1). In the general formula (1), $R^1$ is hydrogen, an alkyl group having 1 to 4 carbon atoms, or an aryl group having 6 to 25 carbon atoms. $R^2$ is an alkyl group having 1 to 4 carbon atoms or an aryl group having 6 to 25 carbon atoms. Each of $R^3$ to $R^5$ is hydrogen or an alkyl group having 1 to 4 carbon atoms. $Ar^1$ is an aryl group having 6 to 25 carbon atoms.

16 Claims, 31 Drawing Sheets

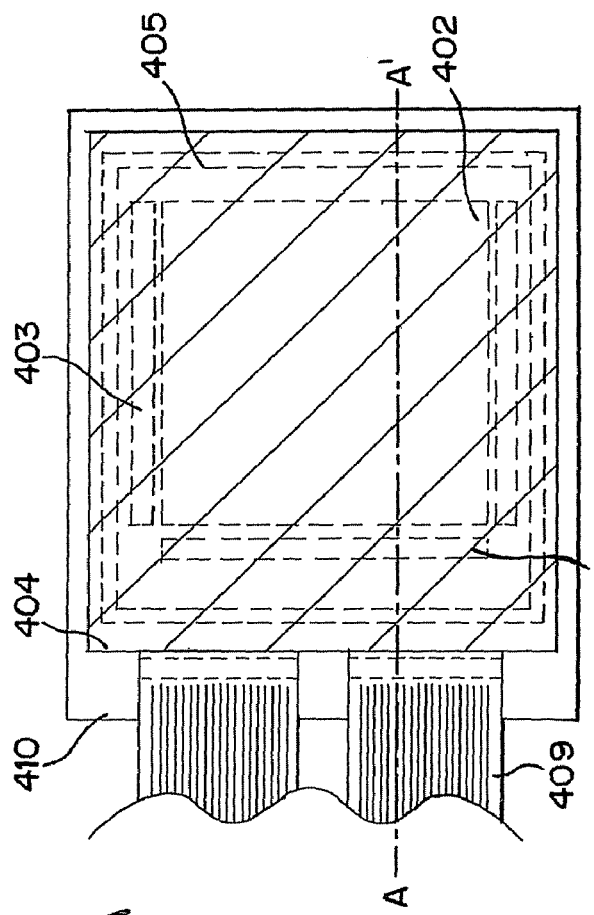
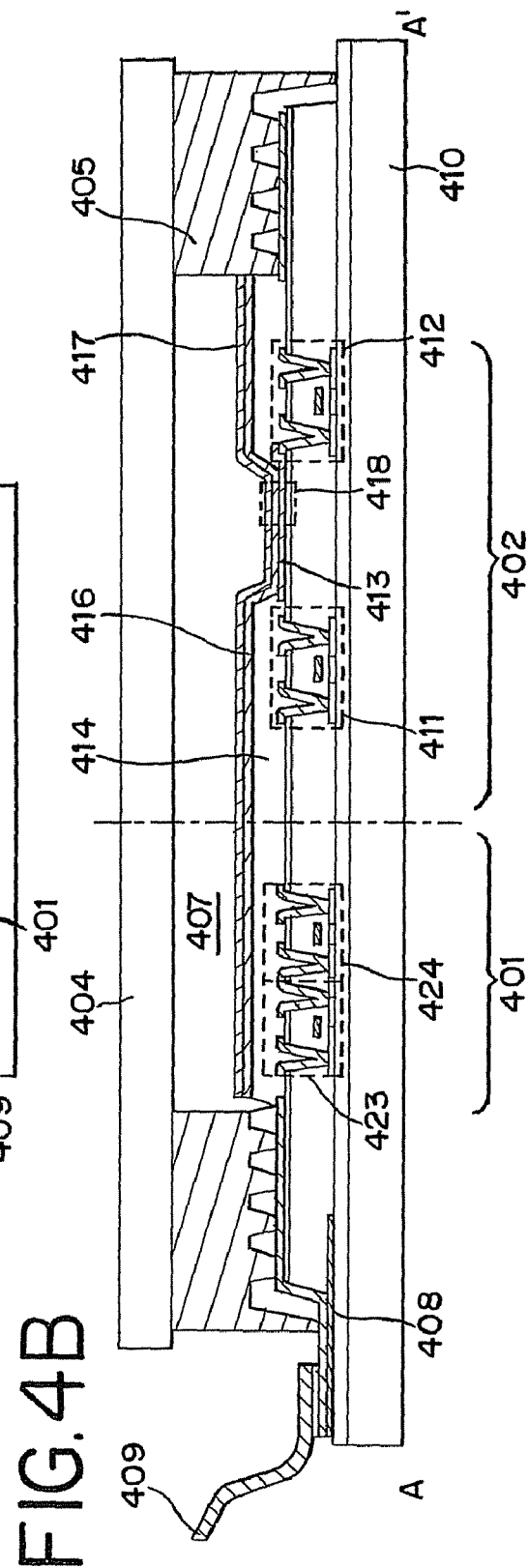
FIG. 4A
FIG. 4B

STILBENE DERIVATIVES, LIGHT-EMITTING ELEMENT AND LIGHT-EMITTING DEVICE

This application is a continuation of U.S. application Ser. No. 12/351,138, filed on Jan. 9, 2009 now U.S. Pat. No. 7,898,171 which is a divisional of U.S. application Ser. No. 11/542,157, filed on Oct. 2, 2006 (now U.S. Pat. No. 7,476,745 issued Jan. 13, 2009) which claims priority of foreign application serial nos. 2005-292366 filed on Oct. 5, 2005 in Japan and 2005-343674 filed on Nov. 29, 2005 in Japan under 35 U.S.C. 119.

TECHNICAL FIELD

The present invention relates to stilbene derivatives, light-emitting elements with the use of stilbene derivatives and light-emitting devices having the light-emitting elements.

BACKGROUND ART

A light-emitting element having features such as thinness, lightweight, and rapid response is expected to be applied to flat panel displays of the next generation. In addition, it is said that a light-emitting device in which light-emitting elements are arranged in matrix is superior to conventional liquid crystal display devices in viewing angle and visibility.

A light-emitting element is formed by interposing a layer including a luminescent substance between a pair of electrodes (an anode and a cathode), and it is said that emission mechanism thereof is as follows: when a voltage is applied between both electrodes, holes injected from the anode and electrons injected from the cathode are recombined in a light-emitting layer in the layer including a luminescent substance, thereby forming a molecular exciton by recombination in an emission center, and energy is released to emit light when the molecular exciton returns to a ground state. By such a mechanism, such a light-emitting element is referred to as a current excitation type light-emitting element. A singlet excitation state and a triplet excitation state can be given as types of an excitation state formed by a luminescent substance. Light emission from a singlet excitation state is referred to as fluorescence and light emission from a triplet excitation state is referred to as phosphorescence.

Emission wavelength of a light-emitting element is determined by energy difference between a ground state and an excited state, that is, a band gap, of a light-emitting molecule included in the light-emitting element. Therefore, various emission colors can be obtained by devising a structure of the light-emitting molecule. By manufacturing a light-emitting device using light-emitting elements capable of emitting red light, blue light, and green light, which are the three primary colors of light, a full-color light-emitting device can be manufactured.

However, until now, there has been a problem in that it is difficult to realize a light-emitting element having high reliability and excellent color purity. As a result of recent development of materials, high reliability and excellent color purity of light-emitting elements for green and red have been achieved. However, in particular, high reliability and excellent color purity of a light-emitting element for blue has not been realized, and many researches have been done (for example, Reference 1: Japanese Published Patent Application No. 2004-75580).

DISCLOSURE OF THE INVENTION

The present invention has been made in view of the above described problems. It is an object of the present invention to provide a novel substance which provides excellent color purity of blue, a light-emitting element and a light-emitting device using the novel substance.

A structure of the present invention is to provide novel stilbene derivatives. A stilbene derivative of the present invention includes a structure shown in the following general formula (1).

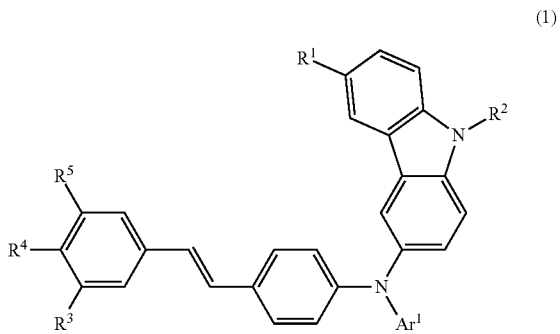

(1)

In the general formula (1), $R^1$ is hydrogen, an alkyl group having 1 to 4 carbon atoms, or an aryl group having 6 to 25 carbon atoms, and the aryl group may have an alkyl group having 1 to 4 carbon atoms. In addition, $R^2$ is an alkyl group having 1 to 4 carbon atoms or an aryl group having 6 to 25 carbon atoms, and the aryl group may have an alkyl group having 1 to 4 carbon atoms. Each of $R^3$ to $R^5$ is hydrogen or an alkyl group having 1 to 4 carbon atoms. Further, $Ar^1$ is an aryl group having 6 to 25 carbon atoms, and the aryl group may have an alkyl group having 1 to 4 carbon atoms.

Also, a stilbene derivative of the present invention includes a structure represented by the following general formula (2).

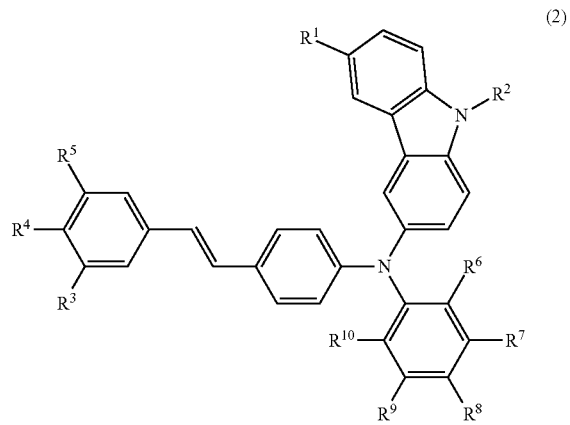

(2)

In the general formula (2), $R^1$ is hydrogen, an alkyl group having 1 to 4 carbon atoms, or an aryl group having 6 to 25 carbon atoms, and the aryl group may have an alkyl group having 1 to 4 carbon atoms. $R^2$ is an alkyl group having 1 to 4 carbon atoms or an aryl group having 6 to 25 carbon atoms, and the aryl group may have an alkyl group having 1 to 4 carbon atoms. Each of $R^3$ to $R^5$ is hydrogen or an alkyl group having 1 to 4 carbon atoms. Further, each of $R^6$ to $R^{10}$ is hydrogen, an alkyl group having 1 to 4 carbon atoms, or an aryl group having 6 to 25 carbon atoms, and the aryl group may have an alkyl group having 1 to 4 carbon atoms.

Also, a stilbene derivative of the present invention includes a structure represented by the following general formula (3).

Further, a stilbene derivative of the present invention includes a structure represented by the following general formula (5).

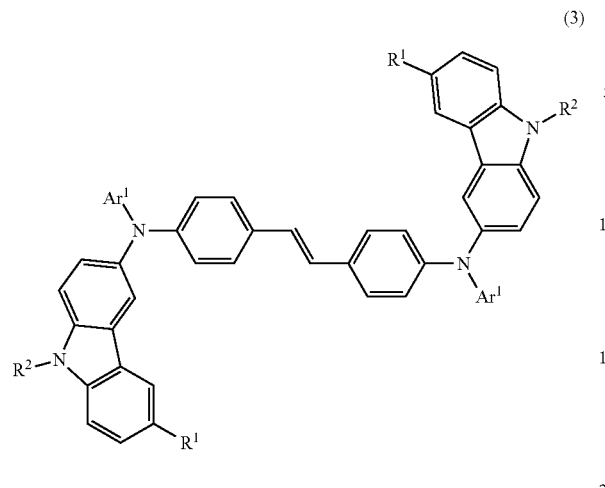

(3)

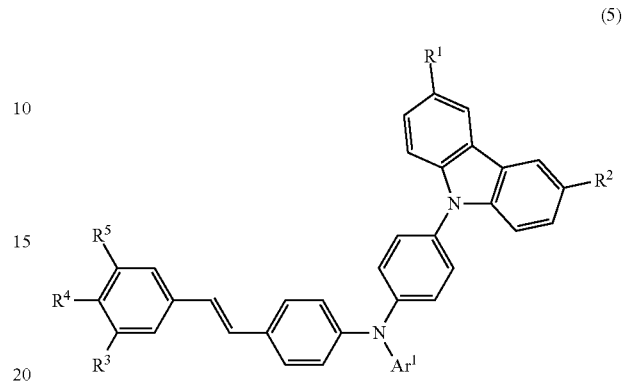

(5)

In the general formula (3), $R^1$ is hydrogen, an alkyl group having 1 to 4 carbon atoms, or an aryl group having 6 to 25 carbon atoms, and the aryl group may have an alkyl group having 1 to 4 carbon atoms. $R^2$ is an alkyl group having 1 to 4 carbon atoms or an aryl group having 6 to 25 carbon atoms, and the aryl group may have an alkyl group having 1 to 4 carbon atoms. $Ar^1$ is an aryl group having 6 to 25 carbon atoms, and the aryl group may have an alkyl group having 1 to 4 carbon atoms.

In addition, a stilbene derivative of the present invention includes a structure represented by the following general formula (4).

In the general formula (5), each of $R^1$ and $R^2$ is hydrogen, an alkyl group having 1 to 4 carbon atoms, or an aryl group having 6 to 25 carbon atoms, and the aryl group may have an alkyl group having 1 to 4 carbon atoms. In addition, each of $R^3$ to $R^5$ is hydrogen or an alkyl group having 1 to 4 carbon atoms. $Ar^1$ is an aryl group having 6 to 25 carbon atoms, and the aryl group may have an alkyl group having 1 to 4 carbon atoms.

Also, a stilbene derivative of the present invention includes a structure represented by the following general formula (6).

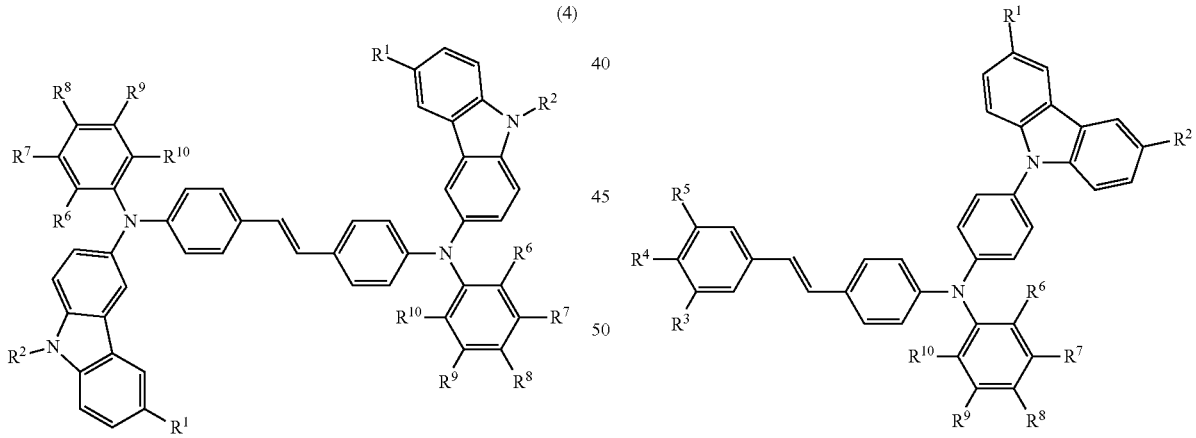

(4)

(6)

In the general formula (4), $R^1$ is hydrogen, an alkyl group having 1 to 4 carbon atoms, or an aryl group having 6 to 25 carbon atoms, and the aryl group may have an alkyl group having 1 to 4 carbon atoms. In addition, $R^2$ is an alkyl group having 1 to 4 carbon atoms or an aryl group having 6 to 25 carbon atoms; and the aryl group may have an alkyl group having 1 to 4 carbon atoms. In addition, each of $R^6$ to $R^{10}$ is hydrogen, an alkyl group having 1 to 4 carbon atoms, or an aryl group having 6 to 25 carbon atoms, and the aryl group may have an alkyl group having 1 to 4 carbon atoms.

In the general formula (6), each of $R^1$ and $R^2$ is hydrogen, an alkyl group having 1 to 4 carbon atoms, or an aryl group having 6 to 25 carbon atoms, and the aryl group may have an alkyl group having 1 to 4 carbon atoms. In addition, each of $R^3$ to $R^5$ is hydrogen or an alkyl group having 1 to 4 carbon atoms, each of $R^6$ to $R^{10}$ is hydrogen, an alkyl group having 1 to 4 carbon atoms, or an aryl group having 6 to 25 carbon atoms, and the aryl group may have an alkyl group having 1 to 4 carbon atoms.

Also, a stilbene derivative of the present invention includes a structure represented by the following general formula (7).

(7)

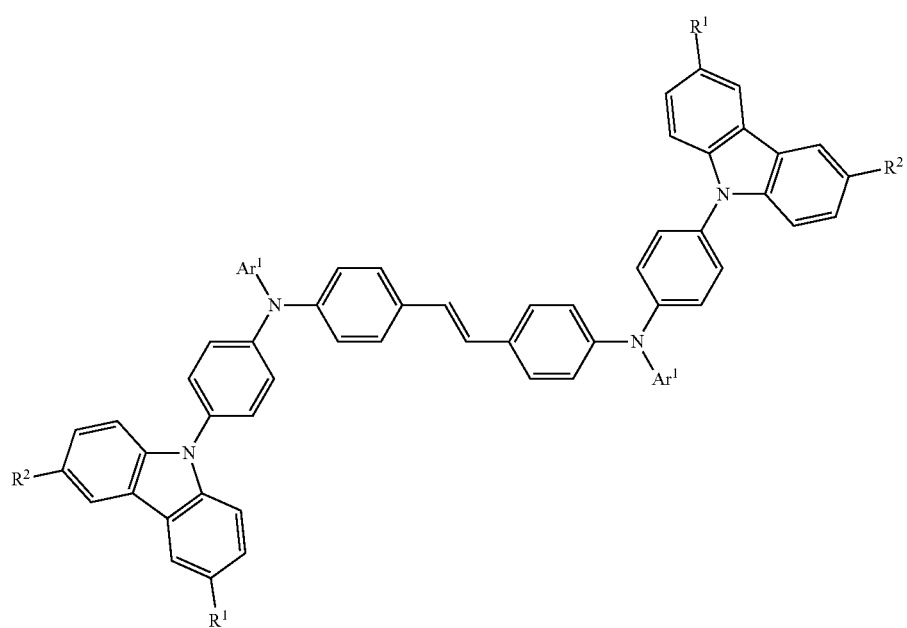

In the general formula (7), each of $R^1$ and $R^2$ is hydrogen, an alkyl group having 1 to 4 carbon atoms, or an aryl group having 6 to 25 carbon atoms, and the aryl group may have an alkyl group having 1 to 4 carbon atoms. In addition, $Ar^1$ is an aryl group having 6 to 25 carbon atoms, and the aryl group may have an alkyl group having 1 to 4 carbon atoms.

Moreover, a stilbene derivative of the present invention includes a structure represented by the following general formula (8).

(8)

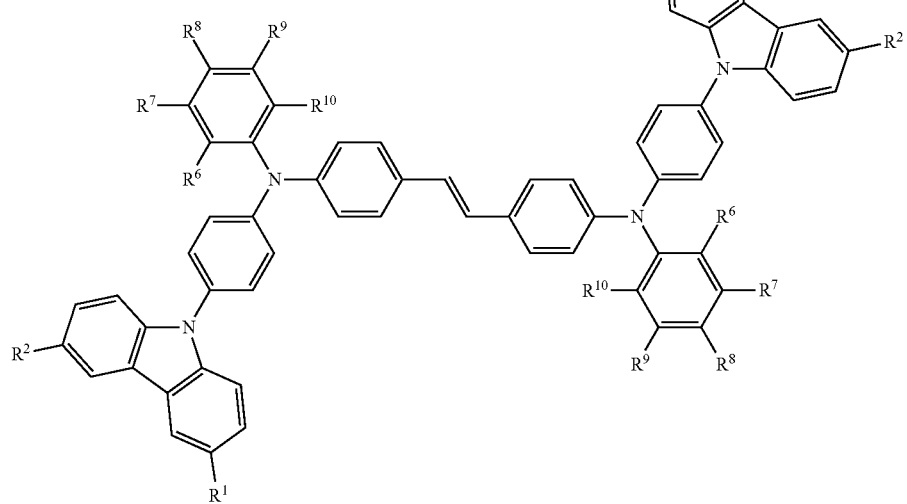

In the general formula (8), each of $R^1$ and $R^2$ is hydrogen, an alkyl group having 1 to 4 carbon atoms, or an aryl group having 6 to 25 carbon atoms, and the aryl group may have an alkyl group having 1 to 4 carbon atoms. In addition, each of $R^6$ to $R^{10}$ is hydrogen, an alkyl group having 1 to 4 carbon atoms, or an aryl group having 6 to 25 carbon atoms, and the aryl group may have an alkyl group having 1 to 4 carbon atoms.

The present invention includes a structure of a light-emitting element which has a light-emitting layer including a stilbene derivative as described above. One feature of a stilbene derivative in accordance with the present invention is to emit blue light with high color purity, and thus, it is mainly used as a guest material and forms a light-emitting layer together with another host material.

In the above structure, fine control of emission color for a stilbene derivative of the present invention is possible, depending on a polarity of a host material, and thus, a desired emission color can be obtained by appropriately selecting a host material.

Furthermore, the present invention includes a structure of a light-emitting device which has a light-emitting element having a light-emitting layer including a stilbene derivative as described above.

By implementing the present invention, blue emission with excellent color purity is obtained and a stilbene derivative with excellent luminous efficiency can be provided. In addition, by manufacturing a light-emitting element using a stilbene derivative as described above, a blue light-emitting element with excellent color purity and a light-emitting device using it can be provided. Moreover, a light-emitting element and a light-emitting device having excellent luminous efficiency can be provided. A light-emitting element and a light-emitting device having a longer lifetime can be provided.

BRIEF DESCRIPTION OF DRAWINGS

In the accompanying drawings:

FIGS. 4A and 4B show a light-emitting device according to an aspect of the present invention.

BEST MODE FOR CARRYING OUT THE INVENTION

Figure 1:
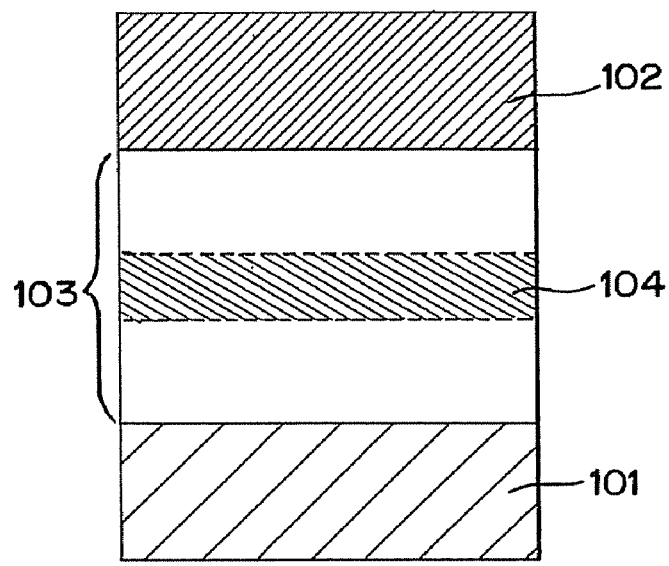
FIG. 1 shows a light-emitting element according to an aspect of the present invention.

Hereinafter, the embodiment modes of the present invention will be described with reference to the accompanying drawings. The present invention can be carried out in many different modes. It is easily understood by those skilled in the art that modes and details herein disclosed can be modified in various ways without departing from the spirit and the scope of the present invention. It should be noted that the present invention should not be interpreted as being limited to the description of the embodiment modes to be given below.

Embodiment Mode 1

Stilbene derivatives of the present invention include structures represented by the following general formulas (1) to (8).

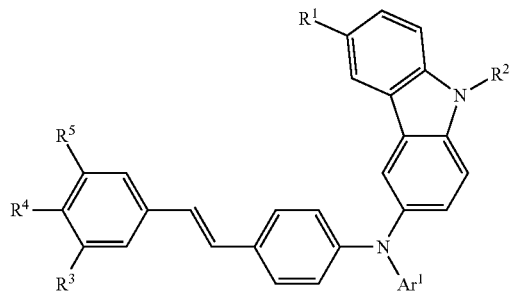

(1)

In the formula, $R^1$ is hydrogen, an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The described aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, $R^2$ is an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, each of $R^3$ to $R^5$ is hydrogen or an alkyl group having 1 to 4 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given.

$Ar^1$ is an aryl group having 6 to 25 carbon atoms. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

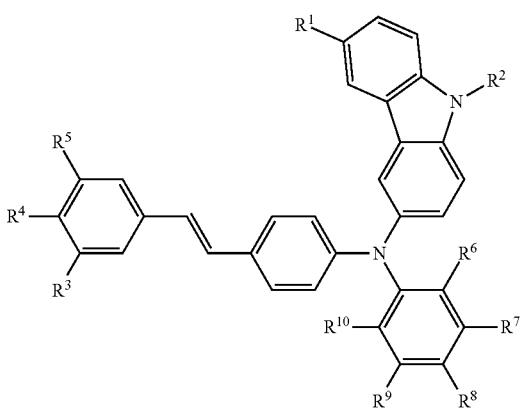

(2)

In the formula, $R^1$ is hydrogen, an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The described aryl group may have a substituent or may not. When such an aryl group has a substituent, the substituent of the -aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, $R^2$ is an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, each of $R^3$ to $R^5$ is hydrogen or an alkyl group having carbon atoms 1 to 4. As the alkyl group having 1 to 4 carbon atoms, a methyl group, an ethyl group, an n-propyl group, an isopropyl group, an n-butyl group, an isobutyl group, an s-butyl group, a t-butyl group and the like are given.

In the formula, each of $R^6$ to $R^{10}$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, $Ar^1$ is an aryl group having 6 to 25 carbon atoms. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

(3)

(4)

In the formula, $R^1$ is hydrogen, an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The described aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, $R^2$ is an alkyl group having 1 to 4 carbon atoms or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, each of $R^6$ to $R^{10}$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

(5)

In the formula, each of $R^1$ and $R^2$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, each of $R^3$ to $R^5$ is hydrogen or an alkyl group having 1 to 4 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given.

In the formula, $Ar^1$ is an aryl group having 6 to 25 carbon atoms. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

(6)

In the formula, each of $R^1$ and $R^2$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, each of $R^3$ to $R^5$ is hydrogen or an alkyl group having 1 to 4 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given.

In the formula, each of $R^6$ to $R^{10}$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

(7)

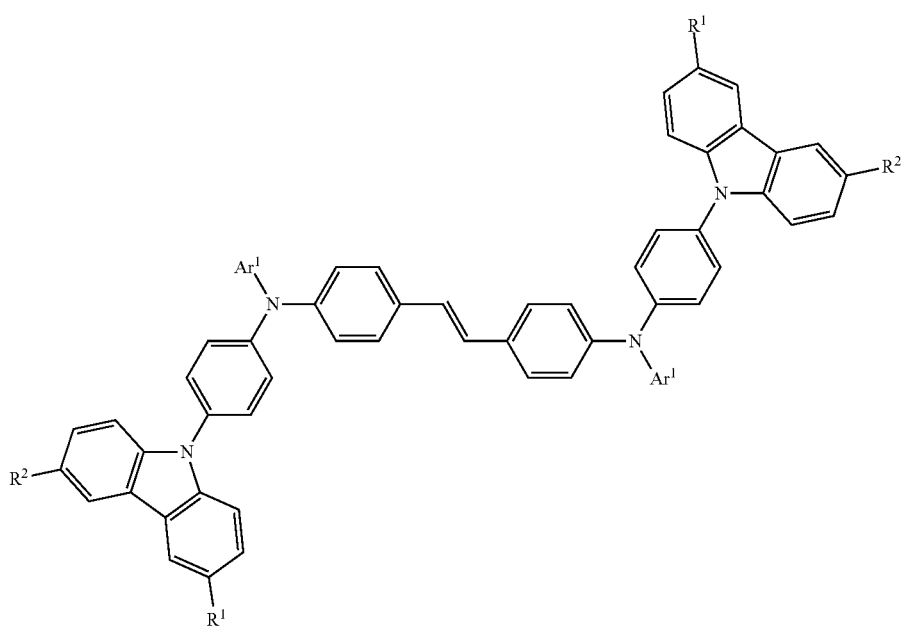

In the formula, each of $R^1$ and $R^2$ is hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

In the formula, $Ar^1$ is an aryl group having 6 to 25 carbon atoms. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

(8)

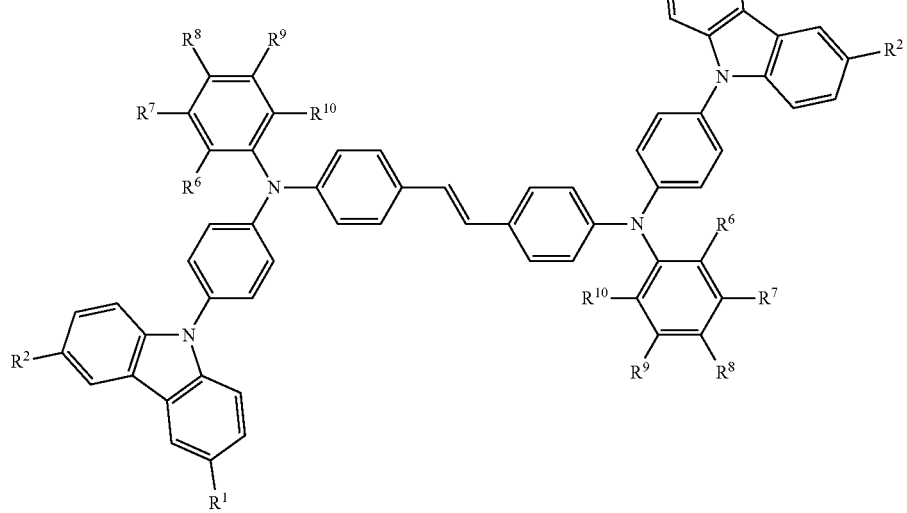

In the formula, $R^1$, $R^2$ and $R^6$ to $R^{10}$ are each hydrogen, an alkyl group having 1 to 4 carbon atoms, or an aryl group having 6 to 25 carbon atoms. As the alkyl group having 1 to 4 carbon atoms, a methyl group, an ethyl group, an n-propyl group, an isopropyl group, an n-butyl group, an isobutyl group, an s-butyl group, a t-butyl group and the like are given. As the aryl group having 6 to 25 carbon atoms, a phenyl group, a naphthyl group, a biphenylyl group, a fluorenyl group and the like are given. The aryl group may have a substituent or may not. When such an aryl group has a substituent, the substituent of the aryl group is preferably an alkyl group having 1 to 4 carbon atoms, specifically, a methyl group, an ethyl group, an n-propyl group, an isopropyl group, an n-butyl group, an isobutyl group, an s-butyl group, a t-butyl group and the like can be given. Among them, the methyl group or the t-butyl group is preferable. In addition, as the fluorenyl group, 9,9-dimethylfluoren-2-yl, or spiro-9,9'-bifluoren-2-yl is preferable.

As a specific mode of the stilbene derivatives represented by the above described general formulas (1) to (8), stilbene derivatives represented by the following structural formulas (9) to (152) are given. Note that stilbene derivatives of the present invention are not limited to these modes.

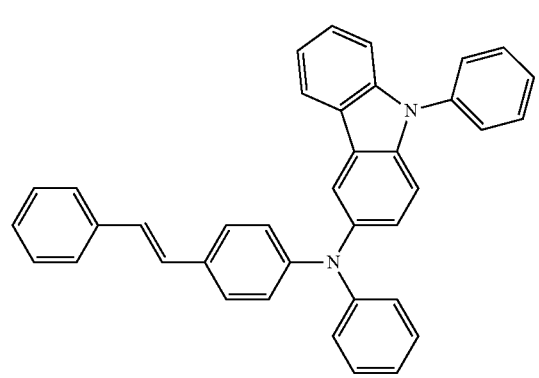

(9)

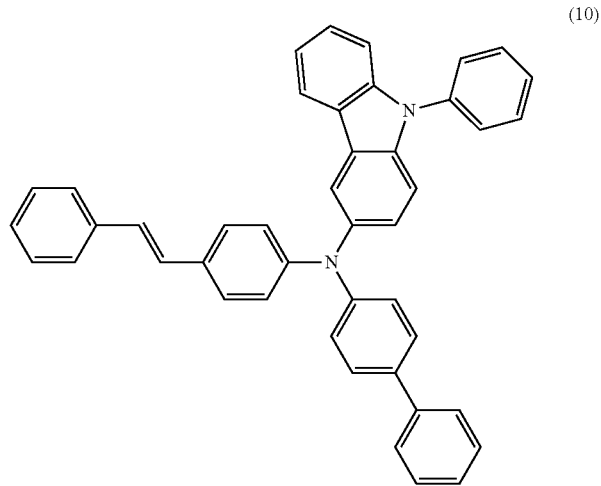

(10)

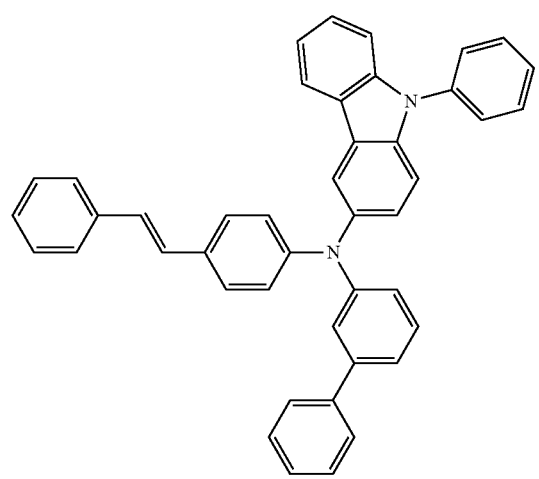

(11)

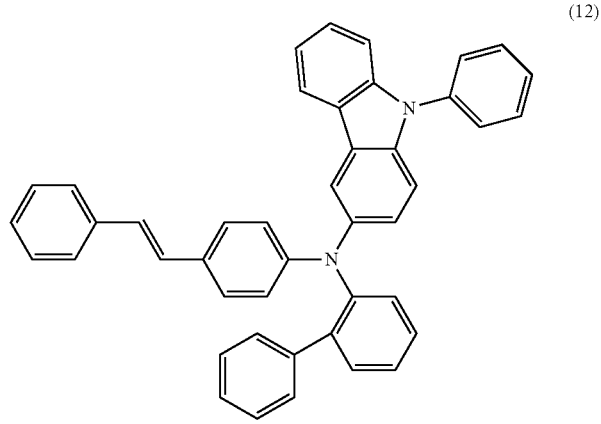

(12)

-continued
(13)
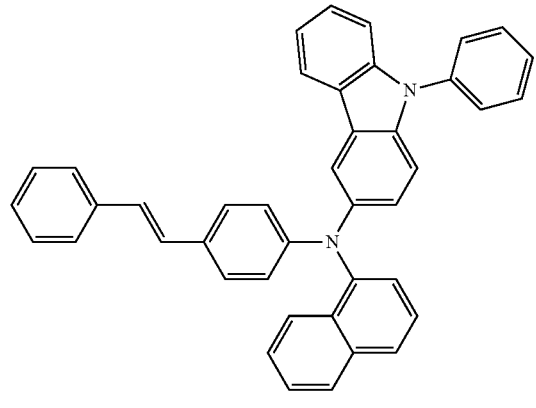
(14)
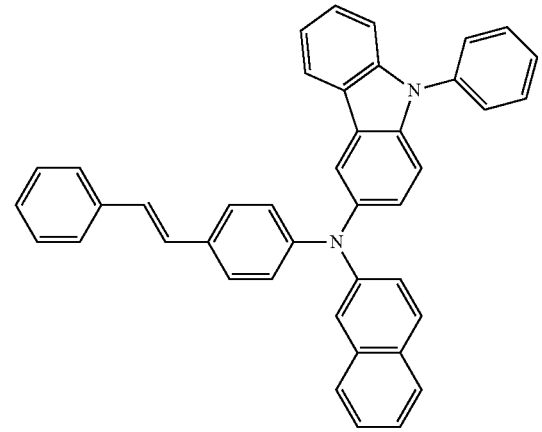
(15)
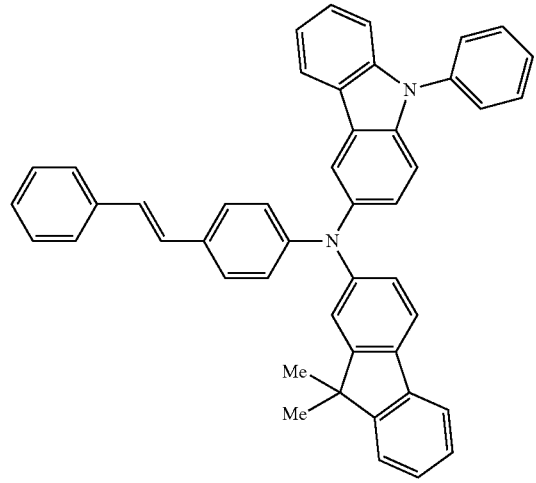
(16)
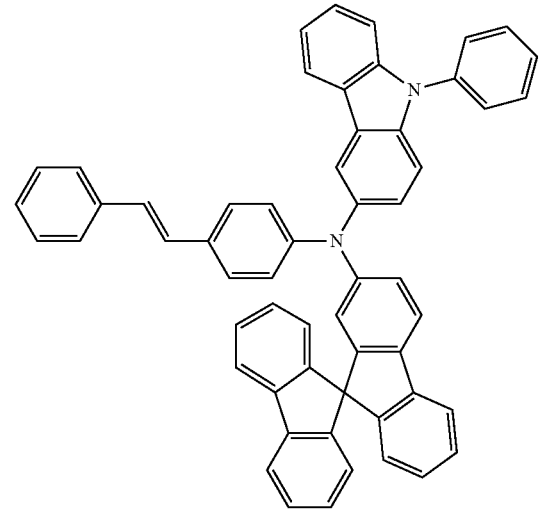
(17)
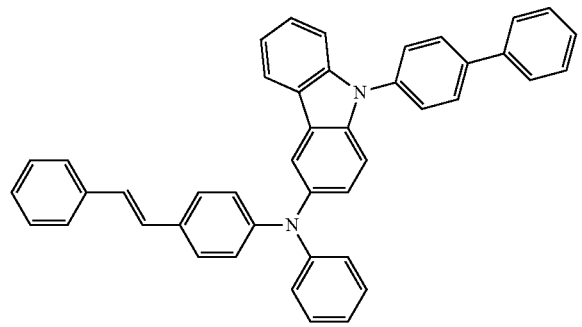
(18)
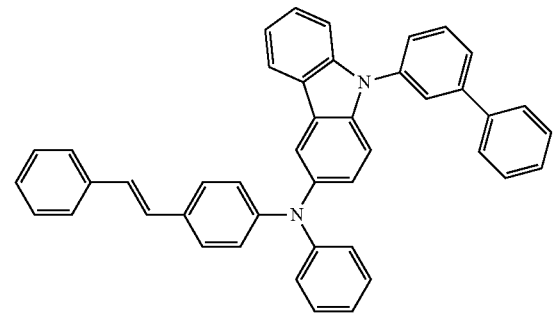
(19)
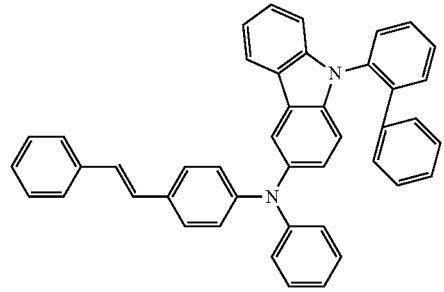
(20)
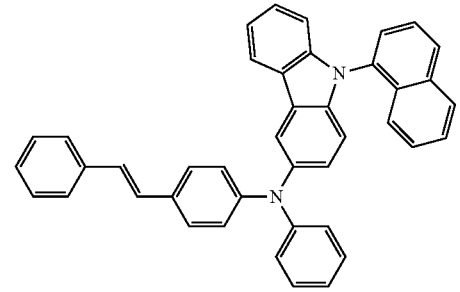

-continued
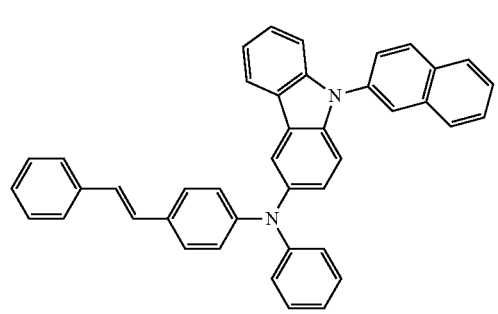
(21)
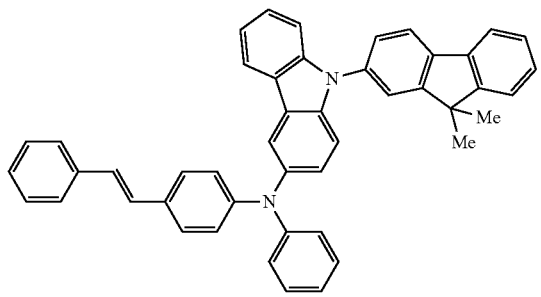
(22)
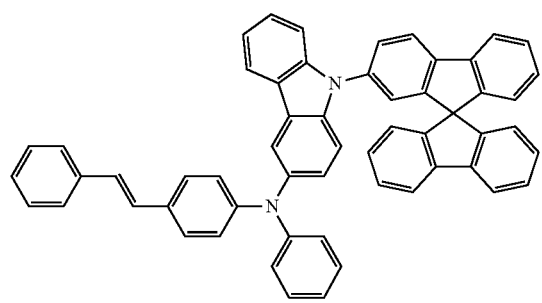
(23)
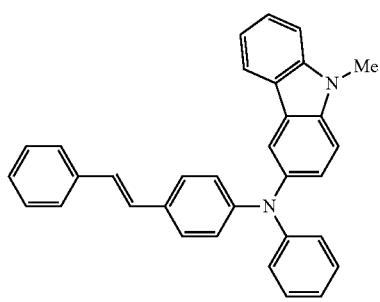
(24)
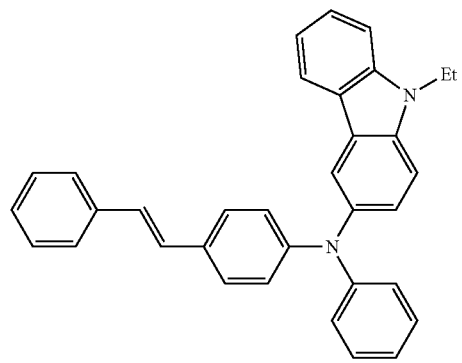
(25)
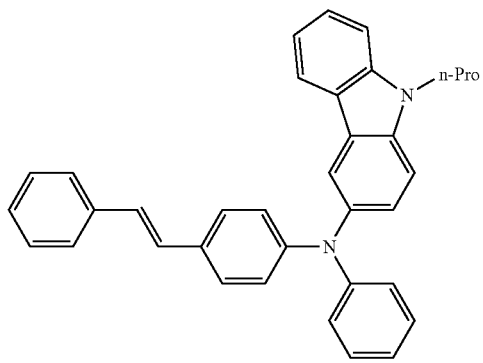
(26)
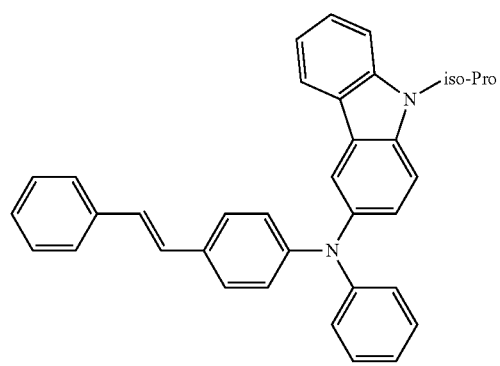
(27)
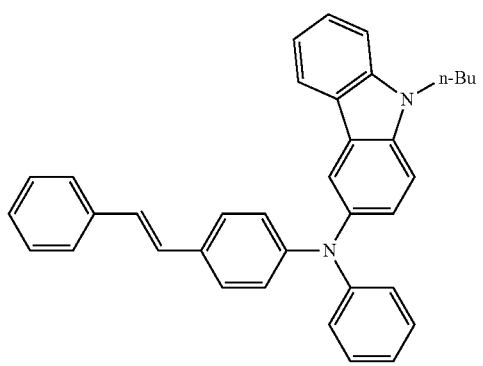
(28)

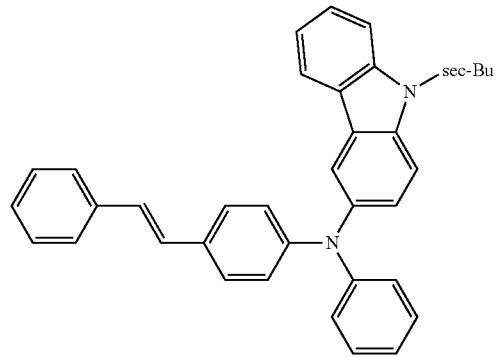
(29)
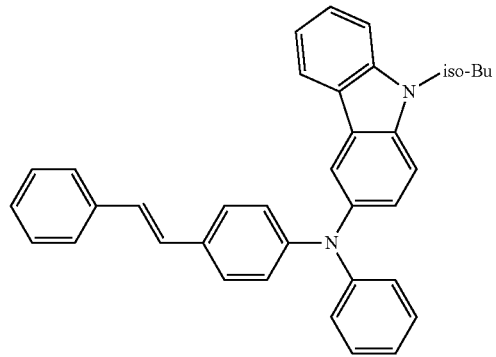
(30)
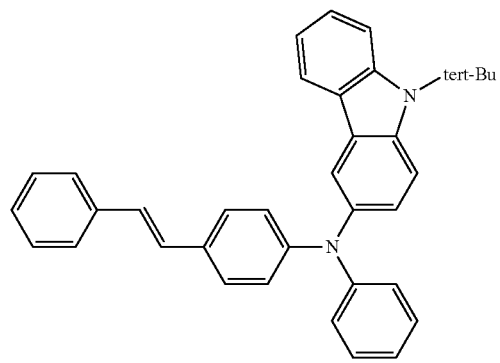
(31)
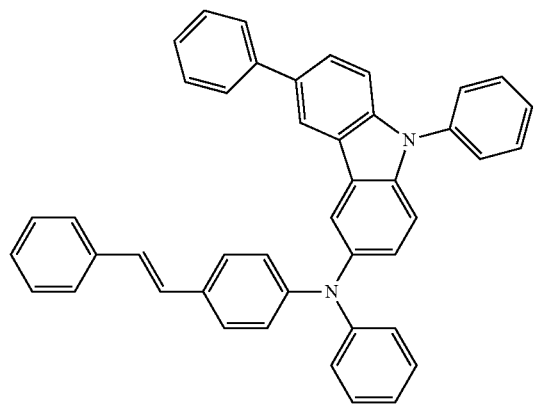
(32)
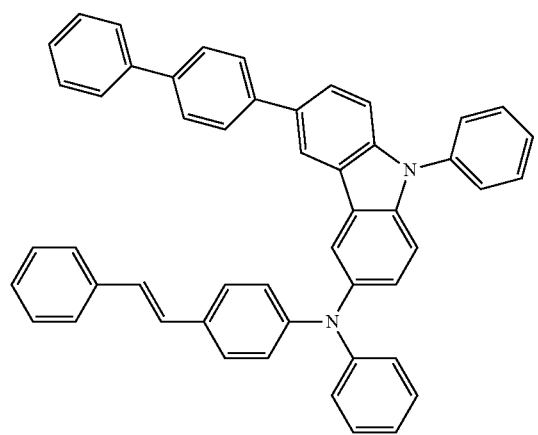
(33)
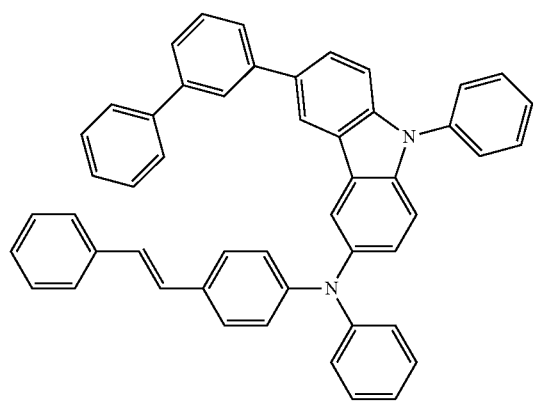
(34)

(35) 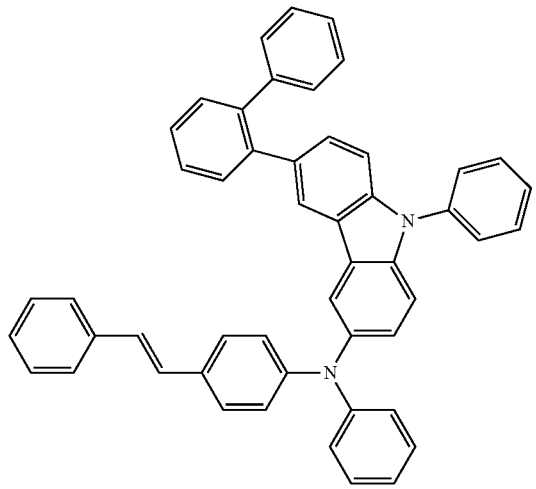
(36) 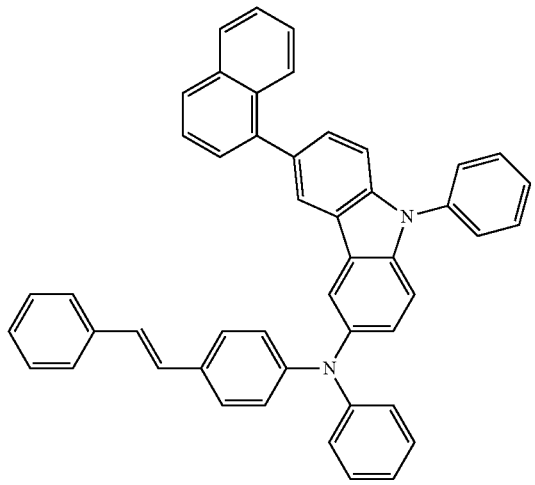
(37) 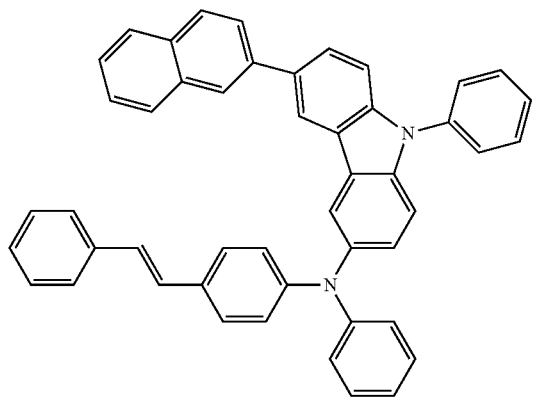
(38) 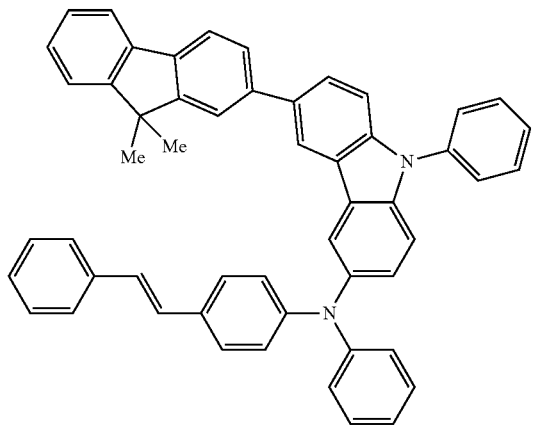
(39) 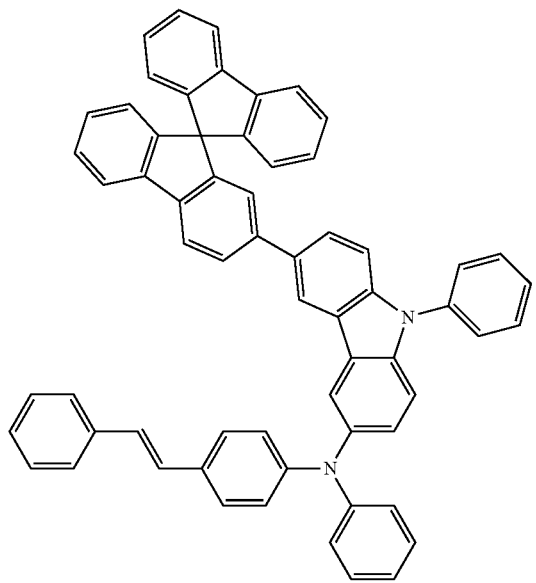
(40) 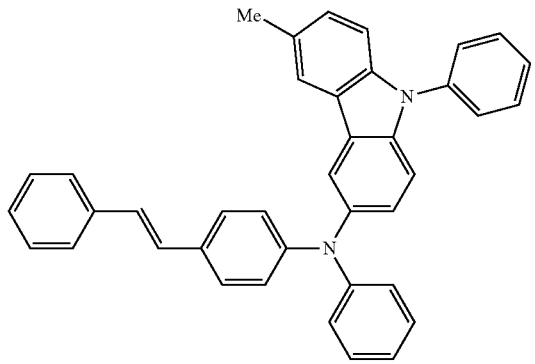

-continued
(41)
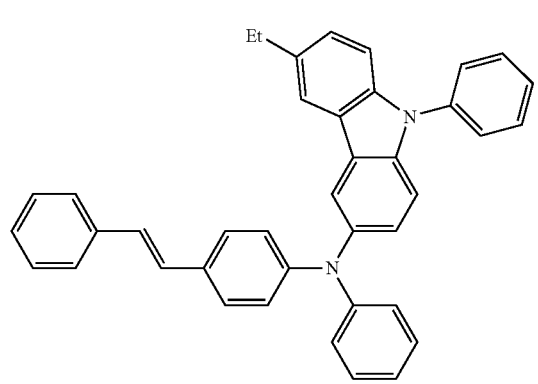
(42)
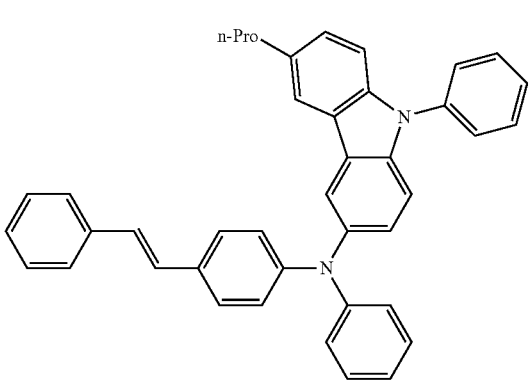
(43)
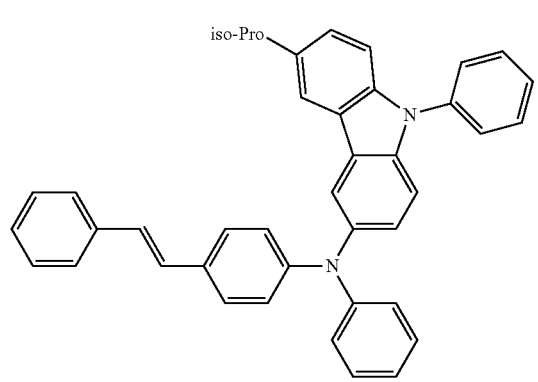
(44)
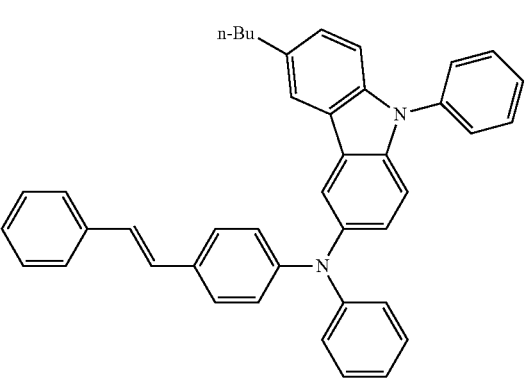
(45)
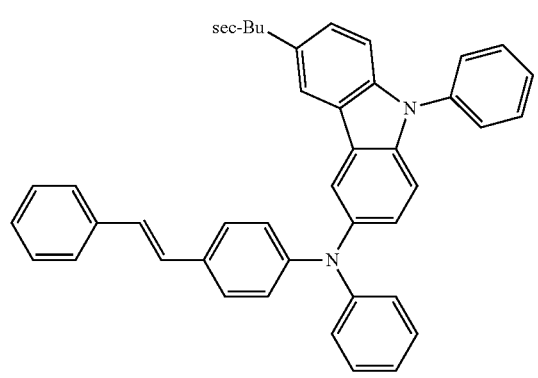
(46)
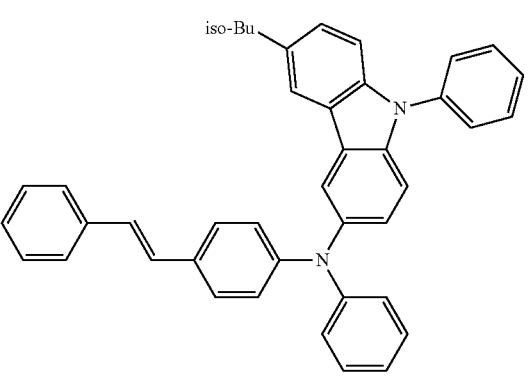
(47)
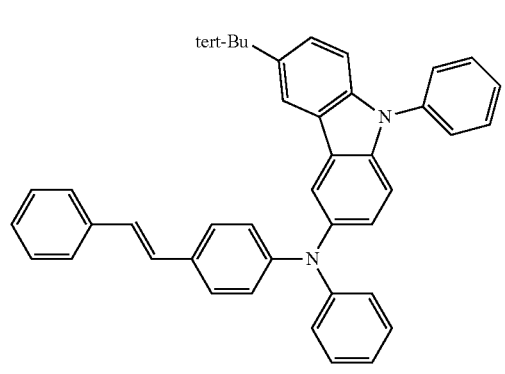
(48)
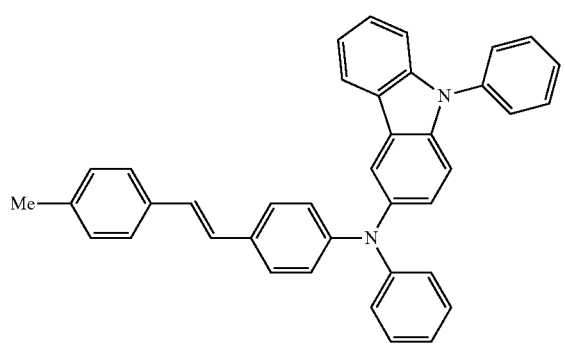

-continued
(49)
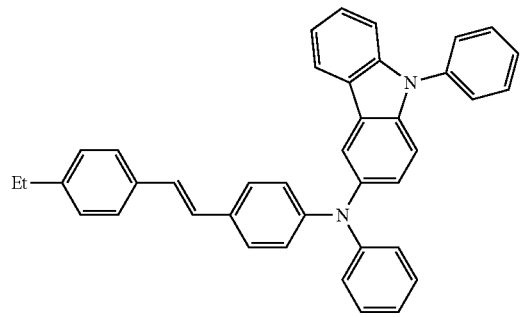
(50)
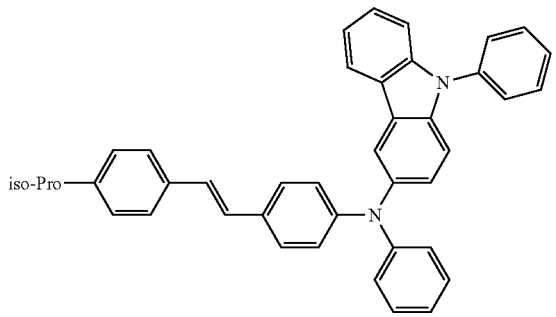
(51)
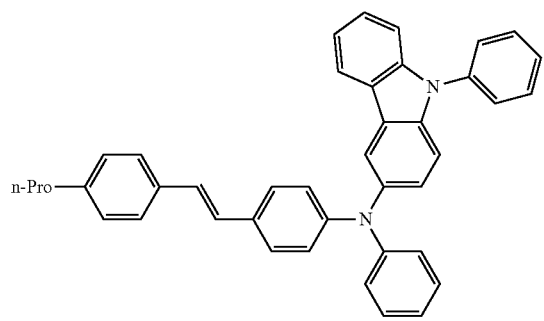
(52)
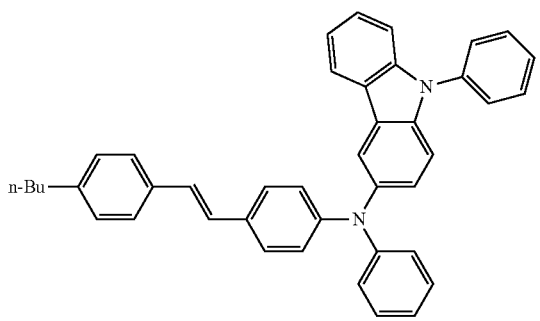
(53)
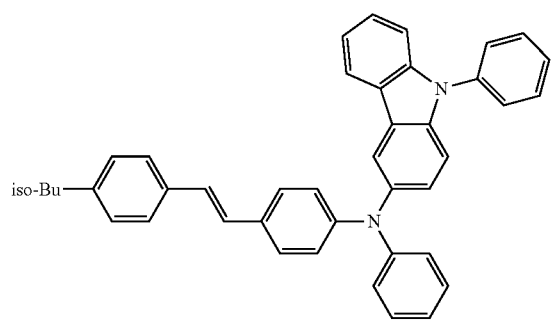
(54)
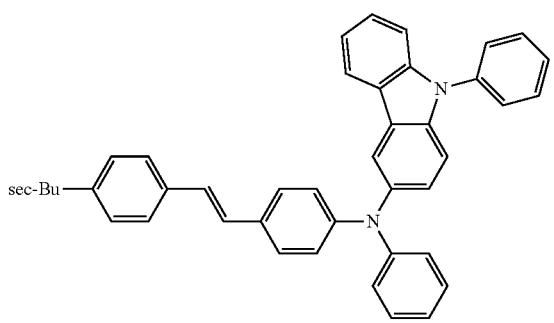
(55)
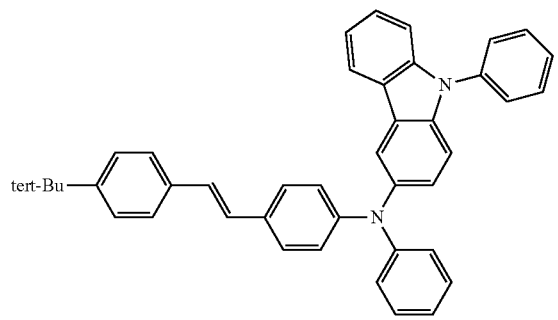
(56)
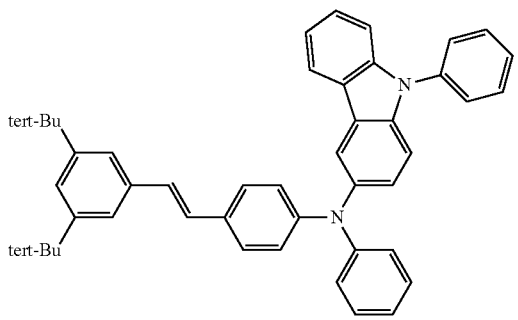

(57)
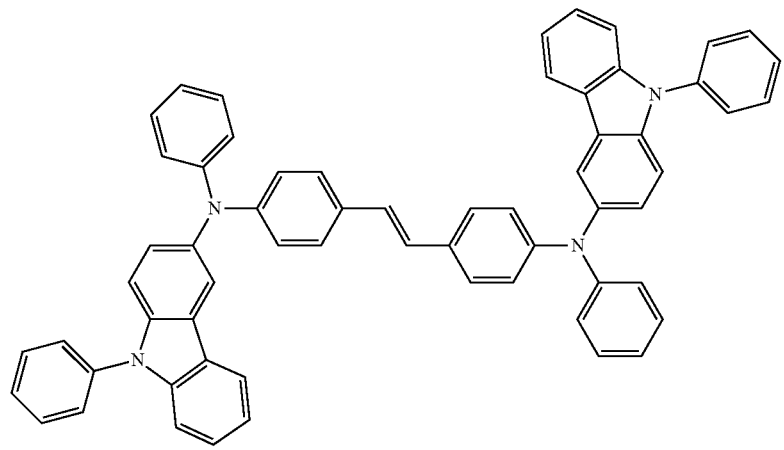
(58)
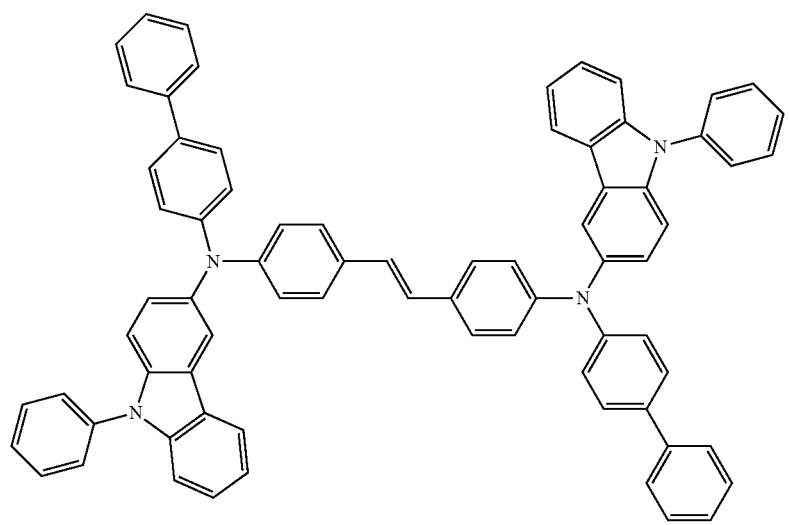
(59)
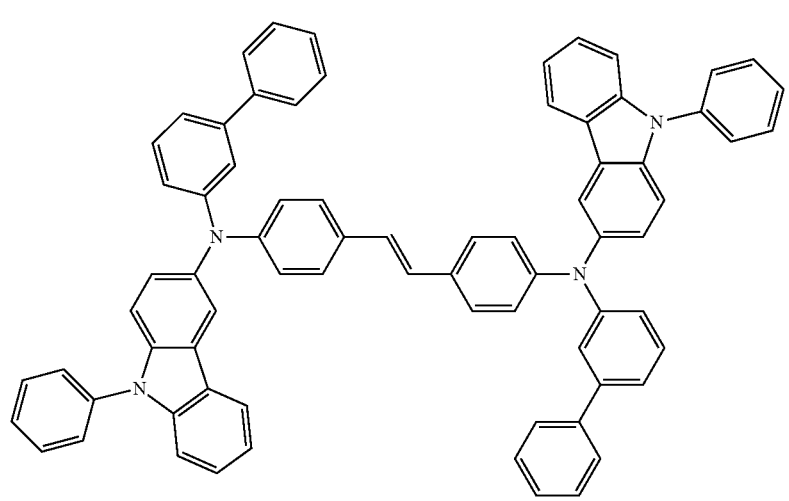

-continued
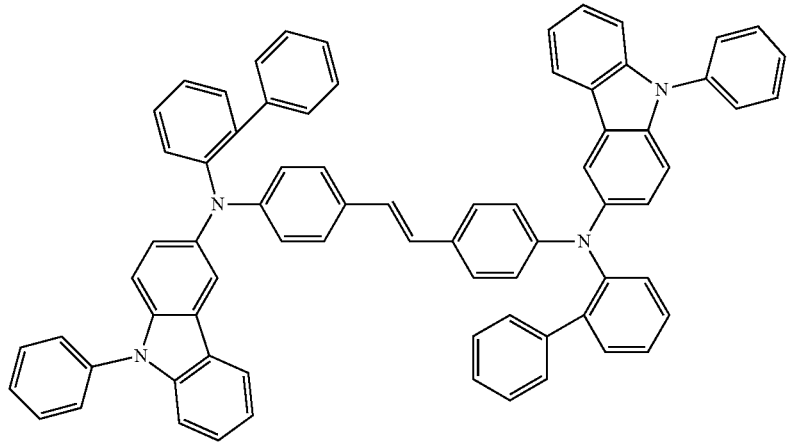
(60)
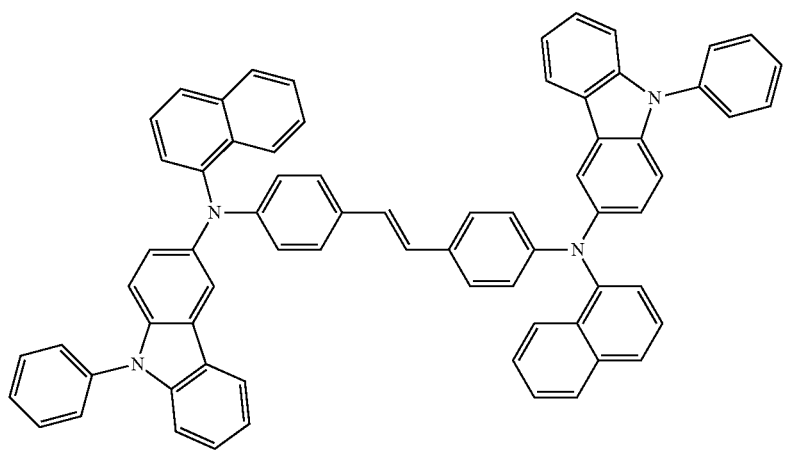
(61)
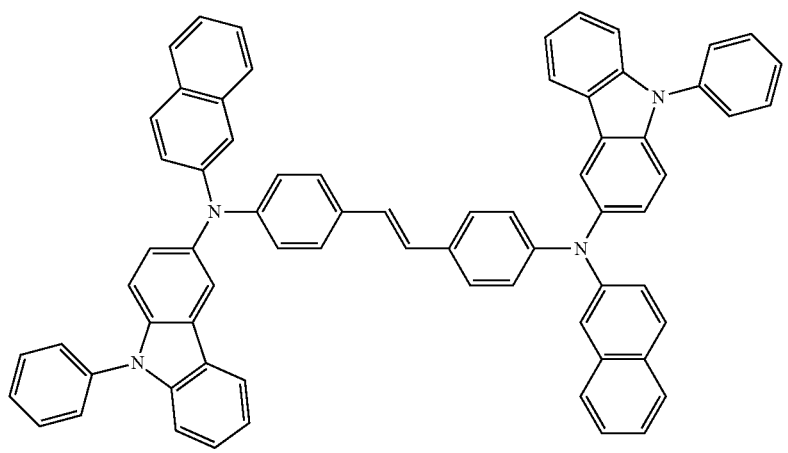
(62)

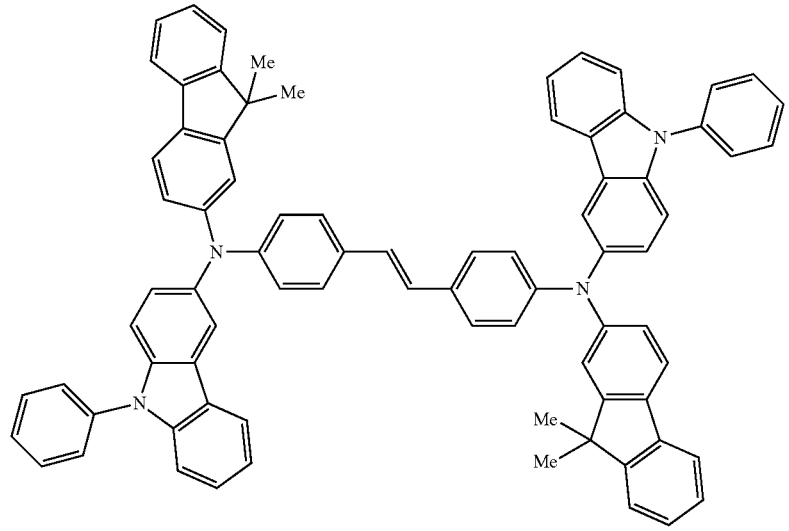
(63)
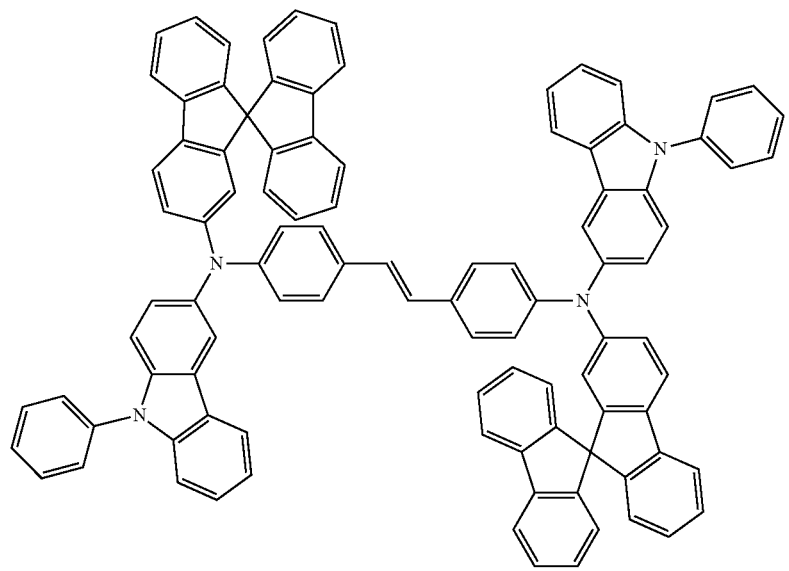
(64)
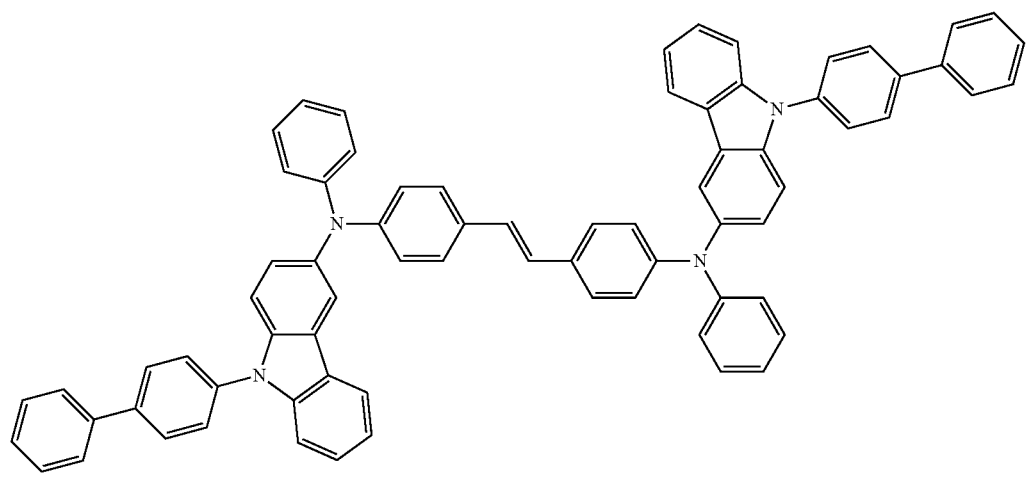
(65)

-continued
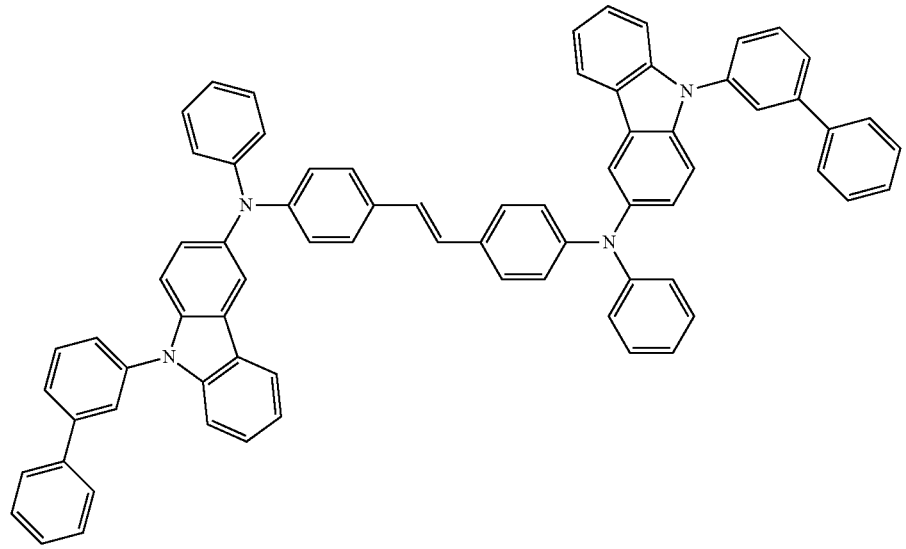
(66)
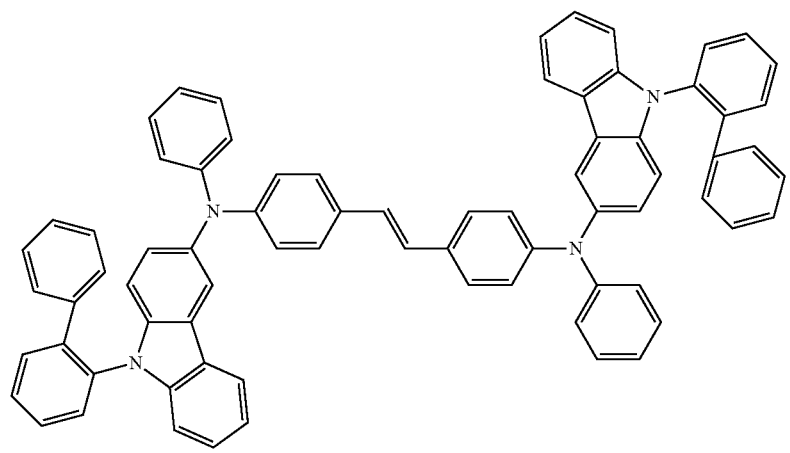
(67)
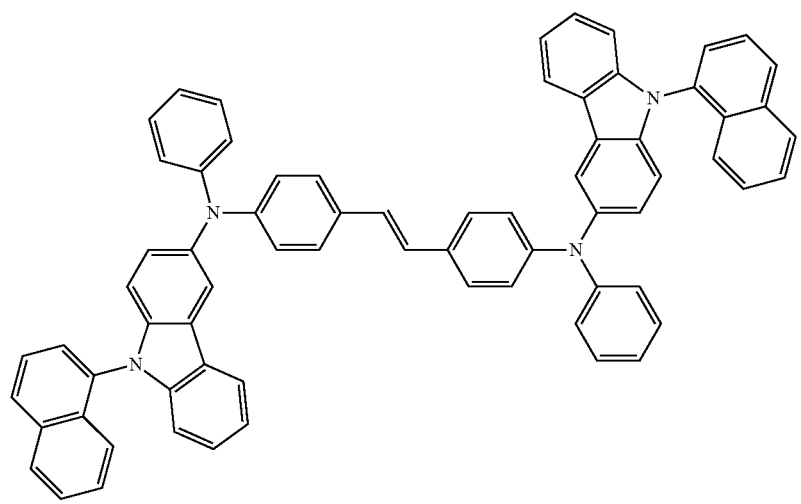
(68)

-continued
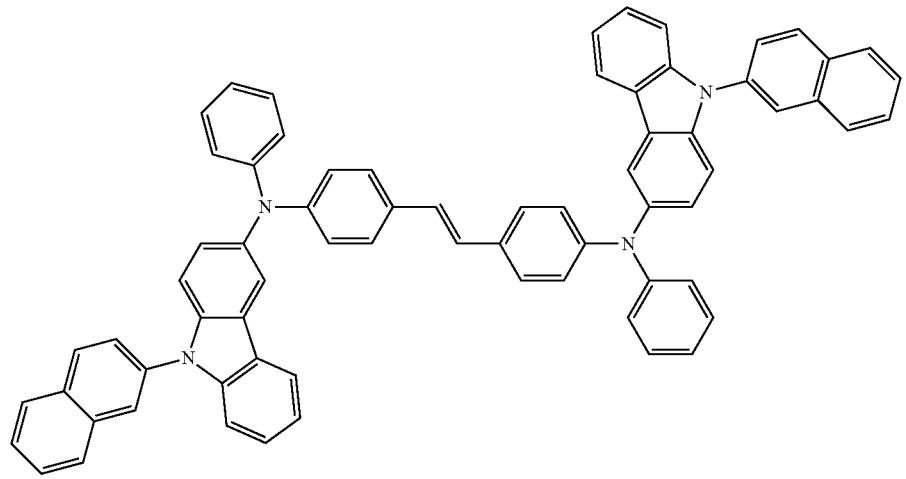
(69)
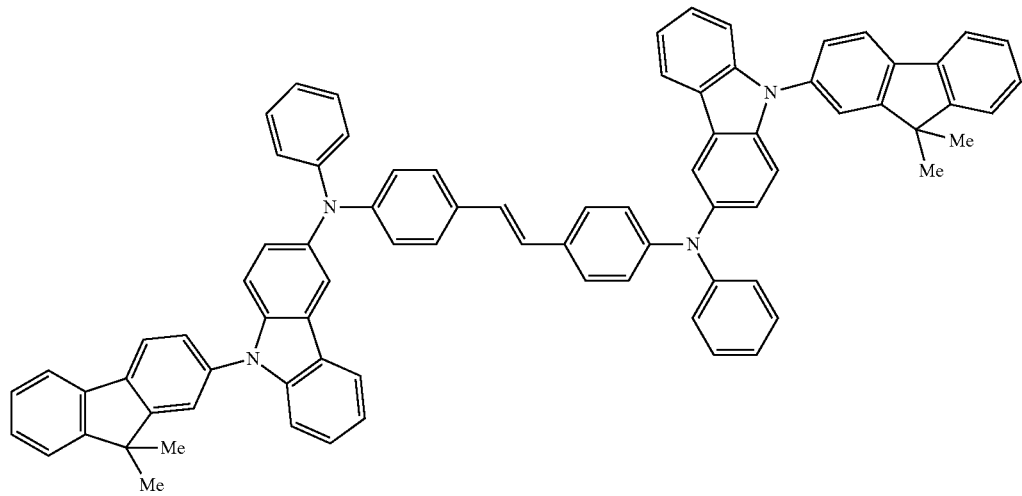
(70)
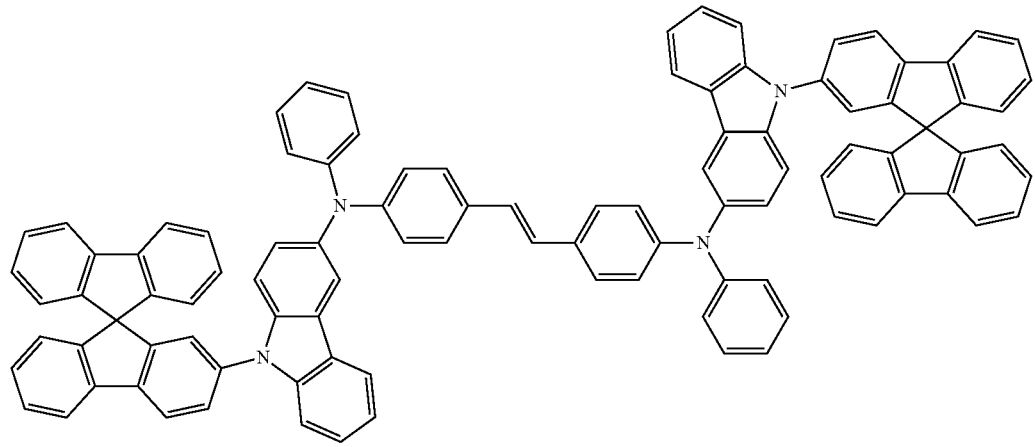
(71)

-continued
(72)
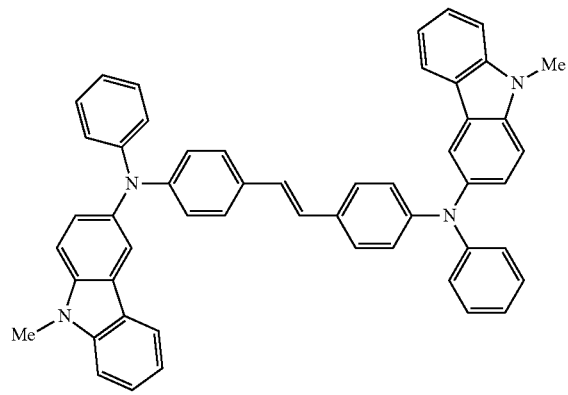
(73)
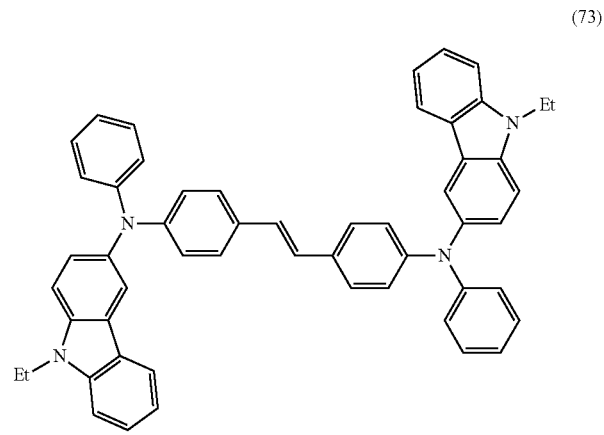
(74)
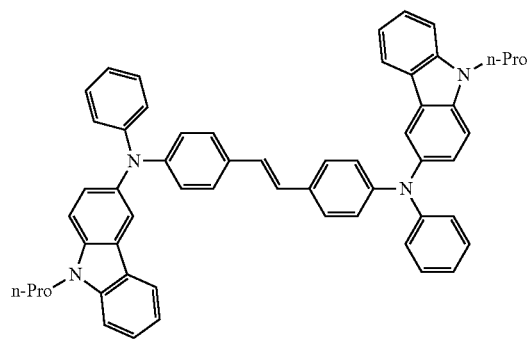
(75)
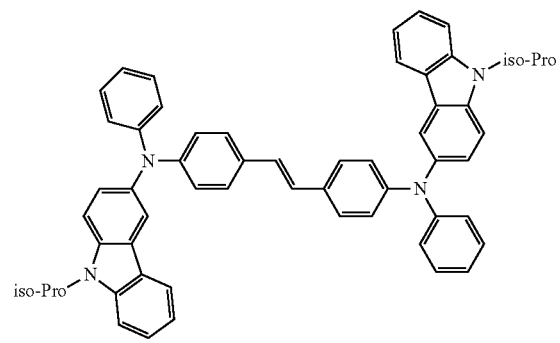
(76)
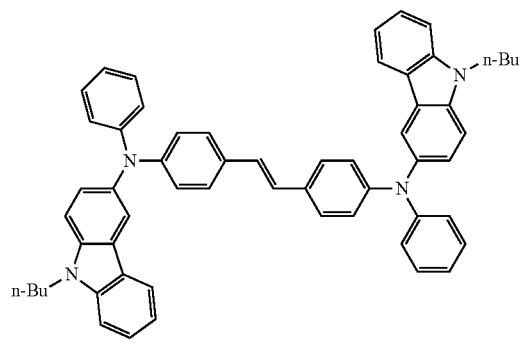
(77)
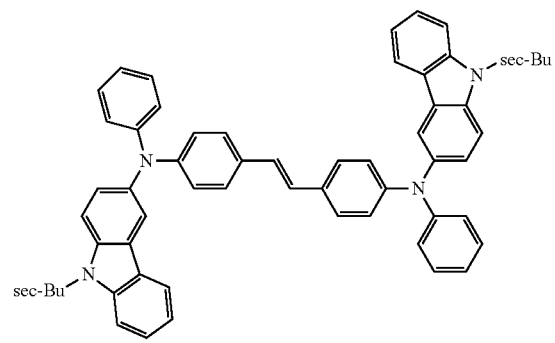
(78)
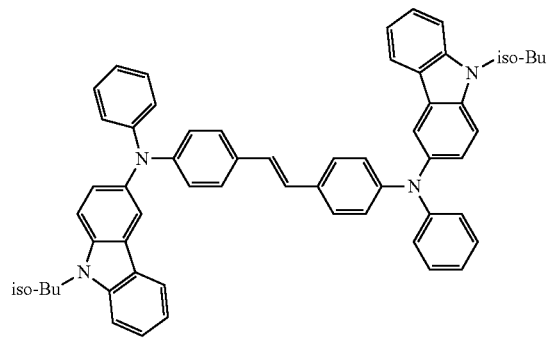
(79)
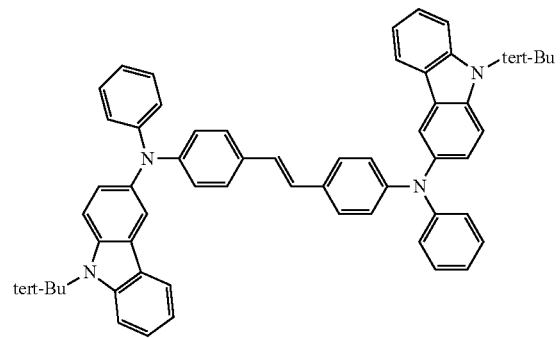

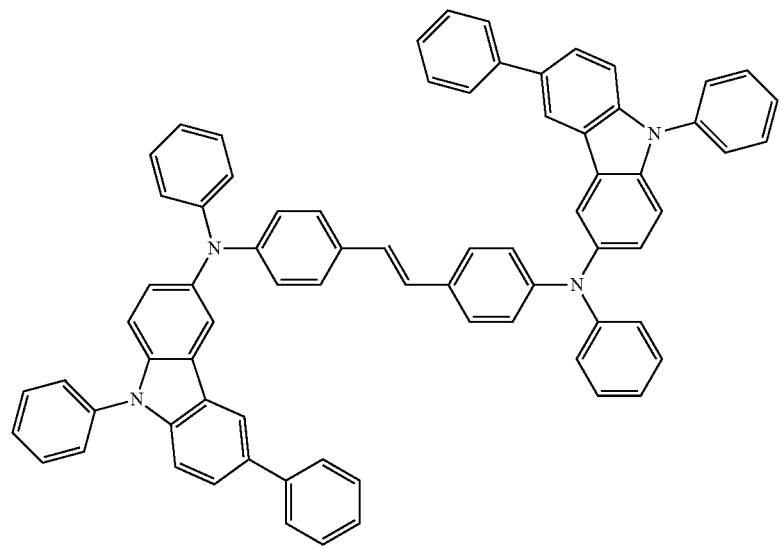
(80)
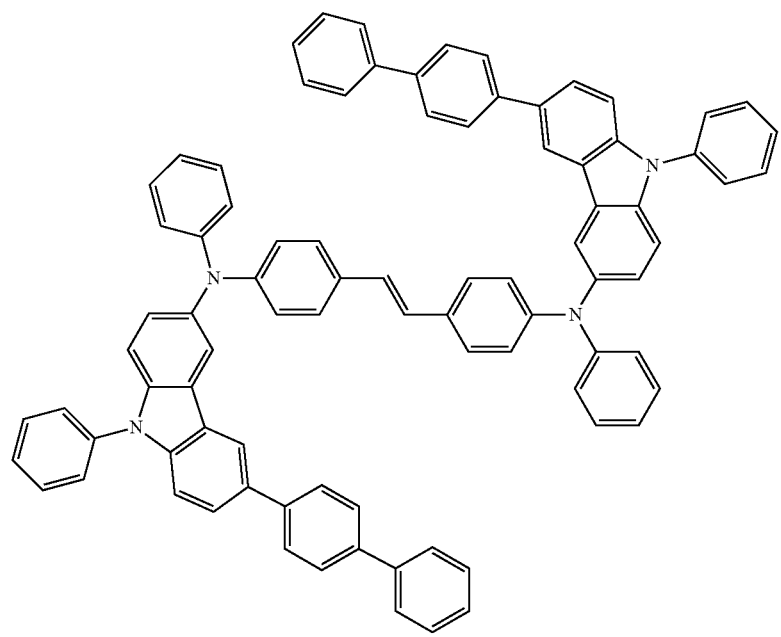
(81)

(82)
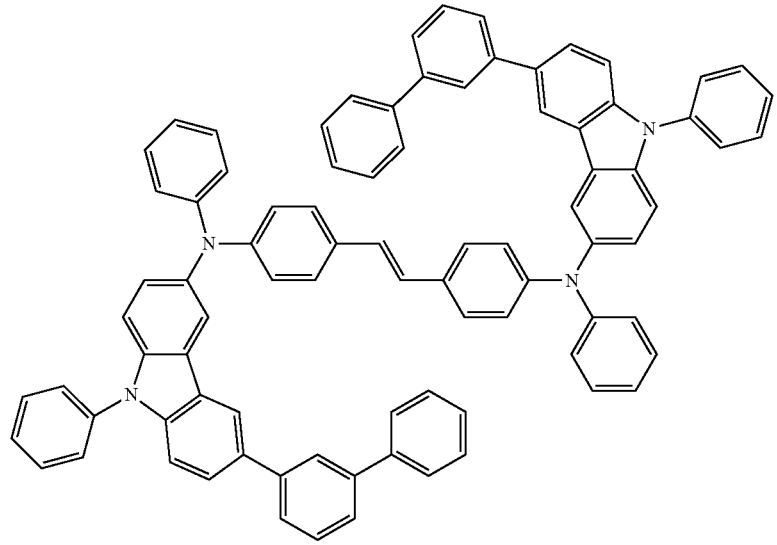
(83)
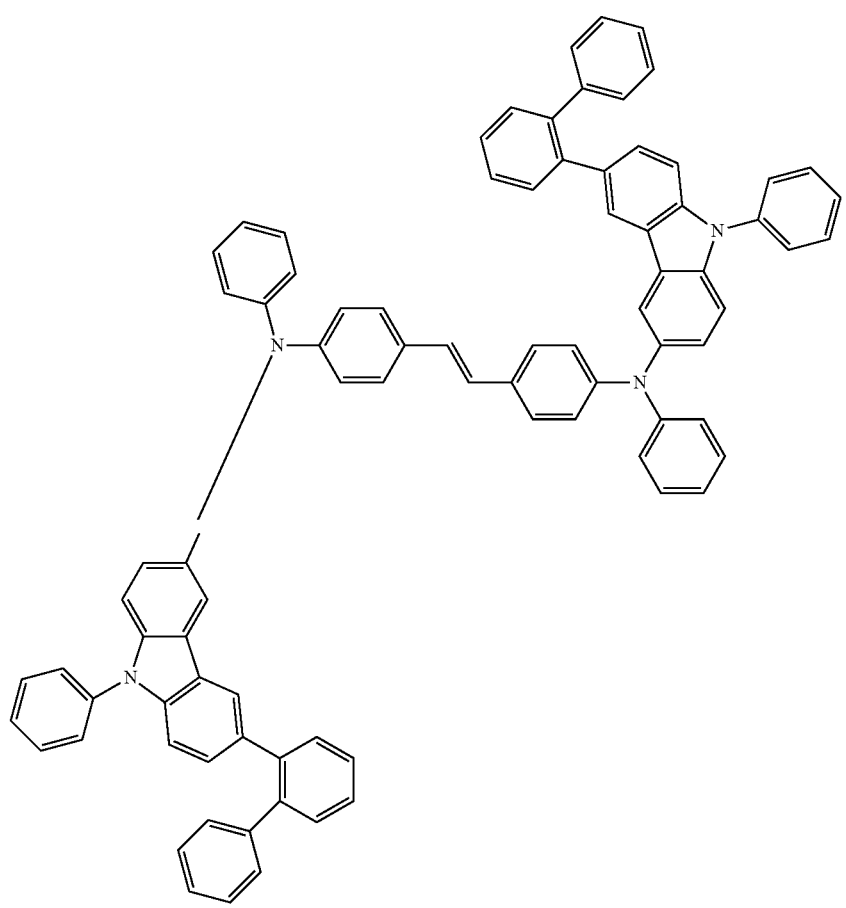

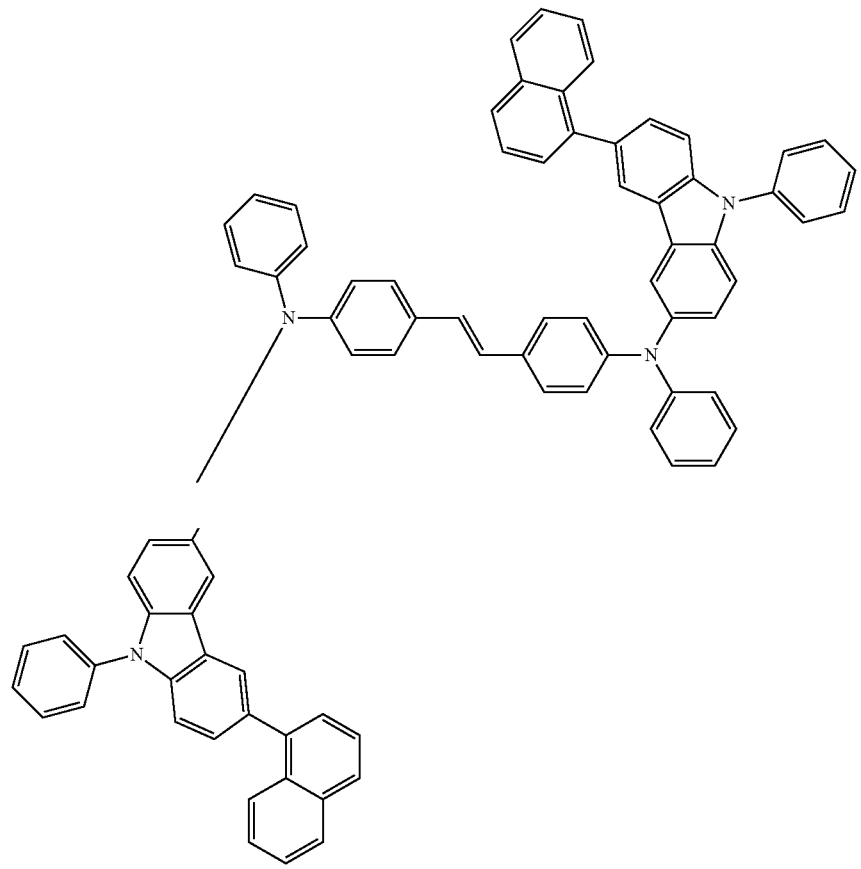
(84)
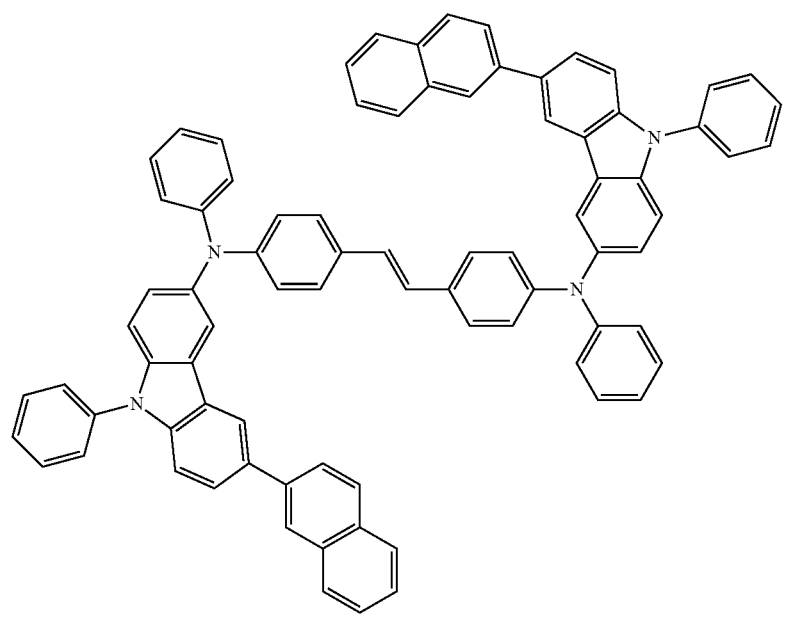
(85)

-continued
(86)
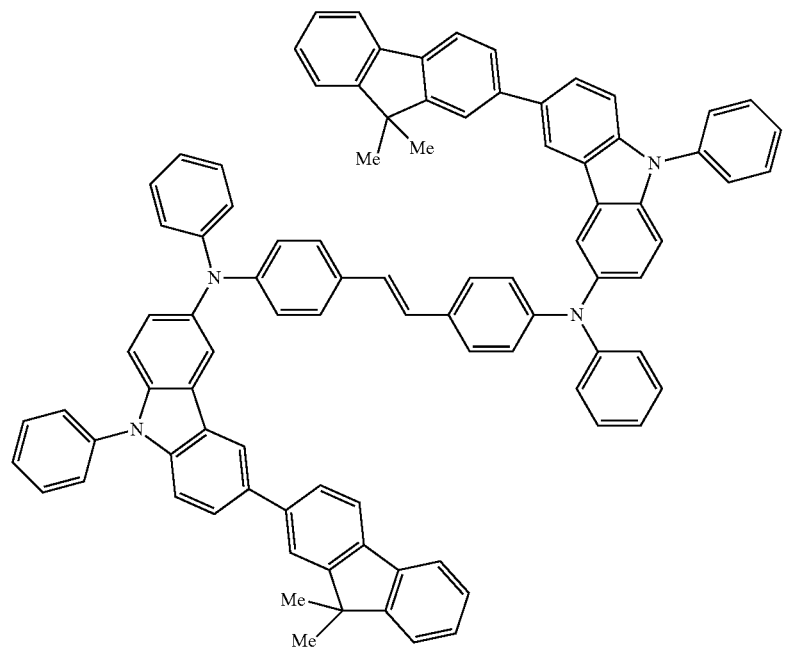
(87)
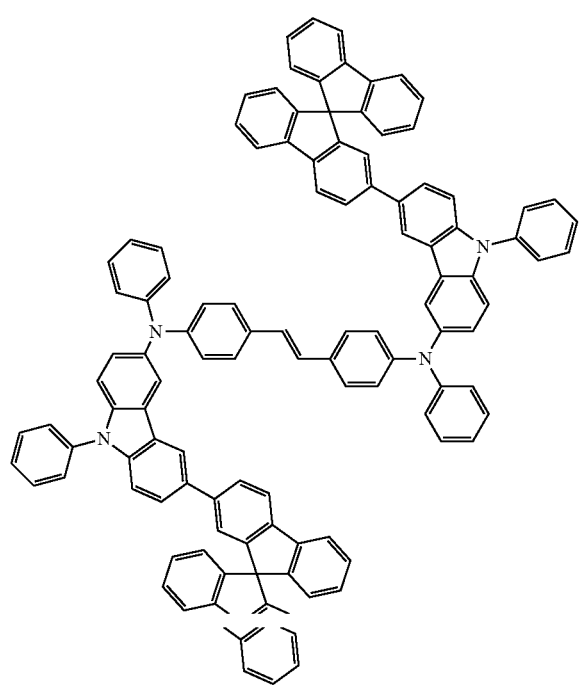

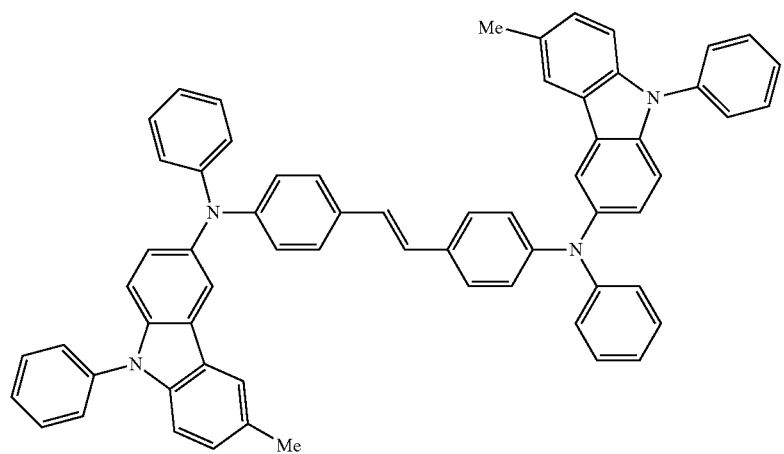
(88)
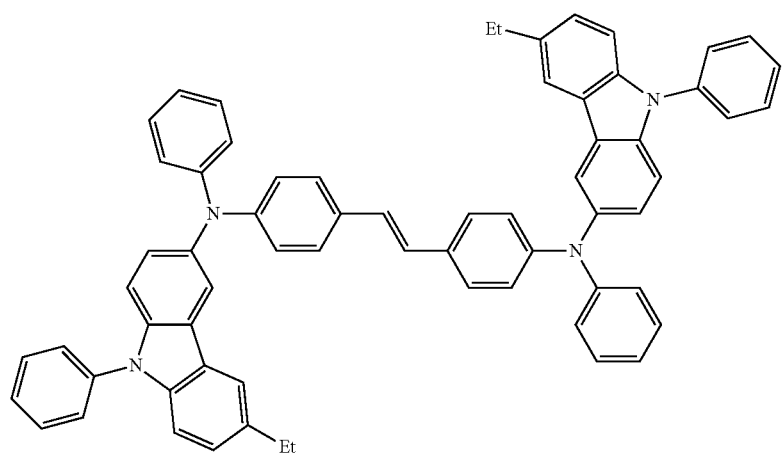
(89)
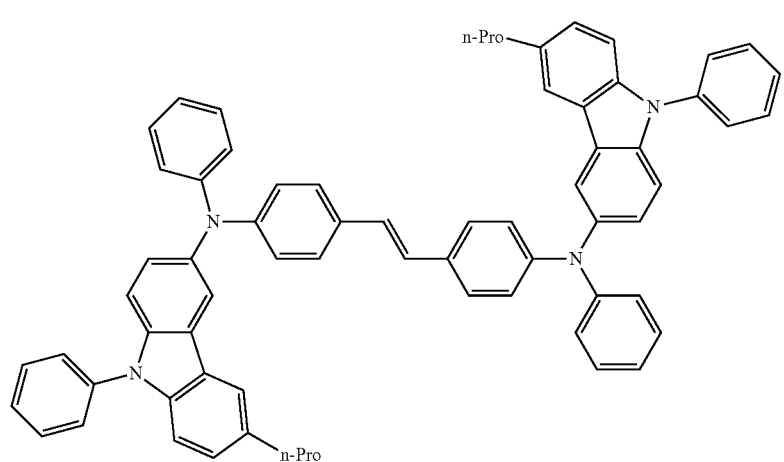
(90)

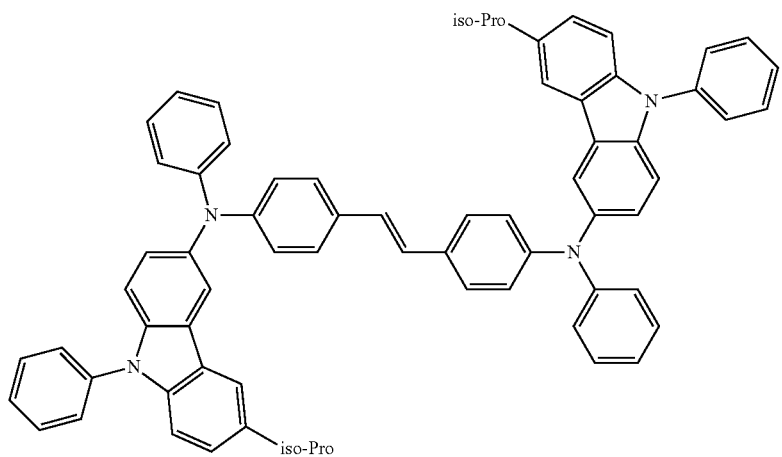
(91)
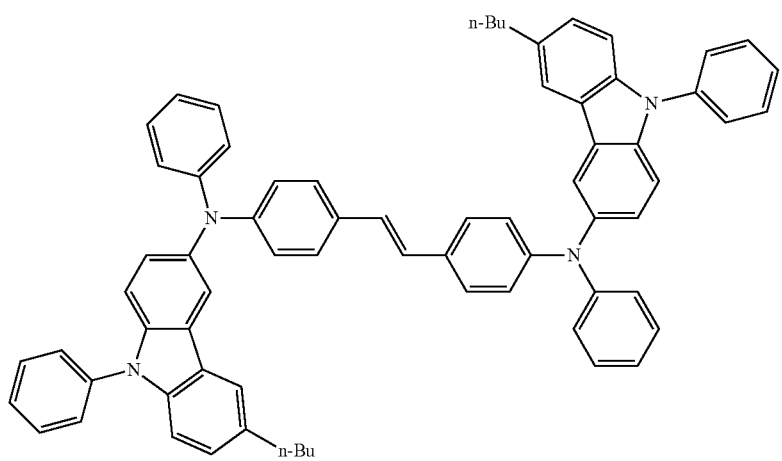
(92)
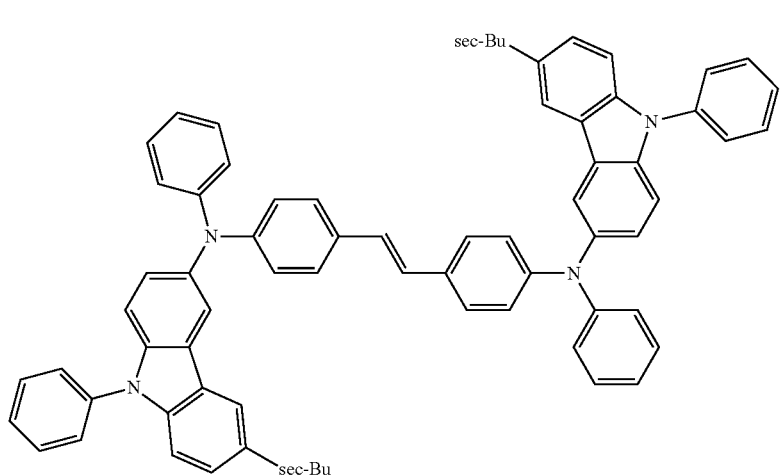
(93)

-continued
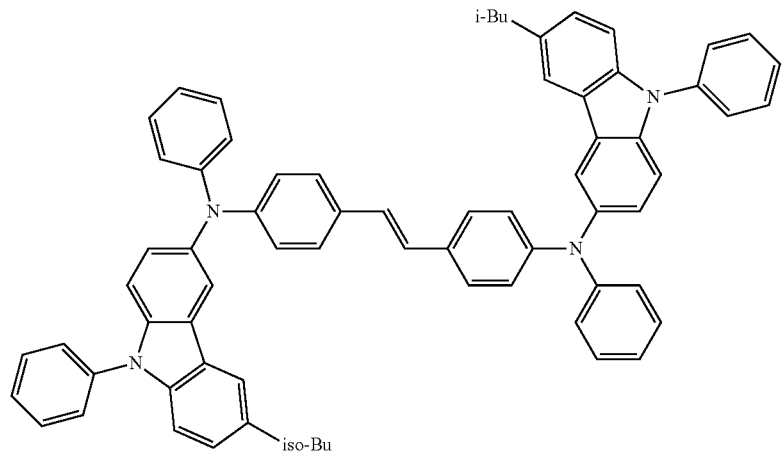
(94)
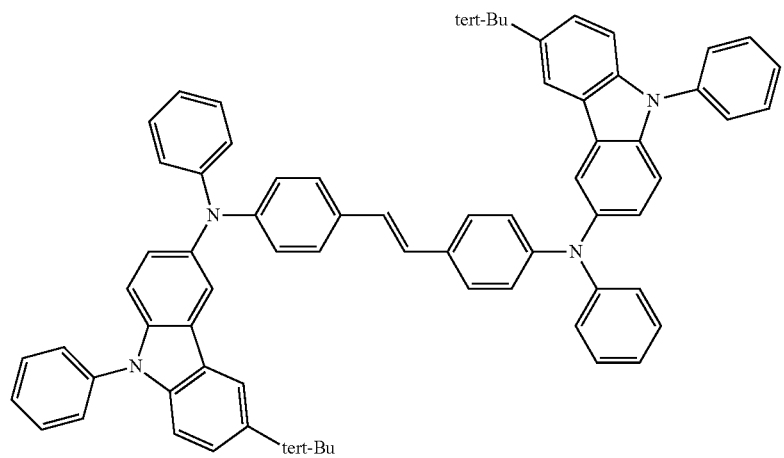
(95)
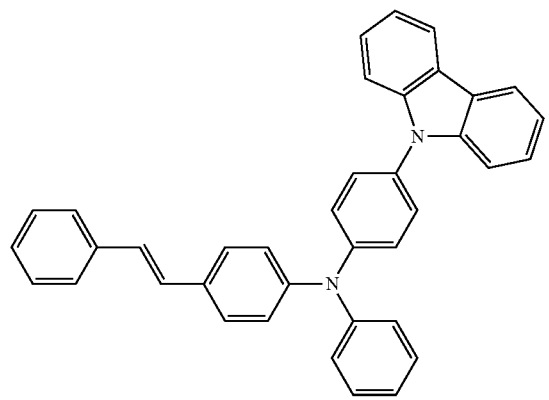
(96)
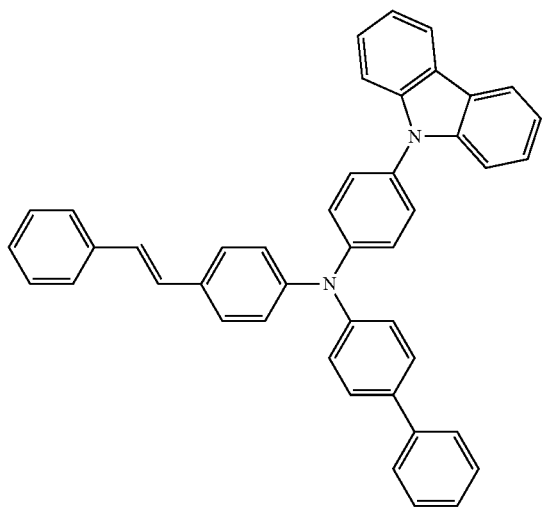
(97)

-continued
(98)
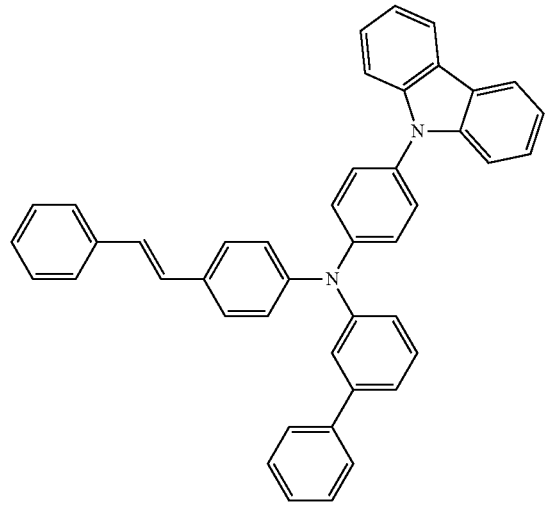
(99)
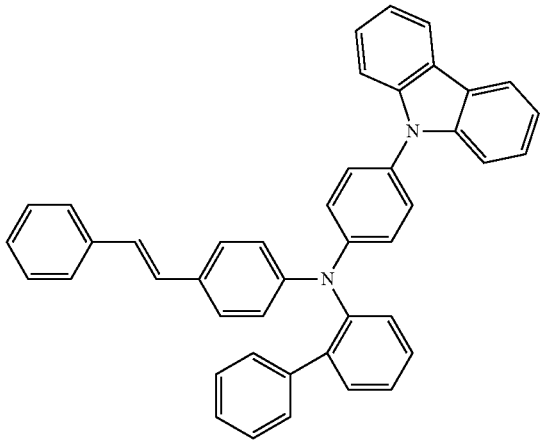
(100)
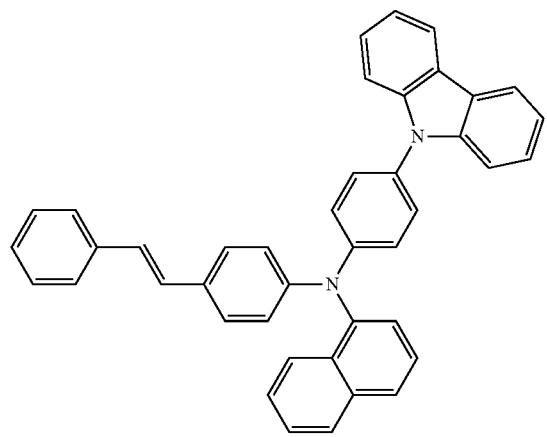
(101)
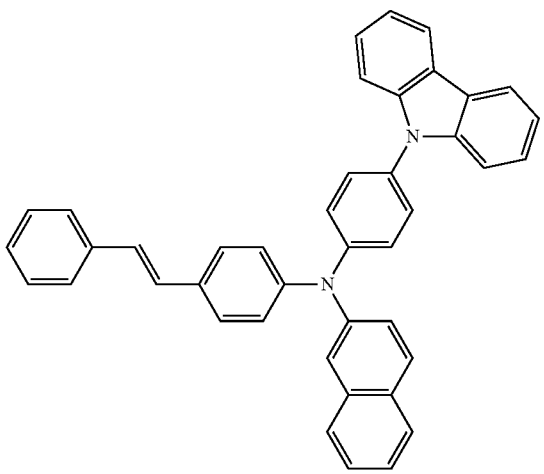
(102)
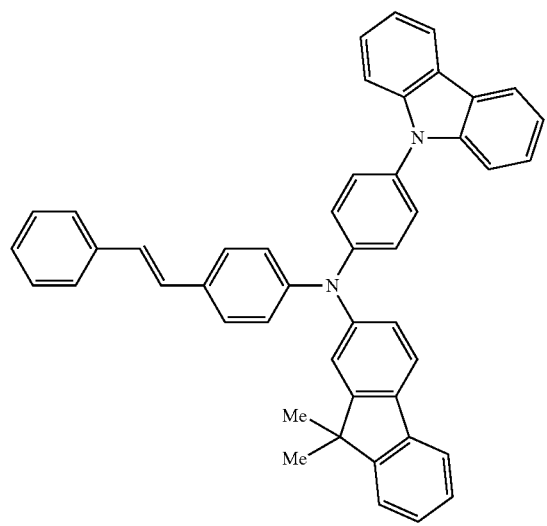
(103)
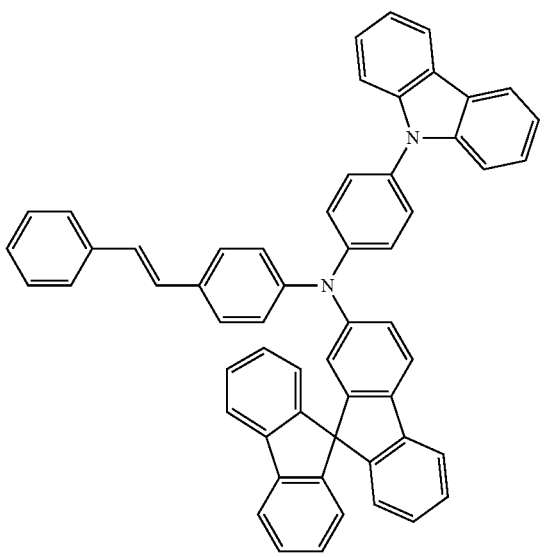

(104)
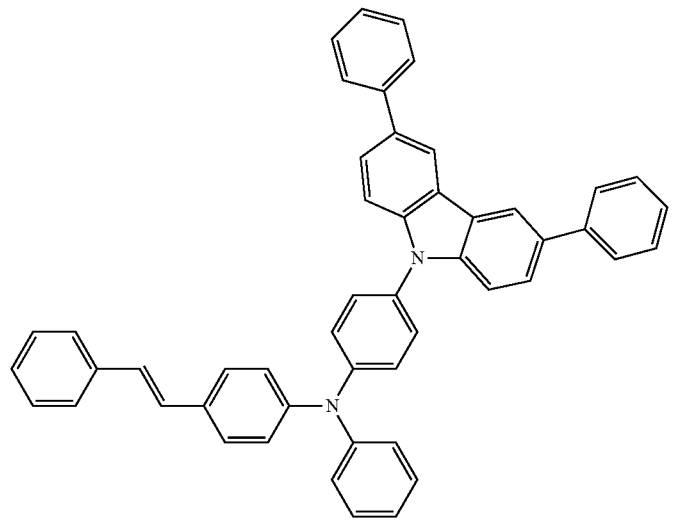
(105)
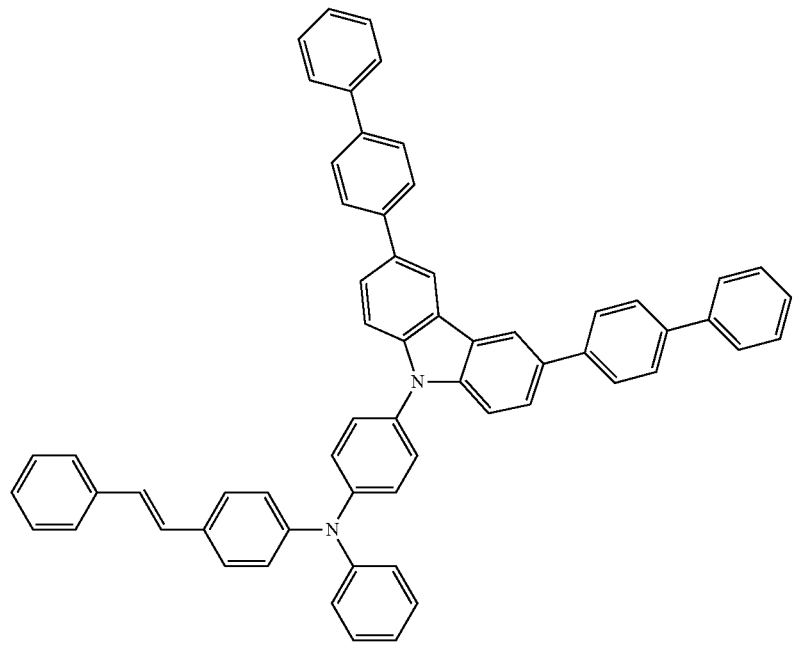
(106)
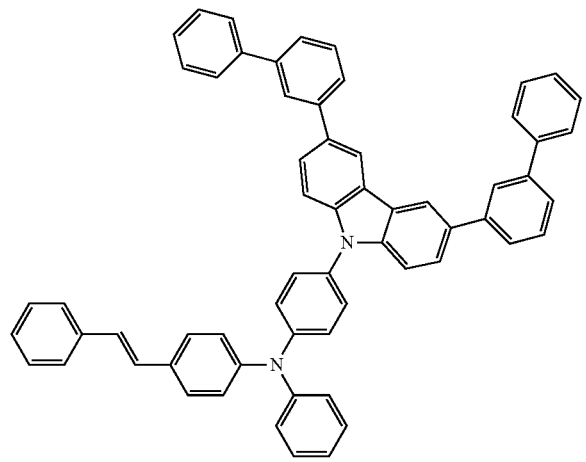
(107)
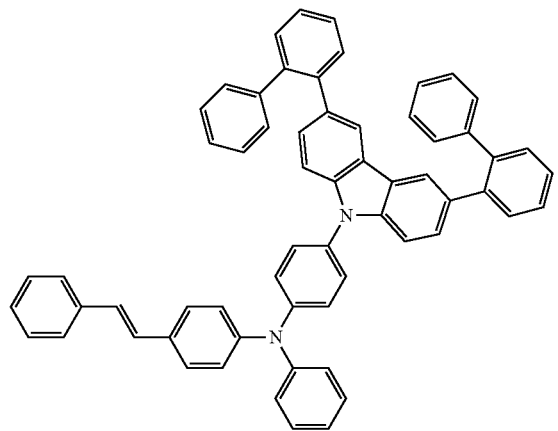

-continued
(108)
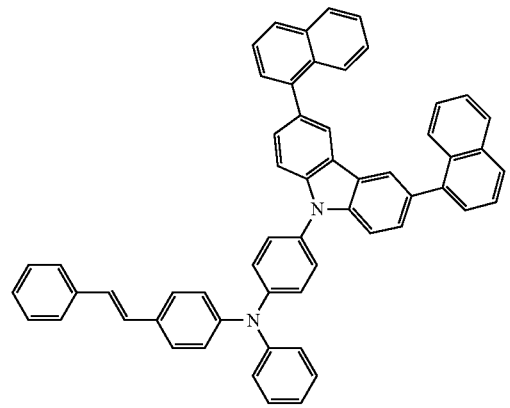
(109)
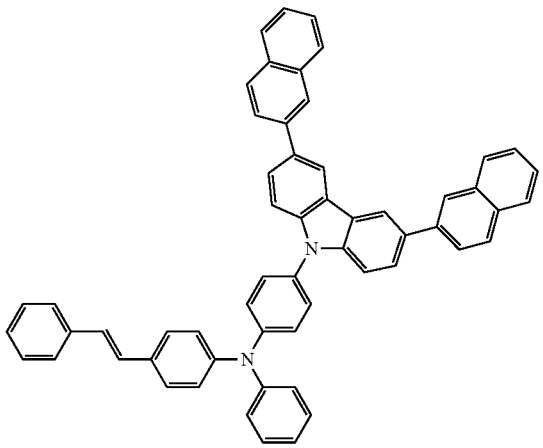
(110)
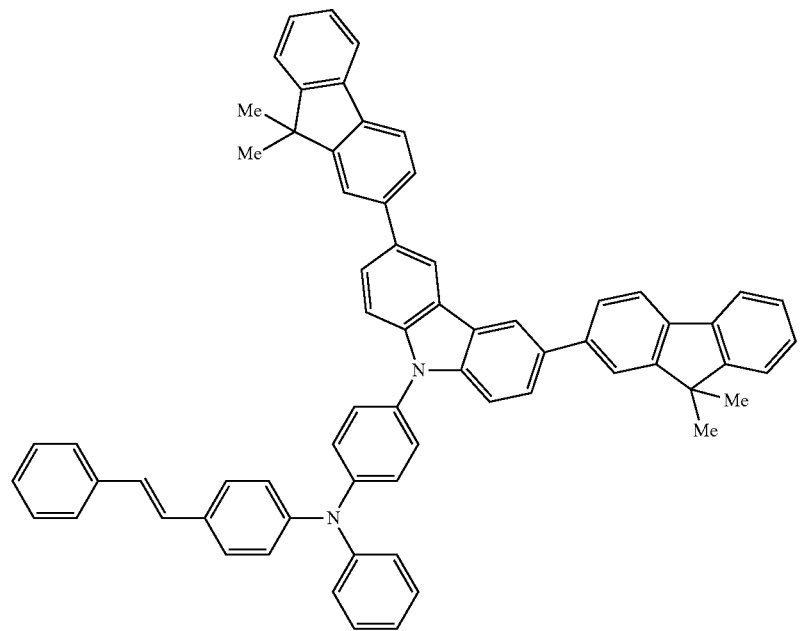

(111)
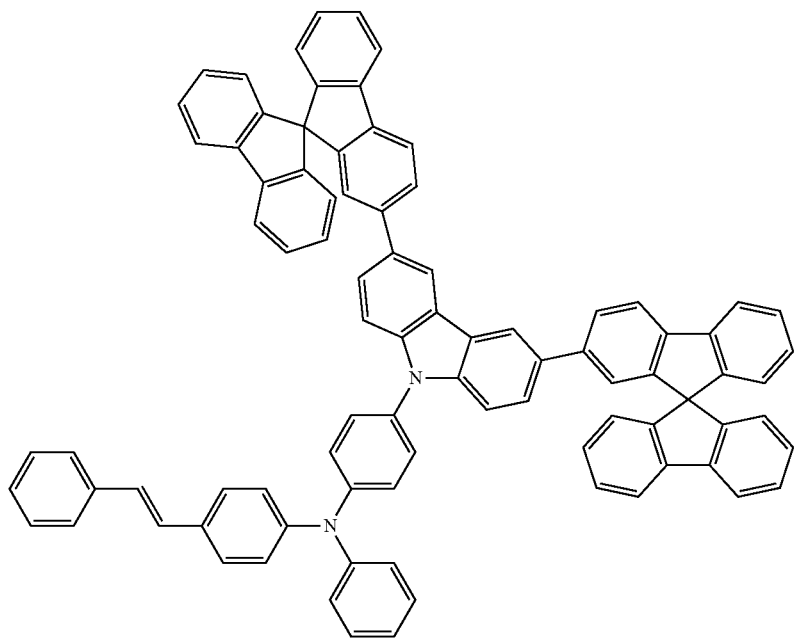
(112) (113)
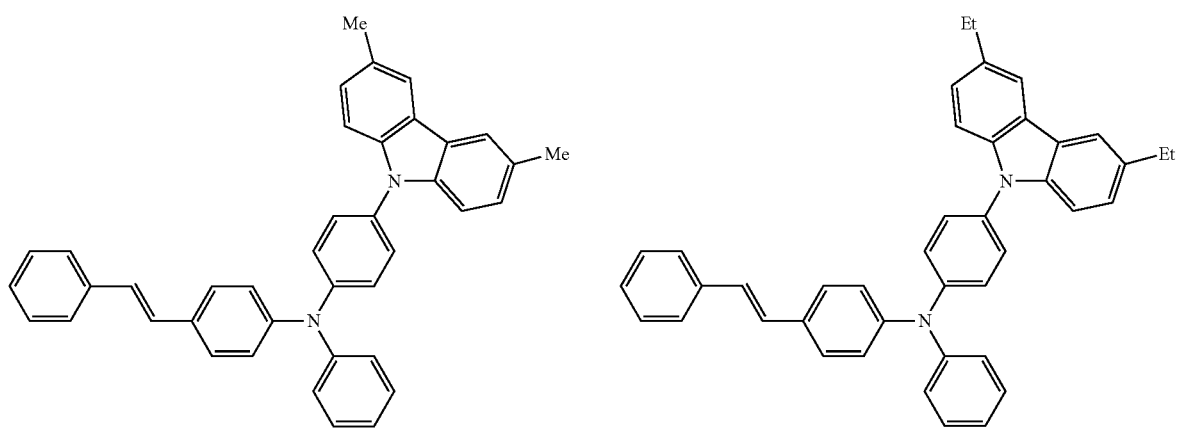
(114) (115)
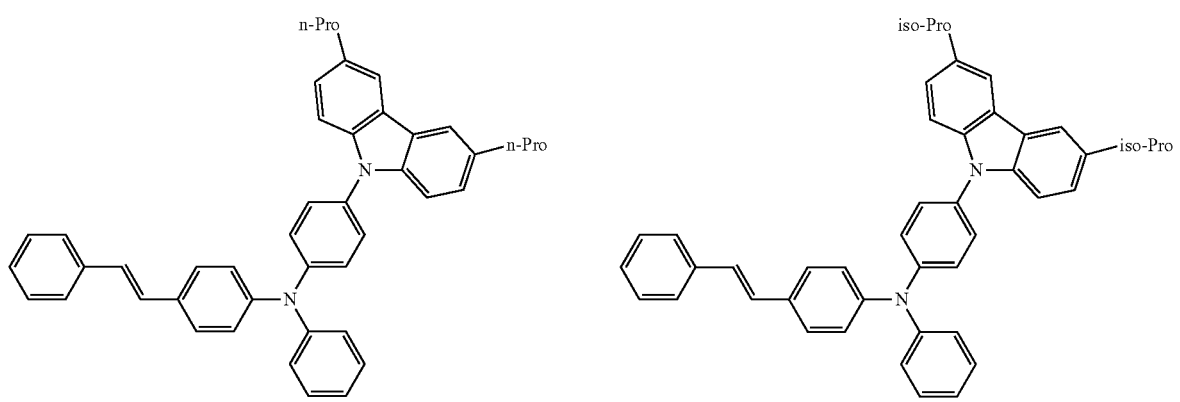

-continued
(116)
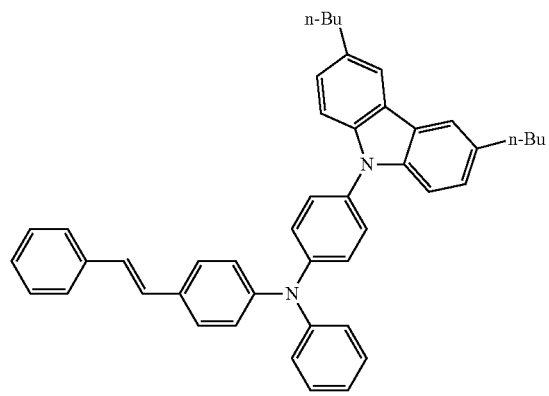
(117)
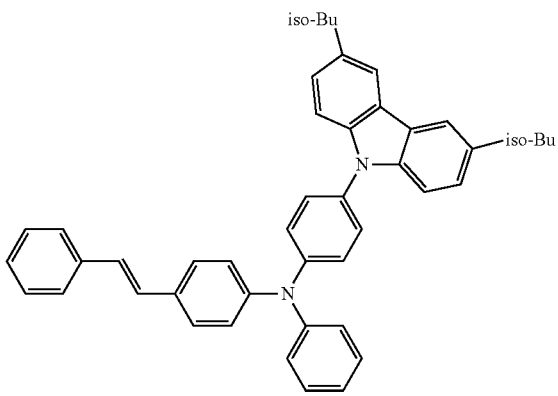
(118)
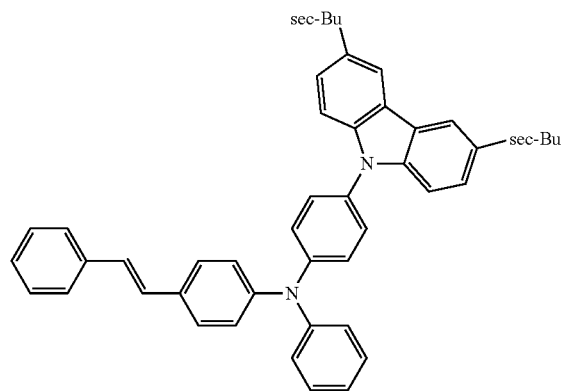
(119)
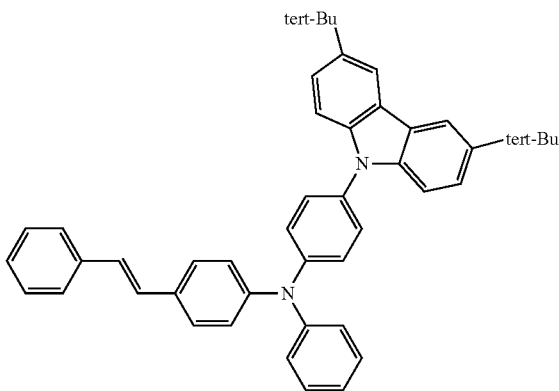
(120)
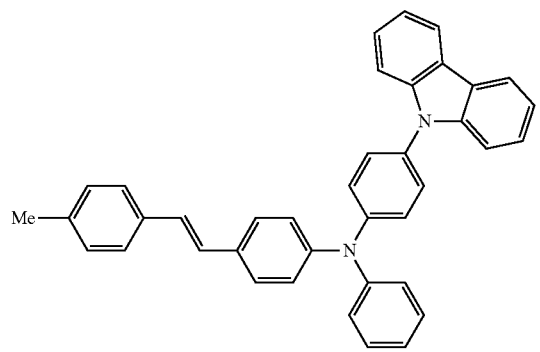
(121)
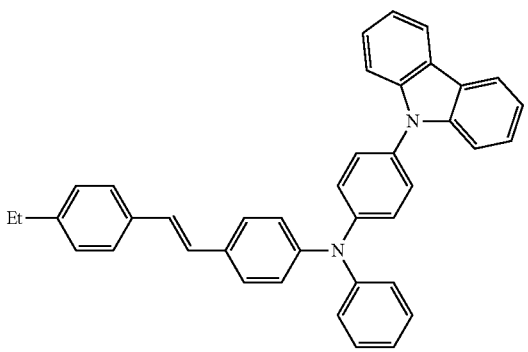
(122)
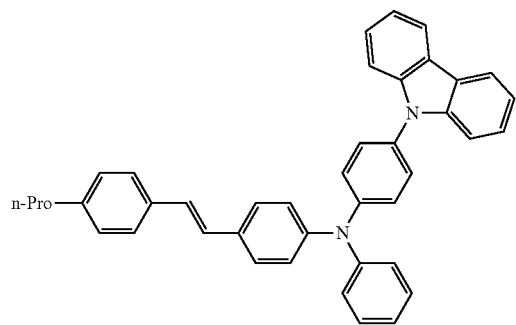
(123)
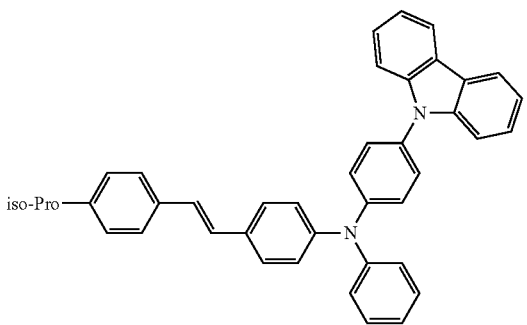

-continued
(124)
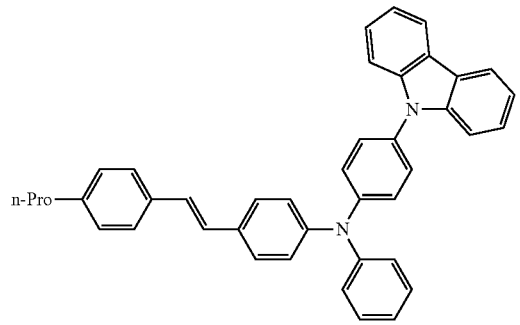
(125)
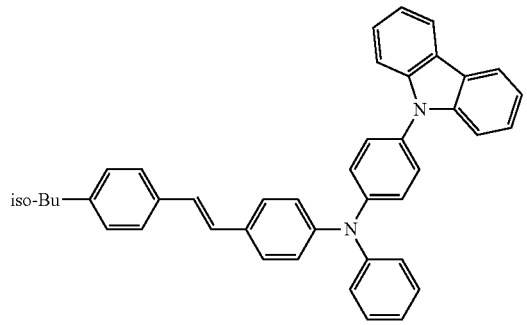
(126)
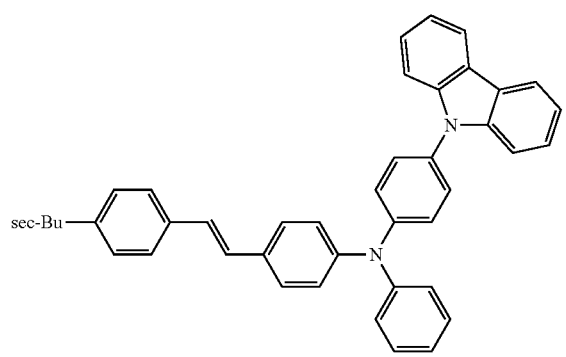
(127)
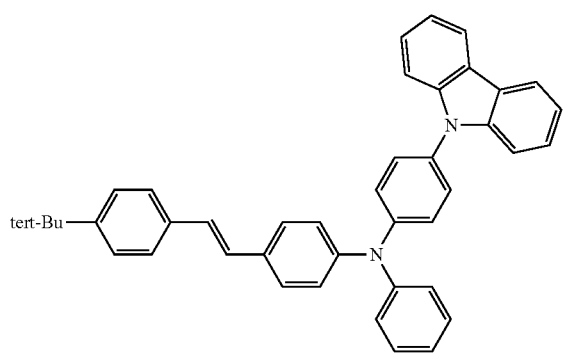
(128)
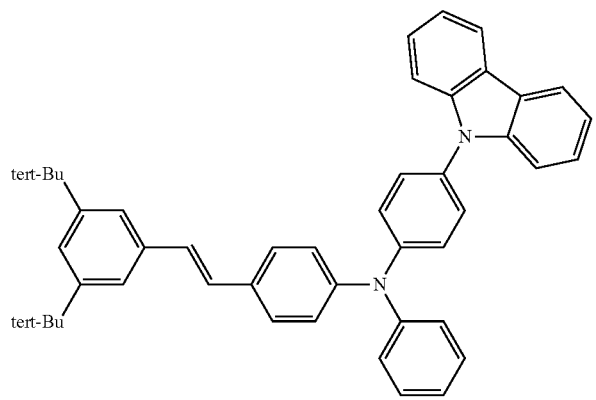
(129)
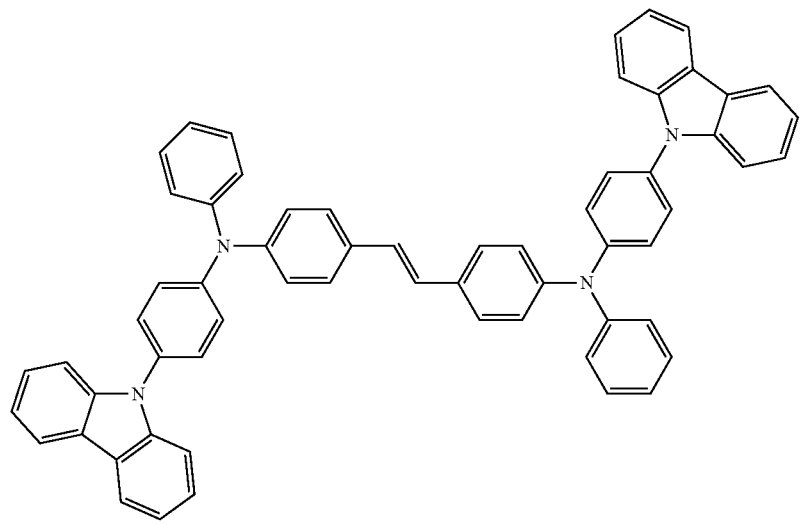

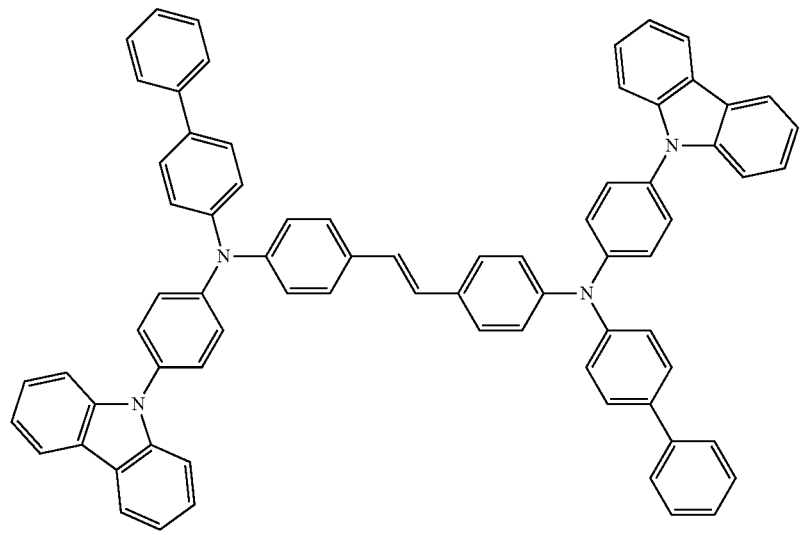
(130)
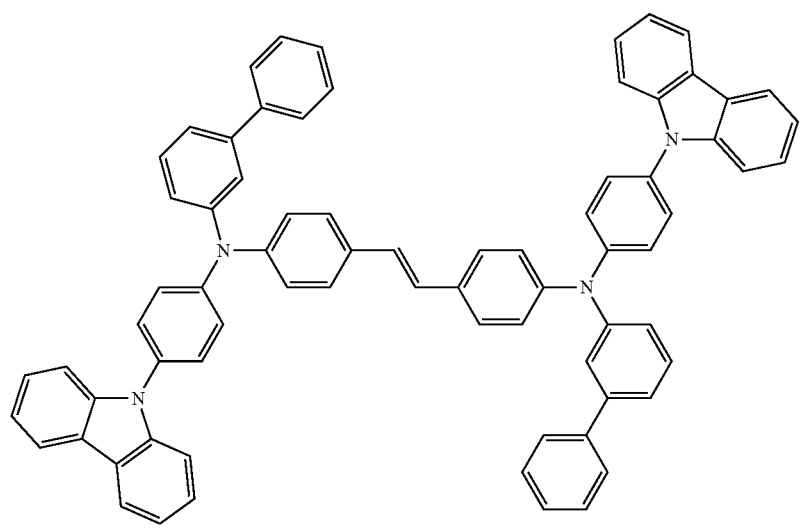
(131)
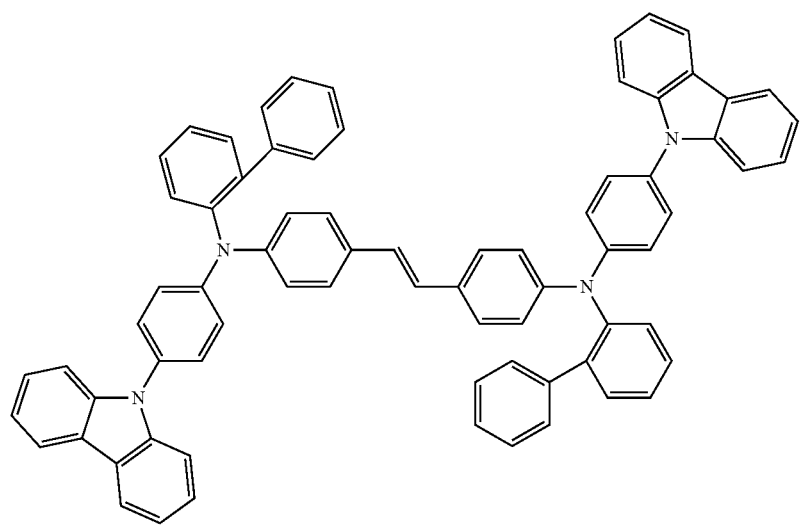
(132)

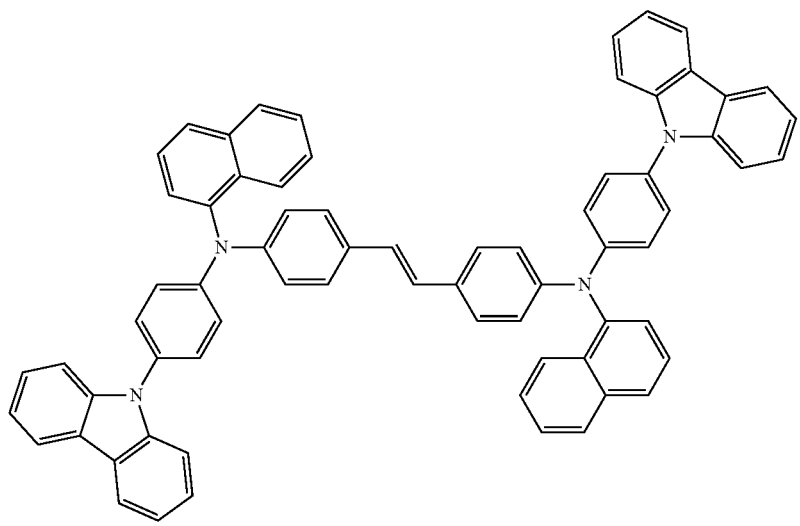 (133)
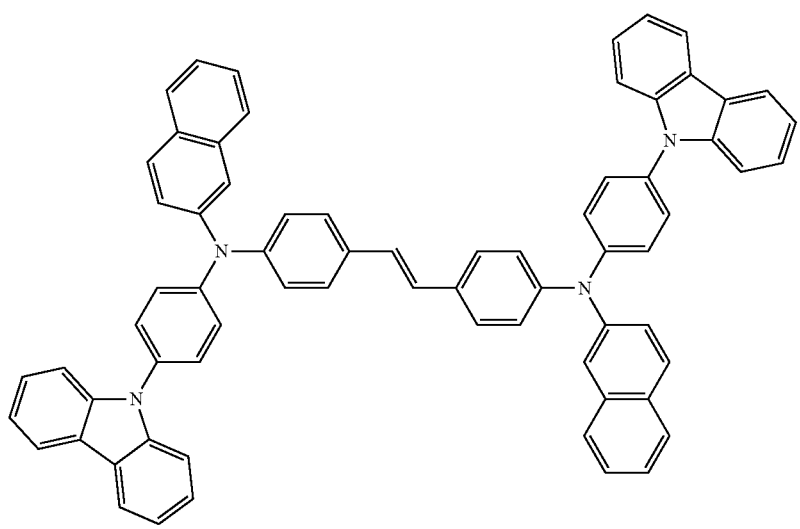 (134)
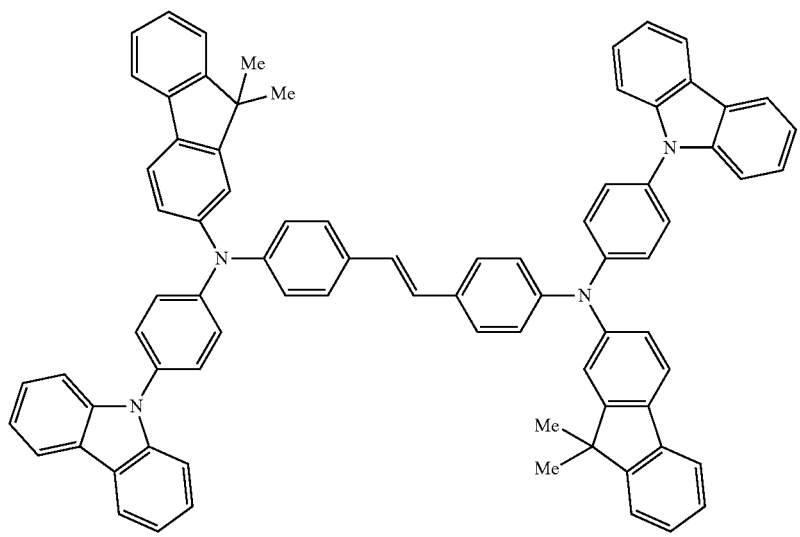 (135)

(136)
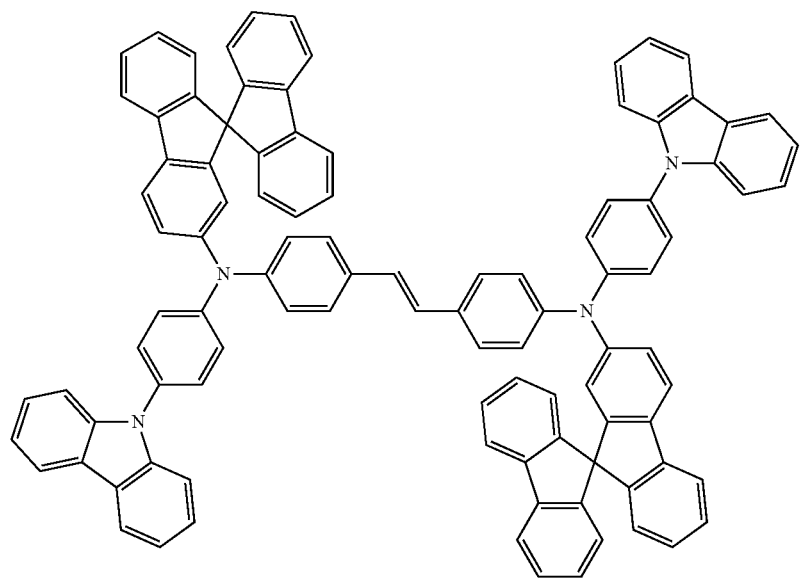
(137)
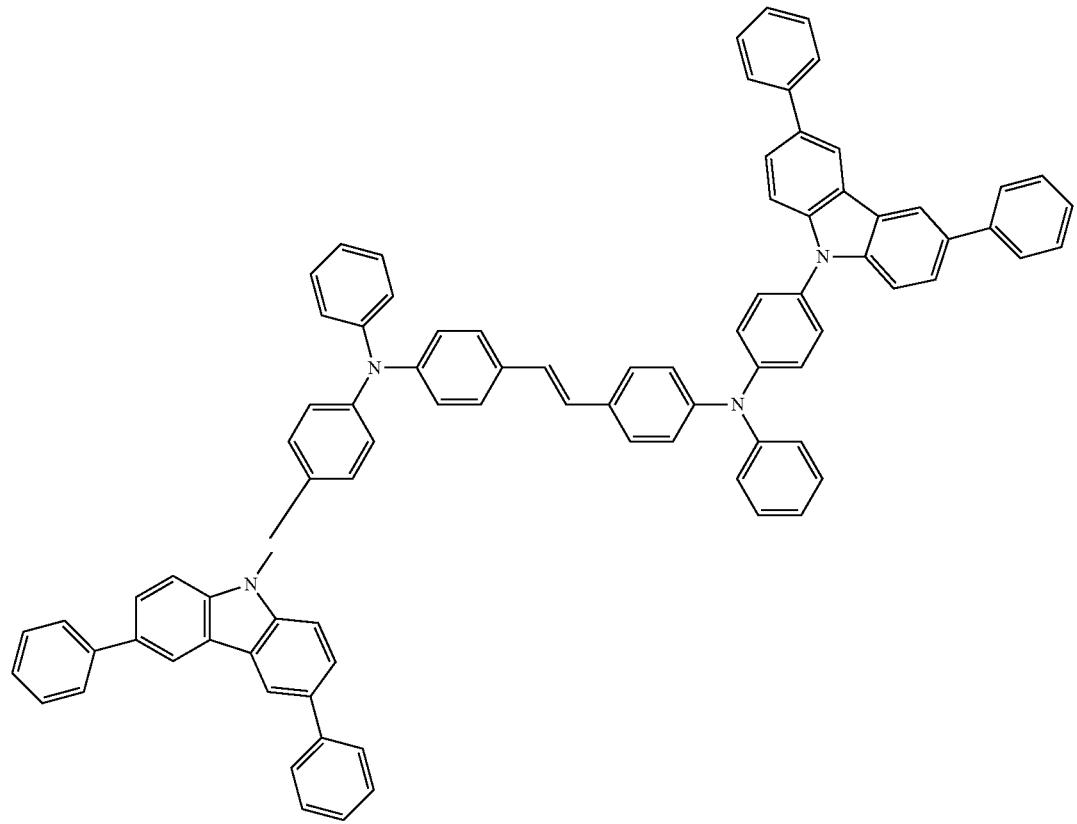

-continued
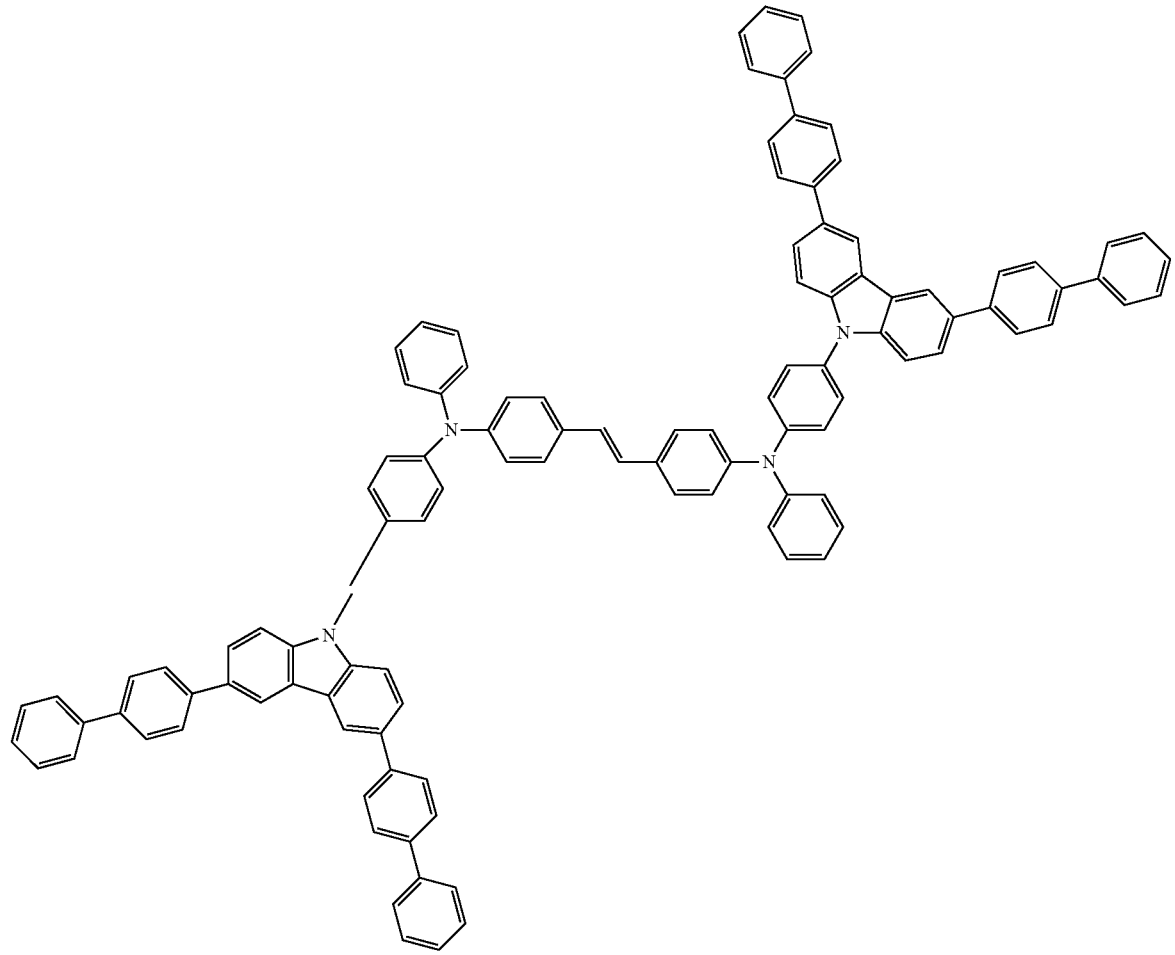
(138)
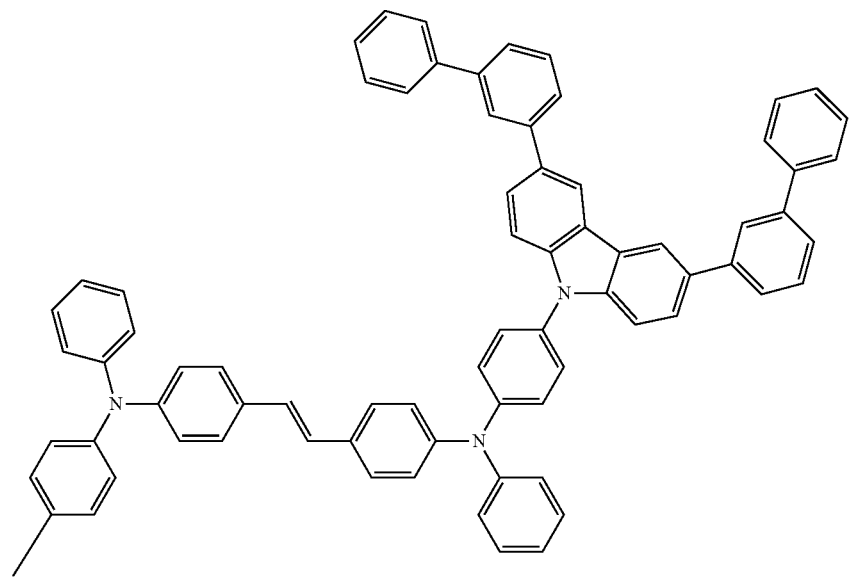
(139)

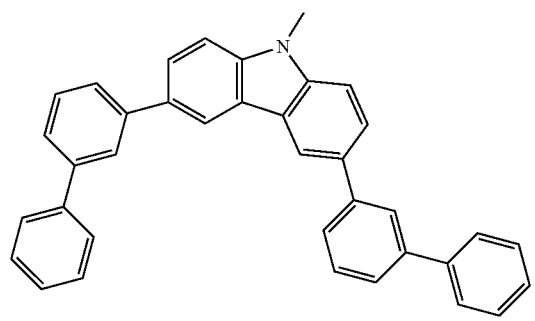
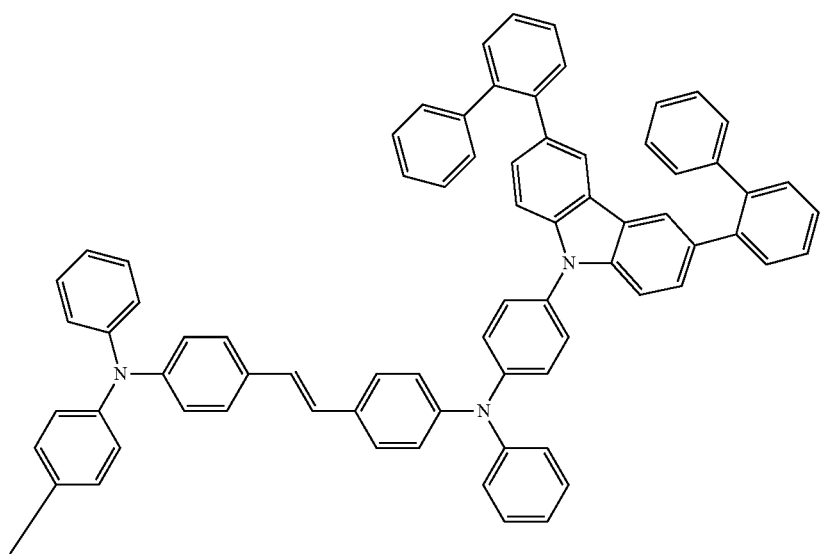
(140)
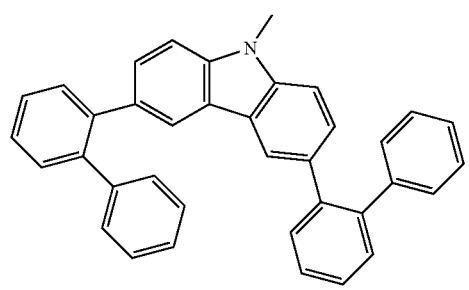

(141)
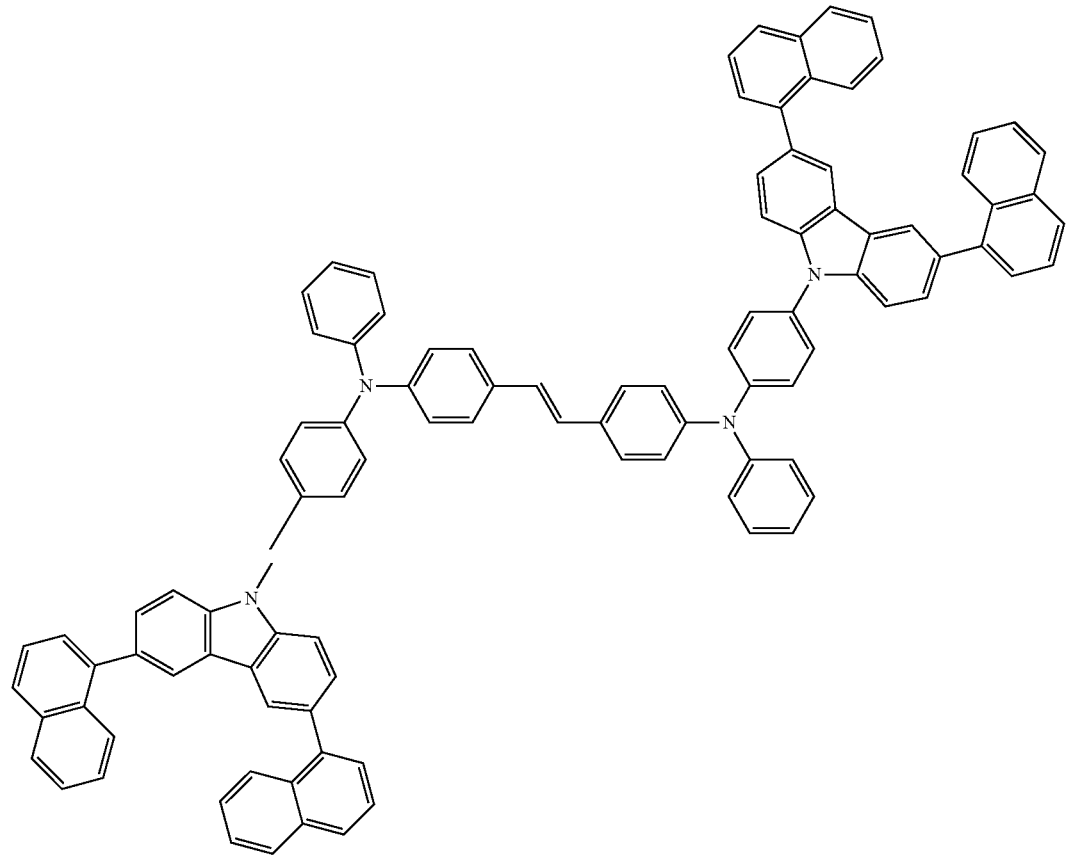
(142)
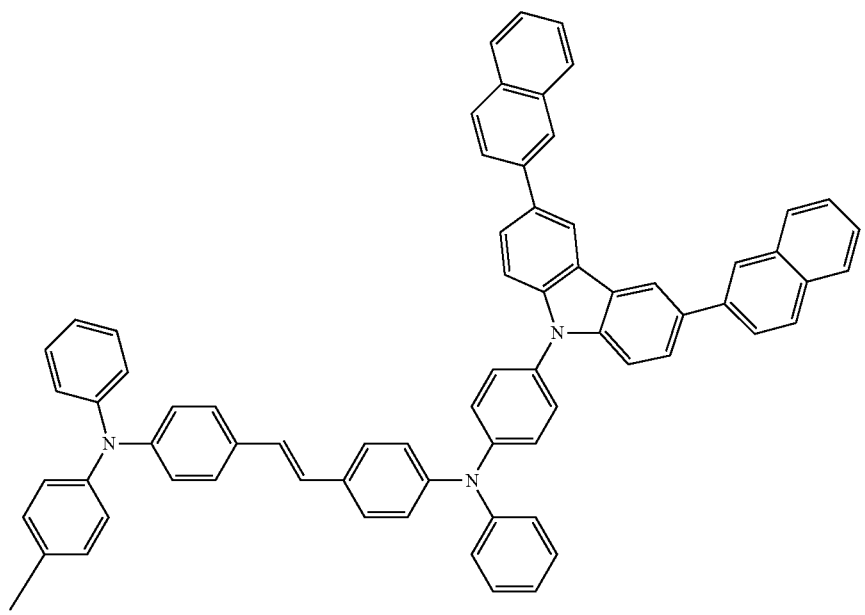

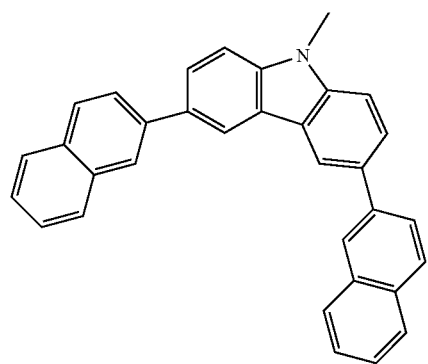
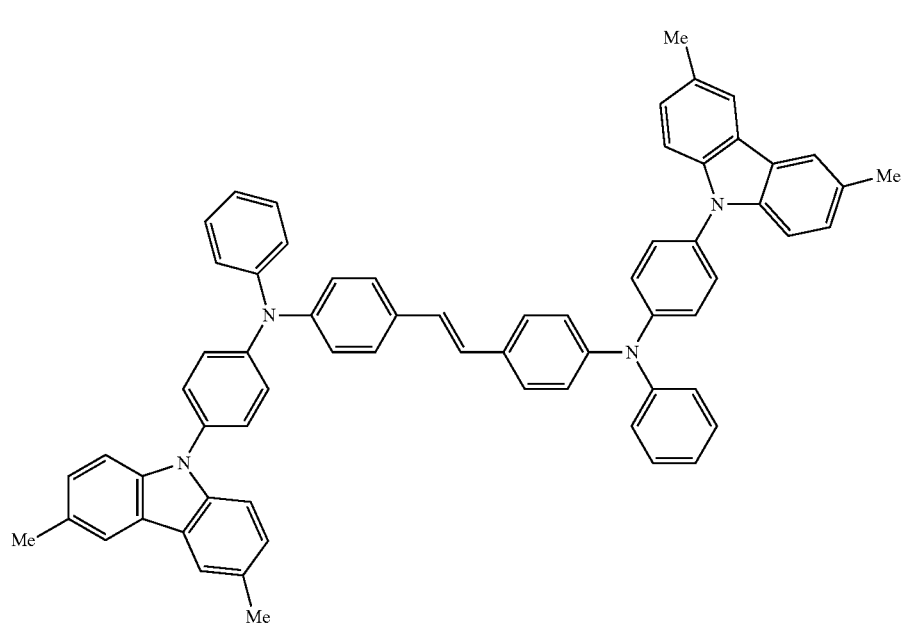
(143)
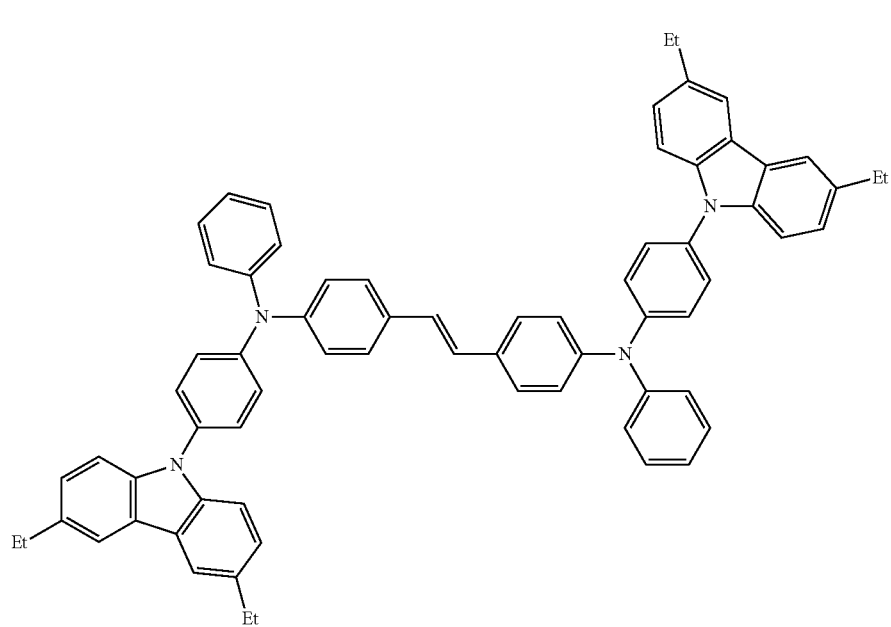
(144)

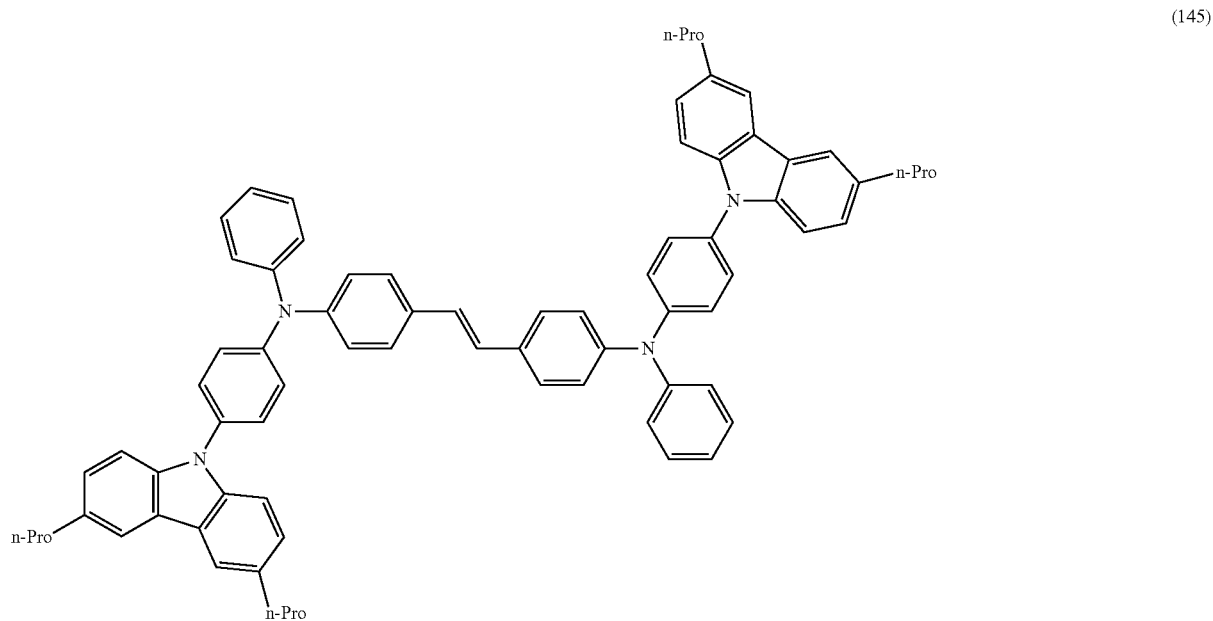
(145)
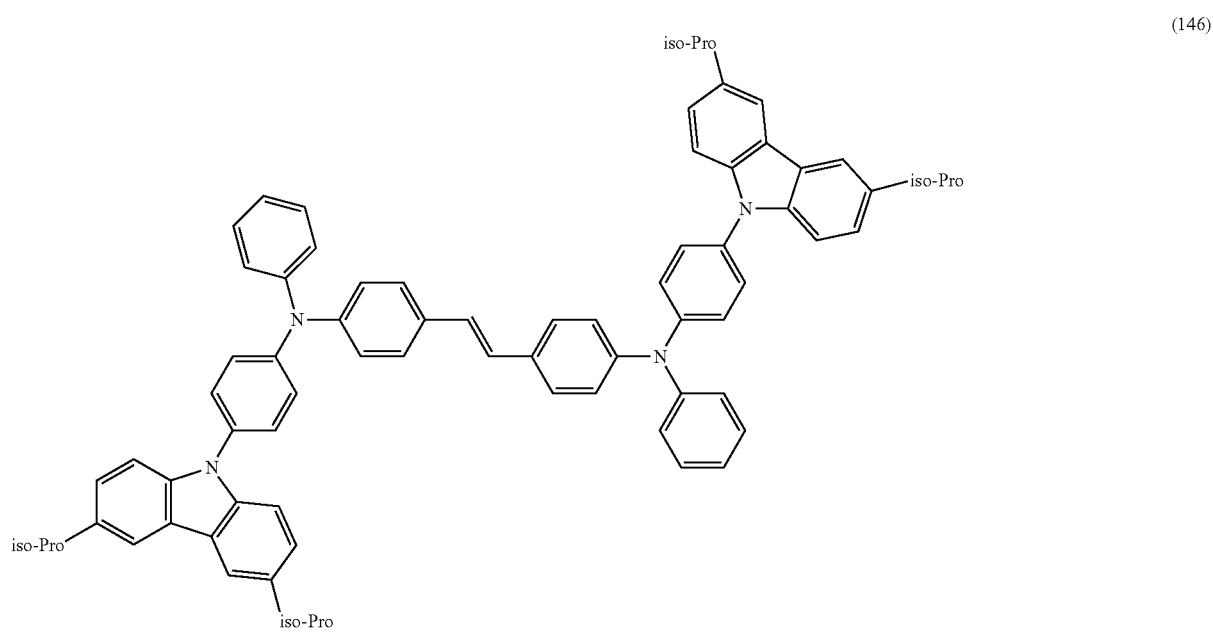
(146)

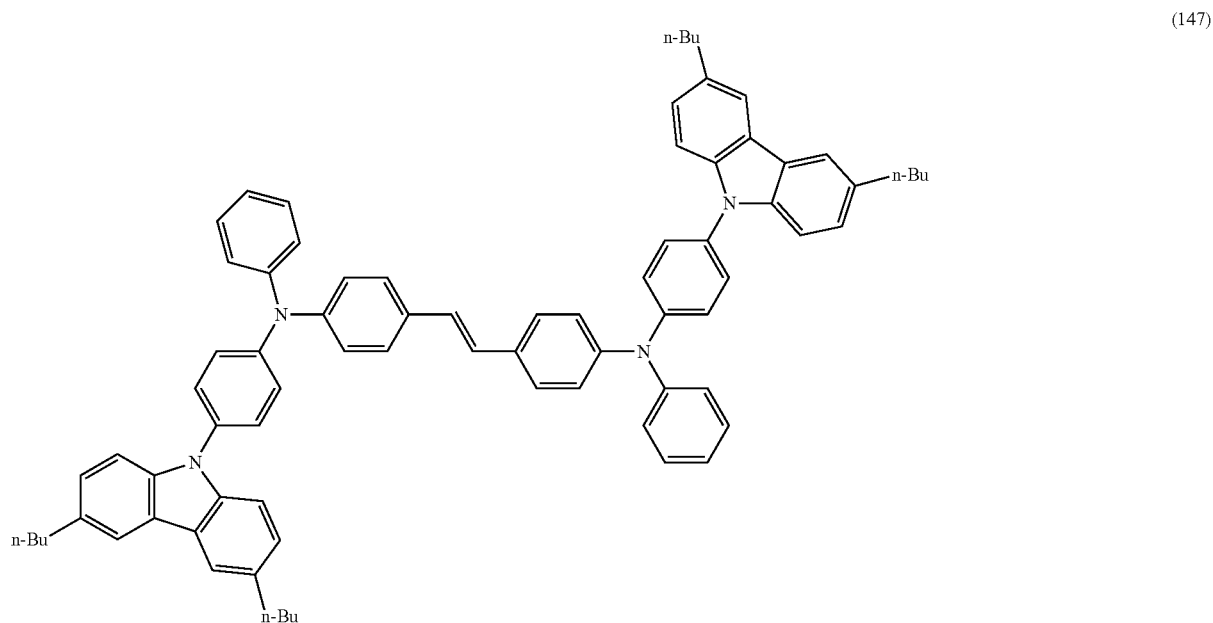
(147)
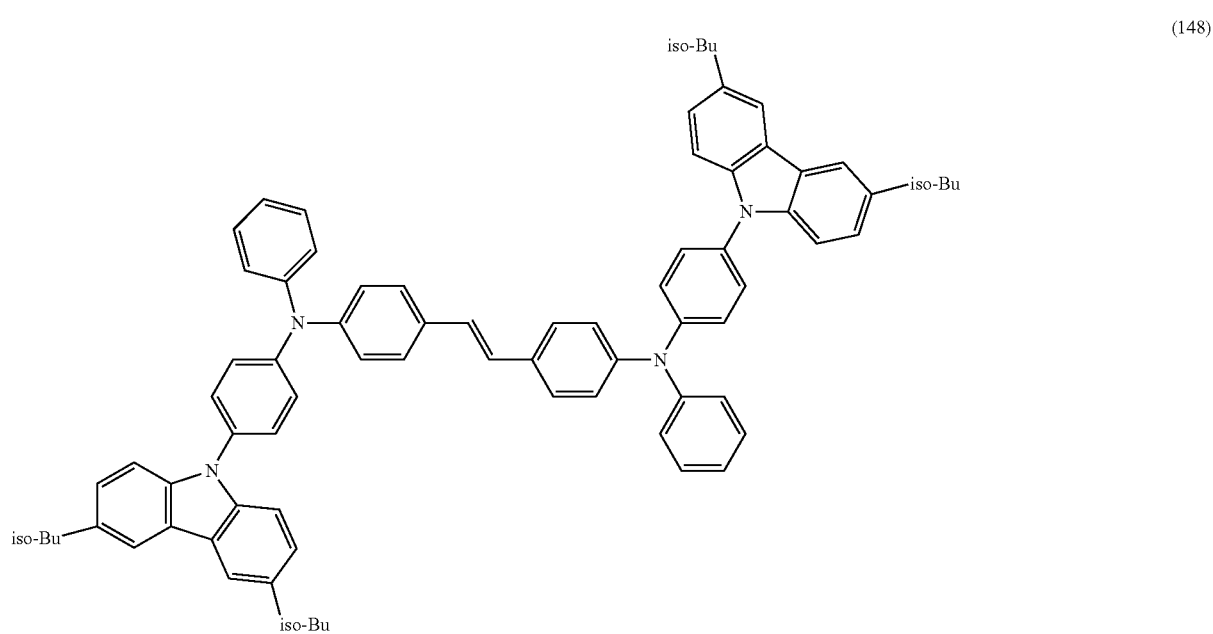
(148)

(149)
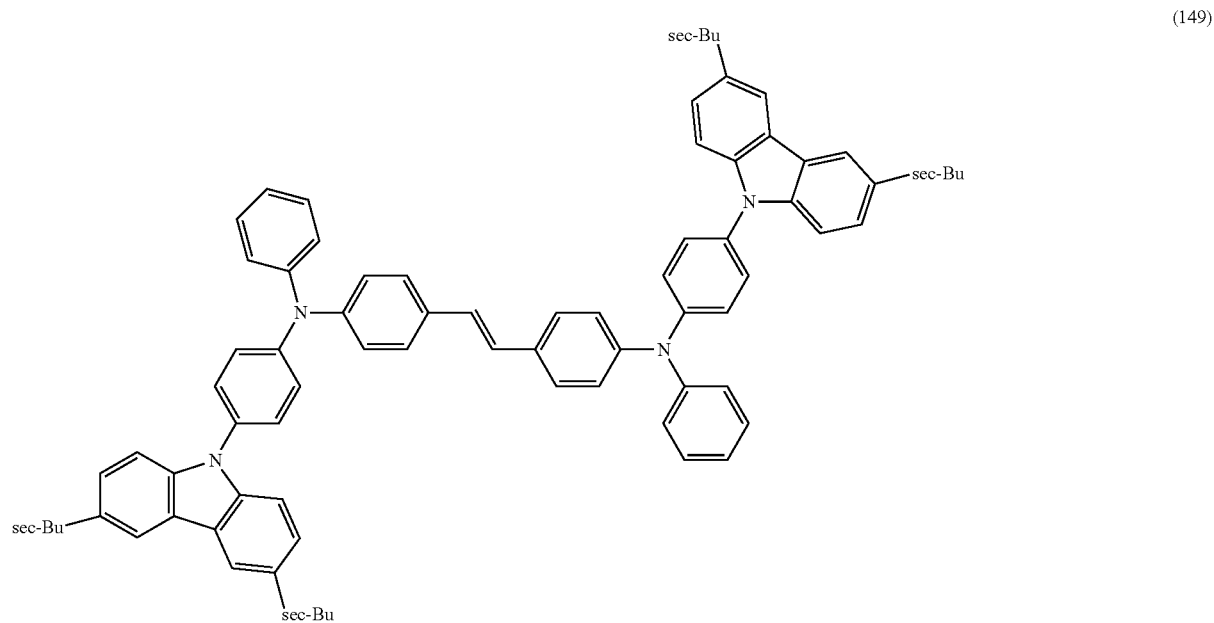
(150)
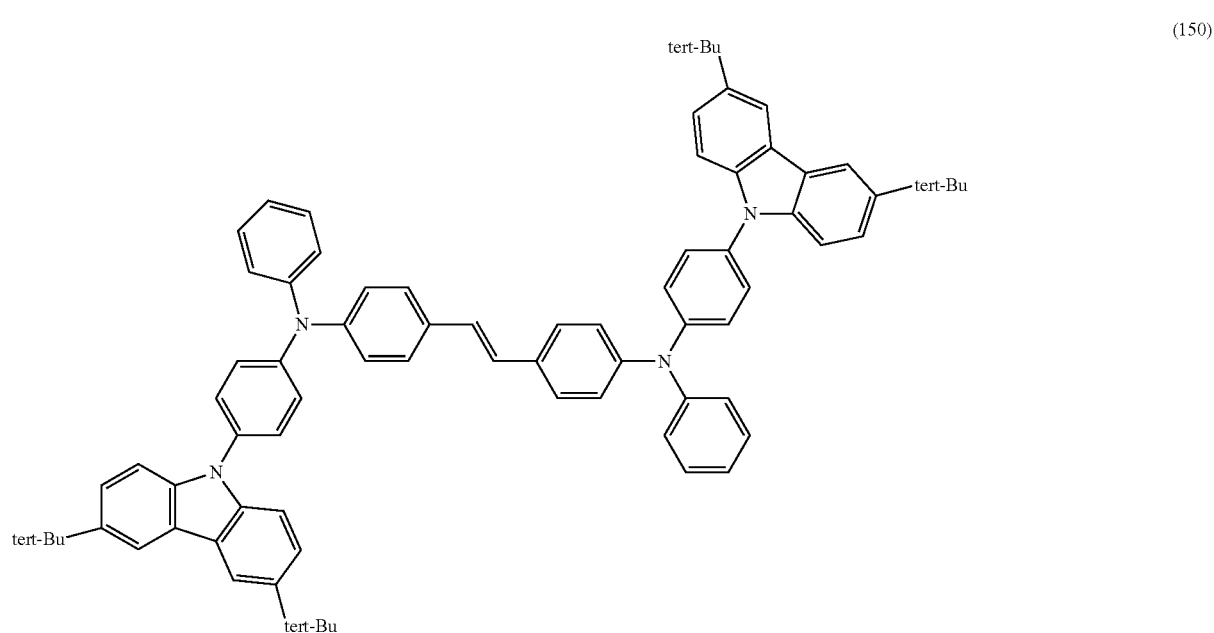

(151)
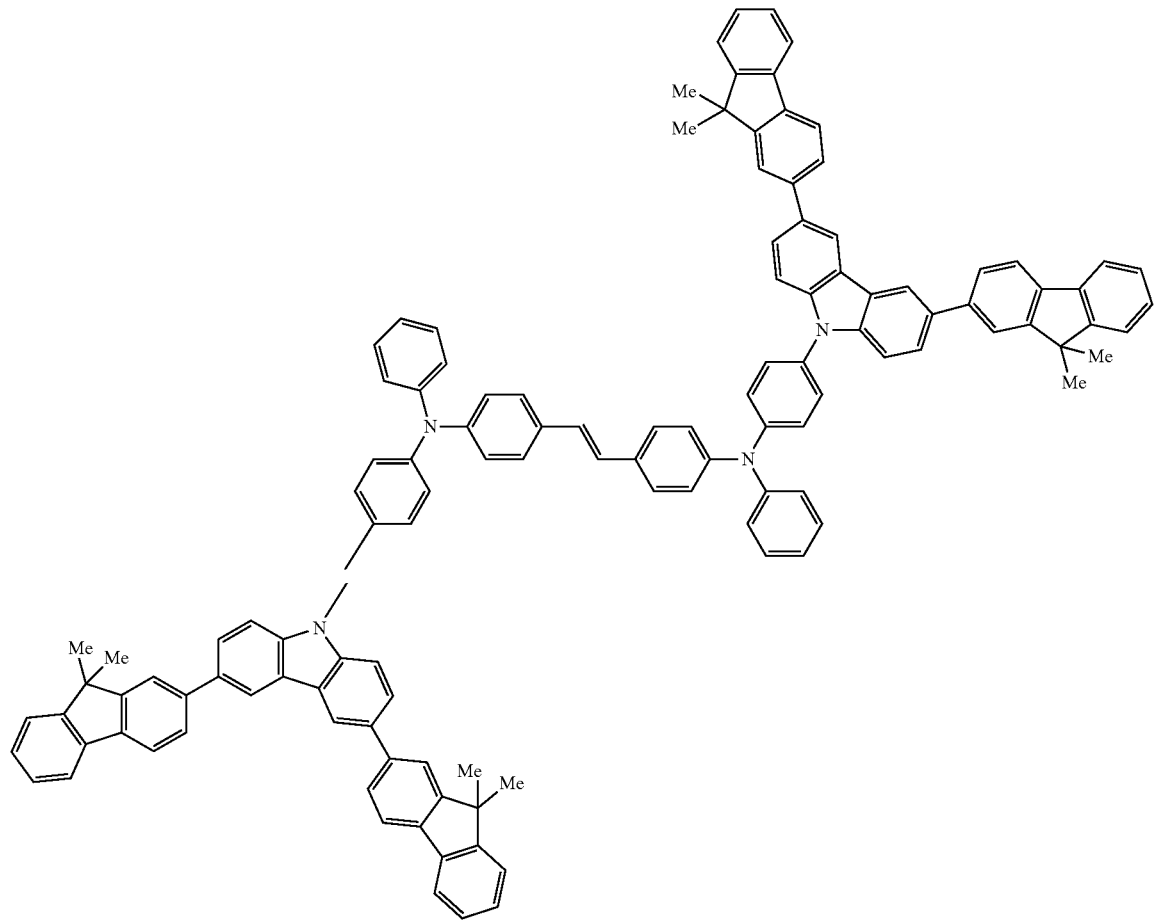
(152)
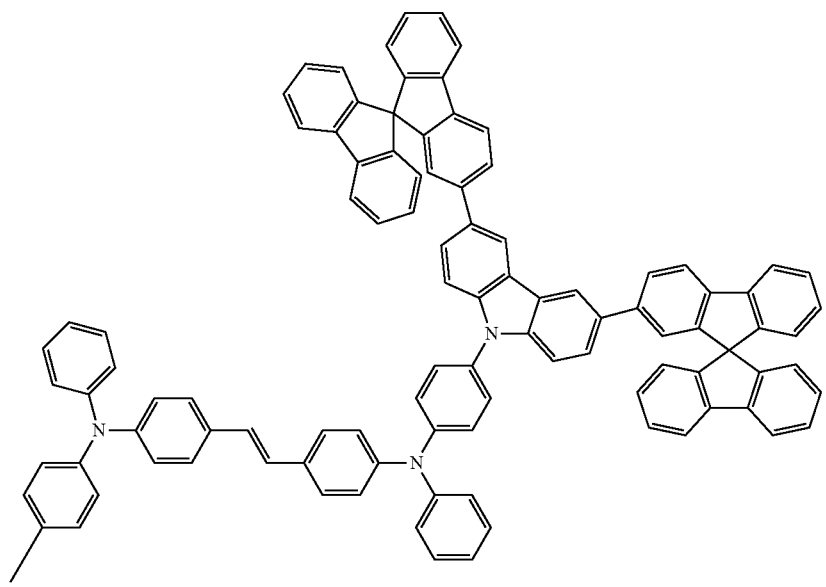

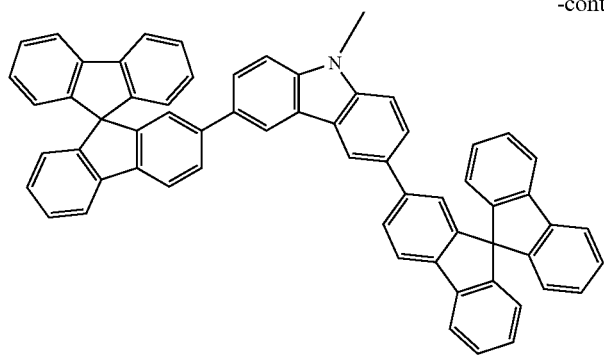

Stilbene derivatives of the present invention have a feature of providing blue emission with excellent color purity and having excellent luminous efficiency.

Embodiment Mode 2

[Synthesis Method of the General Formula (1)]

Hereinafter, an example of a synthesis method for a stilbene derivative of the present invention represented in the following general formula (1) is disclosed.

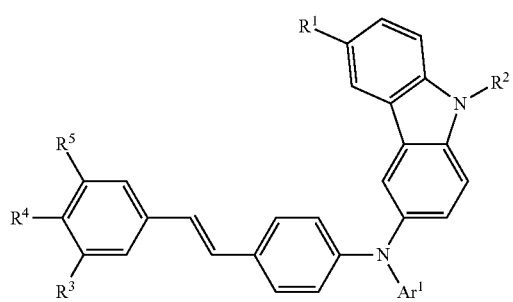

(1)

[Step 1: Synthesis of a Stilbene Derivative (St1) Whose 4-Position is Halogenated]

As represented by the following synthesis scheme (A), by reacting benzyltriphenylphosphonium salt (α1) whose 4-position is halogenated with benzaldehydes (β1) under the presence of a base, so-called, Wittig reaction, a stilbene derivative (St1) whose 4-position is halogenated is obtained. This stilbene derivative (St1) can also be obtained by Horner-Emmons reaction in which phosphonate ester (α2) is used instead of the triphenylphosphonium salt (α1), as shown in a synthesis scheme (A'). As the base, inorganic bases such as potassium carbonate or sodium carbonate, organic bases such as metal alkoxide, or the like can be used.

In addition, the stilbene derivative (St1) can also be obtained as shown by a synthesis scheme (A") by a Wittig reaction in which benzyltriphenylphosphonium salt (α3) which is unsubstituted or at least one of third, fourth and fifth position of which is substituted and benzaldehyde (β2) whose 4-position is halogenated are reacted under the presence of a base. Alternatively, as shown by a synthesis scheme (A'''), this can be obtained by Horner-Emmons reaction in which phosphonate ester (α4) is used instead of the triphenylphosphonium salt (α3).

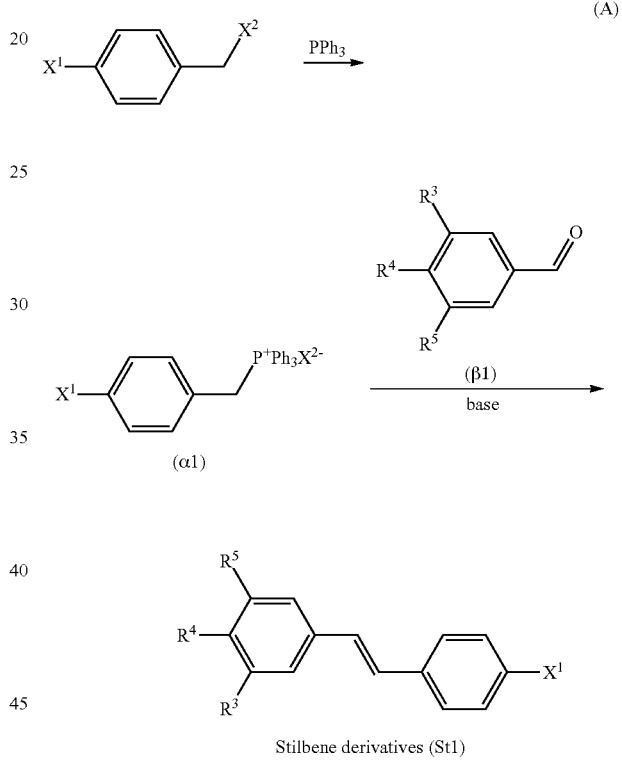

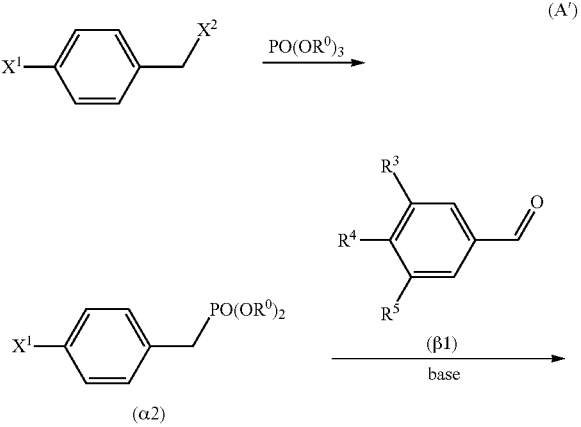

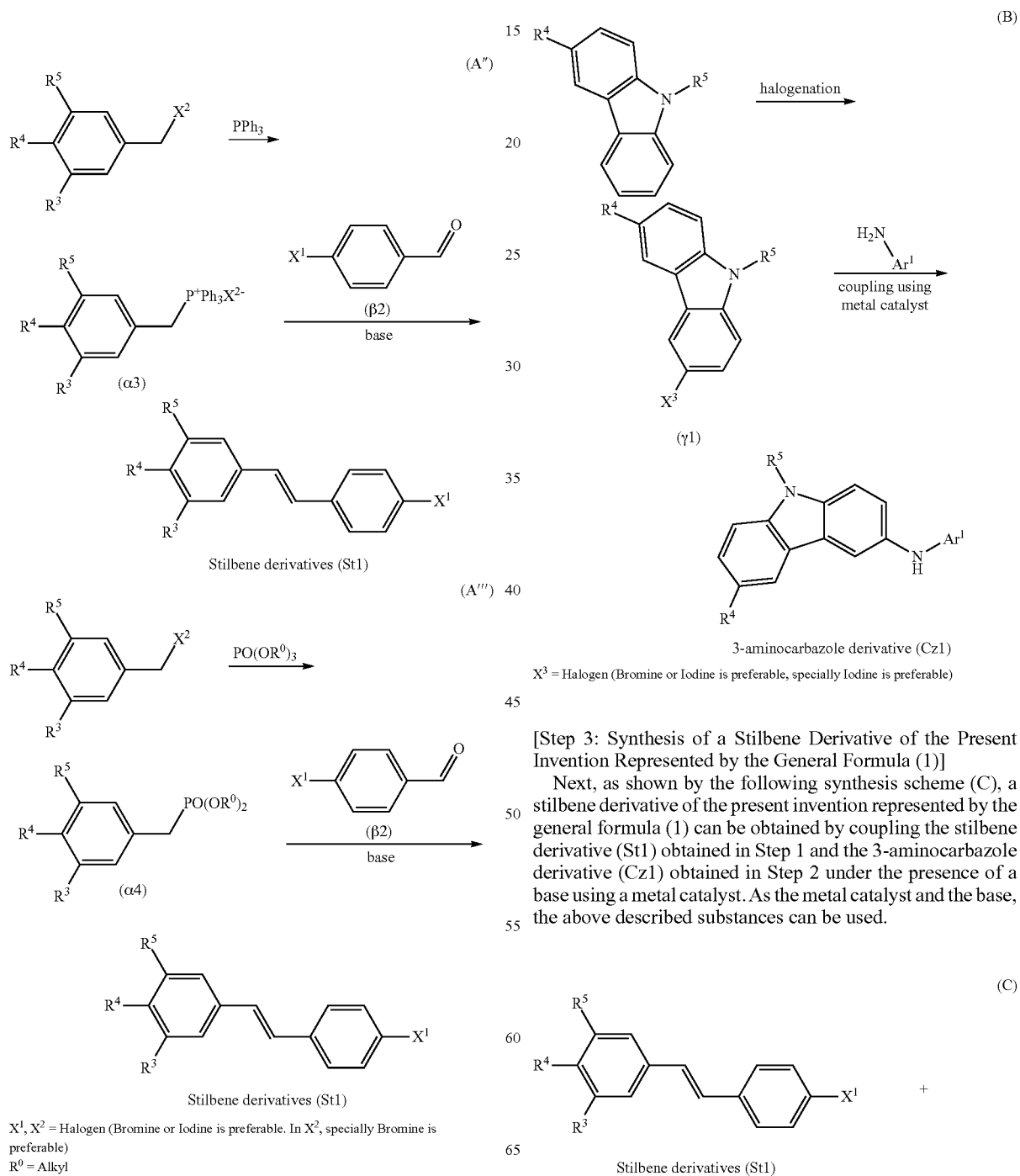

[Step 2: Synthesis of 3-Aminocarbazole Derivative (Cz1)]

Next, as shown by a synthesis scheme (B) below, a 3-aminocarbazole derivative (Cz1) is obtained by coupling a carbazole derivative (γ1) whose third position is halogenated and arylamine under the presence of a base using a metal catalyst. As the metal catalyst at the coupling, a palladium catalyst such as palladium acetate, tetrakis(triphenylphosphine)palladium, or bis(dibenzylideneacetone)palladium, or monatomic copper can be used. As the base, inorganic bases such as potassium carbonate or sodium carbonate, organic bases such as metal alkoxide, or the like can be used.

[Step 3: Synthesis of a Stilbene Derivative of the Present Invention Represented by the General Formula (1)]

Next, as shown by the following synthesis scheme (C), a stilbene derivative of the present invention represented by the general formula (1) can be obtained by coupling the stilbene derivative (St1) obtained in Step 1 and the 3-aminocarbazole derivative (Cz1) obtained in Step 2 under the presence of a base using a metal catalyst. As the metal catalyst and the base, the above described substances can be used.

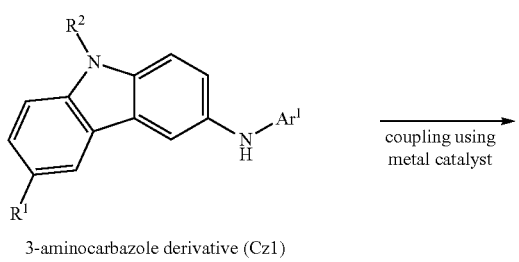

3-aminocarbazole derivative (Cz1)

coupling using metal catalyst

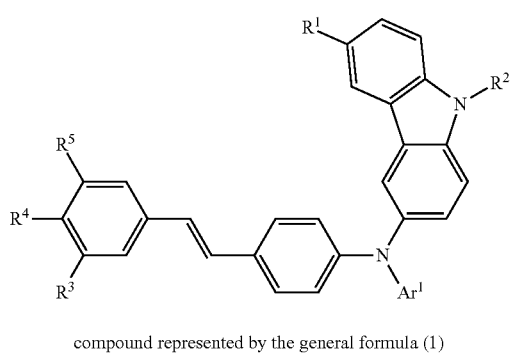

compound represented by the general formula (1)

[Synthesis Method of the General Formula (3)]

Hereinafter, a synthesis method of a stilbene derivative of the present invention represented by the following general formula (3) is shown as one example.

(3)

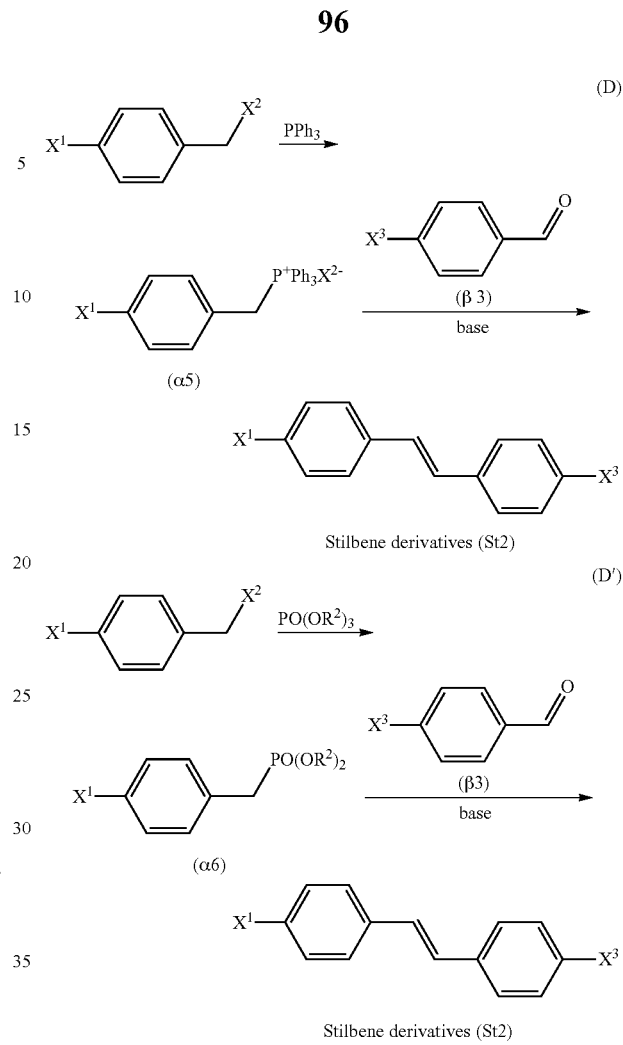

[Step 1: Synthesis of a Stilbene Derivative (St2) Whose 4-Position and 4'-Position are Halogenated]

As shown by the following synthesis scheme (D), a stilbene derivative (St2) whose 4-position and 4'-position are halogenated is obtained first by reacting benzyltriphenylphosphonium salt (α5) whose 4-position is halogenated with benzaldehyde (β3) whose 4-position is halogenated under the presence of a base, so-called Wittig reaction. Alternatively, as represented by the synthesis scheme (D'), this can be obtained by a Horner-Emmons reaction in which phosphonate ester (α6) is used in stead of the triphenylphosphonium salt (α5).

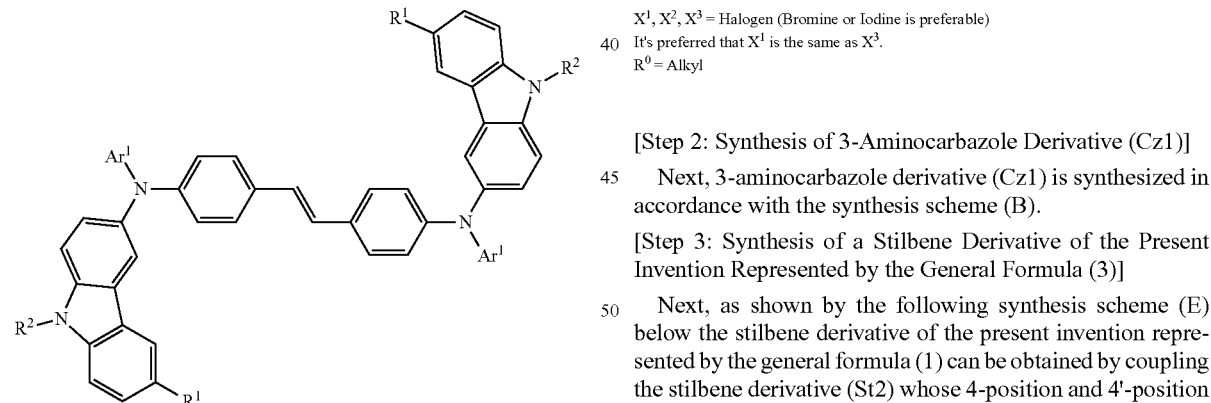

$X^1$, $X^2$, $X^3$ = Halogen (Bromine or Iodine is preferable)
It's preferred that $X^1$ is the same as $X^3$.
$R^0$ = Alkyl

[Step 2: Synthesis of 3-Aminocarbazole Derivative (Cz1)]

Next, 3-aminocarbazole derivative (Cz1) is synthesized in accordance with the synthesis scheme (B).

[Step 3: Synthesis of a Stilbene Derivative of the Present Invention Represented by the General Formula (3)]

Next, as shown by the following synthesis scheme (E) below the stilbene derivative of the present invention represented by the general formula (1) can be obtained by coupling the stilbene derivative (St2) whose 4-position and 4'-position are halogenated with the 3-aminocarbazole derivative (Cz1) under the presence of a base using a metal catalyst. As the metal catalyst and the base, the above described substances can be used.

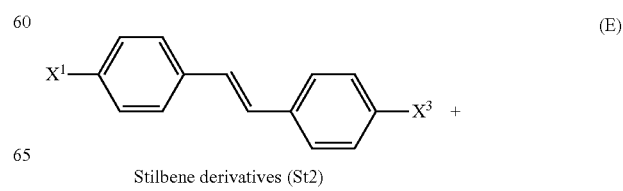

-continued

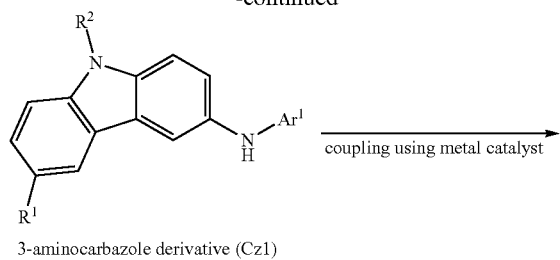

3-aminocarbazole derivative (Cz1)

coupling using metal catalyst

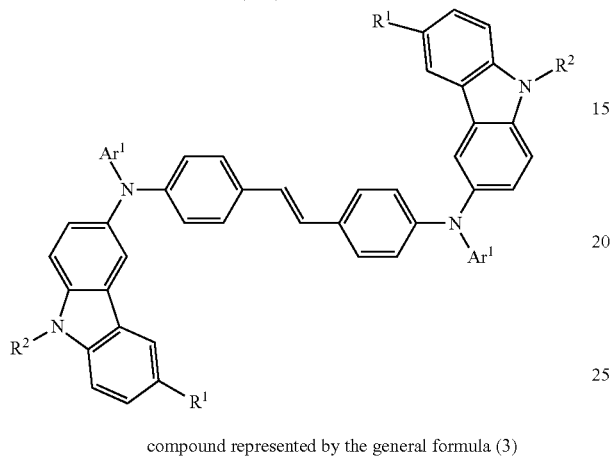

compound represented by the general formula (3)

(γ2)

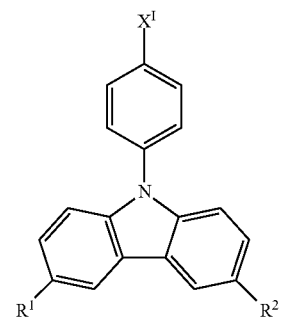

coupling using metal catalyst

[Synthesis Method of the General Formula (5)]

Hereinafter, a synthesis method of a stilbene derivative of the present invention represented by the following general formula (5) is shown as one example.

(5)

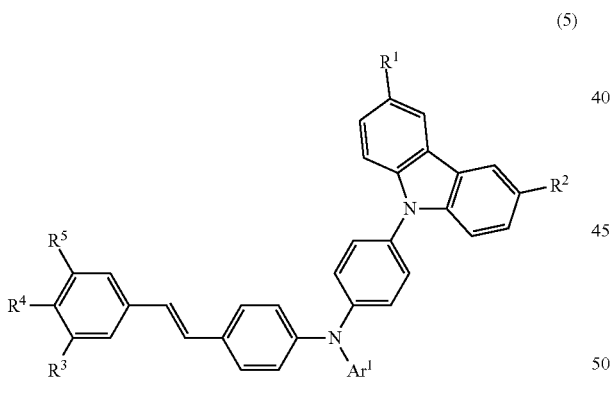

[Step 1: Synthesis of a Stilbene Derivative (St1) Whose 4-Position is Halogenated]

In accordance with any one of the above described synthesis schemes (A) to (A'''), a stilbene derivative (St1) whose 4-position is halogenated is synthesized.

[Step 2: Synthesis of 9-(4-Aminophenyl)Carbazole Derivative (Cz2)]

Next, as shown by the following synthesis scheme (F) below, 9-(4-aminophenyl)carbazole derivative (Cz2) is obtained by coupling 9-phenylcarbazole derivative (γ2) in which the 4-position of a phenyl group is halogenated, with arylamine under the presence of a base using a metal catalyst. As the metal catalyst and the base, the above described substances can be used.

(F)

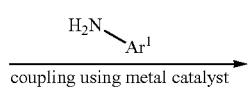

coupling using metal catalyst

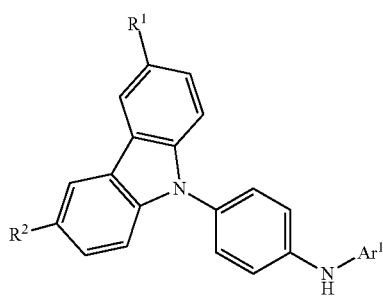

9-(4-aminophenyl) carbazole derivative (Cz2)

$X^1, X^2$ = Halogen (Bromine or Iodine is preferable)

[Step 3: Synthesis of a Stilbene Derivative of the Present Invention Represented by the General Formula (5)]

Next, as shown by the following synthesis scheme (G) below, a stilbene derivative of the present invention represented by the general formula (5) can be obtained by coupling a stilbene derivative (St1) whose 4-position is halogenated, with 9-(4-aminophenyl)carbazole derivative (Cz2) under the presence of a base using a metal catalyst.

(G)

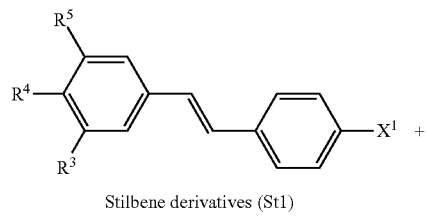

Stilbene derivatives (St1)

+

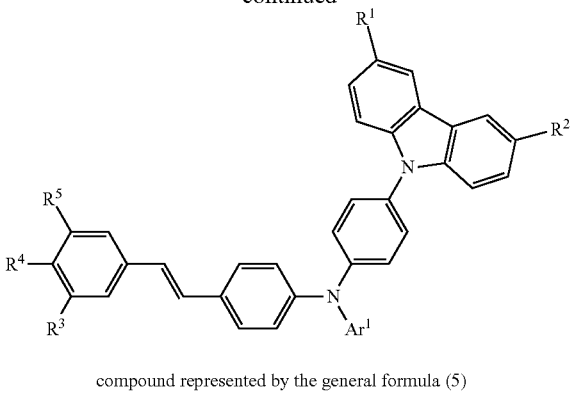

compound represented by the general formula (5)

[Synthesis Method of the General Formula (7)]

Hereinafter, a synthesis method of a stilbene derivative of the present invention represented by the following general formula (7) is shown as one example.

(7)

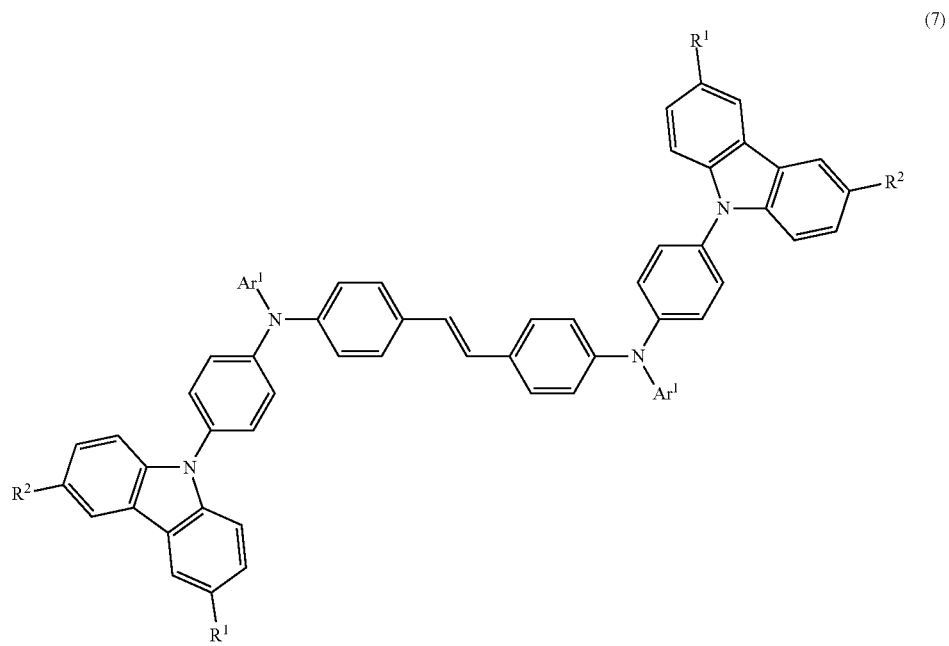

-continued

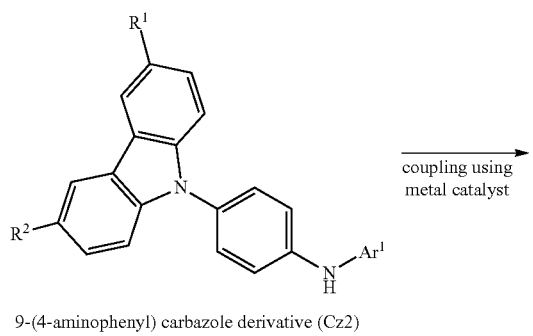

9-(4-aminophenyl) carbazole derivative (Cz2)

coupling using metal catalyst →

[Step 1: Synthesis of a Stilbene Derivative (St2) Whose 4-Position and 4'-Position are Halogenated]

In accordance with any one of the above described synthesis schemes (D) to (D'), a stilbene derivative (St2) whose 4-position and 4'-position are halogenated is synthesized.

[Step 2: Synthesis of 9-(4-Aminophenyl)Carbazole Derivative (Cz2)]

9-(4-aminophenyl)carbazole derivative (Cz2) is synthesized in accordance with the above described synthesis scheme (F).

[Step 3: Synthesis of a Stilbene Derivative of the Present Invention Represented by the General Formula (7)]

Next, as shown by the following synthesis scheme (H) below, a stilbene derivative of the present invention represented by the general formula (7) can be obtained by coupling the stilbene derivative (St2) whose 4-position and 4'-position are halogenated, with the 9-(4-aminophenyl)carbazole derivative (Cz2) under the presence of a base using a metal catalyst.

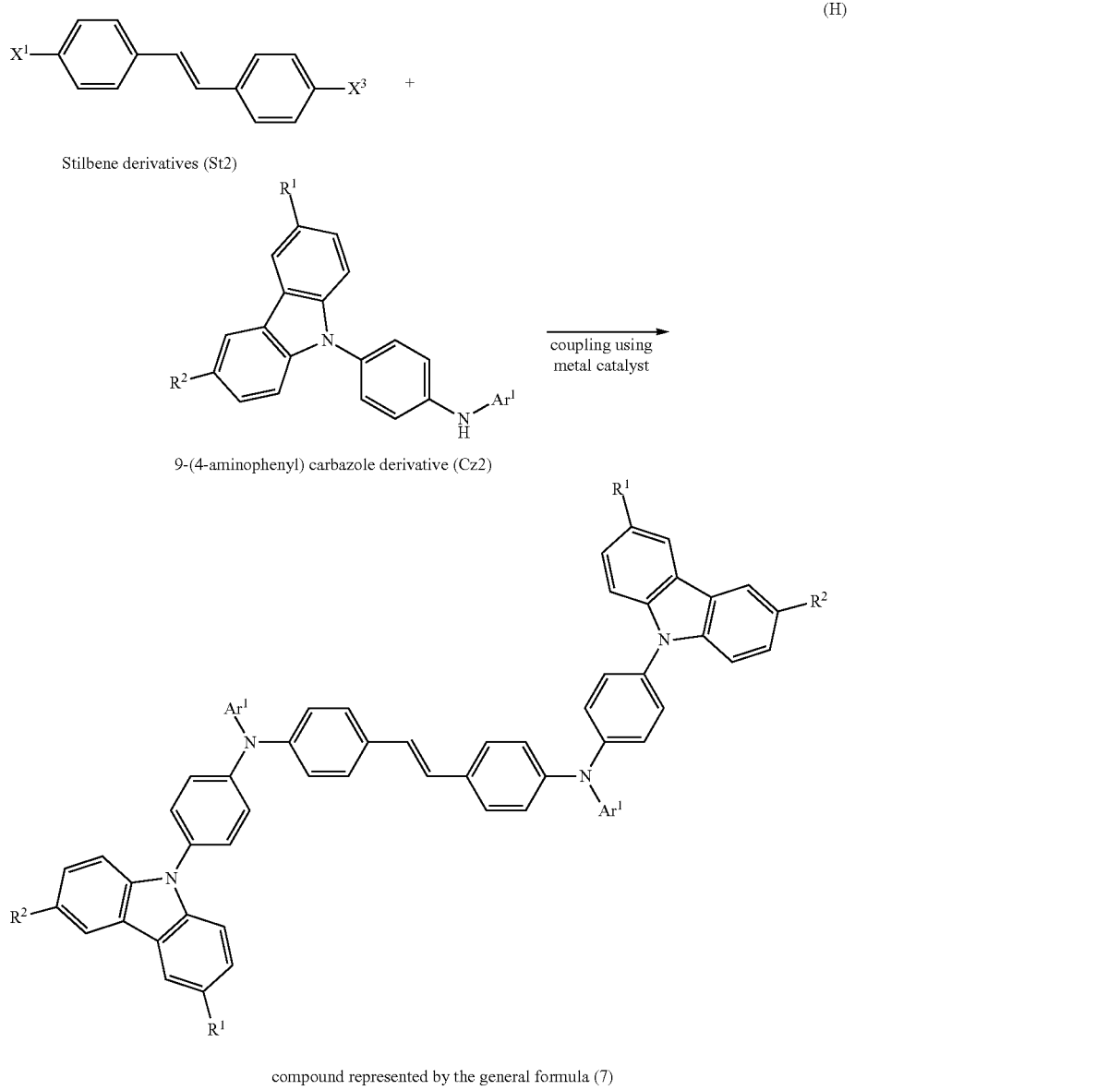

Embodiment Mode 3

In accordance with the present invention, a light-emitting element can be formed using a stilbene derivative as shown in Embodiment Mode 1.

A light-emitting element of the present invention includes an element structure in which a layer including a luminescent substance 103 is sandwiched between a first electrode 101 and a second electrode 102 as shown in FIG. 1. The layer including a luminescent substance 103 includes a stilbene derivative of the present invention. Here, a case is described that the first electrode serves as an anode and the second electrode serves as a cathode. Note that the anode is an electrode which injects holes into the layer including a luminescent substance and the cathode is an electrode which injects electrons into the layer including a luminescent substance.

A structure of the layer including a luminescent substance 103 includes at least a light-emitting layer. As examples of the structure, a stacked structure of a hole injecting layer, a light-emitting layer, and an electron transporting layer in this order, a stacked structure of a hole injecting layer, a hole transporting layer, a light-emitting layer, and an electron transporting layer in this order; a stacked structure of a hole injecting layer, a hole transporting layer, a light-emitting layer, a hole-blocking layer and an electron transporting layer in this order; a stacked structure of a hole injecting layer, a hole transporting layer, a light-emitting layer, a hole-blocking layer, an electron transporting layer and an electron injecting layer in this order, and the like are given. The stilbene derivative of the present invention is preferably used for the light-emitting layer.

The light-emitting element of the present invention is preferably supported over a substrate. The substrate is not particularly limited and those used for conventional light-emitting elements can be employed, including substrates made of glass, quartz, transparent plastic or the like.

As for anode material for the light-emitting element of the present invention, use of a metal, an alloy or an electroconductive compound having a high work function (work function of 4.0 eV or more), or a mixture thereof is preferred.

Specific examples of the anode material include gold (Au), platinum (Pt), titanium (Ti), nickel (Ni), tungsten (W), chromium (Cr), molybdenum (Mo), iron (Fe), cobalt (Co), copper (Cu), palladium (Pd), nitride of metal material (TiN) or the like, in addition to ITO (indium tin oxide), and IZO (indium zinc oxide) including silicon oxide in which indium oxide is mixed with 2 to 20 atomic % of zinc oxide (ZnO).

On the other hand, as for a cathode material, use of metals, alloys or electroconductive compounds having a low work function (work function of 3.8 eV or less), or mixtures thereof are preferred. Specific examples of the cathode material include, in addition to elements in groups I or II of the periodic table of the elements, i.e., alkaline metals such as Li and Cs, alkaline earth metals such as Mg, Ca and Sr, and alloys (Mg:Ag, Al:Li) and compounds (LiF, CsF, $CaF_2$) containing these, transition metals including rare earth metals, and further laminates with metals (including alloys) such as Al, Ag or ITO.

However, in a case that a first buffer layer is provided to be in contact with the anode on the light-emission side of the anode, an ohmic contact with an electrode material having a wide range of work function is possible. Thus, aluminum (Al), silver (Ag), an alkali metal, an alkaline-earth metal such as magnesium (Mg), an alloy thereof (Mg:Ag, Al:Li) or the like which are commonly known as materials having a low work function, can be used as an anode material.

The first buffer layer used here is formed from a metal compound and any one of organic compounds such as an aromatic amine compound, a carbazole derivative, aromatic hydrocarbon including aromatic hydrocarbon including at least one vinyl skeleton.

As the aromatic amine compound described above, for example, 4,4'-bis[N-(1-naphthyl)-N-phenylamino]biphenyl (abbrev.: NPB); 4,4'-bis[N-(3-methylphenyl)-N-phenylamino]biphenyl (abbrev.: TPD); 4,4',4"-tris(N,N-diphenylamino)triphenylamine (abbrev.: TDATA); 4,4',4"-tris[N-(3-methylphenyl)-N-phenylamino]triphenylamine (abbrev.: MTDATA); 4,4'-bis(N-{4-[N,N-bis(3-methylphenyl)amino]phenyl}-N-phenylamino)biphenyl (abbrev.: DNTPD); 1,3,5-tris[N,N-di(m-tolyl)amino]benzene (abbrev.: m-MTDAB); 4,4',4"-tri(N-carbazolyl)triphenylamine (abbrev.: TCTA); 2,3-bis(4-diphenylaminophenyl)quinoxaline (abbrev.: TPAQn); 2,2',3,3'-tetrakis(4-diphenylaminophenyl)-6,6'-bisquinoxaline (abbrev.: D-TriPhAQn); 2,3-bis{-4-[N-(1-naphthyl)-N-phenylamino]phenyl}dibenzo[f,h]quinoxaline (abbrev.: NPADiBzQn); and the like can be given.

As the carbazole derivative, for example, 3-[N-(9-phenylcarbazol-3-yl)-N-phenylamino]-9-phenylcarbazole (abbrev.: PCzPCA1); 3,6-bis[N-(9-phenylcarbazol-3-yl)-N-phenylamino]-9-phenylcarbazole (abbrev.: PCzPCA2); N-(2-naphthyl)carbazole (abbrev.: NCz); 4,4'-di(N-carbazolyl)biphenyl (abbrev.: CBP); 9,10-bis[4-(N-carbazolyl)phenyl]anthracene (abbrev.: BCPA); 3,5-bis[4-(N-carbazolyl)phenyl]biphenyl (abbrev.: BCPBi); 1,3,5-tris[4-(N-carbazolyl)phenyl]benzene (abbrev.: TCPB) and the like can be given.

As the aromatic hydrocarbon (including an aromatic hydrocarbon including at least one vinyl skeleton), aromatic hydrocarbons such as anthracene, 9,10-diphenylanthracene (abbrev.: DPA); 2-tert-butyl-9,10-di(2-naphthyl)anthracene (abbrev.: t-BuDNA); tetracene; rubrene; pentacene; and 4,4'-bis(2,2-diphenylvinyl)biphenyl (abbrev.: DPVBi) can be given.

As the above-described metal compound, an oxide or nitride of a transition metal is preferable, and an oxide or nitride of a metal which belongs to Group 4 to 8 is more preferable. In addition, a material having an electron-accepting property with respect to all of the above-described aromatic amines, carbazole derivatives, and aromatic hydrocarbons (including aromatic hydrocarbons including at least one vinyl skeleton) is preferable. As a metal compound like this, for example, a metal compound such as molybdenum oxide, vanadium oxide, ruthenium oxide, rhenium oxide, titanium oxide, chromium oxide, zirconium oxide, hafnium oxide, tantalum oxide, tungsten oxide, or silver oxide can be used.

In the first buffer layer, the metal compound is preferably contained in an organic compound such as an aromatic amine, a carbazole derivative, or an aromatic hydrocarbon (including an aromatic hydrocarbon including at least one vinyl skeleton) such that a mass ratio is 0.5 to 2 with respect to these, or a molar ratio is 1 to 4 (=metal compound/organic compound). In addition, the first buffer layer may have a thickness of 50 nm or more, because it has a high conductivity.

On the other hand, as a cathode metal, a metal, an alloy, a conductive compound having a low work function (work function of 3.8 eV or less), or a mixture thereof is preferably used. As specific example of the cathode material, an element belonging to Group 1 or 2 of the periodic table, in other words, an alkali metal such as Li or Cs, an alkaline earth metal such as Mg, Ca or Sr, an alloy (Mg:Ag, Al:Li) or a compound (LiF, CsF, or $CaF_2$), a transition metal including a rare earth metal, and further, a stack of metals (including an alloy) such as Al, Ag and ITO (indium tin oxide) can be used.

However, when a second buffer layer is provided to be in contact with the cathode on a light-emitting layer side of the cathode, an ohmic contact with an electrode material having a work function in the wide range is possible, and thus, ITO (indium tin oxide), indium tin oxide including silicon oxide, IZO (indium zinc oxide) including silicon oxide in which indium oxide is mixed with zinc oxide (ZnO) of 2 to 20 atomic %, and the like which are known to be a material with a high work function, can be used as the cathode material.

Furthermore, the second buffer layer used here is constituted by a combination of at least one substance selected from electron transporting substances and bipolar substances, and a substance showing an electron-donating property to these materials (donor). As the electron transporting substance and the bipolar substance, a substance having an electron mobility of $1 \times 10^{-6}$ $cm^2/Vs$ or more is preferable. In addition, materials to be described below can be used for each of the electron transporting substance and the bipolar substance.

An anode and a cathode are made of the anode material and the cathode material described above, respectively, by forming a thin film by an evaporation method, a sputtering method, or the like. Each of the anode and the cathode preferably has a thickness of 10 to 500 nm.

The light-emitting element of the present invention has a structure in which light generated by recombination of carriers in the layer including a luminescent substance is emitted outside from one or both of the anode and the cathode. In other words, the anode is made of a material having a light transmitting property in a case where light is made to be emitted through the anode. The cathode is made of a material having a light transmitting property in a case where light is made to be emitted through the cathode.

For the layer including a luminescent substance, known materials can be used, and any of low molecular compounds and high molecular compounds can be used. The materials for forming the layer including a luminescent substance may include not only an organic compound but also an inorganic compound included in a portion of the layer including a luminescent substance.

The layer including the luminescent substance is formed by combining layers such as the first buffer layer and the second buffer layer described above as well as a hole injecting layer including a hole injecting substance, a hole transporting layer including a hole transporting substance or a bipolar substance, a light-emitting layer including a luminescent substance, a hole blocking layer including a hole blocking substance, an electron transporting layer including an electron transporting substance, and an electron injecting layer including an electron injecting substance.

In the present invention, in the case of using the stilbene derivative for the light-emitting layer, the layer including a luminescent substance interposed between a pair of electrodes can be formed by combining the light-emitting layer and another layer (for example, the hole injecting layer, the hole transporting layer, the hole blocking layer; the electron transporting layer, the electron injecting layer, the first buffer layer and the second buffer layer), and thus, a light-emitting element can be formed. Here are shown specific substances to be used in this case. Description of the first buffer layer and the second buffer layer is omitted here, because it has been described above.

The hole injecting layer is preferably formed using a hole injecting substance. As the hole injecting substance, porphyrin-based compounds are efficient among organic compounds. For example, phthalocyanine (hereinafter, referred to as $H_2$-Pc), copper phthalocyanine (hereinafter, referred to as Cu-Pc), or the like can be used. In addition, a chemically doped conductive high molecular compound such as polyethylene dioxythiophene (hereinafter, referred to as PEDOT) doped with polystyrene sulfonate (hereinafter, referred to as PSS).can be used.

The hole transporting layer is a layer superior in a hole transporting property, and specifically, the hole transporting layer is preferably formed of a hole transporting substance or a bipolar substance, which has hole mobility of $1 \times 10^{-6}$ cm$^2$/Vs or more. The hole transporting substance is a substance having higher hole mobility than electron mobility, and preferably, a substance having a value of a ratio of the hole mobility to the electron mobility (=hole mobility/electron mobility) of more than 100.

As the hole transporting substance, for example, an aromatic amine-based (namely a substance having a bond of benzene ring-nitrogen) nitrogen) compound is preferable. As a substance which is widely used, for example, 4,4'-bis[N-(3-methylphenyl)-N-phenylamino]biphenyl (hereinafter, referred to as TED); 4,4'-bis[N-(1-naphtyl)-N-phenyl-amino] biphenyl (hereinafter, referred to as NPB) which is a derivative thereof; a star burst aromatic amine compound such as 4,4',4"-tris(N-carbazolyl)-triphenylamine (hereinafter, referred to as TCTA); 4,4',4"-tris(N,N-diphenylamino)triphenylamine (hereinafter, referred to as TDATA); or 4,4',4"-tris [N-(3-methylphenyl)-N-phenylamino]triphenylamine (hereinafter, referred to as MTDATA) is given.

The bipolar substance is a substance which is described as follows: when mobility of an electron and mobility of a hole are compared with each other, a value of a ratio of mobility of one carrier to mobility of the other carrier is 100 or less, preferably 10 or less. As the bipolar substance, for example, 2,3-bis(4-diphenylaminophenyl) quinoxaline (abbrev.: TPAQn); 2,3-bis{-4-[N-(1-naphthyl)-N-phenylamino] phenyl}dibenzo[f,h]quinoxaline (abbrev.: NPADiBzQn); and the like are given. In particular, among bipolar substances, a substance having hole mobility and electron mobility of $1 \times 10^{-6}$ cm$^2$/Vs or more is preferably used.

The light-emitting layer includes at least one kind of luminescent substance. A luminescent substance herein represents a substance with excellent luminous efficiency which can emit light of a desired wavelength. The light emitting layer is a layer in which a stilbene derivative is mixed to be dispersed in a layer made of a substance (host substance) having a larger band gap (the energy gap between a LUMO level and a HOMO level) than a band gap of the stilbene derivative sewing as a guest substance, as an aspect of the present invention (in other words, a layer including a host substance and a guest substance).

Thus, by using a stilbene derivative of the present invention to a light-emitting layer, blue emission with excellent color purity can be obtained.

As a host substance which is combined with a stilbene derivative of the present invention to form a light-emitting layer, 9-[4-(N-carbazolyl)phenyl]-10-phenyl anthracene (abbrev.: CzPA), 4,4'-di(N-carbazolyl)biphenyl (abbrev.: CBP), bis[2-(2-hydroxyphenyl)benzoxazolato]zinc (abbrev.: Zn(BOX)$_2$), 9,10-di(2-naphthyl)anthracene (abbrev.: DNA), 4,4',4"-tri(N-carbazolyl)triphenylamine (abbrev.: TCTA), 2,2',2"-(1,3,5-benzenetriyl)-tris(1-phenyl-1H-benzimidazole) (abbrev.: TPBi) or the like can be used.

The electron transporting layer is a layer which is superior in an electron transporting property, and specifically, the electron transporting layer is preferably formed of an electron transporting substance or a bipolar substance, which has electron mobility of $1 \times 10^{-6}$ cm$^2$/Vs or more. The electron transporting substance is a substance having higher electron mobility than hole mobility, and preferably, a substance having a value of a ratio of the electron mobility to the hole mobility (=electron mobility/hole mobility) of more than 100.

As a specific electron transporting substance, a metal complex having a quinoline skeleton or a benzoquinoline skeleton such as tris(8-quinolinolato)aluminum (hereinafter, Alq$_3$), tris(4-methyl-8-quinolinolato)aluminum (hereinafter, Almq$_3$), or bis(10-hydroxybenzo[h]-quinolinato)beryllium (hereinafter, BeBq$_2$); bis(2-methyl-8-quinolinolato)(4-phenylphenolate)aluminum (hereinafter, BAlq) which is a mixed ligand complex; or the like is preferable. In addition, a metal complex having an oxazole-based or thiazole-based ligand such as bis[2-(2-hydroxyphenyl)benzoxazolato]zinc (hereinafter, Zn(BOX)$_2$) or bis[2-(2-hydroxyphenyl)benzothiazolato]zinc (Zn(BTZ)$_2$) can also be used. Furthermore, an oxadiazole derivative such as 2-(4-biphenylyl)-5-(4-tert-butylphenyl)-1,3,4-oxadiazole (hereinafter, referred to as PBD) or 1,3-bis[5-(4-tert-butylphenyl)-1,3,4-oxadiazol-2-yl]benzene (hereinafter, referred to as OXD-7); a triazole derivative such as 3-(4-biphenylyl)-4-phenyl-5-(4-tert-butylphenyl)-1, 2,4-triazole (hereinafter, referred to as TAZ) or 3-(4-biphenylyl)-4-(4-ethylphenyl)-5-(4-tert-butylphenyl)-1,2,4-triazole (hereinafter, referred to as p-EtTAZ); a phenanthroline derivative such as bathophenanthroline (hereinafter, referred to as BPhen) or bathocuproin (hereinafter, referred to as BCP); and, in addition, 4,4-bis(5-methylbenzoxazolyl-2-yl) stilbene (hereinafter, referred to as BzOs); or the like can be used as well as the metal complexes described above. It is to be noted that the substances described above can be used as the bipolar substance.

In addition, as a hole blocking substance, BAlq, OXD-7, TAZ, p-EtTAZ, BPhen, BCP or the like which has been described above can be used.

As described above, by forming a light-emitting element with a light-emitting layer using a stilbene derivative of the present invention, a blue light-emitting element with excellent color purity can be obtained. Further, a light-emitting element with excellent luminous efficiency can be obtained. Moreover, a long lifetime light-emitting element can be obtained.

Embodiment Mode 4

In Embodiment Mode 4, as an example of a thin film transistor (TFT) which can be combined with a light-emitting element including a stilbene derivative of the present invention to manufacture a light-emitting device, a single gate TFT having a top gate structure will be described with reference to FIG. 2.

Figure 2:
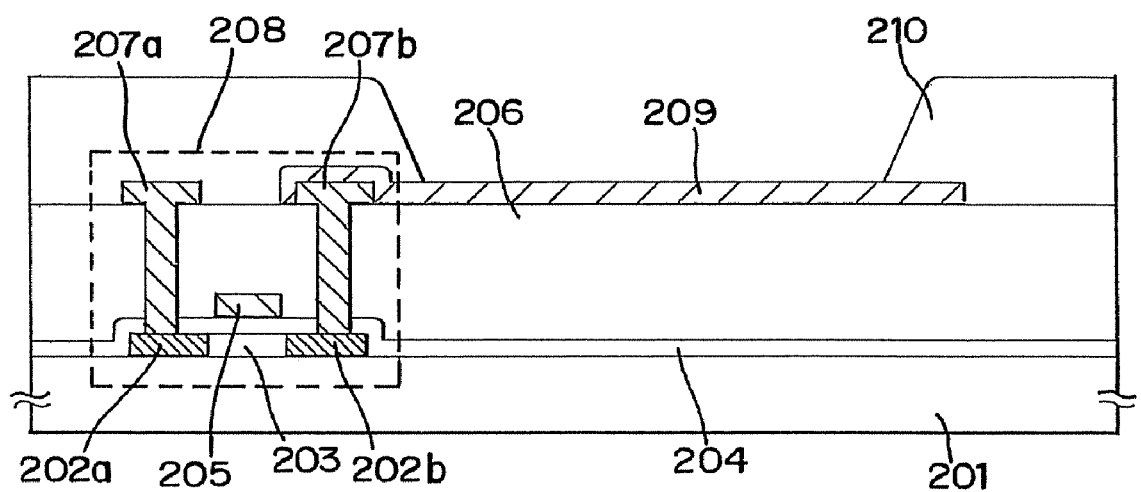
FIG. 2 shows, a light-emitting element according to an aspect of the present invention.

As shown in FIG. 2, a TFT 208 is formed over a substrate 201. A drain electrode 207b of the TFT 208 is electrically connected to a first electrode 209 of a light-emitting element. A second electrode is formed over the first electrode 209 with a layer including a luminescent substance therebetween and thus, the light-emitting element as described in Embodiment Mode 2 is formed. Accordingly, the 208 can control driving of the light-emitting element.

There is no particular limitation on the substrate 201, and flexible materials such as polyethyleneterephthalate (PET), polyethylenenaphthalate (OEN), or polyethersulfone (PES) can be used, in addition to glass, quartz, or the like.

In addition, although not shown here, an insulating film formed of an insulator such as silicon oxide or silicon nitride may be formed over the substrate 201 by a known film-formation method such as plasma CVD or sputtering. Note that the insulating film may be formed to have a single layer structure or a multilayer structure in which plural layers are stacked. By providing an insulating film between the substrate 201 and the TFT 208, impurities can be prevented from diffusing into the TFT 208 from the substrate 201.

A source region 202a, a drain region 202b and a channel forming region 203 in FIG. 2 are formed from a semiconductor film: As the semiconductor film, any of an amorphous semiconductor film having different crystal states, an amorphous semiconductor film including partially a crystal state, and a crystalline semiconductor film, which mainly include silicon, silicon-germanium (SiGe) or the like can be used. In this embodiment mode, the crystalline semiconductor film is used. In addition, the semiconductor film can be formed by a known method such as plasma CVD or sputtering. A thickness of the semiconductor film is preferably 10 to 150 nm, preferably, 30 to 70 nm.

The crystalline semiconductor film can be formed by crystallizing an amorphous semiconductor film by heating or laser irradiation. Alternatively, a crystalline semiconductor film can be formed originally. Specifically, a crystalline semiconductor film can be formed by heat or plasma using a fluorine-based gas such as $GeF_4$ or $F_2$, and a silane-based gas such as $SiH_4$ or $Si_2H_6$.

The source region 202a and the drain region 202b are regions in which an impurity element is added into the crystalline semiconductor film. The impurity element is an element which can impart one conductivity to the semiconductor film, typically, phosphorus (P) or the like is given as an impurity element imparting an n-type conductivity, and boron (B) or the like is given as an impurity element imparting a p-type conductivity. When the first electrode 209 serves as an anode, an impurity element imparting the p-type conductivity is preferably added. On the other hand, when the first electrode 209 serves as a cathode, an impurity element imparting the n-type conductivity is preferably added. In the TFT structure shown in this embodiment mode, after forming a crystalline semiconductor film, an impurity element is added into the crystalline semiconductor film by using a gate electrode 205 to be formed later as a mask.

A gate insulating film 204 formed to cover the source region 202a, the drain region 202b and the channel forming region 203 is formed using an insulator such as silicon oxide, silicon nitride, silicon oxynitride, or silicon nitride oxide by a film-formation method such as plasma CVD or sputtering. The gate insulating film 204 may be formed to have a single layer structure of insulating film or a multilayer structure in which plural insulating films are stacked. A thickness of the gate insulating film 204 is preferably 10 to 150 nm, preferably, 30 to 70 nm.

The gate electrode 205 can be formed using a conductive film made of a metal nitride such as tantalum nitride (TaN) or titanium nitride (TN), in addition to a metal such as tungsten (W), aluminum (Al), molybdenum (Mo), tantalum (Ta), titanium (Ti), copper (Cu), chromium (Cr) or niobium (Nb). In addition, the gate electrode 205 may be formed to have a single layer of conductive film or a multilayer structure in which plural conductive films are stacked. In addition, the conductive film can be formed by a known film-formation method such as sputtering. A thickness of the gate electrode 205 is preferably 200 nm or more, more preferably 300 to 700 nm.

An interlayer insulating film 206 formed to cover the source region 202a, the drain region 202b, the channel forming region 203 and the gate electrode 205 can be formed using an insulator such as silicon oxide, silicon nitride, silicon oxynitride or silicon nitride oxide. Besides, an insulator such as acrylic, polyimide, or siloxane can be used. Note that the siloxane is a compound including an element such as silicon (Si), oxygen (O) or hydrogen (H) and further including Si—O—Si bond (siloxane bond). Note that the insulating film described above can be formed by a known film-formation method such as a plasma CVD method, a sputtering method, an application method, or a spin coating method. Note that a thickness of the interlayer insulating film 206 is preferably 300 nm to 2 μm, further preferably, 500 nm to 1 μm.

A source electrode 207a and a drain electrode 207b formed over the interlayer insulating film 206 are electrically connected to the source region 202a and the drain region 202b, respectively. As the source electrode 207a and the drain electrode 207b, a film formed of a metal element such as silver (Ag), gold (Au), copper (Cu), nickel (Ni), platinum (Pt), palladium (Pd), iridium (It), ruthenium (Ru), tungsten (W), aluminum (Al), tantalum (Ta), molybdenum (Mo), cadmium (Cd), zinc (Zn), iron (Fe), titanium (Ti), silicon (Si), germanium (Ge), zirconium (Zr), or barium (Ba); a film formed of an alloy material containing some of the above-described elements as its main component (for example, an alloy including Al, carbon (C) and Ni; or an alloy including Al, carbon (C) and Mo); or a stacked film including some of the above elements (for example, a stacked film of Mo, Al and Mo, a stacked film of Ti, Al, and Ti, or a stacked film of Ti, titanium nitride (TN), Al and Ti); a film made of a compound material such as a metal nitride; or the like can be given. The above described conductive film can be formed by a known film-formation method such as sputtering. Thicknesses of the source electrode 207a and the drain electrode 207b are preferably 200 nm or more, more preferably, 300 to 700 nm.

In addition, the drain electrode 207b is electrically connected to the first electrode 209 of the light-emitting element. The material for forming the first electrode 209 has been described in Embodiment Mode 3 and the description in Embodiment Mode 3 may be referred to. Description of the material for forming the first electrode 209 is omitted here.

An insulator 210 is formed to cover the source electrode 207a, the drain electrode 207b and an end portion of the first electrode 209. Further, the insulator 210 is preferably formed to have a curvature on its side. The insulator 210 can be formed using acrylic, polyimide, resist, silicon oxide, silicon nitride, siloxane or the like.

This embodiment mode has described the case where the TFT 208 is a single gate type TFT having a top gate structure; however, is not limited to this case. A 111 having a bottom gate structure or a multigate type having plural gate electrodes may be used. Further, a TFT having an LDD (lightly doped drain) structure in which a low concentration impurity region including an impurity element at lower concentration than a drain region is formed, between a channel forming region and a drain region, may be employed. Furthermore, a transistor with a gate-overlapped LDD structure in which a low concentration impurity region formed between a channel forming region and a drain is overlapped with a gate electrode, may be used.

By using a TFT described above and a light-emitting element including a stilbene derivative of the present invention in combination so as to manufacture a light-emitting device, a longer life light-emitting device with excellent luminous efficiency as well as blue emission with excellent color purity can be provided.

Embodiment Mode 5

In Embodiment Mode 5, as an example of a thin film transistor (TFT) which can be combined with a light-emitting element including a stilbene derivative of the present invention to manufacture a light-emitting device, a channel-etch type TFT having a bottom gate structure will be described with reference to FIG. 3A and a channel-stopped type TFT having a bottom gate structure will be described with reference to FIG. 3B.

Figure 3A:
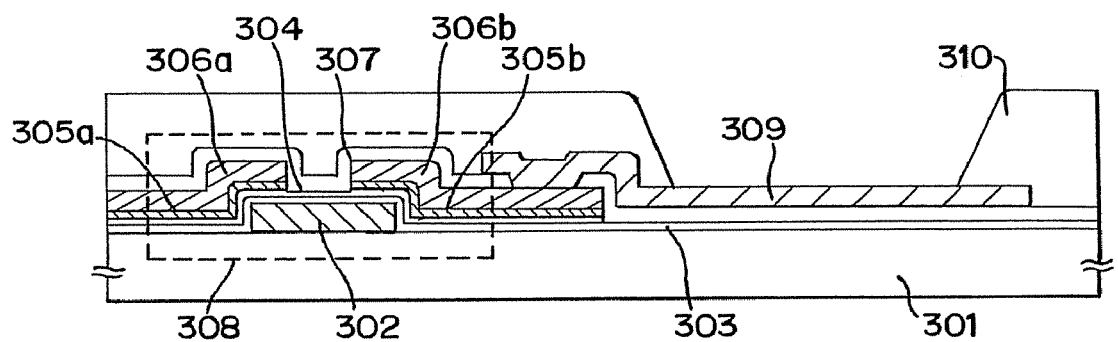
FIGS. 3A and 3B show light-emitting elements according to an aspect of the present invention.

As shown in FIG. 3A, a channel-etch type TFT having a bottom gate structure 308 is formed over a substrate 301. A drain electrode 306*b* of the TFT 308 is electrically connected to a first electrode 309 of a light-emitting element. A second electrode is formed over the first electrode 309 with a layer including a luminescent substance therebetween and thus, the light-emitting element as described in Embodiment Mode 3 is formed. Accordingly, the TFT 308 can control driving of the light-emitting element.

There is no particular limitation on the substrate 301, and the same materials as the substrate 201 shown in Embodiment Mode 3 can be used. In addition, an insulating film which can be formed between the substrate 301 and the TFT 308 can be formed by the same method and using the same material as in Embodiment Mode 4. Note that the effect is the same.

A gate electrode 302 is formed over the substrate 301. A gate insulating film 303 is formed over the gate electrode 302. Note that the gate electrode 302 and the gate insulating film 303 can be formed by the same method and using the same material as the gate electrode 205 and the gate insulating film 204 in Embodiment Mode 4, respectively.

Over a portion where the gate electrode 302 is overlapped with the gate insulating film 303, a channel forming region 304 made of a first semiconductor film is formed. As the first semiconductor film, any of an amorphous semiconductor film, an amorphous semiconductor film including partially a crystal state, and a crystalline semiconductor film, which mainly include silicon, silicon-germanium (SiGe) or the like can be used. In this embodiment mode, an amorphous semiconductor film is used as the first semiconductor film. In addition, the first semiconductor film can be formed by a known method such as plasma CVD or sputtering. A thickness of the first semiconductor film is preferably 10 to 150 nm, more preferably, 30 to 70 nm.

A source region 305*a* and a drain region 305*b* made of a second semiconductor film are formed over the first semiconductor film. As the second semiconductor film, any of an amorphous semiconductor film, an amorphous semiconductor film including partially a crystal state, and a crystalline semiconductor film, which mainly include silicon, silicon-germanium (SiGe) or the like and includes an impurity element imparting an n-type or a p-type conductivity, can be used. In this embodiment mode, an amorphous semiconductor film is used as the second semiconductor film. The semiconductor film is an amorphous semiconductor film including beforehand an impurity element imparting an n-type or p-type conductivity. In addition, the second semiconductor film can be formed by a known method such as plasma CVD or sputtering. A thickness of the second semiconductor film is preferably 10 to 150 nm, more preferably, 30 to 70 nm.

A source electrode 306*a* is formed on and in contact with the source region 305*a* and a drain electrode 306*b* is formed on and in contact with the drain region 305*b*. Note that the source electrode 306*a* and the drain electrode 306*b* are formed by the same method, using the same material and with the same thickness as the source electrode 207*a* and the drain electrode 207*b* shown in Embodiment Mode 3.

The TFT 308 as described above includes the gate electrode 302, the gate insulating film 303, the channel forming region 304, the source region 305*a*, the drain region 305*b*, the source electrode 306*a*, and the drain electrode 306*b*, and an interlayer insulating film 307 is formed to cover the TFT 308. Note that the interlayer insulating film 307 can be formed using the same material as the interlayer insulating film 206 shown in Embodiment Mode 3.

The drain electrode 306*b* is electrically connected to the first electrode 309 of the light-emitting element through an opening portion which is formed in a part of the interlayer insulating film 307. The method, material and thickness for forming the first electrode 309 have been described in Embodiment Mode 3 and the description in Embodiment Mode 3 may be referred to. Description of the method, material and thickness for forming the first electrode 309 is omitted here.

An insulator 310 formed to cover the TFT 308 and an end portion of the first electrode 309 can be formed by the same method, using the same material and with the same thickness as the insulator 310 shown in Embodiment Mode 3.

Figure 3B:
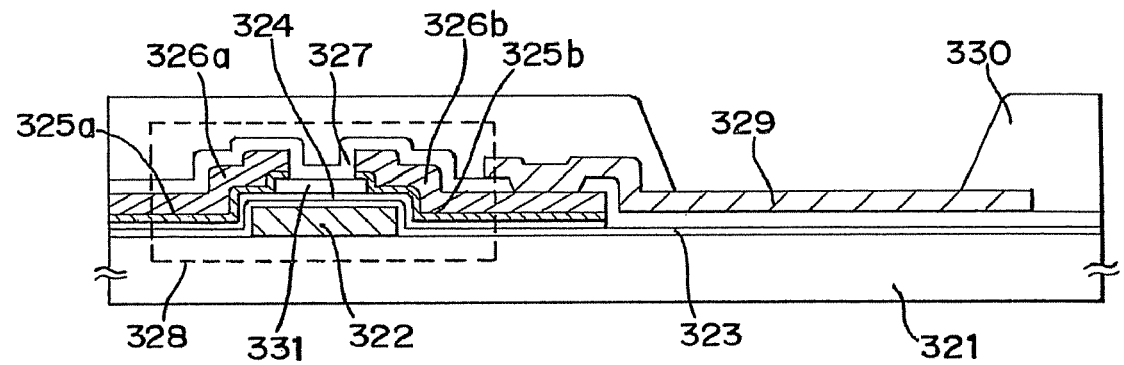

A channel-stop type TFT 328 having a bottom gate structure has the structure as shown in FIG. 3B. In other words, the TFT 328 is formed over a substrate 321, and a drain electrode 326*b* of the TFT 328 is electrically connected to the first electrode 329 of the light-emitting element. A second electrode is formed over the first electrode 329 with a layer including a luminescent substance therebetween and thus, the light-emitting element as described in Embodiment Mode 2 is formed. Accordingly, the TFT 328 can control driving of the light-emitting element.

In the channel-stop type TFT 328 having a bottom gate structure shown in FIG. 3B, a protective film 331 is provided over the channel forming region 324, in a position which is overlapped with the gate electrode.

Note that the protective film 331 is a film having a function of protecting the first semiconductor film in order to prevent the first semiconductor film forming the channel forming region 324 from being etched when the second semiconductor film and the conductive film are processed to form the source region 325*a*, the drain region 325*b*, the source electrode 326*a*, and the drain electrode 326*b*. The protective film 331 may be formed of an insulating film such as silicon oxide, silicon nitride, silicon oxynitride or silicon nitride oxide by a film-formation method such as plasma CVD or sputtering.

In addition, in the TFT 328 shown in FIG. 3B, the gate electrode 322, the gate insulating film 323, the channel forming region 324, the source region 325*a*, the drain region 325*b*, the source electrode 326*a*, the drain electrode 326*b*, the interlayer insulating film 327, the first electrode 329 and the insulator 330 may be formed by the same method, using the same material and with the same thickness as the gate electrode 302, the gate insulating film 303, the channel forming region 304, the source region 305a, the drain region 305b, the source electrode 306a, the drain electrode 306b, the interlayer insulating film 307, the first electrode 309 and the insulator 310 shown in FIG. 3A, and thus, description made in FIG. 3A is referred to, and description of the method, material and thickness thereof is omitted here.

By using a TFT as described above and a light-emitting element including a stilbene derivative of the present invention in combination so as to manufacture a light-emitting device, a longer life light-emitting device with excellent luminous efficiency as well as blue emission with excellent color purity can be provided.

Embodiment Mode 6

In Embodiment Mode 6, a light-emitting device having the light-emitting element of the present invention in a pixel portion will be described with reference to FIGS. 4A and 4B. Note that the structure of a light-emitting device of the present invention includes a control means such as a driver circuit for driving the light-emitting element, as well as the light-emitting element in accordance with the present invention. FIG. 4A is a top view showing the light-emitting device, and FIG. 4B is a sectional view taken along the section A-A' of FIG. 4A. A source driver circuit is denoted by Reference numerals 401, 402 and 403, which are shown by a dotted line; denote a driver circuit portion (a source driver circuit), a pixel portion, and a driver circuit portion (a gate driver circuit), respectively. Reference numeral 404 denotes a sealing substrate; reference numeral 405 denotes a sealant; and an inner side region enclosed by the sealant 405 is a space 407.

Reference numeral 408 denotes a wire for transmitting signals input to the source driver circuit 401 and the gate driver circuit 403 and receives a video signal, a clock signal, a start signal, a reset signal, and the like from an FPC (Flexible Printed Circuit) 409 serving as an external input terminal In addition, though only the FPC is indicated in the drawing, a printed wire board (PWB) may be attached to the FPC. In this specification, the light-emitting device includes the light-emitting device on which the FPC or the PWB is mounted as well as the light-emitting device itself.

Next, a sectional structure will be described using FIG. 4B. The driver circuit portion and the pixel portion are formed over a substrate 410. Here, the source driver circuit 401 of the driver circuit portion and the pixel portion 402 are shown.

As the source driver circuit 401, a CMOS circuit which is obtained by combining an n-channel ITT 423 and a p-channel TFT 424 is formed. The TFT forming the driver circuit may be a known CMOS circuit, PMOS circuit or NMOS circuit. Though the driver-integrated type, which the driver circuit is formed over the substrate, is used in this embodiment mode, the driver circuit may be formed outside the substrate.

The pixel portion 402 is formed of a plurality of pixels having a switching TFT 411, a current control TFT 412, and a first electrode 413 electrically connected to a drain of the current control TFT 412. An insulator 414 is formed to cover an end portion of the first electrode 413. The insulator 414 is formed by using a positive type photosensitive acryl resin film.

Over the first electrode 413, a layer including a luminescent substance 416 and a second electrode 417 are formed. It is desirable to use a material having a high work function as a material for forming the first electrode 413 functioning as the anode. For instance, a single layer film of an ITO (indium tin oxide) film, an indium zinc oxide (IZO) film, a titanium nitride film, a chromium film, a tungsten film, a Zn film, a Pt film, or the like, a stacked film of a film mainly containing titanium nitride and a film mainly comprising aluminum, a three layer structure of a titanium nitride film, a film mainly containing aluminum, and a titanium nitride film, or the like may be used. The stacked structure reduces a wire resistance and achieves a good ohmic contact, so that the stacked structure is capable of functioning as the anode.

The layer including a luminescent substance 416 is formed by an evaporation method using an evaporation mask or an inkjet method. The layer including a luminescent substance 416 includes a light-emitting layer, an electron generating layer, a hole transporting layer, an electron transporting layer, a hole blocking layer, a hole injecting layer, an electron injecting layer, a buffer layer or the like. Note that a low-molecular material, an intermediate-molecular material (including oligomer and dendrimer) or a high-molecular material can be used for forming the above described layers. Further, though a single layer of an organic compound or a stack of organic compound layers is generally used for the layer including a luminescent substance, the present invention includes a structure which an inorganic compound is used for a part of a film formed from an organic compound.

In the present invention, the buffer layer is provided to be in contact with one electrode of the both electrodes (an anode and a cathode) of the light-emitting element, to be in contact with the both electrodes, or to be in contact with neither of the both electrodes.

A second electrode (cathode) 417 is formed over the layer including a luminescent substance 416.

By joining the sealing substrate 404 and the element substrate 410 with the sealant 405, a structure where the light-emitting element 418 is provided in the space 407 surrounded by the element substrate 410, the sealing substrate 404, and the sealant 405 is formed. Structures wherein the space 407 is filled with an inert gas (nitrogen or argon) and the space 407 is filled with the sealant 405 are included in the present invention.

It is preferable to use an epoxy-based resin as the sealant 405. Also, it is desirable that the material to be used should not permeate moisture and oxygen as much as possible. Further, as a material to be used for the sealing substrate 404, a plastic substrate made from FRP (Fiberglass-Reinforced Plastics), PVF (polyvinyl fluoride), mylar, polyester, or acryl may be used, in addition to a glass substrate, and a quartz substrate.

As described above, by manufacturing a light-emitting device including a stilbene derivative of the present invention, a longer life light-emitting device with excellent luminous efficiency as well as blue emission with excellent color purity can be provided.

The light-emitting device shown in this embodiment mode can be freely combined with any of the structures shown in Embodiment Modes 1 to 5.

Embodiment Mode 7

Embodiment Mode 7 will describe examples of electronic devices including a stilbene derivative with reference to FIGS. 5A to 5E.

Figure 5A:
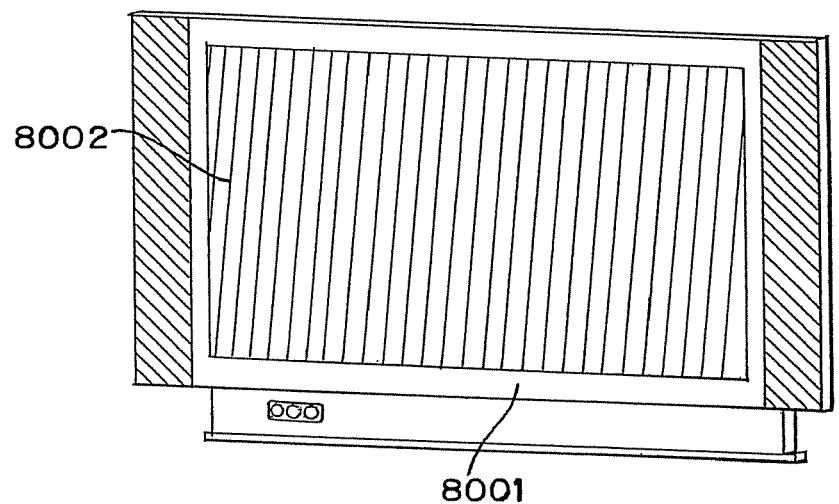
FIGS. 5A to 5E show electronic devices according to an aspect of the present invention.

A television device shown in FIG. 5A includes a main body 8001, a display portion 8002, and the like. In the display portion 8002, each of pixels includes a light-emitting element in which a stilbene derivative is included in a layer including a luminescent substance, and the pixels are arranged in matrix. For example, the light-emitting device of Embodiment Mode 6 can be applied to the display portion 8002. By forming the display portion 8002 including the stilbene derivative, a longer life television device with excellent luminous efficiency as well as blue color reproductivity and low power consumption can be provided.

Figure 5B:
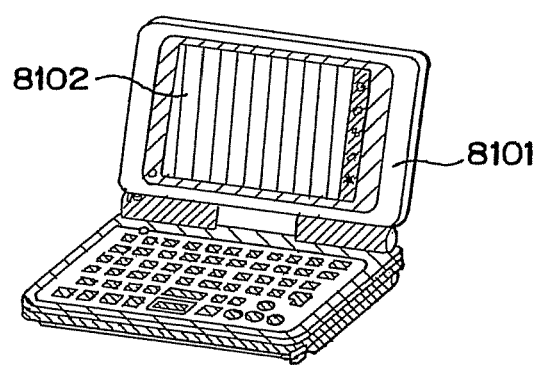

A portable information terminal device shown in FIG. 5B includes a main body 8101, a display portion 8102, and the like. In the display portion 8102, pixels are formed using a light-emitting element in which a stilbene derivative is included in a layer including a luminescent substance, and the pixels are arranged in matrix. For example, the light-emitting device of Embodiment Mode 6 can be applied to the display portion 8102. By forming the display portion 8102 including the stilbene derivative, a longer life portable information terminal device with excellent luminous efficiency as well as blue color reproductivity and low power consumption can be provided.

Figure 5C:
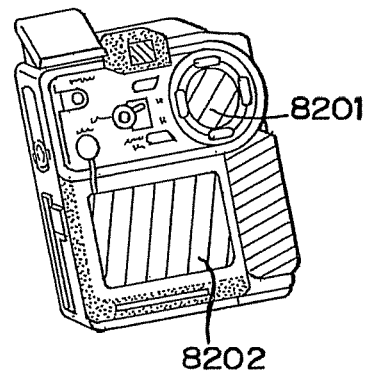

A video camera shown in FIG. 5C includes a main body 8201, a display portion 8202, and the like. In the display portion 8202, pixels are formed using a light-emitting element in which a stilbene derivative is included in a layer including a luminescent substance, and the pixels are arranged in matrix. For example, the light-emitting device of Embodiment Mode 6 can be applied to the display portion 8202. By forming the display portion 8202 including the stilbene derivative, a longer life video camera with excellent luminous efficiency as well as blue color reproductivity and low power consumption can be provided.

Figure 5D:
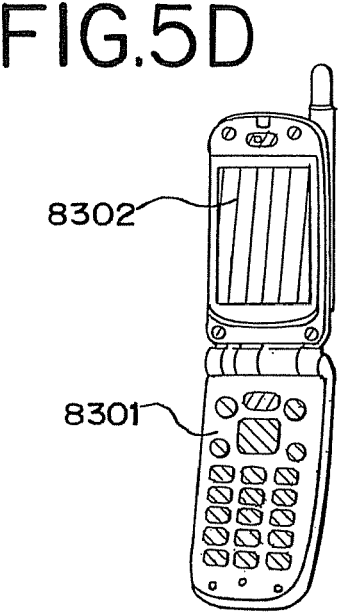

A telephone shown in FIG. 5D includes a main body 8301, a display portion 8302, and the like. In the display portion 8302, pixels are formed using a light-emitting element in which a stilbene derivative is included in a layer including a luminescent substance, and the pixels are arranged in matrix. For example, the light-emitting device of Embodiment Mode 6 can be applied to the display portion 8302. By forming the display portion 8302 including the stilbene derivative, a longer life telephone with excellent luminous efficiency as well as blue color reproductivity and low power consumption can be provided.

Figure 5E:
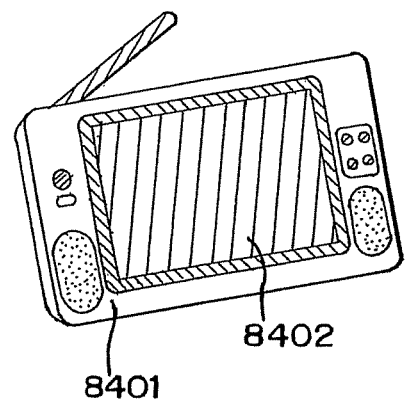

A portable television device shown in FIG. 5E includes a main body 8401, a display portion 8402, and the like. In the display portion 8402, pixels are formed using a light-emitting element in which a stilbene derivative is included in a layer including a luminescent substance, and the pixels are arranged in matrix. For example, the light-emitting device of Embodiment Mode 6 can be applied to the display portion 8402. By forming the display portion 8402 including the stilbene derivative, a longer life portable television device with excellent luminous efficiency as well as blue color reproductivity and low power consumption can be provided. In addition, the light-emitting device of the present invention can be widely applied to various television devices such as a small sized one incorporated in a portable terminal such as a cellular phone handset, a medium sized one which is portable, and a large sized one (for example, 40 inches or more in size).

The electronic devices according to the present invention are not limited to those shown in FIGS. 5A to 5E, and electronic devices in which a stilbene derivative is included in a display portion or a light-emitting portion are also included. For example, an electronic device in which a light-emitting element including a stilbene derivative is used as lighting for showing a position of a switch or a status can be provided. In addition, a light-emitting element including a stilbene derivative can be used for a light-source of a traffic signal machine.

By including a display portion or the like including a stilbene derivative, a longer life electronic device with excellent luminous efficiency as well as blue emission with excellent color purity can be provided.

Example 1

Hereinafter, Synthesis Examples and Examples of a stilbene derivative of the present invention will be described; however, the present invention is not limited thereto.

Synthesis Example 1

Synthesis Example 1 will describe a synthesis method of 4-[N-(9-phenylcarbazol-3-yl)-N-phenylamino]stilbene (abbrev.: PCAS) represented by the structural formula (9), as an example of a stilbene derivative of the present invention.

[Step 1: Synthesis of 4-bromostilbene]

(i) A Synthetic Method of 4-bromobenzyltriphenylphosphoniumbromide is Described Below.

First, 25.36 g (101.5 mmol) of 4-bromobenzylbromide and 100 mL of acetone were put in a 100 mL conical flask, and 29.28 g (111.6 mmol) of triphenylphosphine was added thereto. The mixture was stirred for 24 hours at room temperature. After the reaction, a precipitate in the reaction mixture was collected by suction filtration, and 50 g of a white powdered solid of 4-bromobenzyltriphenylphosphoniumbromide was obtained in a yield of 96%.

(ii) A Synthetic Method of 4-bromostilbene is Described Below.

25.3 g (49.5 mmol) of 4-bromobenzyltriphenylphosphoniumbromide, which was obtained in (i), and 5.25 g (49.5 mmol) of benzaldehyde were put in a 500 mL conical flask, and nitrogen substitution was carried out. Then, 150 mL of dehydrated tetrahydrofuran (abbrev.: THF) was added thereto, and was cooled. Then, 6.10 g (54.4 mmol) of potassium tert-butoxide dissolved in 50 mL, of dehydrated THF was dropped to this, and was stirred for 24 hours at room temperature. After the reaction, the solution was washed with water and separated into an organic layer and an aqueous layer. This aqueous layer was extracted with ethyl acetate, and the obtained extraction solution was combined with the organic layer and then dried with magnesium sulfate. Suction filtration of the mixed solution was carried out, and the filtrate was concentrated. The obtained residue was washed with methanol, and then a precipitate in the mixture was collected by suction filtration, and 3.75 g of a white solid, which was the target substance, was obtained in a yield of 29%.

Next, a synthesis scheme (a-1) of 4-bromostilbene is shown.

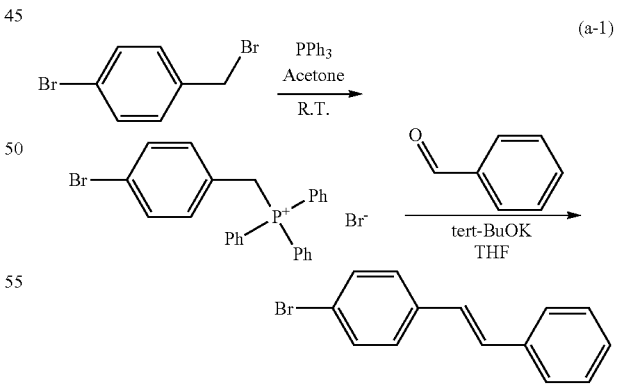

(a-1)

[Step 2: Synthesis of 3-(N-phenylamino)-9-phenylcarbazole (Abbrev.: PCA)]

(i) A Synthetic Method of 3-bromo-9-phenylcarbazole is Described Below.

First, 24.3 g (100 mmol) of N-phenylcarbazole was dissolved in 600 mL of gracial acetic acid, and 17.8 g (100 mmol) of N-bromosuccinimide was slowly added thereto.

Then, the mixture was stirred for 24 hours at room temperature. This gracial acetic acid solution was dropped into 1 L of ice water while being stirred. The precipitated white solid was washed with water three times. This solid was dissolved in 150 mL of diethylether, and washed with a saturated sodium hydrogen carbonate solution and water in this order.

This organic layer was dried with magnesium sulfate and then filtrated to obtain a filtrate. The filtrate was concentrated. The obtained residue was added with about 50 mL of methanol and was irradiated with ultrasonic waves so as to be dissolved uniformly. This solution was left at rest, and a white solid was precipitated. This solution was filtered, and the precipitate was dried to obtain 28.4 g (in a yield of 88%) of a white powder, which was 3-bromo-9-phenylcarbazole.

(ii) A Synthetic Method of 3-(N-phenylamino)-9-phenylcarbazole (Abbrev.: PCA) is Described Below.

Under a nitrogen atmosphere, 110 mL of dehydrated xylene and 7.0 g (75 mmol) of aniline were added into a mixture containing 19 g (60 mmol) of 3-bromo-9-phenylcarbazole obtained in (i), 340 mg (0.6 mmol) of bis(dibenzylideneacetone)palladium(0) (abbrev.: Pd(dba)$_2$), 1.6 g (3.0 mmol) of 1,1-bis(diphenylphosphino)ferrocene (abbrev.: DPPF) and 13 g (180 mmol) of sodium tert-butoxide (abbrev.: tert-BuONa). This mixed solution was heated and stirred under a nitrogen atmosphere at 90° C. for 7.5 hours.

After the reaction, about 500 mL of toluene which had been heated to 50° C. was added into this suspension and then, filtered through florisil, alumina and celite. The obtained filtrate was concentrated, and hexane-ethyl acetate was added into this residue, and was irradiated with ultrasonic waves. The obtained suspension was filtered, and this filtrate was dried to obtain 15 g (in a yield of 75%) of a cream-colored powder. By a nuclear magnetic resonance method ($^1$H NMR), this cream-colored powder was ascertained to be 3-(N-phenylamino)-9-phenylcarbazole (abbrev.: PCA).

Figure 6A:
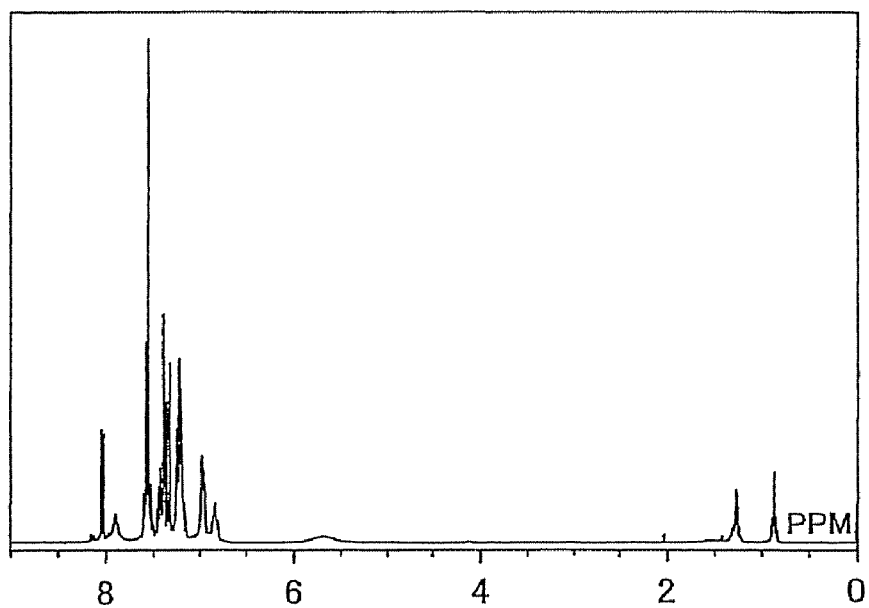
FIGS. 6A and 6B are $^1$NMR charts of PCA.
Figure 6B:
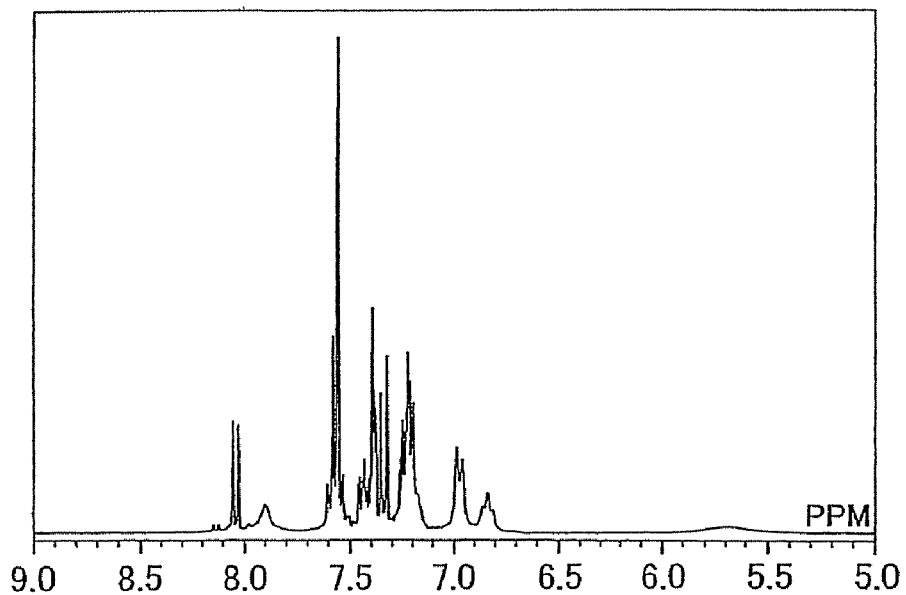

Next, $^1$H NMR of this compound is shown. In addition, FIGS. 6A and 6B show $^1$H NMR charts. FIG. 6B is an enlarged chart showing a range of 5 ppm to 9 ppm of FIG. 6A.

$^1$H NMR (300 MHz, CDCl$_3$); δ=6.84 (t, J=6.9 Hz, 1H), 6.97 (d, J=7.8 Hz, 2H), 7.20-7.61 (m, 13H), 7.90 (s, 1H), 8.04 (d, J=7.8 Hz, 1H).

Figure 52A:
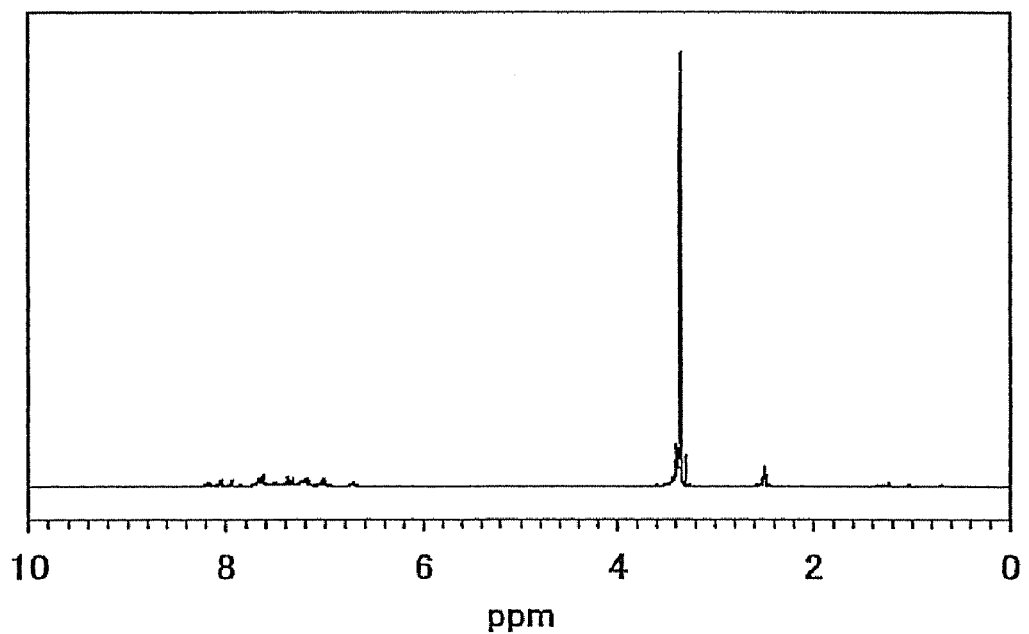
FIGS. 52A and 52B are $^1$NMR charts of PCA.
Figure 52B:
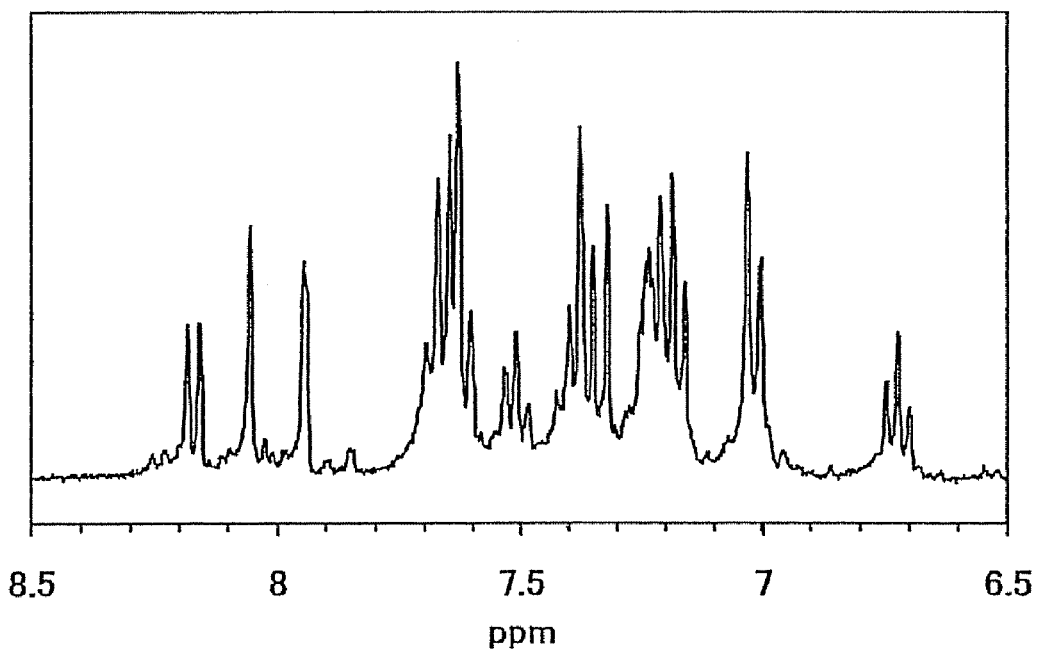

Next, $^1$H NMR of this compound is shown. In addition, FIGS. 52A and 52B show $^1$H NMR charts. FIG. 52B is an enlarged chart showing a range of 6.5 ppm to 8.5 ppm of FIG. 52A.

$^1$H NMR (300 MHz, DMSO-d$_6$); δ=6.73 (t, J=7.5 Hz, 1H), 7.02 (d, J=8.1 Hz, 2H), 7.16-7.70 (m, 12H), 7.95 (s, 1H), 8.06 (s, 1H), 8.17 (d, J=7.8 Hz).

Figure 53A:
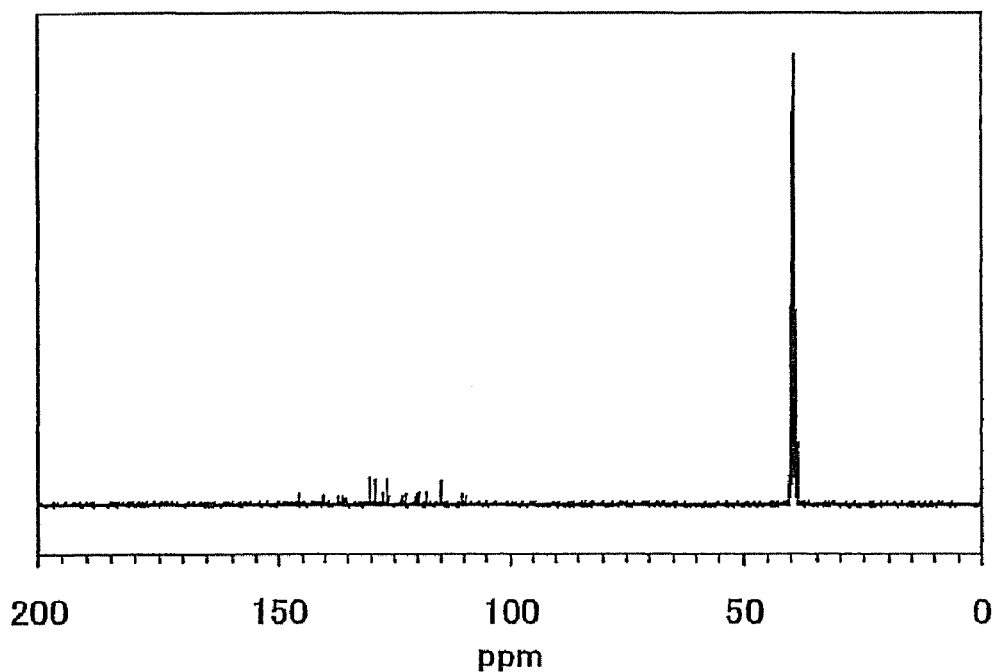
FIGS. 53A and 53B are $^1$NMR charts of PCA.
Figure 53B:
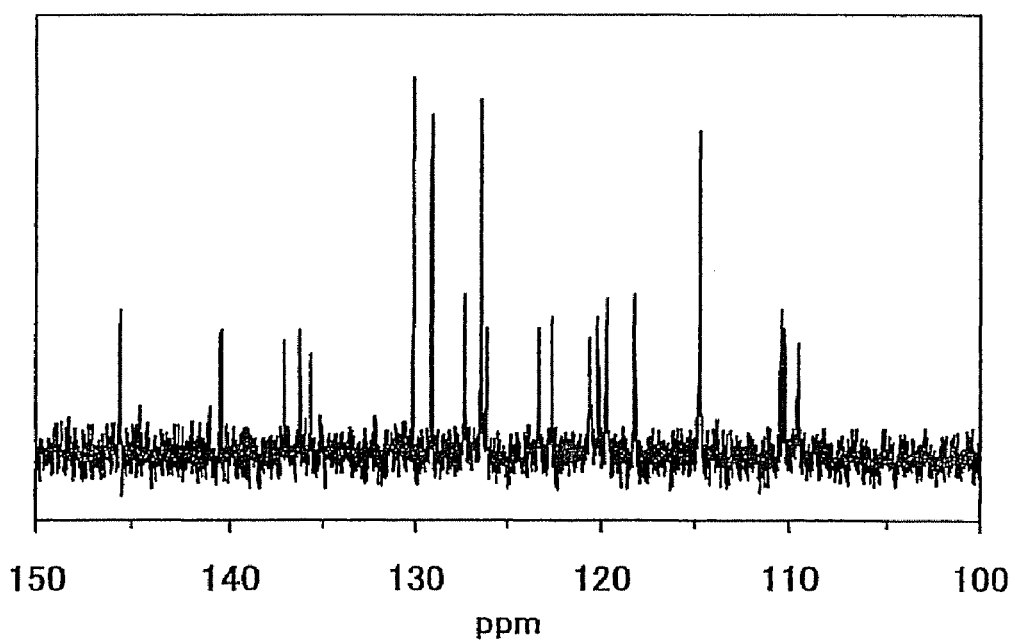

Further, $^{13}$C NMR is shown next. In addition, FIGS. 53A and 53B show $^{13}$C NMR charts. FIG. 53B is an enlarged chart showing a range of 100 ppm to 150 ppm of FIG. 53A.

$^{13}$C NMR (75.5 MHz, DMSO-d$_6$); δ=109.55, 110.30, 110.49, 114.71, 118.22, 119.70, 120.14, 120.61, 122.58, 123.35, 126.18, 126.48, 127.37, 129.15, 130.14, 135.71, 136.27, 137.11, 140.41, 145.61.

Next, a synthesis scheme (b-1) of 3-(N-phenylamino)-9-phenylcarbazole (abbrev.: PCA) is shown.

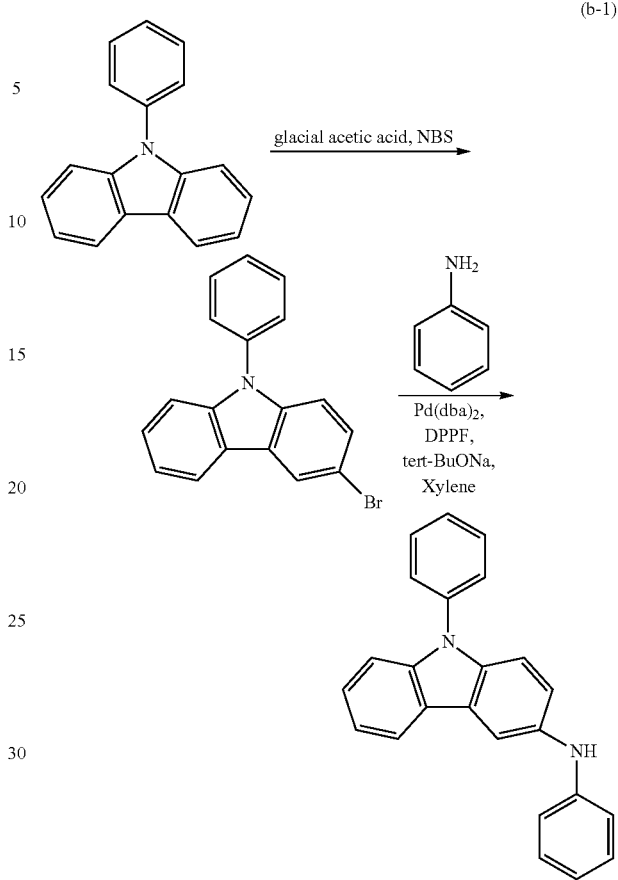

(b-1)

[Step 3: Synthesis of 4-[N-(9-phenylcarbazol-3-yl)-N-phenylamino]stilbene (Abbrev.: PCAS)]

1.00 g (3.86 mmol) of 4-bromostilbene, 1.29 g (3.86 mmol) of 3-(N-phenylamino)-9-phenylcarbazole (abbrev.: PCA), 0.11 g (0.193 mmol) of bis(dibenzylideneacetone)palladium, and 1.85 g (19.3 mmol) of sodium tert-butoxide were put in a 100 mL three-necked flask, and nitrogen substitution was carried out. Then, 20 mL of toluene and 0.39 g (0.193 mmol) of tri(tert-butyl)phosphine (10% hexane solution) were added thereto, and heated to be stirred for 7 hours at 80° C.

After the reaction, the solution was washed with water and separated into an organic layer and an aqueous layer. This aqueous layer was extracted with toluene, and the obtained extraction solution was dried with magnesium sulfate together with the organic layer. The mixed solution was filtered, and the filtrate was concentrated. The obtained residue was purified by silica gel column chromatography (toluene-hexane mixed solution), and the residue was recrystallized with the toluene-hexane mixed solution to obtain 1.34 g of a yellow solid in a yield of 68%. By a nuclear magnetic resonance method ($^1$H NMR), this compound was ascertained to be 4-[N-(9-phenylcarbazol-3-yl)-N-phenylamino]stilbene (abbrev.: PCAS).

Figure 7:
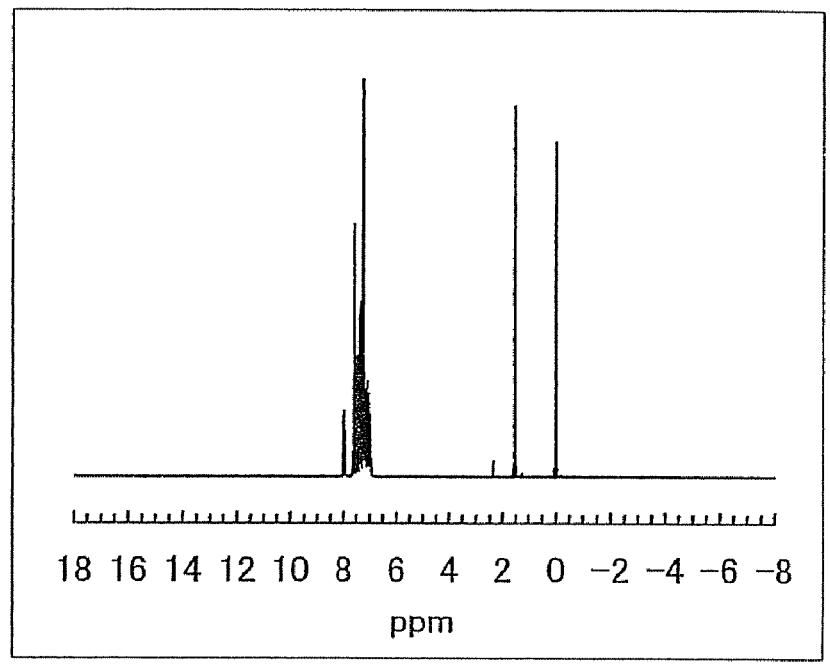
FIG. 7 is a $^1$NMR chart of PCAS according to an aspect of the present invention.

$^1$H NMR of this compound is shown below. In addition, FIG. 7 shows a $^1$H NMR chart. $^1$H NMR (300 MHz, CDCl$_3$); δ=7.90 (d, J=7.8 Hz, 1H), 7.94 (s, 1H), 7.61-7.31 (m, 14H), 7.25-7.00 (m, 12H)

Next, a synthesis scheme (c-1) of 4-[N-(9-phenylcarbazol-3-yl)-N-phenylamino]stilbene (abbrev.: PCAS) is shown.

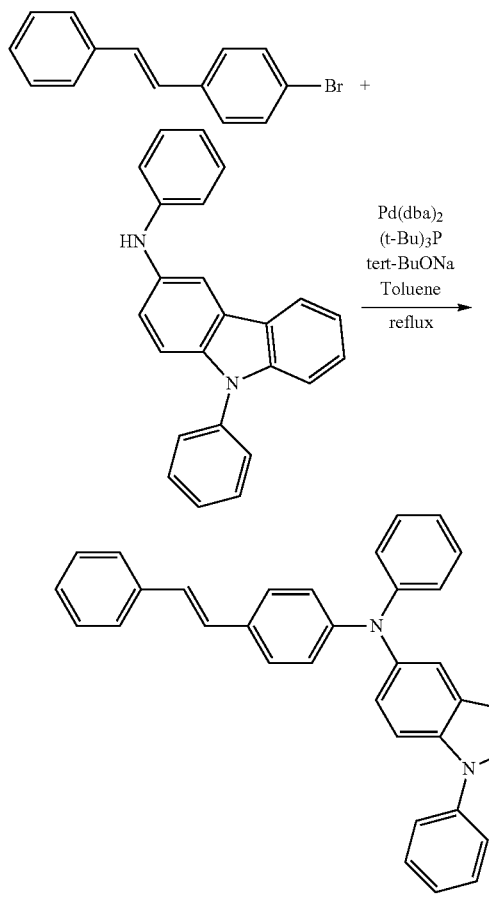

(c-1)

Figure 8:
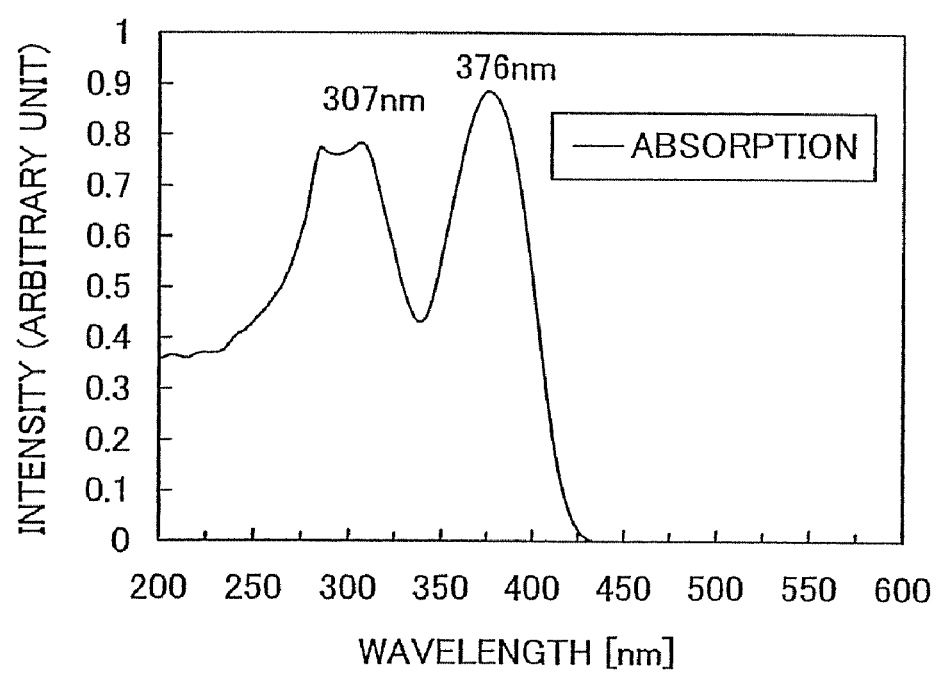
FIG. 8 shows an absorption spectrum of PCAS according to an aspect of the present invention.

An absorption spectrum of 4-[N-(9-phenylcarbazol-3-yl)-N-phenylamino]stilbene (hereinafter referred to as PCAS) is shown in FIG. 8. In FIG. 8, the horizontal axis indicates a wavelength (nm) and the vertical axis indicates intensity (no unit). Note that FIG. 8 shows an absorption spectrum in a state where PCAS was dissolved in a toluene solution.

Figure 9:
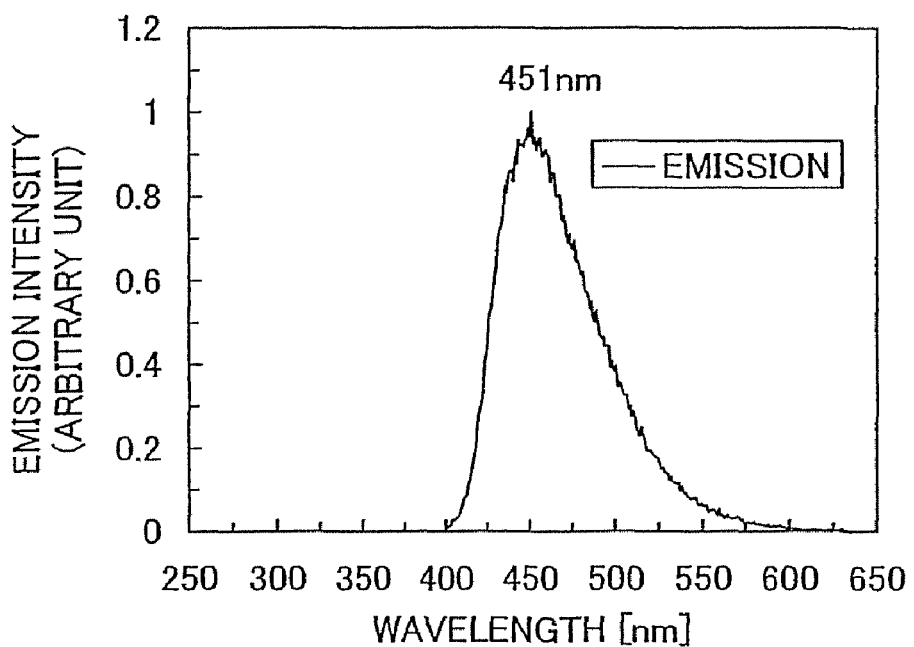
FIG. 9 shows an emission spectrum of PCAS according to an aspect of the present invention.

An emission spectrum of PCAS is shown in FIG. 9. In FIG. 9, the horizontal axis indicates a wavelength (nm) and the vertical axis indicates emission intensity (arbitrary unit). Note that FIG. 9 shows an emission spectrum (excitation wavelength: 393 nm) in a state where PCAS was dissolved in a toluene solution. From FIG. 9, it is found that emission from PCAS in a toluene solution has a peak at 451 nm. The emission was recognized as a bluish emission color.

A film of the obtained PCAS was formed by an evaporation method. An ionization potential of the compound in a thin film state was measured with a photoelectron spectrometer (manufactured by Riken Keiki Co.; Ltd., AC-2) and was found to be −5.30 eV. In addition, an absorption spectrum of the compound in a thin film state was measured with a UV/VIS spectrophotometer (manufactured by JASCO Corporation, V-550), an absorption edge on a longer wavelength side of the absorption spectrum was obtained from a tauc plot, and a LUMO level was measured considering an energy of the absorption edge as a band gap (2.91 eV). The LUMO level was found to be −2.39 eV.

Further, a decomposition temperature $T_d$ of the obtained PCAS was measured with a thermo-gravimetric/differential thermal analyzer (TG/DTA 320, manufactured by Seiko Instruments Inc.), and the $T_d$ was found to be 359° C. Thus, it was found that PCAS had excellent heat resistance.

An optimal molecular structure of PCAS in a ground state was calculated with B3LYP/6-311 (d, p) of a density functional theory (DFT). The accuracy of calculation of the DFT is higher than that of a Hartree-Fock (HF) method which does not consider electron correlation. In addition, the calculation cost of the DFT is lower than that of a method of perturbation (MP) which has the same level accuracy of calculation as the DFT. Therefore, the MT was employed in the present calculation. The calculation was performed using a high performance computer (HPC) (manufactured by SGI Japan, Ltd., Altix3700 DX). From this calculation result, a HOMO level value of PCAS was obtained to be −5.00 eV.

In addition, a singlet excitation energy (band gap) of PCAS was calculated by employing B3LYP/6-311 (d, p) of a time-dependent density functional theory (TDDFT) for the molecular structure whose structure was optimized by the DFT.: The singlet excitation energy was calculated to be 3.04 eV.

Synthesis Example 2

Synthesis Example 2 will describe a synthetic method of 4-tert-butyl-4'[N-(9-phenylcarbazol-3-yl)-N-phenylamino]stilbene (abbrev.: PCATBS) represented by the structural formula (55), as an example of a stilbene derivative of the present invention.

[Step 1: Synthesis of 4-bromo-4'-tert-butylstilbene]

Similarly to (i) in Step 1 of Synthesis Example 1, 4-bromobenzyltriphenylphosphoniumbromide was obtained. Then, 15 g (29.28 mmol) of 4-bromobenzyltriphenylphosphoniumbromide and 7.12 g (43.92 mmol) of 4-tert-butylbenzaldehyde were put in a 500 mL three-necked flask. Nitrogen substitution was carried out, and 150 mL of THF was added and then cooled with ice. Into this, 3.94 g (35.14 mmol) of potassium tert-butoxide which was dissolved in 50 mL of THF was dropped, and then stirred for 24 hours at room temperature.

After the reaction, the solution was washed with water and separated into an organic layer and an aqueous layer. The aqueous layer was extracted with ethyl acetate, and the extraction solution was dried with magnesium sulfate together with the organic layer. The mixed solution was filtered, and the filtrate was concentrated. The obtained residue was washed with methanol, and a precipitate in the mixed solution was collected by suction filtration. Then, 3.30 g of a white solid which was a target substance, was obtained in a yield of 35%.

Next, a synthesis scheme (a-2) of 4-bromo-4'-tert-butylstilbene is shown.

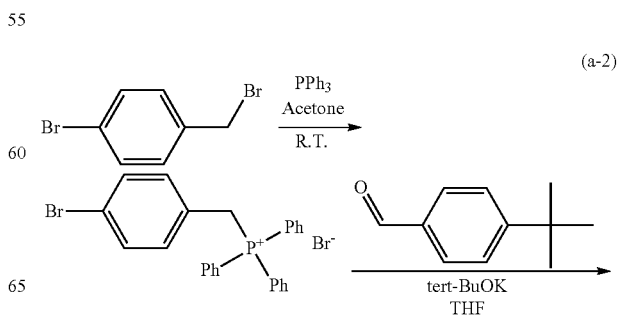

(a-2)

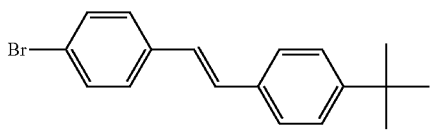

[Step 2: Synthesis of 3-(N-phenylamino)-9-phenylcarbazole (Abbrev.: PCA)]

3-(N-phenylamino)-9-phenylcarbazole synthesized in Step 2 of Synthesis Example 2 is the same substance as the one described in Step 2 of Synthesis Example 1; accordingly, the description thereof is omitted here.

[Step 3: Synthesis of 4-tert-butyl-4'[N-(9-Ppenylcarbazol-3-yl)-N-phenylamino]stilbene (Abbrev.: PCATBS)]

1.0 g (3.17 mmol) of 4-bromo-4'-tert-butylstilbene, 1.06 g (3.17 mmol) of 3-(N-phenylamino)-9-phenylcarbazole (abbrev.: PCA), 0.09 g (0.159 mmol) of bis(dibenzylideneacetone)palladium, and 1.52 g (15.86 mmol) of sodium tert-butoxide were put in a 100 mL three-necked flask, and nitrogen substitution was carried out. Then, into the mixed solution, 20 mL of dehydrated toluene and 0.32 g (0.159 mmol) of tri(tert-butyl)phosphine (10% hexane solution) were added and heated at 80° C. for 3 hours.

After the reaction, the solution was washed with water and separated into an organic layer and an aqueous layer. The aqueous layer was extracted with toluene, and the extraction solution was dried with magnesium sulfate together with the organic layer. The mixed solution was filtered, and the filtrate was concentrated to obtain a residue. The obtained residue was purified by silica gel column chromatography (toluene, hexane) and recrystallized with toluene and hexane to obtain 0.67 g of a yellow solid which was a target substance in a yield of 37%. By a nuclear magnetic resonance method ($^1$H NMR), this compound was ascertained to be 4-tert-butyl-4'-[N-(9-phenylcarbazol-3-yl)-N-phenylamino]stilbene (abbrev.: PCATBS).

Figure 10:
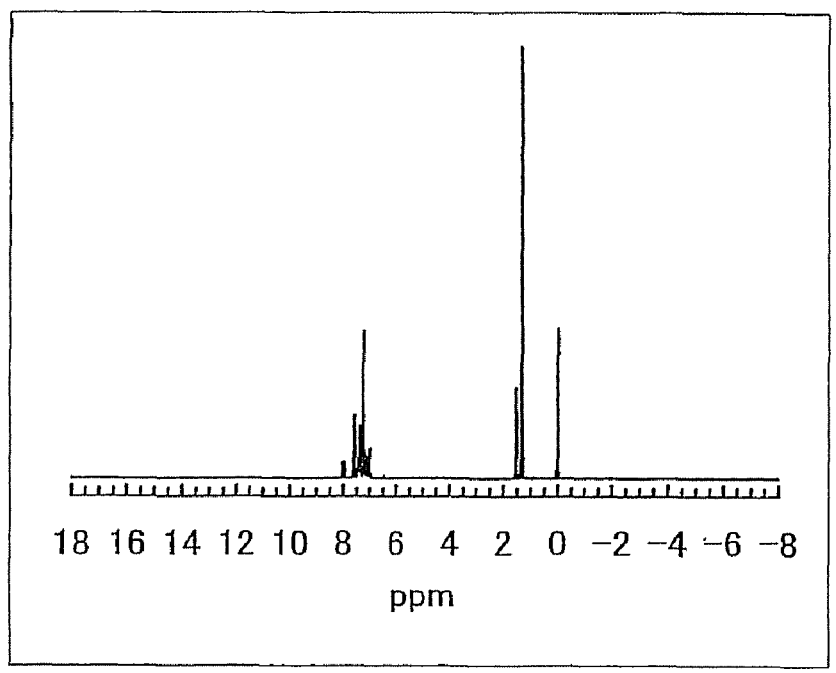
FIG. 10 is a $^1$NMR Chart of PCATBS according to an aspect of the present invention.

$^1$H NMR of this compound is shown below. In addition, FIG. 10 shows a $^1$H NMR chart.

$^1$H NMR (300 MHz, CDCl$_3$); δ=8.00 (d, J=7.8 Hz, 1H), 7.94 (s, 1H), 7.64-7.33 (m, 14H), 7.27-6.99 (m, 11H), 1.32 (s, 9H)

Next, a synthesis scheme (c-2) of 4-tert-butyl-4'[N-(9-phenylcarbazol-3-yl)-N-phenylamino]stilbene (abbrev.: PCATBS) is shown.

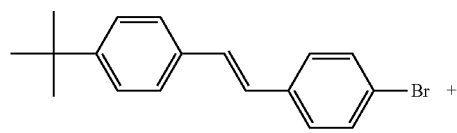

(c-2)

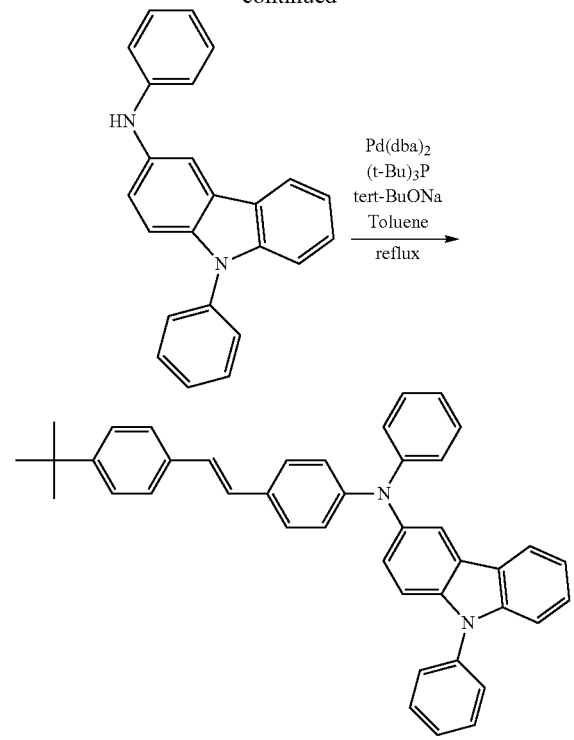

Figure 11:
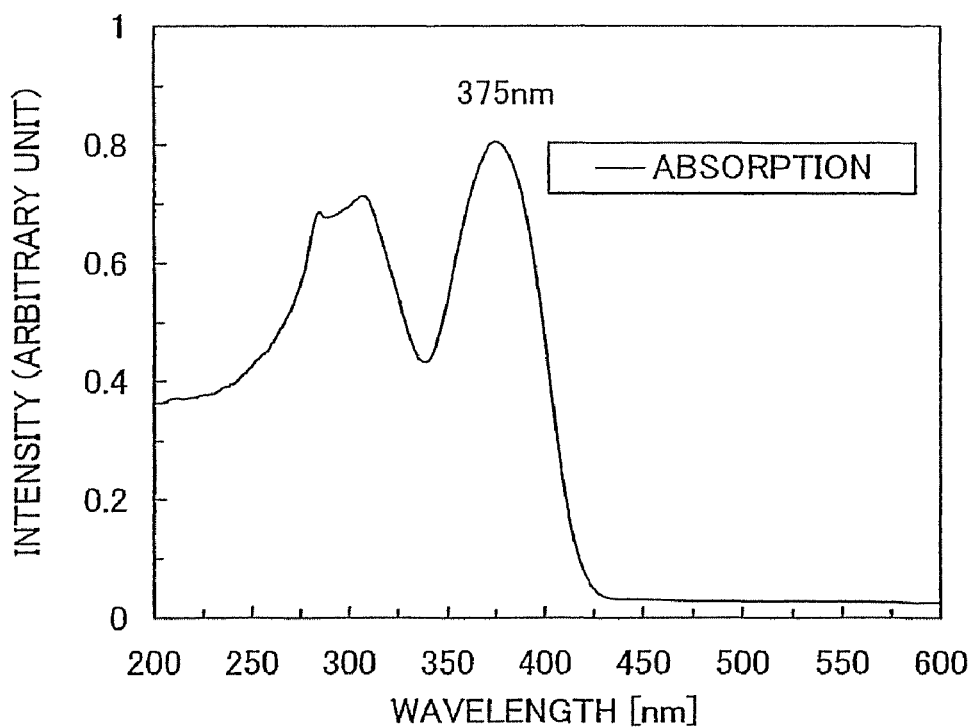
FIG. 11 shows an absorption spectrum of PCATBS according to an aspect of the present invention.

FIG. 11 shows an absorption spectrum of 4-tert-butyl-4'[N-(9-phenylcarbazol-3-yl)-N-phenylamino]stilbene (hereinafter referred to as PCATBS). In FIG. 11, the horizontal axis indicates a wavelength (nm) and the vertical axis indicates intensity (no unit). Note that FIG. 11 shows an absorption spectrum in a state where PCATBS was dissolved in a toluene solution.

Figure 12:
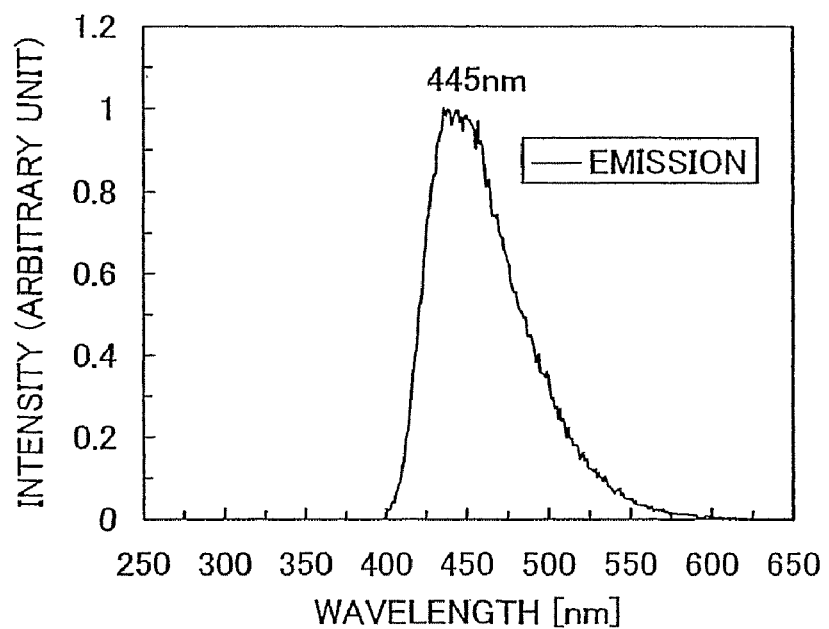
FIG. 12 shows an emission spectrum of PCATBS according to an aspect of the present invention.

FIG. 12 shows an emission spectrum of PCATBS. In FIG. 12, the horizontal axis indicates a wavelength (nm) and the vertical axis indicates emission intensity (arbitrary unit). FIG. 12 shows an emission spectrum (excitation wavelength: 391 nm) in a state where PCATBS was dissolved in a toluene solution. According to FIG. 12, it is found that emission from PCATBS in a toluene solution has a peak at 445 nm. The emission was realized as a bluish emission color.

A film of the obtained PCATBS was formed by an evaporation method. An ionization potential of the compound in a thin film state was measured with a photoelectron spectrometer (manufactured by Riken Keiki Co., Ltd., AC-2) and was found to be −5.26 eV. In addition, an absorption spectrum of the compound in a thin film state was measured with a UV/VIS spectrophotometer (manufactured by JASCO Corporation, V-550), an absorption edge on a longer wavelength side of the absorption spectrum was obtained from a tauc plot, and a LUMO level was measured considering an energy of the absorption edge as a band gap (2.93 eV). The LUMO level was found to be −2.33 eV.

Further, a decomposition temperature $T_d$ of the obtained PCATBS was measured with a thermo-gravimetric/differential thermal analyzer (manufactured by Seiko Instruments Inc., TG/DTA 320), and the $T_d$ was found to be 381° C. Thus, it was found that PCATBS had excellent heat resistance.

Synthesis Example 3

Synthesis Example 3 will describe a synthetic method of 4,4'-bis[N-(9-phenylcarbazol-3-yl)-N-phenylamino]stilbene (abbrev.: PCA2S) shown by the structural formula (57), as an example of a stilbene derivative of the present invention.

[Step 1: Synthesis of 4,4'-dibromostilbene]

Similarly to (i) in Step 1 of Synthesis Example 1, 4-bromobenzyltriphenylphosphoniumbromide was obtained. Then, 48.05 g (93.80 mmol) of 4-bromobenzyltriphenylphosphoniumbromide and 20.83 g (112.6 mmol) of 4-bromobenzaldehyde were put in a 1 L three-necked flask, and nitrogen substitution was carried out. 300 mL of dehydrated THF was added into the mixed solution and cooled with ice. Into this, 12.63 g (112.6 mmol) of potassium tert-butoxide which was dissolved in 100 ml of THF was dropped and stirred for 24 hours at room temperature.

After the reaction, the solution was washed with water and separated into an organic layer and an aqueous layer. The aqueous layer was extracted with ethyl acetate, and the extraction solution was dried with magnesium sulfate together with the organic layer. The mixed solution was filtered, and the filtrate was concentrated. The obtained residue was washed with methanol, and a precipitate in the mixed solution was collected by suction filtration. Accordingly, 10.77 g of a white solid which was a target substance was obtained in a yield of 34%.

Next, a synthesis scheme (d-1) of 4,4'-dibromostilbene is shown.

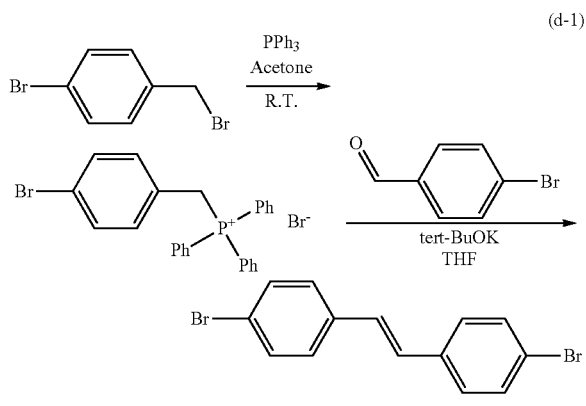

(d-1)

[Step 2: Synthesis of 3-(N-phenylamino)-9-phenylcarbazole (Abbrev.: PCA)]

3-(N-phenylamino)-9-phenylcarbazole synthesized in Step 2 of Synthesis Example 3 is the same substance as the one described in Step 2 of Synthesis Example 1; accordingly, the description thereof is omitted here.

[Step 3: Synthesis of 4,4'-bis[N-(9-phenylcarbazol-3-yl)-N-phenylamino]stilbene (Abbrev.: PCA2S)]

1.00 g (2.95 mmol) of 4,4'-dibromostilbene, 2.19 g (6.56 mmol) of 3-(N-phenylamino)-9-phenylcarbazole, 0.189 g (0.328 mmol) of bis(dibenzylideneacetone)palladium, and 3.15 g (32.8 mmol) of sodium tert-butoxide were put in a 100 mL three-necked flask, and nitrogen substitution was carried out. 20 mL of dehydrated toluene and 0.66 g (0.328 mmol) of tri(tert-butyl)phosphine (10% hexane solution) were added thereto and heated at 80° C. for 7 hours.

After the reaction, the solution was washed with water and separated into an organic layer and an aqueous layer. The aqueous layer was extracted with ethyl acetate, and the extraction solution was dried with magnesium sulfate together with the organic layer. The mixed solution was filtered, and the filtrate was concentrated to obtain a residue. The obtained residue was purified by silica gel column chromatography (toluene, hexane) and was recrystallized with chloroform and hexane; accordingly, 1.19 g of a yellow solid which was a target substance was obtained in a yield of 47%. By a nuclear magnetic resonance method ($^1$H NMR), this compound was ascertained to be 4,4'-bis[N-(9-phenylcarbazol-3-yl)-N-phenylamino]stilbene (abbrev.: PCA2S).

Figure 13:
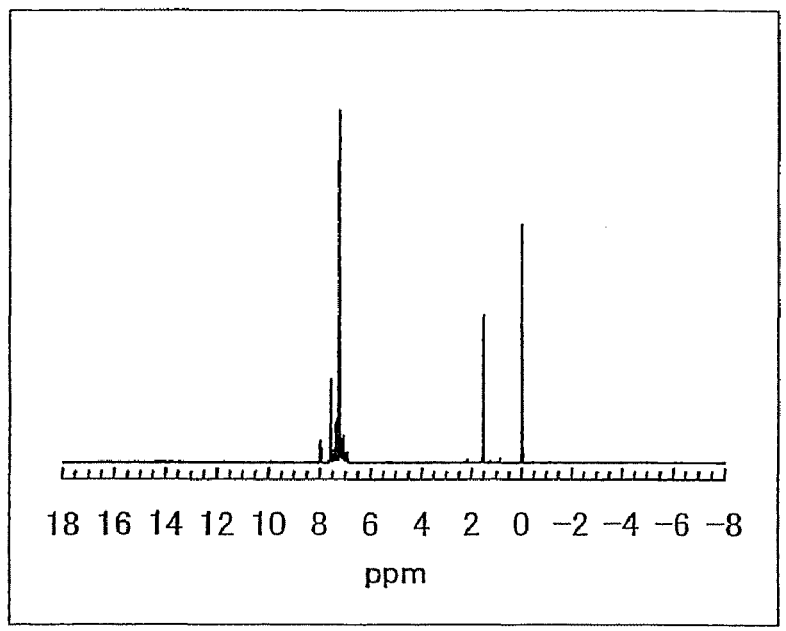
FIG. 13 is a $^1$NMR chart of PCA2S according to an aspect of the present invention.

$^1$H NMR of this compound is shown below. In addition, FIG. 13 shows a $^1$H NMR chart.

$^1$H NMR (300 MHz, CDCl$_3$): δ=8.00 (d, J=7.8 Hz, 2H), 7.94 (s, 2H), 7.62-7.33 (m, 20H), 7.24-6.94 (m, 10H)

Next, a synthesis scheme (e-1) of 4,4'-bis[N-(9-phenylcarbazol-3-yl)-N-phenylamino]stilbene (abbrev.: PCA2S) is shown.

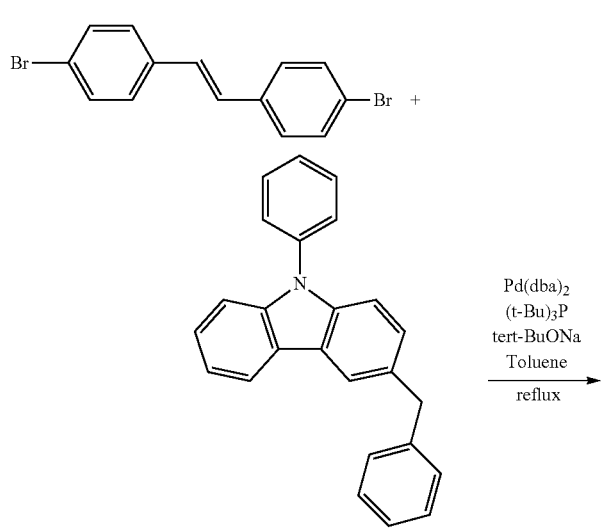

(e-1)

-continued

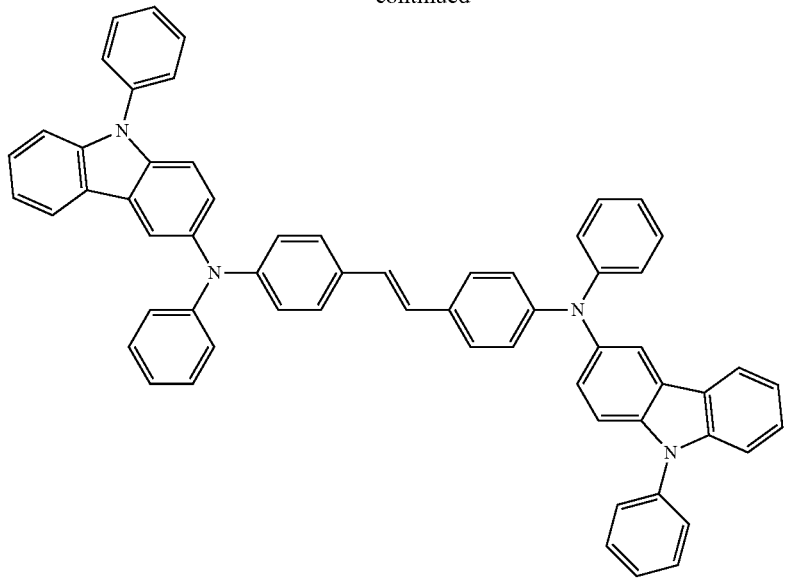

Figure 14:
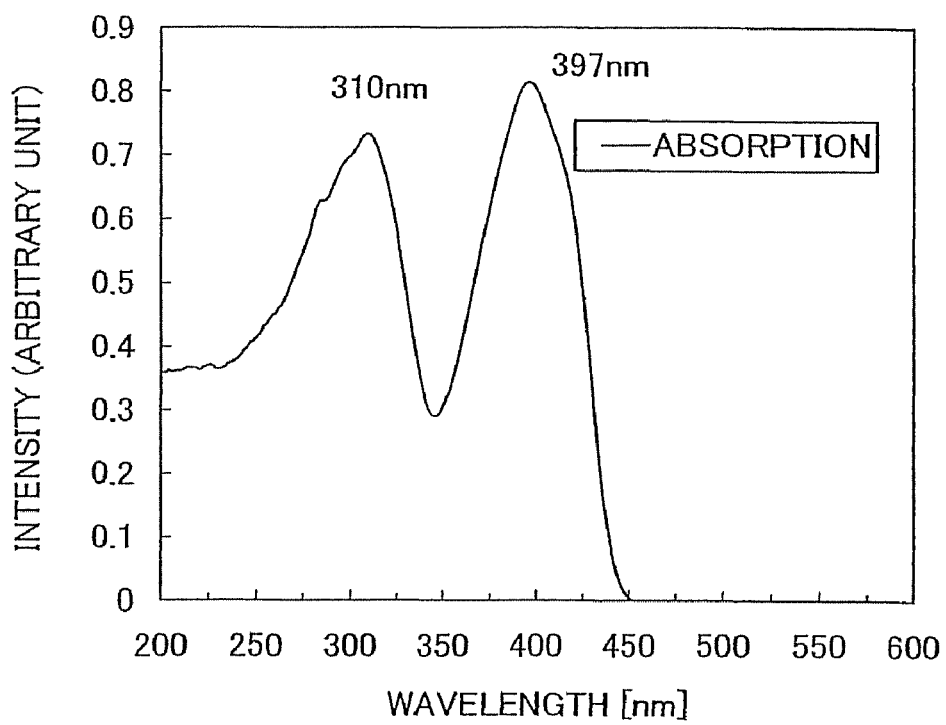
FIG. 14 shows an absorption spectrum of PCA2S according to an aspect of the present invention.

FIG. 14 shows an absorption spectrum of 4,4'-bis[N-(9-phenylcarbazol-3-yl)-N-phenylamino]stilbene (hereinafter referred to as PCA2S). In FIG. 14, the horizontal axis indicates a wavelength (nm) and the vertical axis indicates intensity (no unit). Note that FIG. 14 shows an absorption spectrum in a state where PCA2S was dissolved in a toluene solution.

Figure 15:
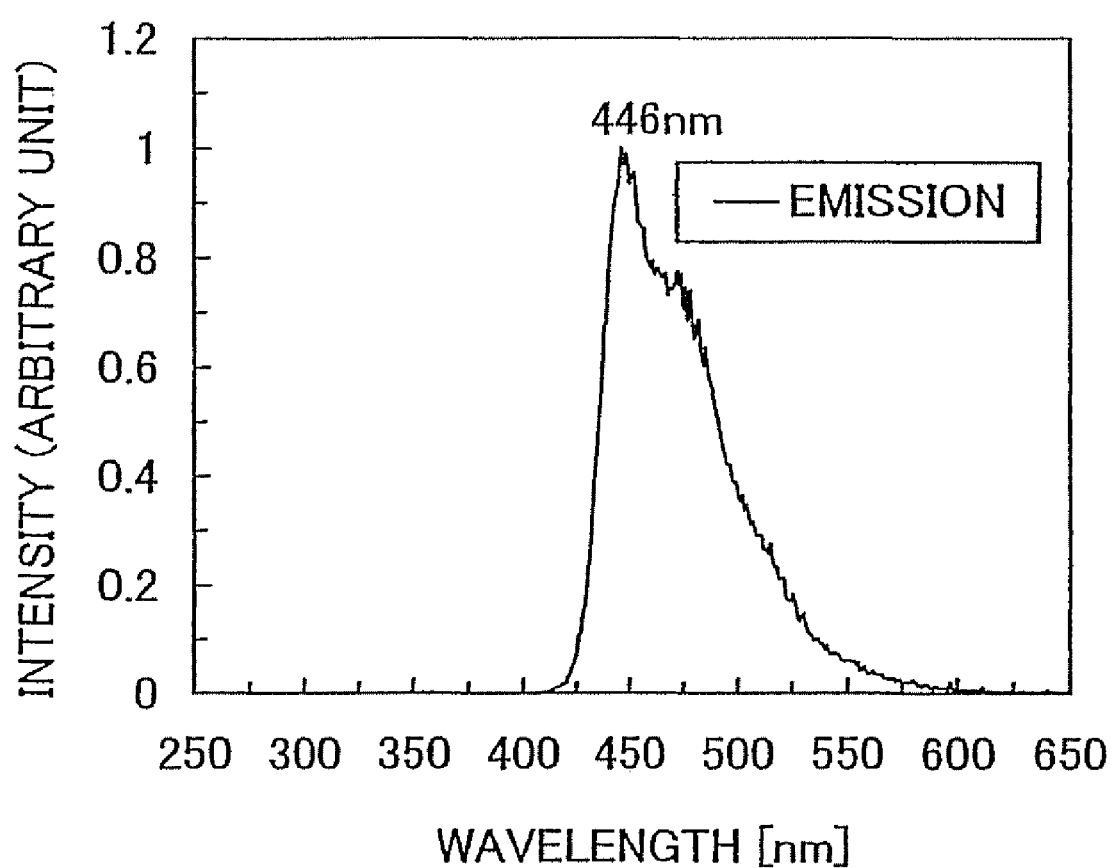
FIG. 15 shows an emission spectrum of PCA2S according to an aspect of the present invention.

FIG. 15 shows an emission spectrum of PCA2S. In FIG. 15, the horizontal axis indicates a wavelength (nm) and the vertical axis indicates emission intensity (arbitrary unit). FIG. 15 shows an emission spectrum (excitation wavelength: 397 nm) in a state where PCA2S was dissolved in a toluene solution. According to FIG. 15, it is found that emission from PCA2S in a toluene solution has a peak at 446 nm. The emission was realized as a bluish emission color.

A film of the obtained PCA2S was formed by an evaporation method. An ionization potential of the compound in a thin film state was measured with a photoelectron spectrometer (manufactured by Riken Keiki Co., Ltd., AC-2) and was found to be −5.20 eV. In addition, an absorption spectrum of the compound in a thin film state was measured with a UV/VIS spectrophotometer (manufactured by JASCO Corporation, V-550), an absorption edge on a longer wavelength side of the absorption spectrum was obtained from a tauc plot, and a LUMO level was measured considering an energy of the absorption edge as a band gap (2.74 eV). The LUMO level was found to be −2.46 eV.

Further, a decomposition temperature $T_d$ of the obtained PCA2S was measured with a thereto-gravimetric/differential thermal analyzer (manufactured by Seiko Instruments Inc., TG/DTA 320), and the $T_d$ was found to be 484° C. From this, it was found that PCA2S had excellent heat resistance.

An optimal molecular structure of PCA2S in a ground state was calculated in a similar manner to that in Synthesis Example 1. From this calculation result, a HOMO level value of PCA2S was obtained to be −4.63 eV.

In addition, when singlet excitation energy (band gap) of PCA2S was calculated in a similar manner to that in Synthesis Example 1, the singlet excitation energy was calculated to be 2.84 eV.

Synthesis Example 4

Synthesis Example 4 will describe a synthetic method of 4-{N-[4-(carbazol-9-yl)phenyl]-N-phenylamino}stilbene (abbrev.: YGAS) represented by the structural formula (96), as an example of a stilbene derivative of the present invention.
[Step 1: Synthesis of 4-bromostilbene]
4-bromostilbene synthesized in Step 1 of Synthesis Example 4 is the same substance as the one described in Step 1 of Synthesis Example 1; accordingly, the description thereof is omitted here.
[Step 2: Synthesis of 9-[4-(N-phenylamino)phenyl]carbazole (abbrev.: YGA)]
(i) A Synthetic Method of N-(4-bromophenyl)carbazole is Described Below.

56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were put in a 300 mL three-necked flask, and nitrogen substitution was carried out. 8 mL of 1,3-dimethyl-3,4,5,6-tetrahydro-2(1H)-pyrimidinone (abbrev.: DMPU) was added thereto, and stirred for 6 hours at 180° C. under a nitrogen atmosphere.

After the reaction mixture was cooled to room temperature, a precipitate was removed by suction filtration. The filtrate was washed with dilute hydrochloric acid, saturated sodium hydrogen carbonate, and saturated saline in this order, and dried with magnesium sulfate. After drying, the reaction mixture was naturally filtered, and the obtained filtrate was concentrated to obtain an oily substance. The obtained oily substance was purified by silica gel column chromatography (hexane:ethyl acetate=9:1), and was recrystallized with chloroform and hexane. Then, 20.7 g of light brown plate-shaped crystal, which was a target substance, was obtained in a yield of 35%. By a nuclear magnetic resonance method, this compound was ascertained to be N-(4-bromophenyl)carbazole.

Next, $^1$H NMR of this compound is shown.
$^1$H NMR (300 MHz, DMSO-d$_6$) δ=8.14 (d, J=7.8 Hz, 2H), 7.73 (d, J=8.7 Hz, 2H), 7.46 (d, J=8.4 Hz, 2H), 7.42-7.26 (m, 6H)

(ii) Synthesis of 9-[4-(N-phenylamino)phenyl]carbazole (Abbrev.: YGA)

Next, 5.4 g (17.0 mmol) of N-(4-bromophenyl)carbazole which was obtained in (i), 1.8 mL (20.0 mmol) of aniline, 100 mg (0.17 mmol) of bis(dibenzylideneacetone)palladium(0) (abbrev.: Pd(dba)$_2$), and 3.9 g (40 mmol) of sodium tert-butoxide (tert-BuONa) were put in a 200 mL, three-necked flask, and nitrogen substitution was carried out. Then, 0.1 mL of 10% hexane solution of tri(tert-butyl)phosphine (abbrev.: P(tert-Bu)$_3$) and 50 mL of dehydrated toluene were added thereto and stirred for 6 hours at 80° C. under a nitrogen atmosphere.

The reaction mixture was filtered through florisil, celite and alumina, and the filtrate was washed with water and saturated saline, and dried with magnesium sulfate. The reaction mixture was naturally filtered, and the filtrate was concentrated to obtain an oily substance. The obtained oily substance was purified by silica gel column chromatography (hexane:ethyl acetate=9:1); accordingly, 4.1 g of a target substance was obtained in a yield of 73%. By a nuclear magnetic resonance method ($^1$H NMR), this compound was ascertained to be 9-[4-(N-phenylamino)phenyl]carbazole (abbrev.: YGA).

Figure 16A:
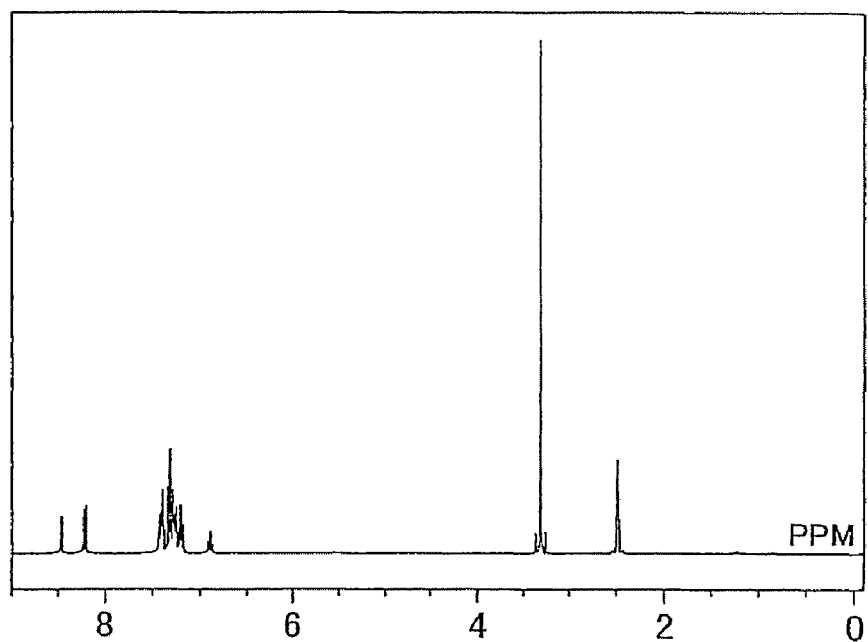
FIGS. 16A and 16B are $^1$MNR charts of YGA.
Figure 16B:
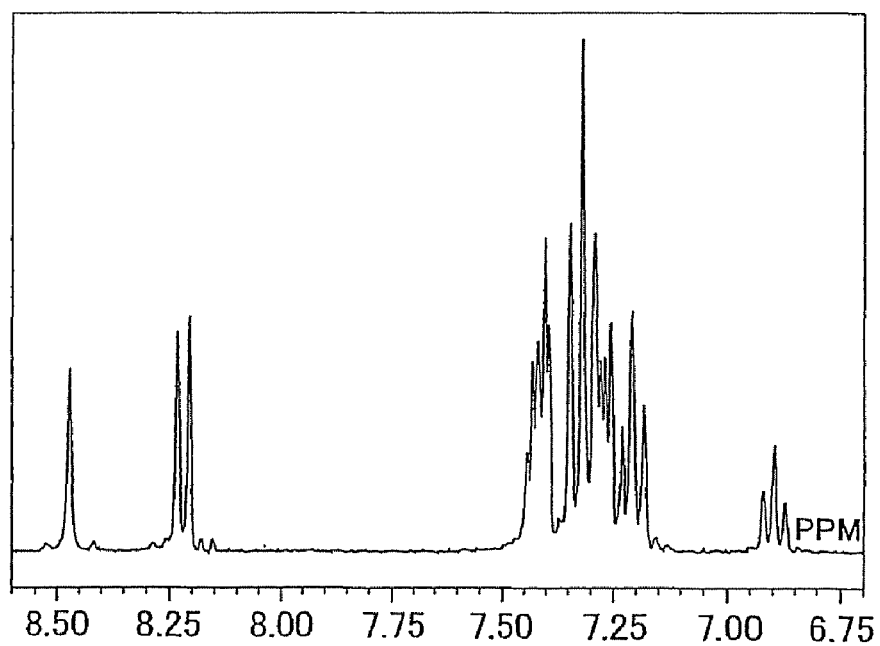

Next, $^1$H NMR of this compound is shown. In addition, FIGS. 16A and 16B show $^1$H NMR charts.

$^1$H NMR (300 MHz, DMSO-d$_6$) δ=8.47 (s, 1H), 8.22 (d, J=7.8 Hz, 2H), 7.44-7.16 (m, 14H), 6.92-6.87 (m, 1H)

Next, a synthesis scheme (f-1) of 9-[4-(N-phenylamino)phenyl]carbazole is shown.

[Step 3: Synthesis of 4-{N[4-(carbazol-9-yl)phenyl]-N-phenylamino}stilbene (Abbrev.: YGAS)]

0.62 g (2.38 mmol) of 4-bromostilbene, 0.88 g (2.62 mmol) of 9-[4-(N-phenylamino)phenyl]carbazole, 0.068 g (0.119 mmol) of bis(dibenzylideneacetone)palladium, and 1.14 g (11.9 mmol) of sodium tert-butoxide were put in a 100 mL three-necked flask, and nitrogen substitution was carried out. Then, 15 mL of dehydrated toluene and 0.24 g (0.119 mmol) of tri(tert-butyl)phosphine (10% hexane solution) were added thereto, and stirred for 7 hours at 80° C.

After the reaction, the solution was washed with water and separated into an organic layer and an aqueous layer. The aqueous layer was extracted with toluene, and the extraction solution was combined with the organic layer and was dried with magnesium sulfate. The mixed solution was filtered, and the filtrate was concentrated to obtain a residue. The obtained residue was dissolved in chloroform, and the solution was filtered through celite, florisil and alumina. The filtrate was concentrated and recrystallized with toluene and hexane. Accordingly, 1.0 g of a yellow solid, which was a target substance, was obtained in a yield of 80%.

Figure 17:
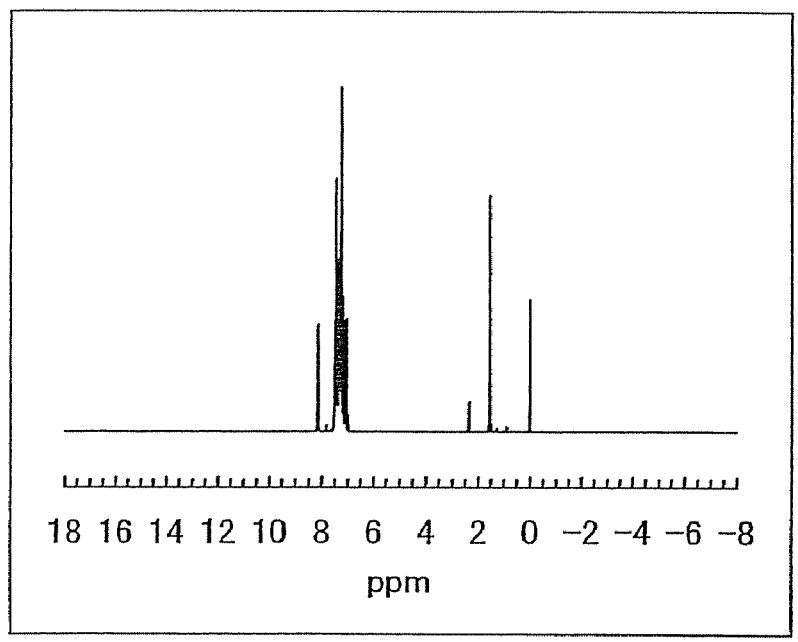
FIG. 17 is a $^1$NMR chart of YGAS according to an aspect of the present invention.

$^1$H NMR of this compound is shown below. In addition, FIG. 17 shows a $^1$H NMR chart.

$^1$H NMR (300 MHz, CDCl$_3$); δ=8.14 (d, J=7.8 Hz, 2H), 7.52-7.26 (m, 19H), 7.22-7.06 (m, 7H)

Next, a synthesis scheme (g-1) of 4-{N-[4-(carbazol-9-yl)phenyl]-N-phenylamino}stilbene (abbrev.:YGAS) is shown.

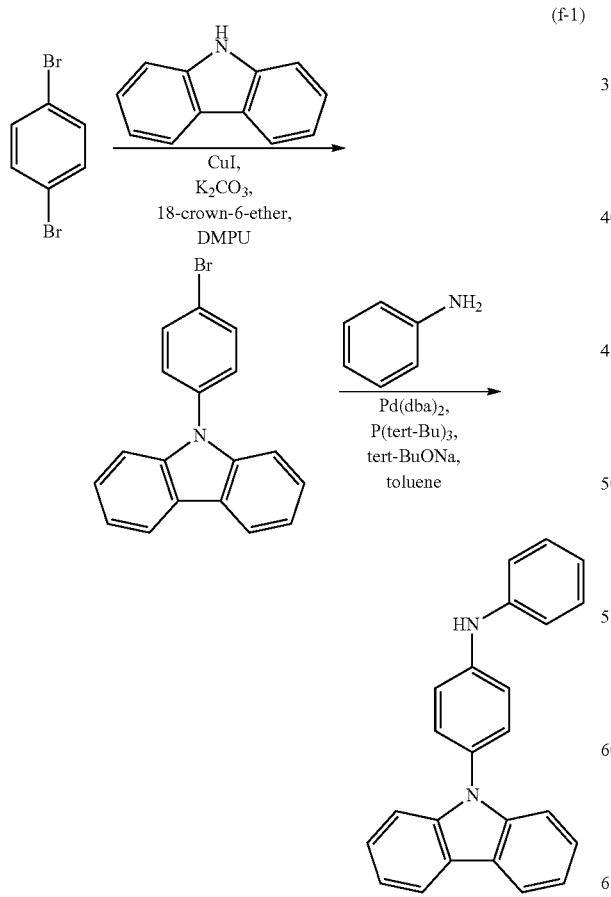

(f-1)

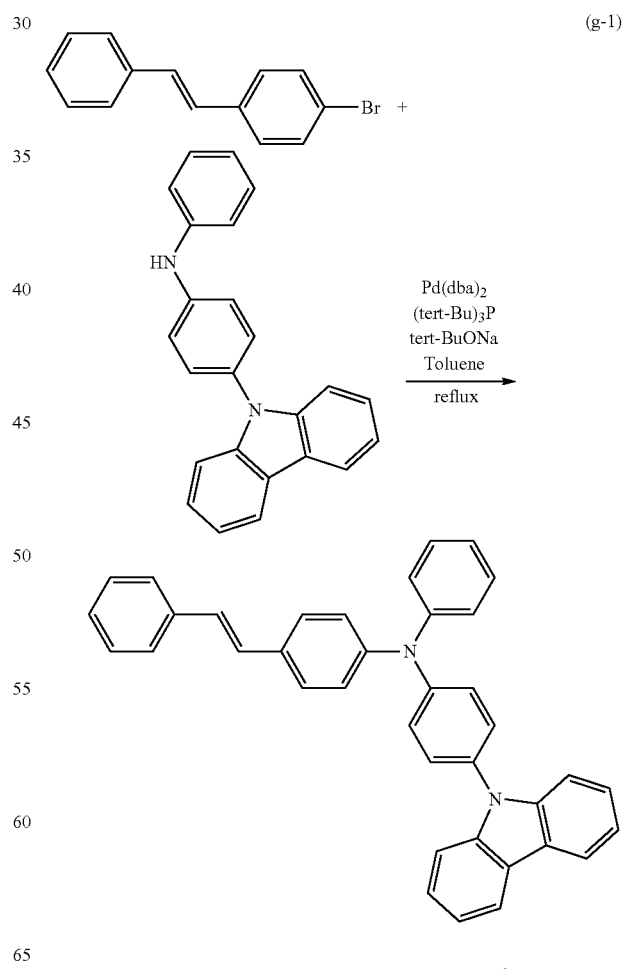

(g-1)

Figure 18:
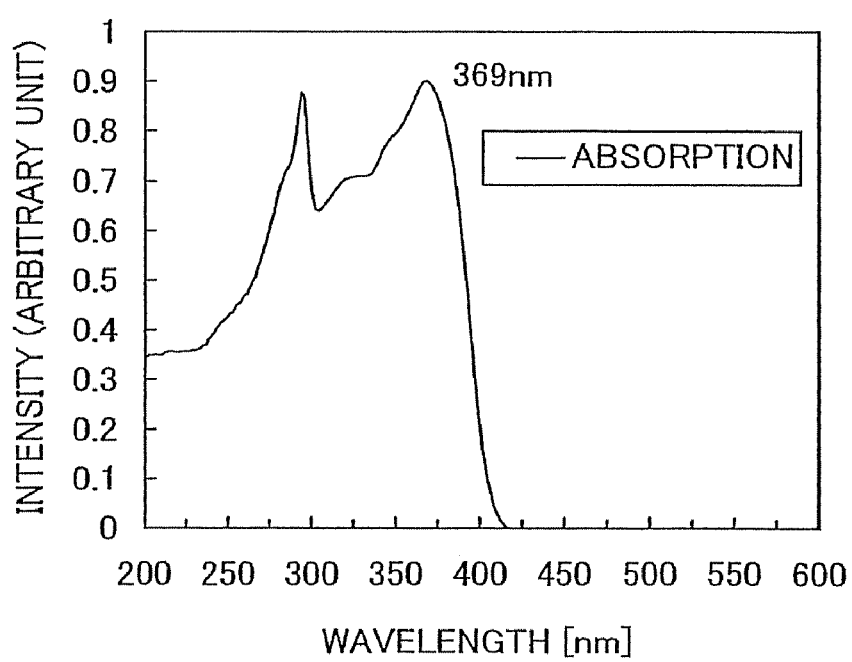
FIG. 18 shows an absorption spectrum of YGAS according to an aspect of the present invention.

FIG. 18 shows an absorption spectrum of 4-{N[4-(carbazol-9-yl)phenyl]-N-phenylamino}stilbene (hereinafter referred to as YGAS). In FIG. 18, the horizontal axis indicates a wavelength (nm) and the vertical axis indicates intensity (no unit). Note that FIG. 18 shows an absorption spectrum in a state where YGAS was dissolved in a toluene solution.

Figure 19:
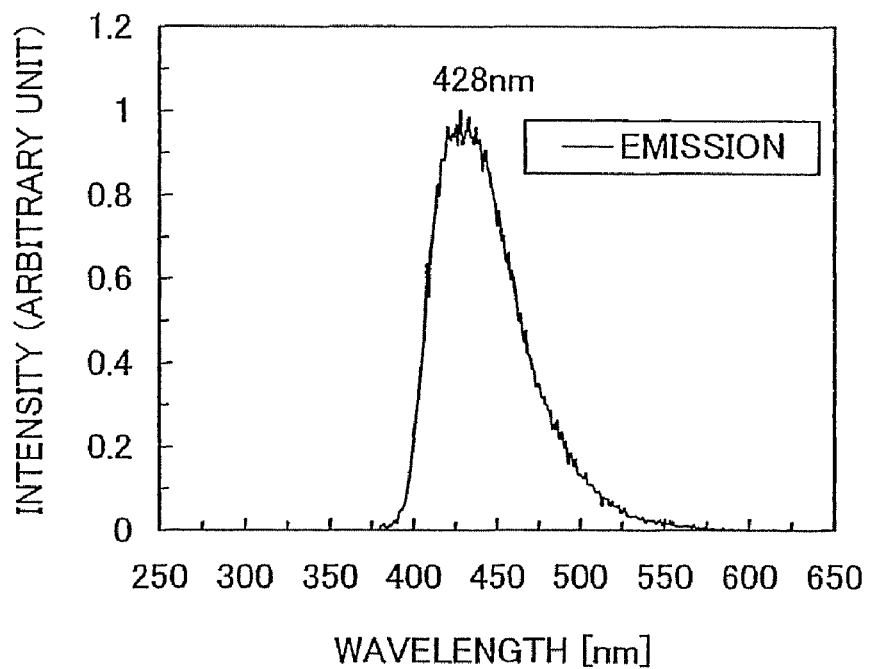
FIG. 19 shows an emission spectrum of YGAS according to an aspect of the present invention.

FIG. 19 shows an emission spectrum of YGAS. In FIG. 19, the horizontal axis indicates a wavelength (nm) and the vertical axis indicates emission intensity (arbitrary unit). FIG. 19 shows an emission spectrum (excitation wavelength: 382 nm) in a state where YGAS was dissolved in a toluene solution. According to FIG. 19, it is found that emission from YGAS in a toluene solution has a peak at 428 nm. The emission was realized as a bluish emission color.

A film of the obtained YGAS was formed by an evaporation method. An ionization potential of the compound in a thin film state was measured with a photoelectron spectrometer (manufactured by Riken Keiki Co., Ltd., AC-2) and was found to be −5.65 eV. In addition, an absorption spectrum of the compound in a thin film state was measured with a UV/VIS spectrophotometer (manufactured by JASCO Corporation, V-550), an absorption edge on a longer wavelength side of the absorption spectrum was obtained from a tauc plot, and a LUMO level was measured considering an energy of the absorption edge as a band gap (2.99 eV). The LUMO level was found to be −2.66 eV.

Further, a decomposition temperature $T_d$ of the obtained YGAS was measured with a thermo-gravimetric/differential thermal analyzer (manufactured by Seiko Instruments Inc., TG/DTA 320), and the $T_d$ was found to be 384° C. Thus, it was found that YGAS had excellent heat resistance.

An optimal molecular structure of YGAS in a ground state was calculated in a similar manner to that in Synthesis Example 1. From this calculation result, a HOMO level value of YGAS was obtained to be −5.10 eV.

In addition, when a singlet excitation energy (band gap) of YGAS was calculated in a similar manner to that in Synthesis Example 1, the singlet excitation energy was calculated to be 3.09 eV.

Synthesis Example 5

Synthesis Example 5 will describe a synthetic method of 4,4'-bis{N-[4-(carbazol-9-yl)phenyl]-N-phenylamino}stilbene (abbrev.: YGA2S) represented by the structural formula (129), as an example of a stilbene derivative of the present invention.

[Step 1: Synthesis of 4,4'-dibromostilbene]

4,4'-dibromostilbene synthesized in Step 1 of this Synthesis Example 5 is the same substance as the one described in Step 1 of Synthesis Example 3; accordingly, the description thereof is omitted here.

[Step 2: Synthesis of 9-[4-(N-phenylamino)phenyl]carbazole (Abbrev.: YGA)]

9-[4-(N-phenylamino)phenyl]carbazole synthesized in Step 2 of this Synthesis Example 5 is the same substance as the one described in Step 2 of Synthesis Example 4; accordingly, the description thereof is omitted here.

[Step 3: Synthesis of 4,4'-bis{N-[4-(carbazol-9-yl)phenyl]-N-phenylamino}stilbene (Abbrev.: YGA2S)]

1.00 g (2.95 mmol) of 4,4'-dibromostilbene, 2.19 g (6.56 mmol) of 9-[4-(N-phenylamino)phenyl]carbazole, 0.189 g (0.328 mmol) of bis(dibenzylideneacetone)palladium, and 3.15 g (32.8 mmol) of sodium tert-butoxide were put in a 100 mL three-necked flask, and nitrogen substitution was carried out. Then, 20 mL of dehydrated toluene and 0.66 g (0.328 mmol) of tri(tert-butyl)phosphine (10% hexane solution) were added thereto and heated at 80° C. for 7 hours.

After the reaction, the solution was washed with water and was separated into an organic layer and an aqueous layer. Then a precipitate in the mixed solution was collected by suction filtration. The filtrate was dissolved in chloroform and the solution was filtered through celite, florisil and alumina. The filtrate was concentrated and recrystallized with chloroform and hexane. Accordingly, 1.51 g of a yellow solid which was a target substance was obtained in a yield of 60%.

Figure 20:
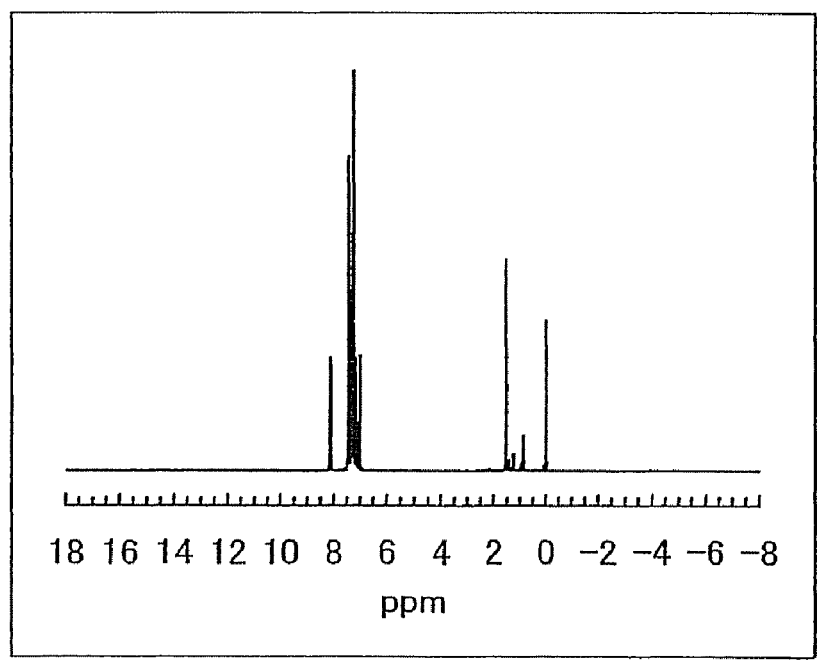
FIG. 20 is a $^1$NMR chart of YGA2S according to an aspect of the present invention.

$^1$H NMR of this compound is described below. In addition, FIG. 20 is a $^1$H NMR chart.

$^1$H NMR (300 MHz, CDCl$_3$); δ=8.14 (d, J=7.8 Hz, 4H), 7.47-7.28 (m, 28H), 7.25-7.08 (m, 10H), 7.02 (s, 2H)

Next, a synthesis scheme (h-1) of 4,4'-bis{N[4-(carbazol-9-yl)phenyl]-N-phenylamino}stilbene (abbrev.: YGA2S) is shown.

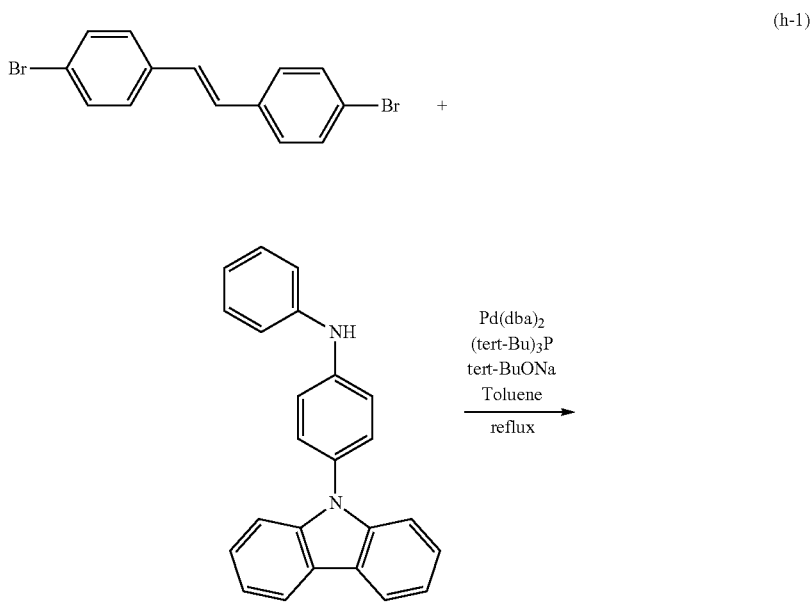

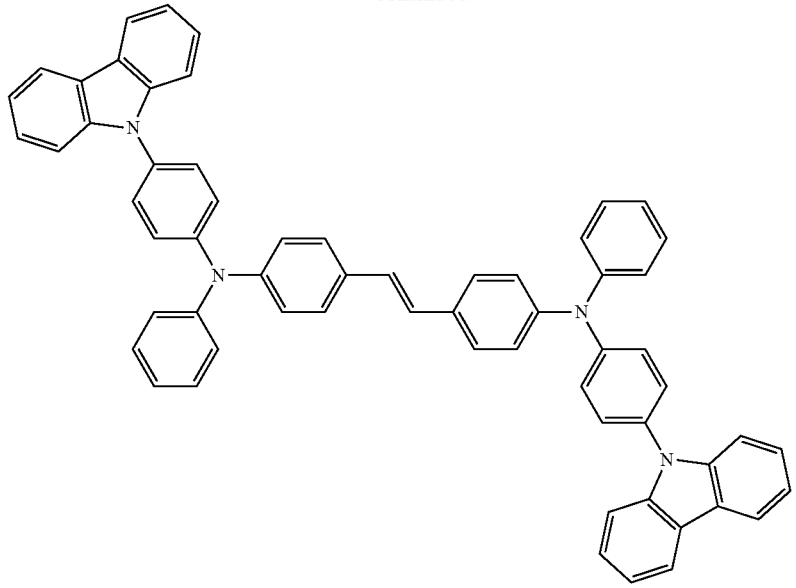

Figure 21:
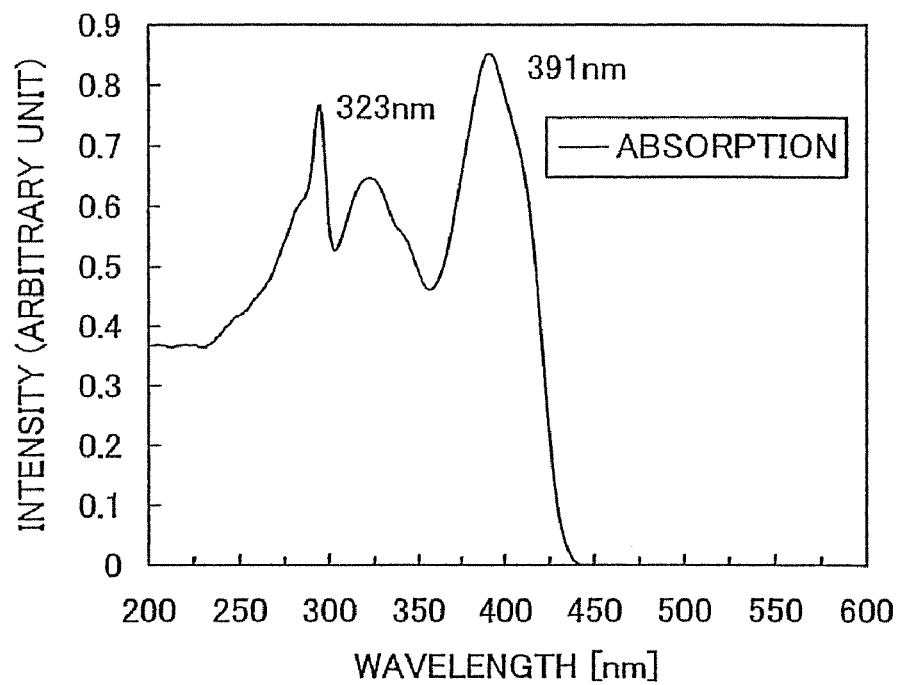
FIG. 21 shows an absorption spectrum of YGA2S according to an, aspect of the present invention.

FIG. 21 shows an absorption spectrum of 4,4'-bis{N[4-(carbazol-9-yl)phenyl]-N-phenylamino}stilbene (hereinafter referred to as YGA2S). In FIG. 21, the horizontal axis indicates a wavelength (nm) and the vertical axis indicates intensity (no unit). Note that FIG. 21 shows an absorption spectrum in a state where YGA2S was dissolved in a toluene solution.

Figure 22:
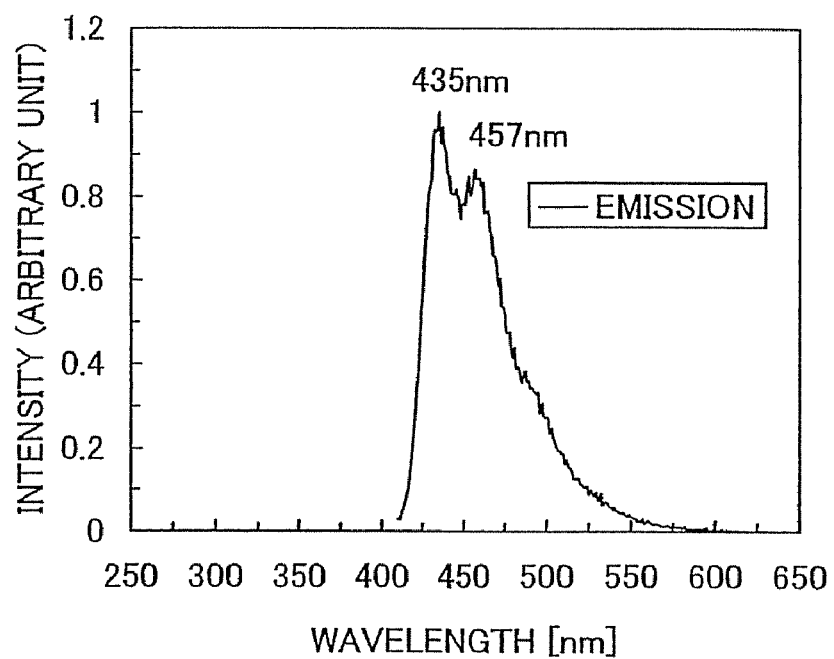
FIG. 22 shows an emission spectrum of YGA2S according to an aspect of the present invention.

FIG. 22 shows an emission spectrum of YGA2S. In FIG. 22, the horizontal axis indicates a wavelength (nm) and the vertical axis indicates emission intensity (arbitrary unit). FIG. 22 shows an emission spectrum (excitation wavelength: 395 nm) in a state where YGA2S was dissolved in a toluene solution. From FIG. 22, it is found that emission from YGA2S in a toluene solution has a peak at 435 nm. The emission was realized as a bluish emission color.

A film of the obtained YGA2S was formed by an evaporation method. An ionization potential of the compound in a thin film state was measured with a photoelectron spectrometer (manufactured by Riken Keiki Co., Ltd., AC-2) and was found to be −5.77 eV. In addition, an absorption spectrum of the compound in a thin film state was measured with a UV/VIS spectrophotometer (manufactured by JASCO Corporation, V-550), an absorption edge on a longer wavelength side of the absorption spectrum was obtained from a tauc plot, and a LUMO level was measured considering an energy of the absorption edge as a band gap (2.81 eV). The LUMO level was found to be −2.96 eV.

Further, a decomposition temperature $T_d$ of the obtained YGA2S was measured with a thermo-gravimetric/differential thermal analyzer (manufactured by Seiko Instruments Inc., TG/DTA 320), and the $T_d$ was found to be 483° C. Thus, it was found that YGA2S had excellent heat resistance.

An optimal molecular structure of YGA2S in a ground state was calculated in a similar manner to that in Synthesis Example 1. From this calculation result, a HOMO level value of YGA2S was obtained to be −5.20 eV.

In addition, when singlet excitation energy (band gap) of YGA2S was calculated in a similar manner to that in Synthesis Example 1, the singlet excitation energy was calculated to be 2.87 eV.

Example 2

Example 2 will describe a case where a light-emitting element is manufactured using a stilbene derivative of the present invention in a part of a layer including a luminescent substance. Specifically, a light-emitting element which is manufactured using a stilbene derivative of the present invention as a guest material of a light-emitting layer of a layer including a luminescent substance, is described.

First, a first electrode of a light-emitting element was formed over a substrate. In this example, ITSO (indium tin oxide containing silicon oxide obtained by a sputtering method by using a target which is ITO containing 2 to 10 wt % of silicon oxide), which was a transparent conductive film, was used for the first electrode. ITO was formed with a thickness of 110 nm by a sputtering method, and etched such that the first electrode had a shape of 2 mm×2 mm.

Next, as a pretreatment for forming the light-emitting element over the first electrode, a surface of the substrate was washed with a porous resin (typically formed of PVA (polyvinyl alcohol), nylon or the like), and a heat treatment was then conducted at 200° C. for 1 hour under atmosphere air. Then, a UV ozone treatment was conducted for 370 seconds, and a heat treatment was further conducted at 170° C. for 30 minutes under reduced pressure.

Next, a layer including a luminescent substance was formed over the first electrode. Note that the layer including a luminescent substance in this example was formed by sequentially stacking a hole injecting layer, a hole transporting layer, a light-emitting layer, an electron transporting layer, and an electron injecting layer by a vacuum evaporation method.

First, the hole injecting layer was formed at 50 nm by coevaporation such that a mass ratio of 4,4'-bis(N-{4-[N,N-bis(3-methylphenyl)amino]phenyl}-N-phenylamino)biphenyl (abbrev.: DNTPD) to molybdenum oxide became 4:2. The hole transporting layer was formed at 10 nm by evaporating NPB.

Next, the light-emitting layer was formed. The thickness thereof was 30 nm. The structure of the light-emitting layer will be described later.

Further, the electron transporting layer was formed at 10 nm by evaporating bathocuproin (abbrev.: BCP). The electron injecting layer was formed at 20 nm by coevaporation such that a mass ratio of $Alq_3$ to lithium became 1:0.01.

Then, Al was formed at 200 nm by vacuum evaporation, as a second electrode; accordingly, the element was completed. Sealing was conducted by using a sealing substrate under a nitrogen atmosphere, so as not to expose the element formed over the substrate to atmosphere.

Here, the following elements were examined: Element 1 is an element including, as the light-emitting layer in the above-described structure, a layer which was formed by coevaporation such that a mass ratio of 4,4'-di(N-carbazolyl)biphenyl (abbrev.: CBP) to PCAS, a stilbene derivative of the present invention, became 1:0.1; Element 2 is an element including, as the light-emitting layer in the above-described structure, a layer which was formed by coevaporation such that a mass ratio of CBP to PCATBS, a stilbene derivative of the present invention, became 1:0.1; Element 3 is an element including, as the light-emitting layer in the above-described structure, a layer which was formed by coevaporation such that a mass ratio of CBP to PCA2S, a stilbene derivative of the present invention, became 1:0.1; Element 4 is an element including, as the light-emitting layer in the above-described structure, a layer which was formed by coevaporation such that a mass ratio of CBP to YGAS, a stilbene derivative of the present invention, became 1:0.05; and Element 5 is an element including, as the light-emitting layer in the above-described structure, a layer which was formed by coevaporation such that a mass ratio of CBP to YGA2S, a stilbene derivative of the present invention, became 1:0.05.

The light-emitting elements manufactured in the above-described manner (elements 1 to 5) were applied with a voltage so as to be driven, and characteristics of the elements were measured.

Figure 23:
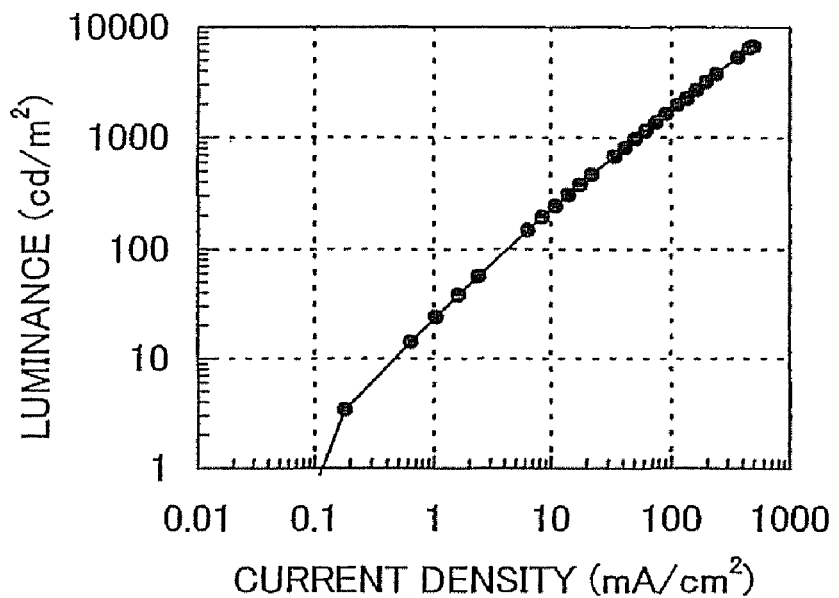
FIG. 23 shows element characteristics of a light-emitting element manufactured using PCAS.
Figure 24:
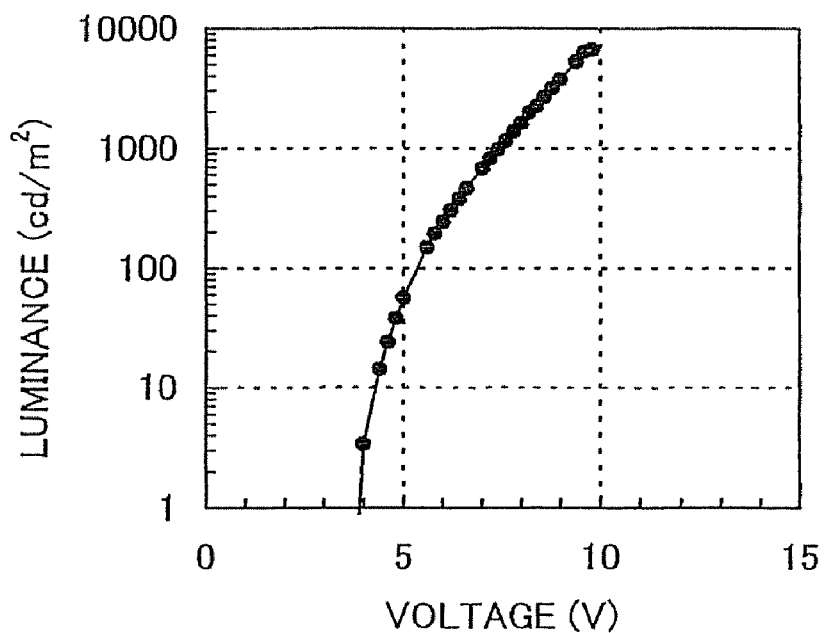
FIG. 24 shows element characteristics of a light-emitting element manufactured using PCAS.
Figure 25:
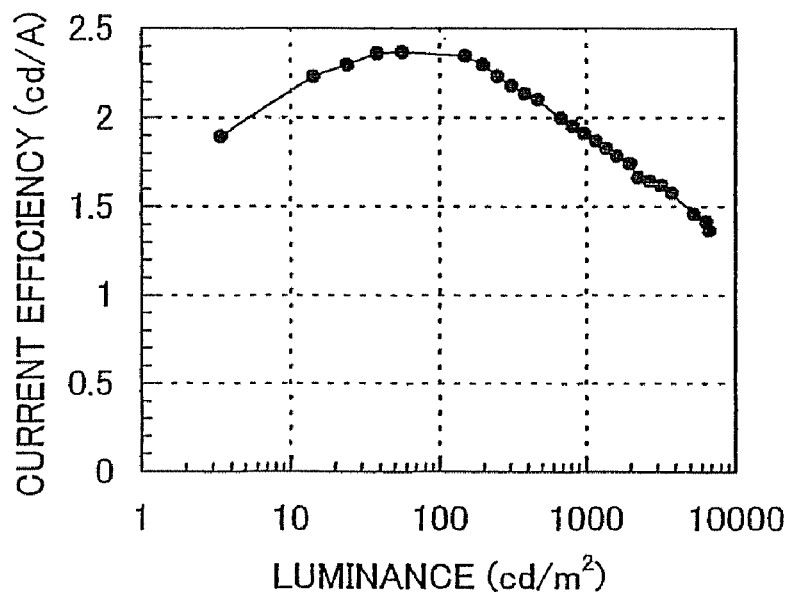
FIG. 25 shows element characteristics of a light-emitting element manufactured using PCAS.
Figure 26:
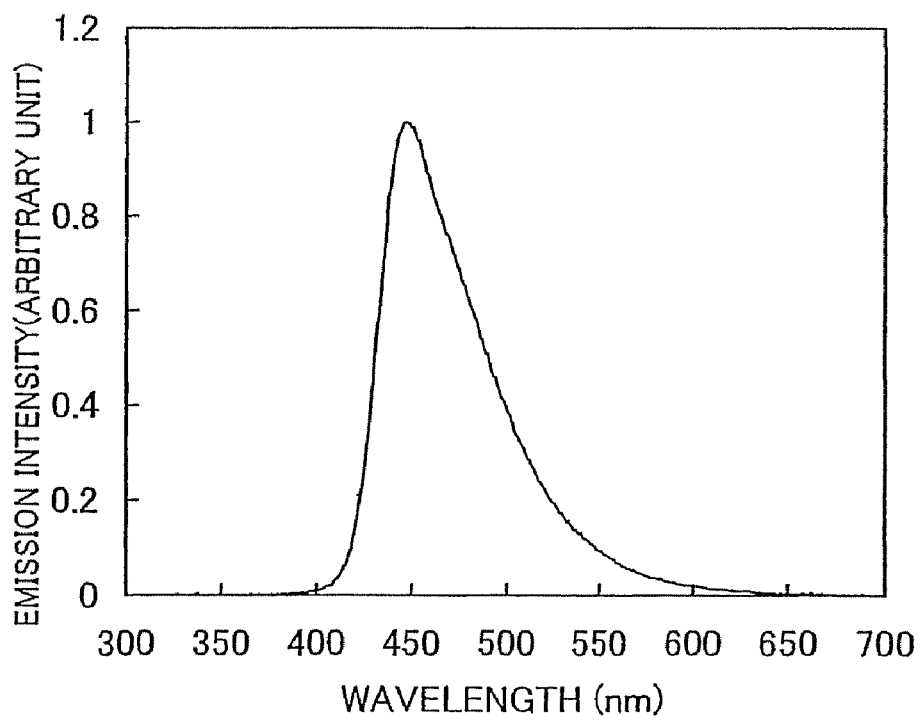
FIG. 26 shows element characteristics of a light-emitting element manufactured using PCAS.

FIG. 23 shows luminance-current density characteristics of the element 1, FIG. 24 shows luminance-voltage characteristics of the element 1, FIG. 25 shows current efficiency-luminance characteristics of the element 1, and FIG. 26 shows an emission spectrum of the element 1. When the element 1 was applied with a voltage of 7.4 V, the current density was 50.9 $mA/cm^2$, the luminance was 972 $cd/cm^2$, and the current efficiency was 1.91 cd/A. In addition, the element 1 had a peak at 448 nm, and CIE chromaticity coordinates were (x, y)=(0.15, 0.13), which was an excellent color purity, and the element 1 exhibited blue light emission.

Figure 27:
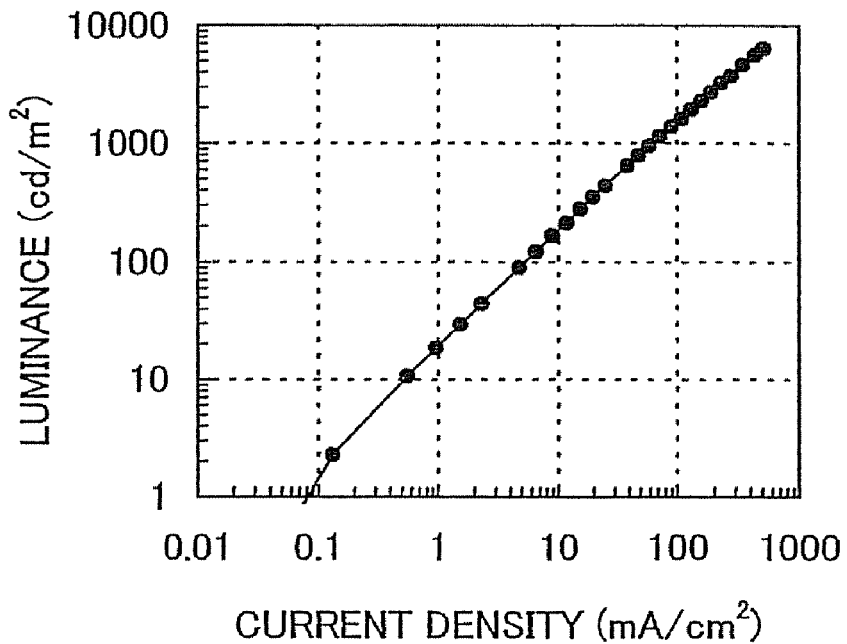
FIG. 27 shows element characteristics of a light-emitting element manufactured using PCATBS.
Figure 28:
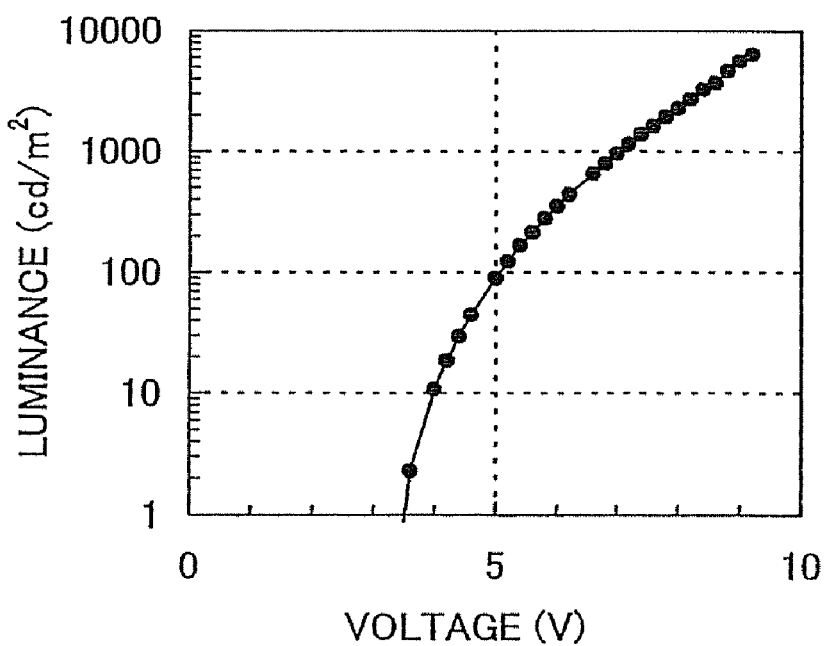
FIG. 28 shows element characteristics of a light-emitting element manufactured using PCATBS.
Figure 29:
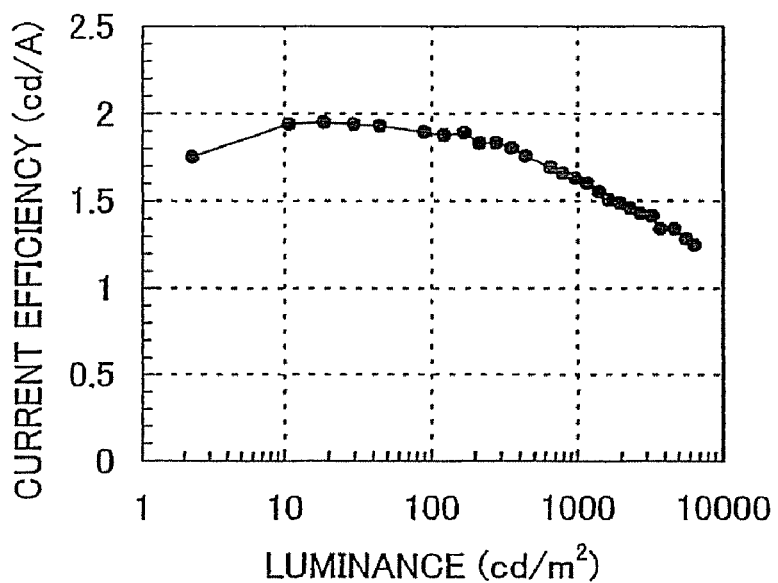
FIG. 29 shows element characteristics of a light-emitting element manufactured using PCATBS.
Figure 30:
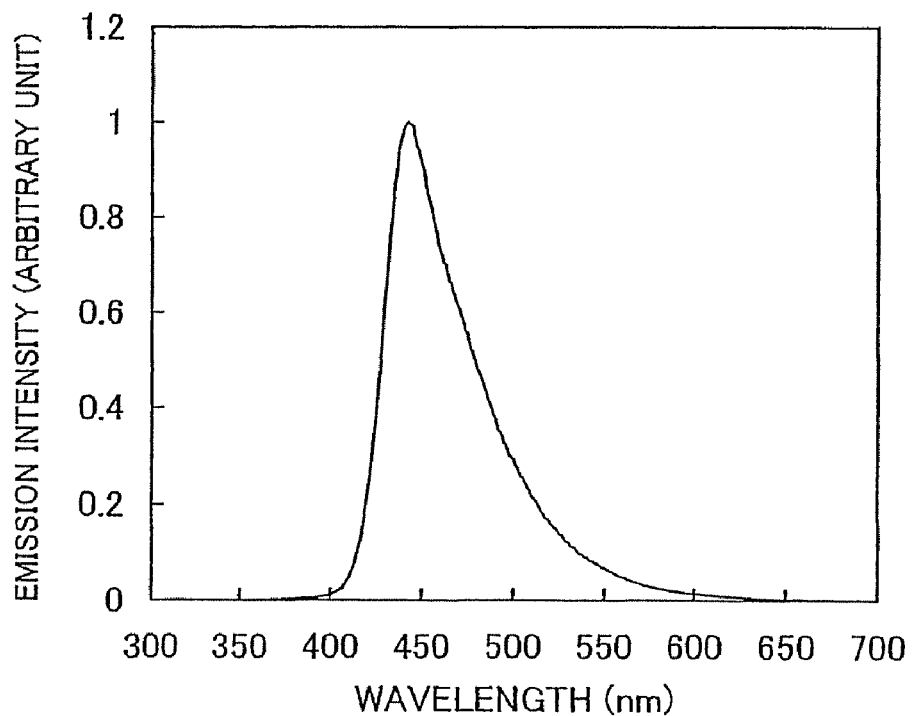
FIG. 30 shows element characteristics of a light-emitting element manufactured using PCATBS.

FIG. 27 shows luminance-current density characteristics of the element 2, FIG. 28 shows luminance-voltage characteristics of the element 2, FIG. 29 shows current efficiency-luminance characteristics of the element 2, and FIG. 30 shows an emission spectrum of the element 2. When the element 2 was applied with a voltage of 7.0 V, the current density was 58.7 $mA/cm^2$, the luminance was 957 $cd/cm^2$, and the current efficiency was 1.63 cd/A. In addition, the element 2 had a peak at 442 nm, and CIE chromaticity coordinates were (x, y)=(0.15, 0.10), which was an excellent color purity, and the element 2 exhibited blue light emission.

Figure 31:
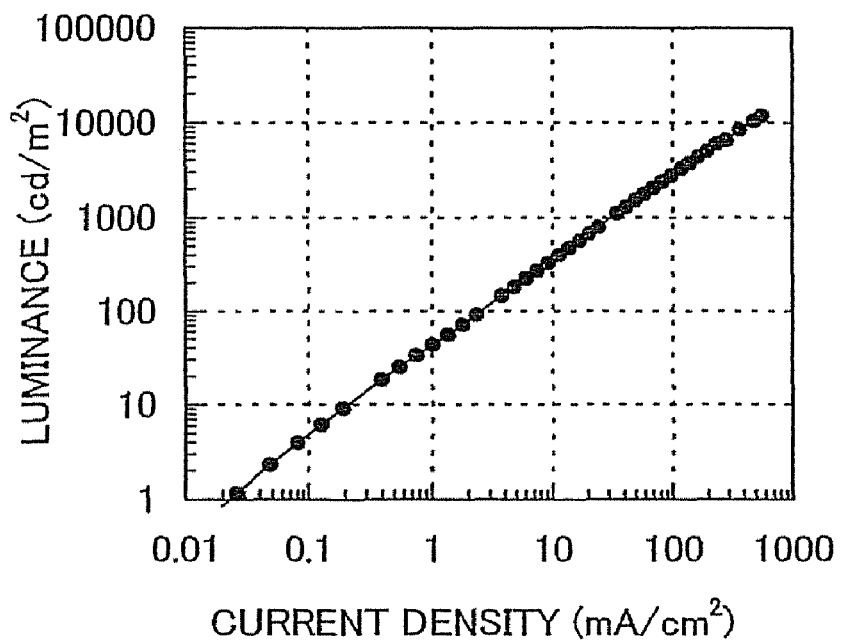
FIG. 31 shows element characteristics of a light-emitting element manufactured using PCA2S.
Figure 32:
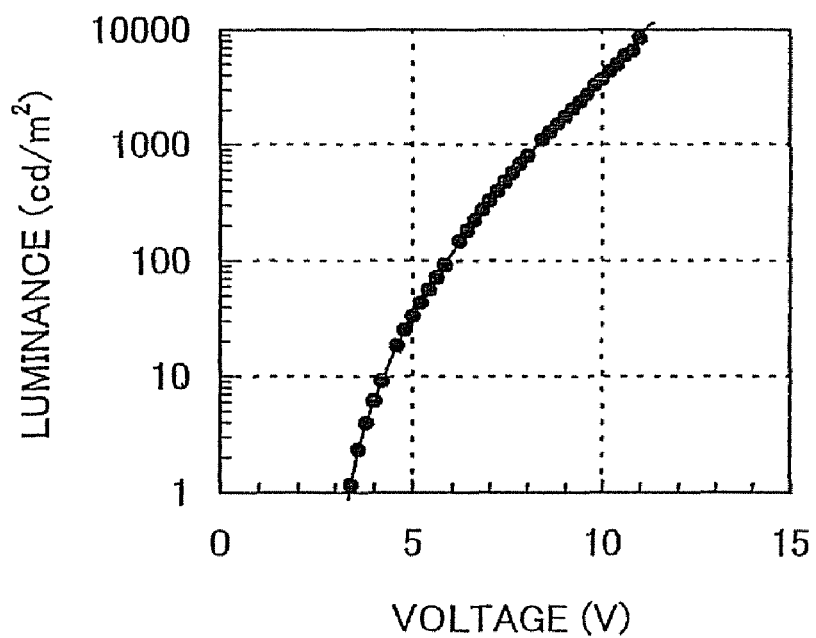
FIG. 32 shows element characteristics of a light-emitting element manufactured using PCA2S.
Figure 33:
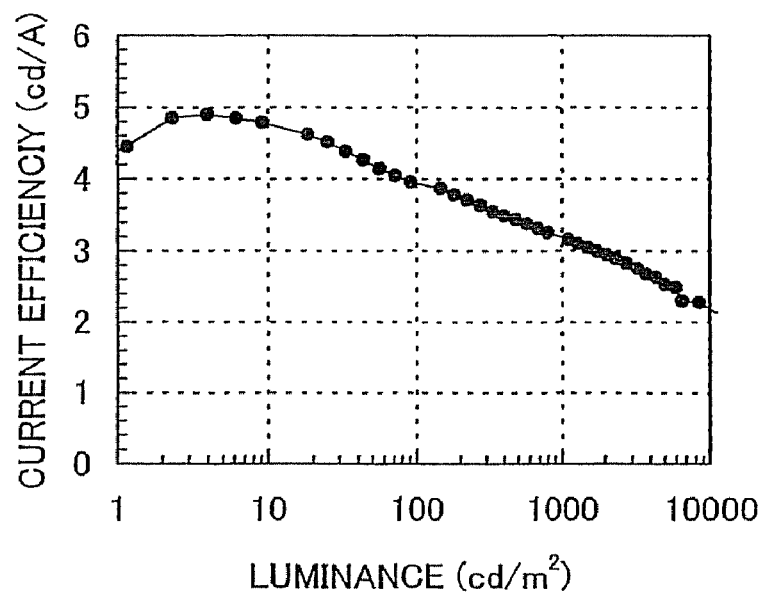
FIG. 33 shows element characteristics of a light-emitting element manufactured using PCA2S.
Figure 34:
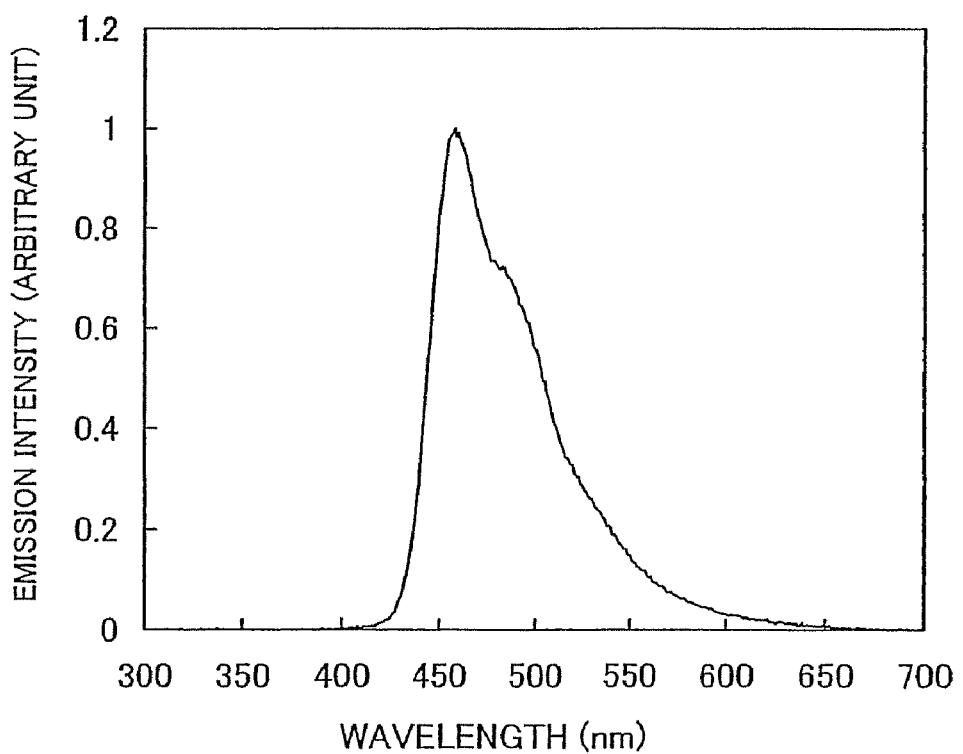
FIG. 34 shows element characteristics of a light-emitting element manufactured using PCA2S.

FIG. 31 shows luminance-current density characteristics of the element 3, FIG. 32 shows luminance-voltage characteristics of the element 3, FIG. 33 shows current efficiency-luminance characteristics of the element 3, and FIG. 34 shows an emission spectrum of the element 3. When the element 3 was applied with a voltage of 8.4 V, the current density was 34.9 $mA/cm^2$, the luminance was 1100 $cd/cm^2$, and the current efficiency was 3.16 cd/A. In addition, the element 3 had a peak at 458 nm, and CIE chromaticity coordinates were (x, y)=(0.16, 0.20), and the element 3 exhibited blue light emission.

Figure 35:
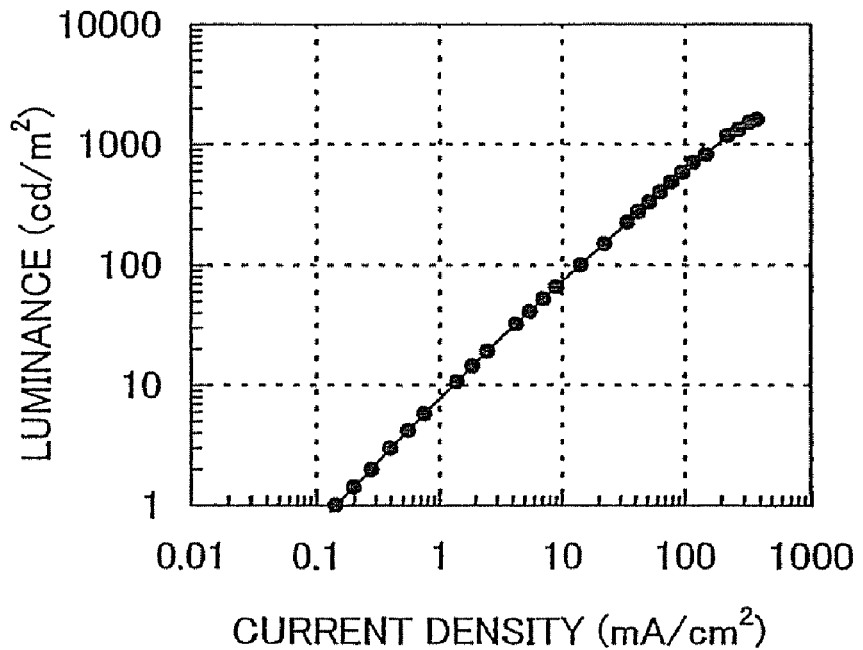
FIG. 35 shows element characteristics of a light-emitting element manufactured using YGAS.
Figure 36:
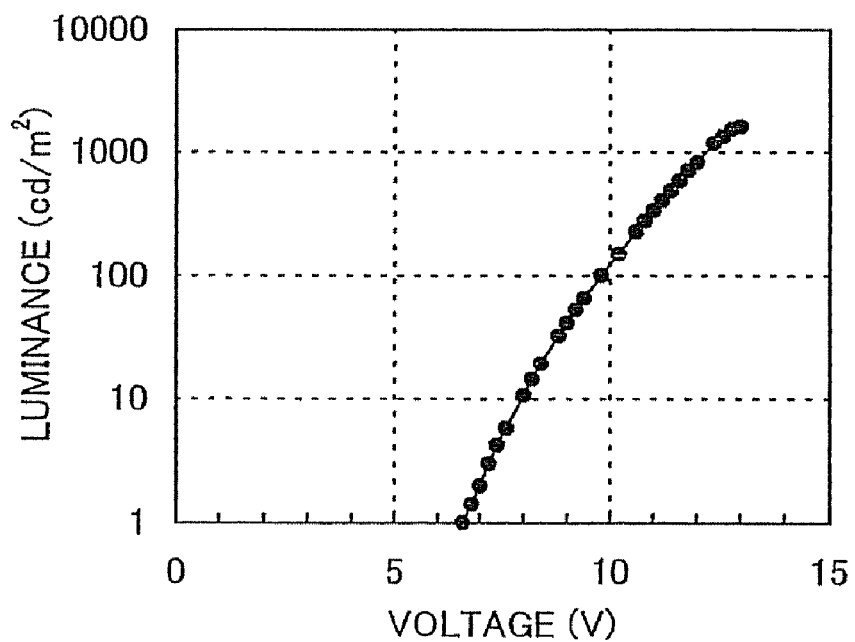
FIG. 36 shows element characteristics of a light-emitting element manufactured using YGAS.
Figure 37:
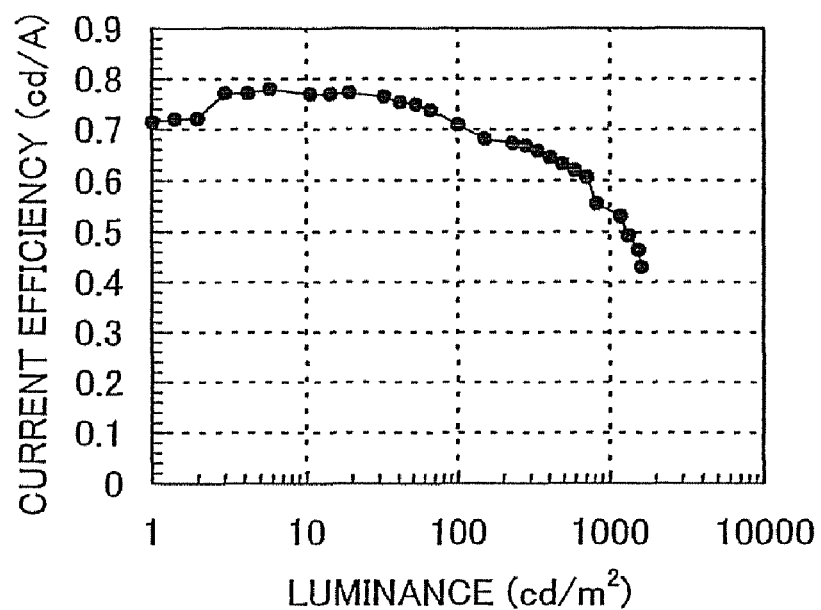
FIG. 37 shows element characteristics of a light-emitting element manufactured using YGAS.
Figure 38:
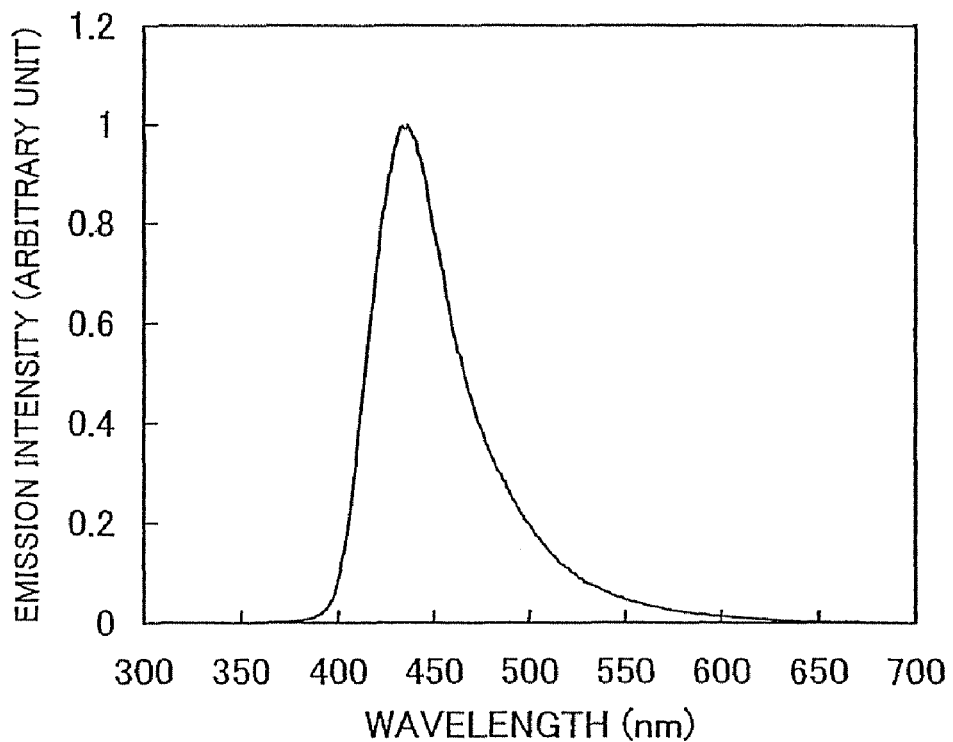
FIG. 38 shows element characteristics of a light-emitting element manufactured using YGAS.

FIG. 35 shows luminance-current density characteristics of the element 4, FIG. 36 shows luminance-voltage characteristics of the element 4, FIG. 37 shows current efficiency-luminance characteristics of the element 4, and FIG. 38 shows an emission spectrum of the element 4. When the element 4 was applied with a voltage of 12.2 V, the current density was 180 $mA/cm^2$, the luminance was 941 $cd/cm^2$, and the current efficiency was 0522 cd/A. In addition, the element 4 had a peak at 436 nm, and CIE chromaticity coordinates were (x, y)=(0.15, 0.07), which was an excellent color purity, and the element 2 exhibited deep blue light emission.

Figure 39:
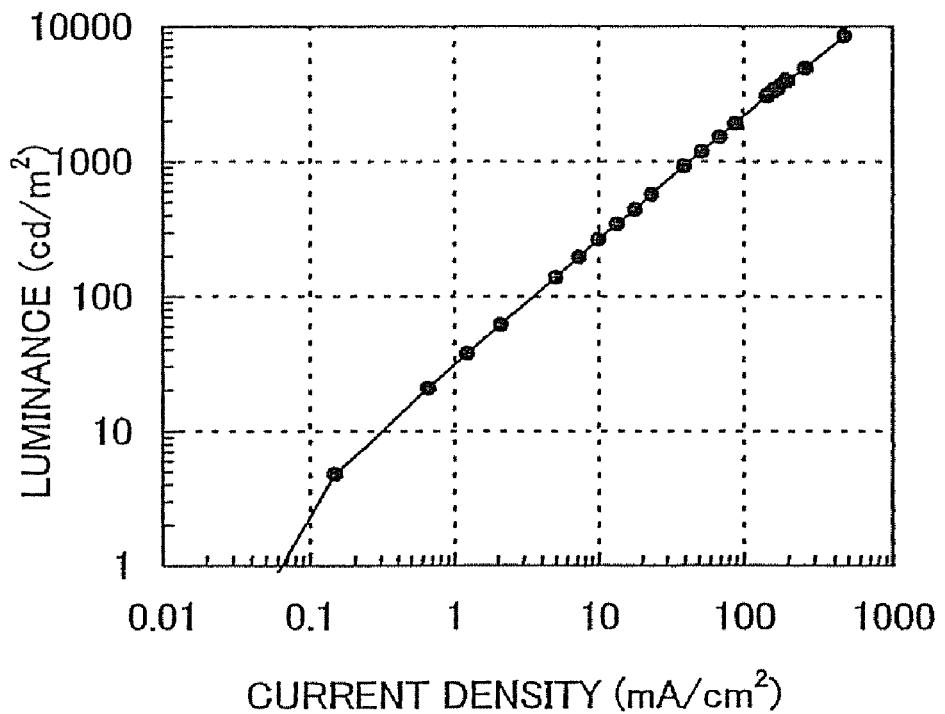
FIG. 39 shows element characteristics of a light-emitting element manufactured using YGA2S.
Figure 40:
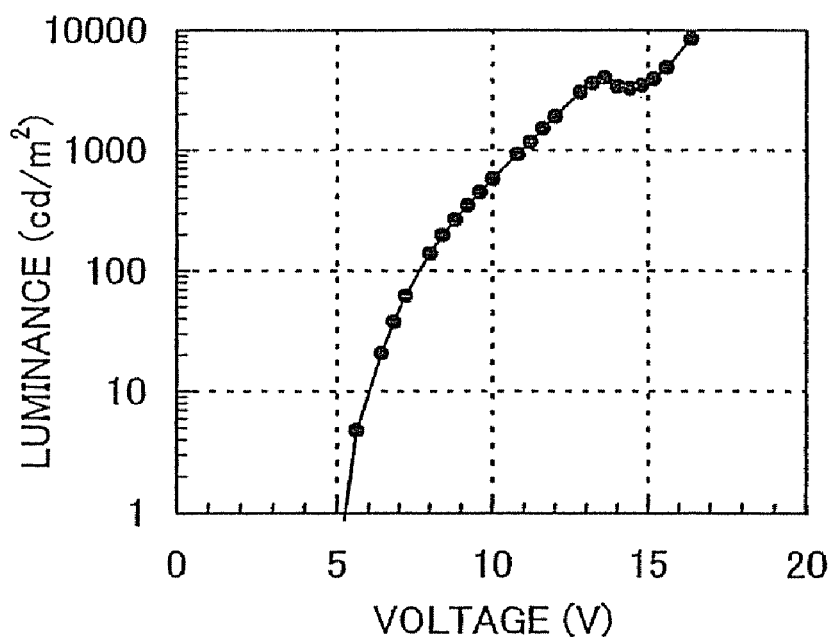
FIG. 40 shows element characteristics of a light-emitting element manufactured using YGA2S.
Figure 41:
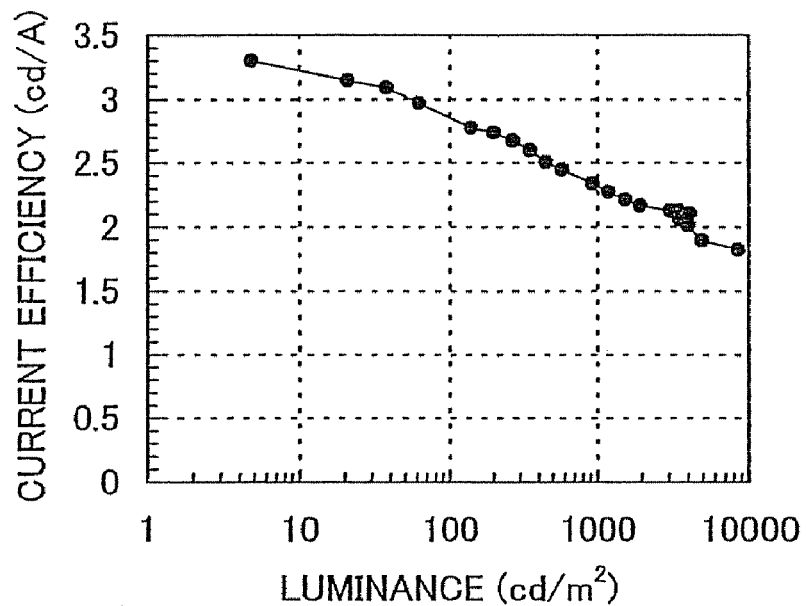
FIG. 41 shows element characteristics of a light-emitting element manufactured using YGA2S.
Figure 42:
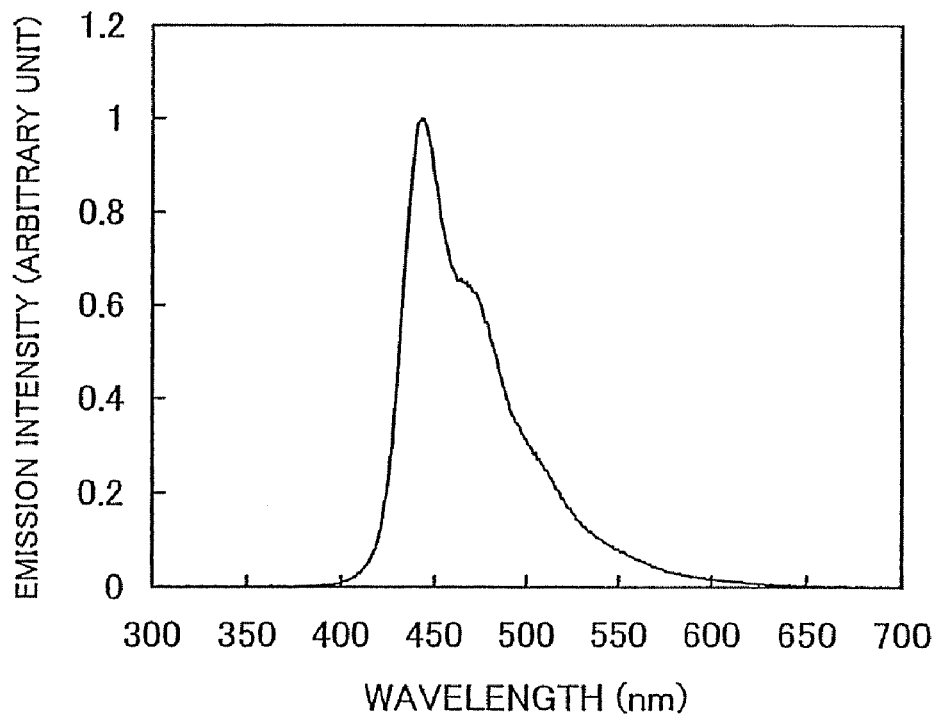
FIG. 42 shows element characteristics of a light-emitting element manufactured using YGA2S.

FIG. 39 shows luminance-current density characteristics of the element 5, FIG. 40 shows luminance-voltage characteristics of the element 5, FIG. 41 shows current efficiency-luminance characteristics of the element 5, and FIG. 42 shows an emission spectrum of the element 5. When the element 5 was applied with a voltage of 10.8 V, the current density was 39.4 $mA/cm^2$, the luminance was 922 $cd/cm^2$, and the current efficiency was 2.34 cd/A. In addition, the element 5 had a peak at 443 nm, and CIE chromaticity coordinates were (x, y)=(0.15, 0.11), which was a favorable color purity, and the element 5 exhibited blue light emission.

In this example, an element was formed as Element 6, in which CzPA was used instead of CBP in the light-emitting layer of Element 5 describe above, and coevaporation was conducted such that a mass ratio of CzPA to YGA2S became 1:0.05 and in which $Alq_3$ was used instead of BCP for the electron transporting layer. Further, an element formed in a similar manner as the element 6 except that the hole injecting layer was formed at 50 nm by coevaporation such that a mass ratio of NPB to molybdenum oxide became 4:1 was manufactured as Element 7. Element characteristics thereof were measured similarly.

Figure 43:
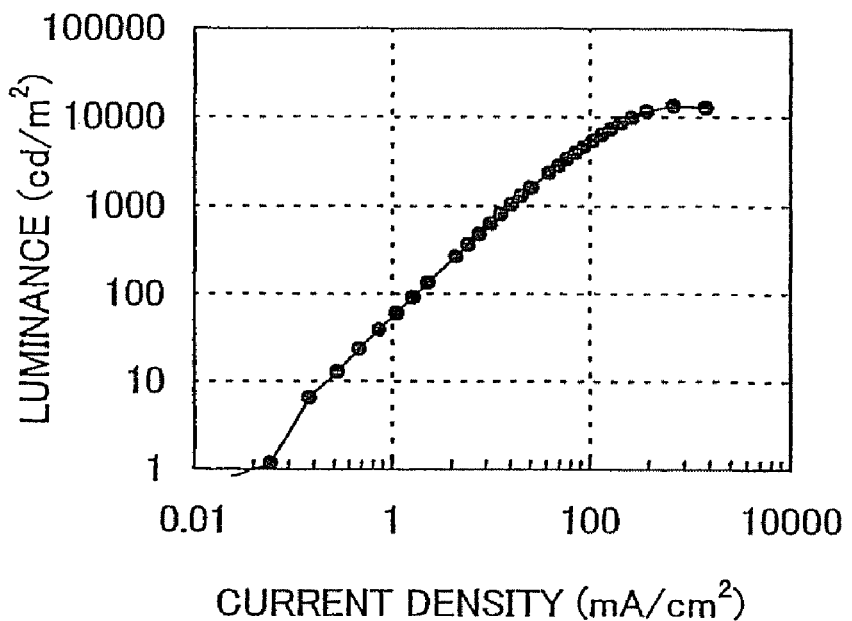
FIG. 43 shows element characteristics of a light-emitting element manufactured using YGA2S.
Figure 44:
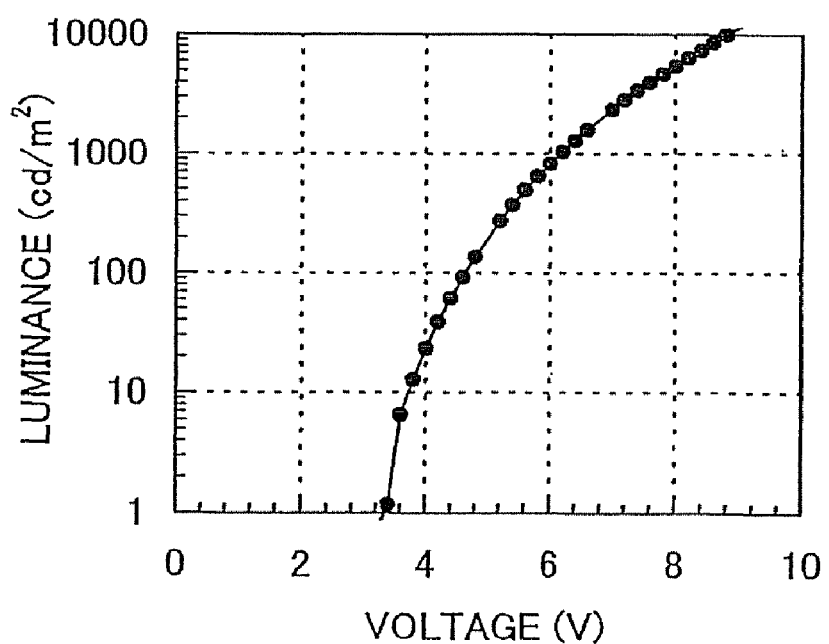
FIG. 44 shows element characteristics of a light-emitting element manufactured using YGA2S.
Figure 45:
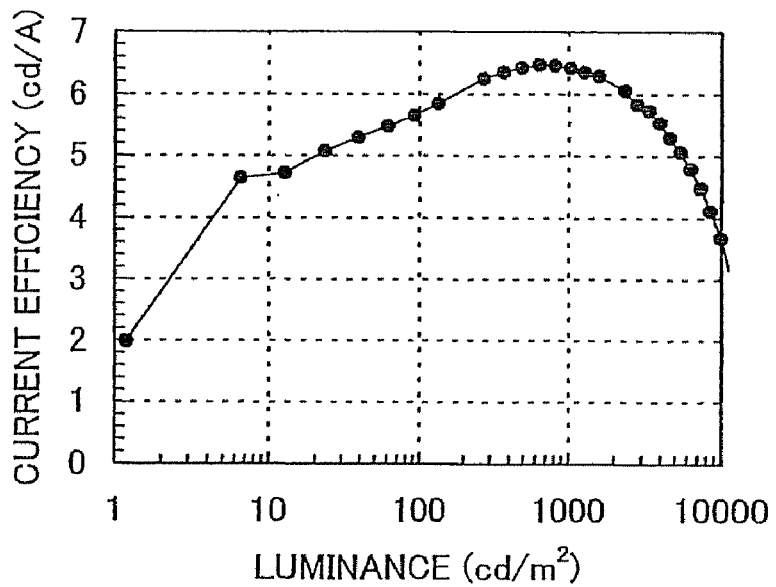
FIG. 45 shows element characteristics of a light-emitting element manufactured using YGA2S.
Figure 46:
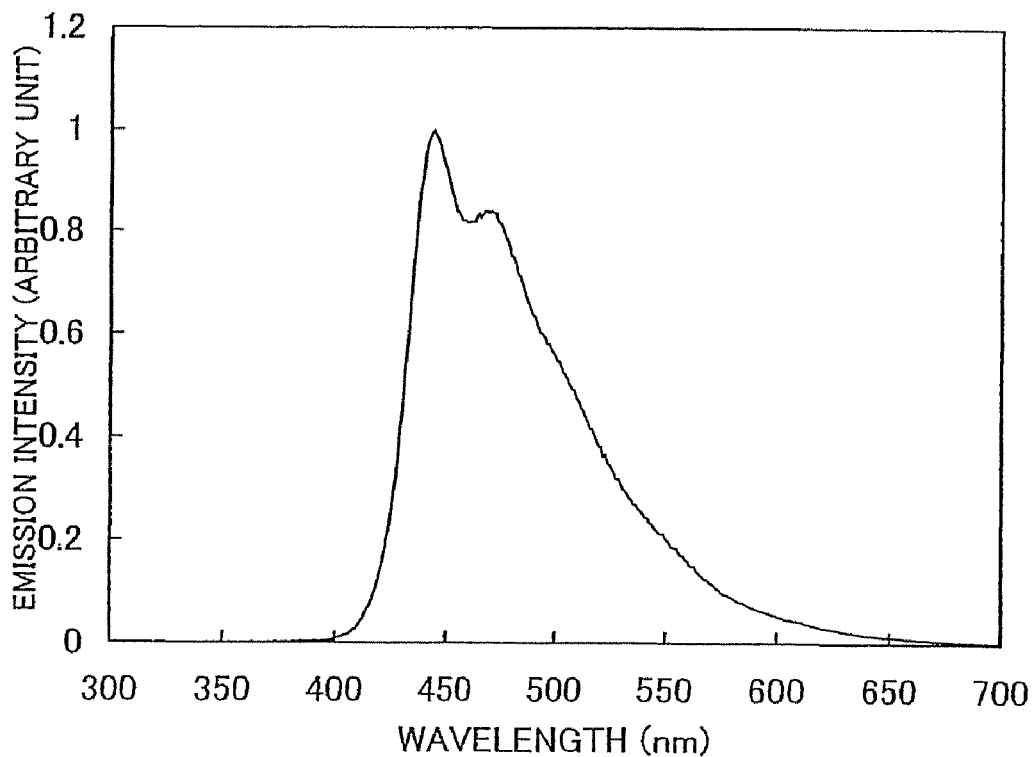
FIG. 46 shows element characteristics of a light-emitting element manufactured using YGA2S.

FIG. 43 shows luminance-current density characteristics of the element 6, FIG. 44 shows luminance-voltage characteristics of the element 6, FIG. 45 shows current efficiency-luminance characteristics of the element 6, and FIG. 46 shows an emission spectrum of the element 6. When the element 6 was applied with a voltage of 6.2 V, the current density was 16.1 $mA/cm^2$, the luminance was 1040 $cd/cm^2$, and the current efficiency was 6.42 cd/A. In addition, the element 6 had a peak at 444 nm, and CIE chromaticity coordinates were (x, y)=(0.17, 0.18), which was an excellent color purity, and the element 6 exhibited blue light emission. From this result, it can be realized that the element 6 has higher efficiency than the above-described elements 1 to 5.

Figure 47:
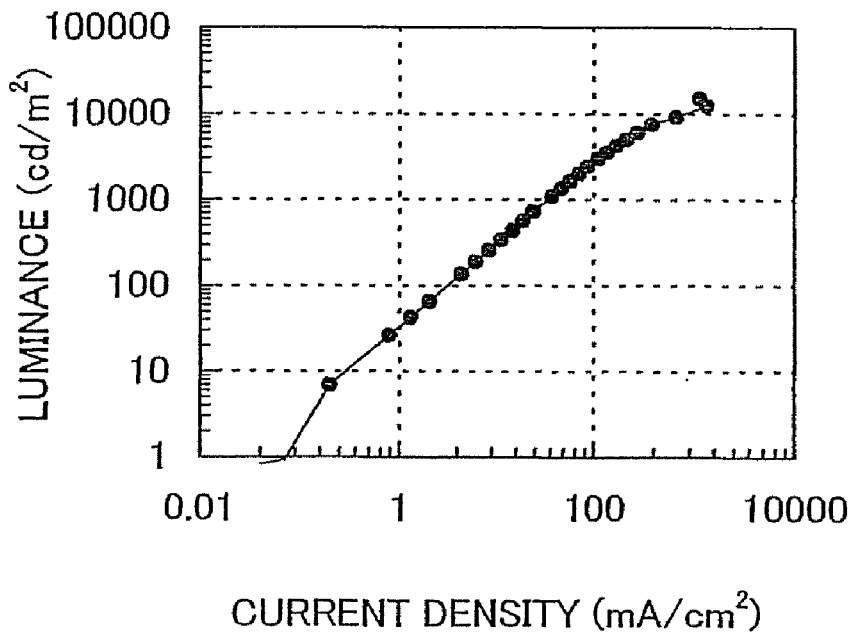
FIG. 47 shows element characteristics of a light-emitting element manufactured using YGA2S.
Figure 48:
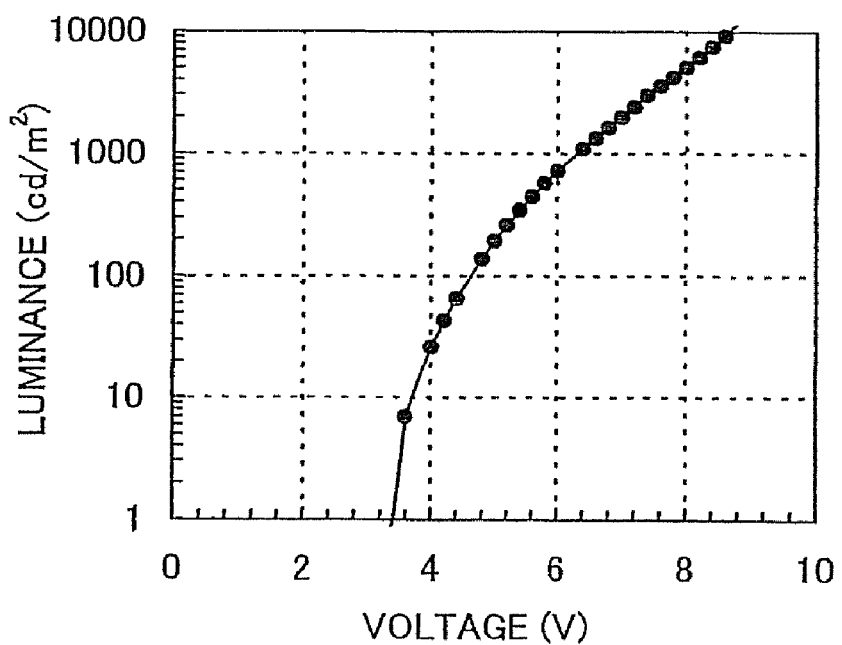
FIG. 48 shows element characteristics of a light-emitting element manufactured using YGA2S.
Figure 49:
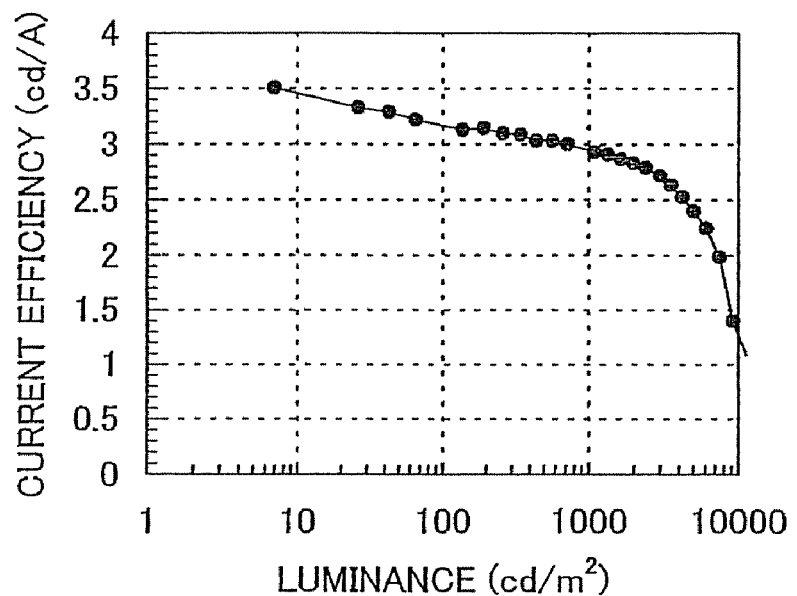
FIG. 49 shows element characteristics of a light-emitting element manufactured using YGA2S.
Figure 50:
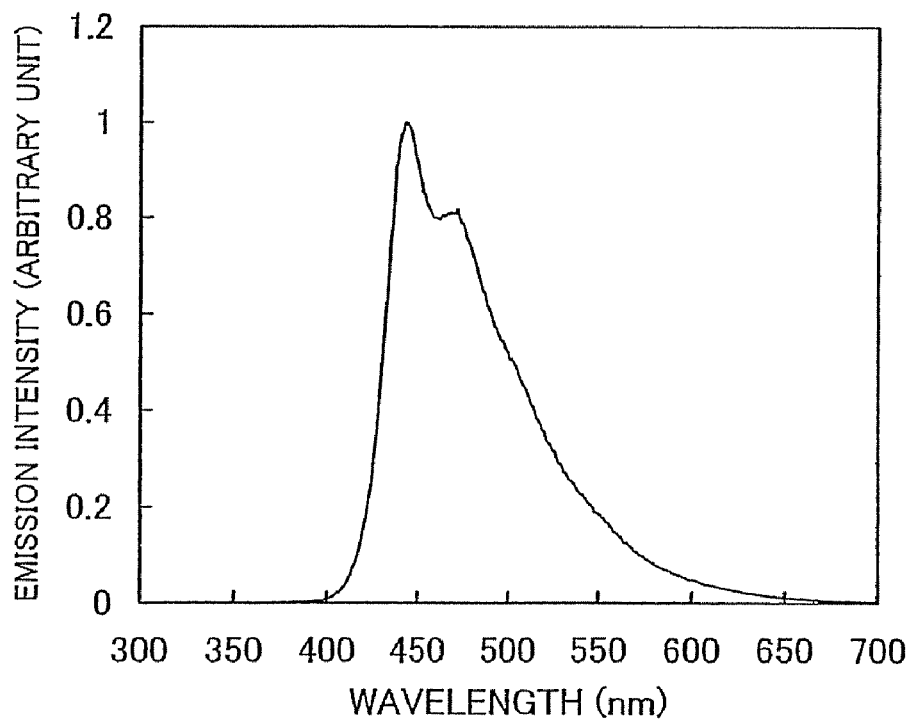
FIG. 50 shows element characteristics of a light-emitting element manufactured using YGA2S.

FIG. 47 shows luminance-current density characteristics of the element 7, FIG. 48 shows luminance-voltage characteristics of the element 7, FIG. 49 shows current efficiency-luminance characteristics of the element 7, and FIG. 50 shows an emission spectrum of the element 7. When the element 7 was applied with a voltage of 6.4 V, the current density was 37.3 $mA/cm^2$, the luminance was 1090 $cd/cm^2$, and the current efficiency was 2.93 cd/A. In addition, the element 7 had a peak at 444 nm, and CIE chromaticity coordinates were (x, y)=(0.16, 0.17), which was an excellent color purity, and the element 7 exhibited blue light emission.

An initial luminance of the element 7 was set at 500 $cd/m^2$, and the element 7 was driven under a condition of constant current density. After a lapse of 200 hours, the element 7 had 86% (relative luminance) of the initial luminance (500 $cd/m^2$).

Figure 51:
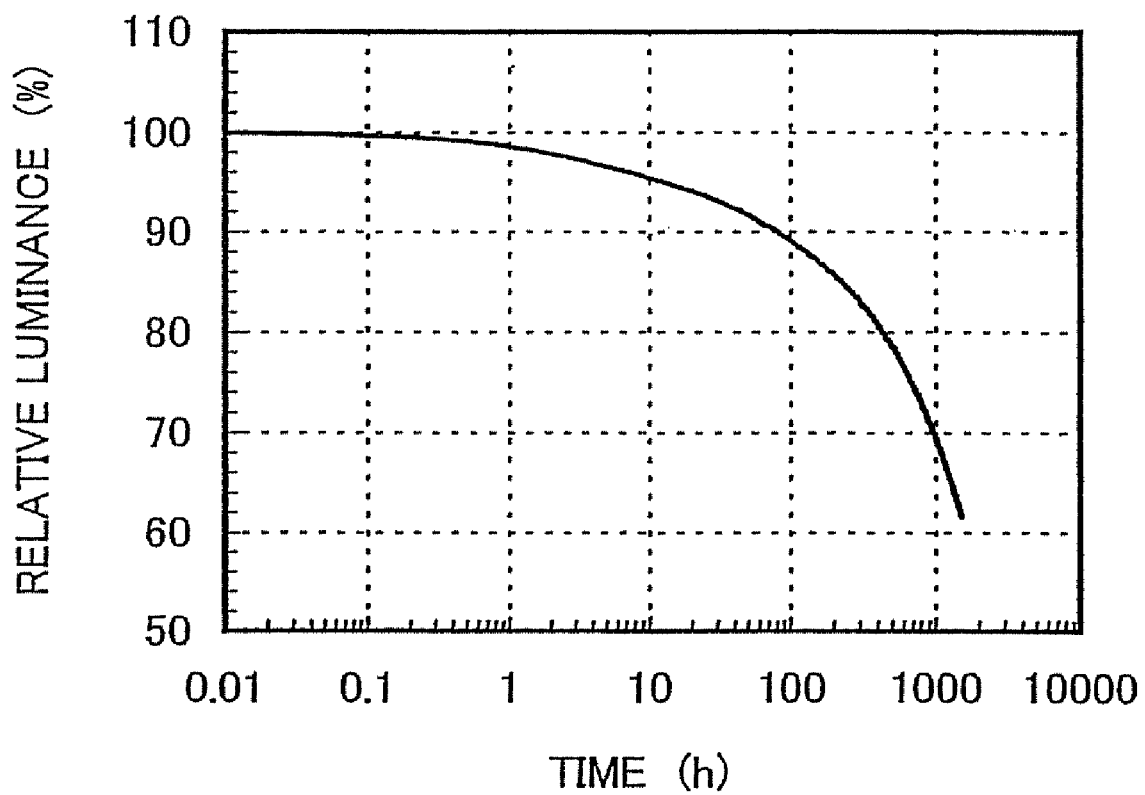
FIG. 51 shows a result of a reliability test of a light-emitting element manufactured using YGA2S.

Further, the above-described test was continued and the result as shown in FIG. 51 was obtained. In FIG. 51, the horizontal axis indicates a driving time (h), and the vertical axis indicates a relative luminance (%) when 500 cd/m² of the luminance was considered as 100%. According to FIG. 51, the predicted half-life period of the luminance, in the case where the initial luminance was 500 cd/m², was 2800 hours. Accordingly, it can be said that the element 7 has an excellent long life.

This application is based on Japanese Patent Application serial Nos. 2005-292366 filed in Japan Patent Office on Oct. 5, 2005, and 2005-343674 filed in Japan Patent Office on Nov. 29, 2005, the entire contents of which are hereby incorporated by references.

Explanation of Reference

101: first electrode, 102: second electrode, 103: layer including a luminescent substance, 104: light-emitting layer, 201: substrate, 202a: source region, 202b: drain region. 203: channel forming region, 204: gate insulating film, 205: gate electrode, 206: interlayer insulating film, 207a: source electrode, 207b: drain electrode, 208: TFT, 209: first electrode, 210: insulator, 301: substrate, 302: gate electrode, 303: gate insulating film, 304: channel forming region, 305a: source region, 305b: drain region, 306a: source electrode, 306b: drain electrode, 307: interlayer insulating film, 308: TFT, 309: first electrode, 310: insulator, 321: substrate, 322: gate electrode, 323: gate insulating film, 324: channel forming region, 325a: source region, 325b: drain region, 326a: source electrode, 326b: drain electrode, 327: interlayer insulating film, 328: TFT, 329: first electrode, 330: insulator, 331: protective layer, 401: driver circuit portion (source driver circuit), 402: pixel portion, 403: driver circuit portion (gate driver circuit), 404: sealing substrate, 405: sealant, 407: space, 408: wire, 409: FPC (flexible printed circuit), 410: element substrate, 411: switching TFT, 412: current control TFT, 413: first electrode, 414: insulator, 416: layer including a luminescent substance, 417: second electrode, 418: light-emitting element, 423: n-channel TFT, 424: p-channel TFT 8001: main body, 8002: display portion, 8101: main body, 8102: display portion, 8201: main body, 8202: display portion, 8301: main body, 8302: display portion, 8401: main body, and 8402: display portion.

The invention claimed is:

1. A light-emitting device comprising:
   a first electrode over a substrate;
   a second electrode over the first electrode; and
   a layer between the first electrode and the second electrode, the layer including a stilbene derivative represented by a general formula (1),

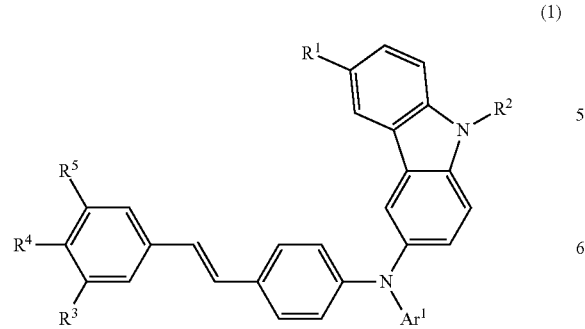

(1)

wherein $R^1$ is hydrogen, an alkyl group having 1 to 4 carbon atoms, or an aryl group having 6 to 25 carbon atoms;

wherein $R^2$ is an alkyl group having 1 to 4 carbon atoms or an aryl group having 6 to 25 carbon atoms;

wherein each of $R^3$ to $R^5$ is hydrogen or an alkyl group having 1 to 4 carbon atoms; and wherein $Ar^1$ is an aryl group having 6 to 25 carbon atoms.

2. The light-emitting device according to claim 1,
wherein the layer including a stilbene derivative represented by a general formula (2),

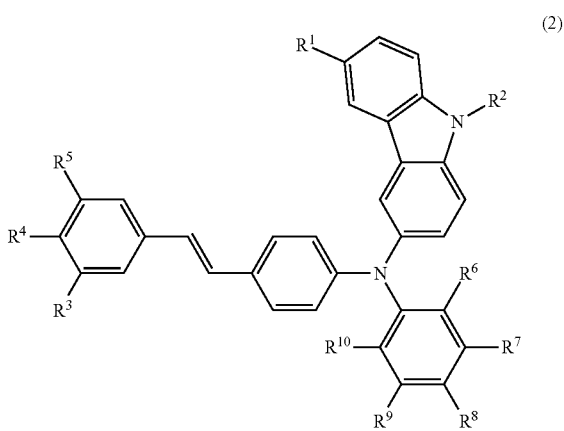

(2)

wherein $R^1$ is hydrogen, an alkyl group having 1 to 4 carbon atoms, or an aryl group having 6 to 25 carbon atoms;

wherein $R^2$ is an alkyl group having 1 to 4 carbon atoms or an aryl group having 6 to 25 carbon atoms;

wherein each of $R^3$ to $R^5$ is hydrogen or an alkyl group having 1 to 4 carbon atoms; and wherein each of $R^6$ to $R^{10}$ is hydrogen, an alkyl group having 1 to 4 carbon atoms, or an aryl group having 6 to 25 carbon atoms.

3. A light-emitting device comprising:
   a first electrode over a substrate;
   a second electrode over the first electrode; and
   a layer between the first electrode and the second electrode, the layer including a stilbene derivative represented by a general formula (3),

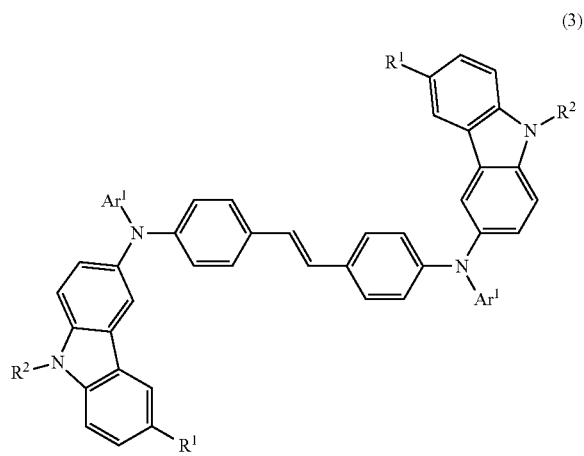

(3)

wherein $R^1$ is hydrogen, an alkyl group having 1 to 4 carbon atoms, or an aryl group having 6 to 25 carbon atoms;

wherein $R^2$ is an alkyl group having 1 to 4 carbon atoms or an aryl group having 6 to 25 carbon atoms; and wherein $Ar^1$ is an aryl group having 6 to 25 carbon atoms.

4. The light-emitting device according to claim 3, wherein the layer including a stilbene derivative represented by a general formula (4),

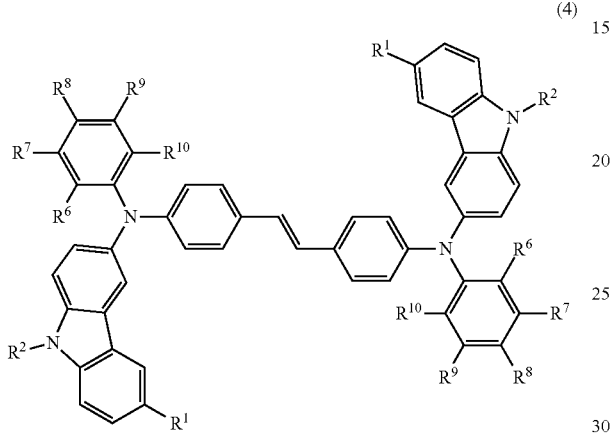

(4)

wherein $R^1$ is hydrogen, an alkyl group having 1 to 4 carbon atoms, or an aryl group having 6 to 25 carbon atoms;

wherein $R^2$ is an alkyl group having 1 to 4 carbon atoms or an aryl group having 6 to 25 carbon atoms; and wherein each of $R^6$ to $R^{10}$ is hydrogen, an alkyl group having 1 to 4 carbon atoms, or an aryl group having 6 to 25 carbon atoms.

5. A light-emitting device comprising:
a first electrode over a substrate;
a second electrode over the first electrode; and
a layer between the first electrode and the second electrode, the layer including a stilbene derivative represented by a general formula (5),

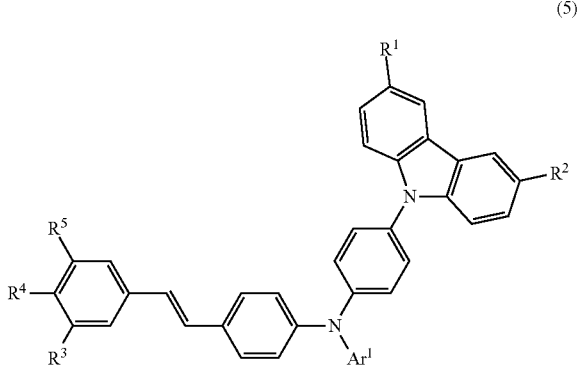

(5)

wherein each of $R^1$ and $R^2$ is hydrogen, an alkyl group having 1 to 4 carbon atoms, or an aryl group having 6 to 25 carbon atoms;

wherein each of $R^3$ to $R^5$ is hydrogen or an alkyl group having 1 to 4 carbon atoms; and wherein $Ar^1$ is an aryl group having 6 to 25 carbon atoms.

6. The light-emitting device according to claim 5, wherein the layer including a stilbene derivative represented by a general formula (6),

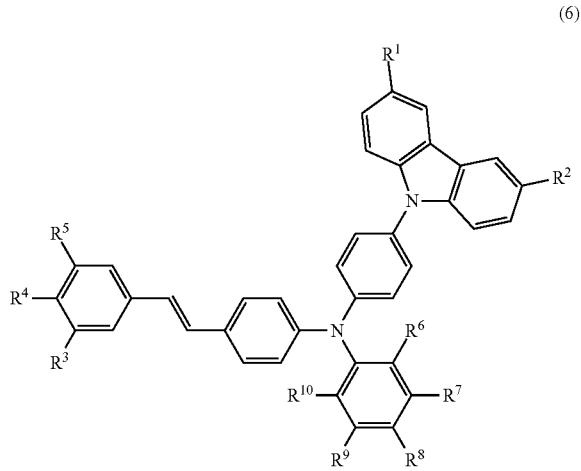

(6)

wherein each of $R^1$ and $R^2$ is hydrogen, an alkyl group having 1 to 4 carbon atoms, or an aryl group having 6 to 25 carbon atoms;

wherein each of $R^3$ to $R^5$ is hydrogen or an alkyl group having 1 to 4 carbon atoms; and wherein each of $R^6$ to $R^{10}$ is hydrogen, an alkyl group having 1 to 4 carbon atoms, or an aryl group having 6 to 25 carbon atoms.

7. A light-emitting device comprising:

a first electrode over a substrate;

a second electrode over the first electrode; and a layer between the first electrode and the second electrode, the layer including a stilbene derivative represented by a general formula (7),

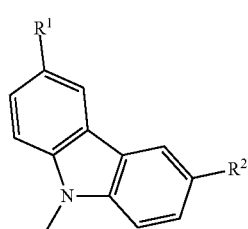
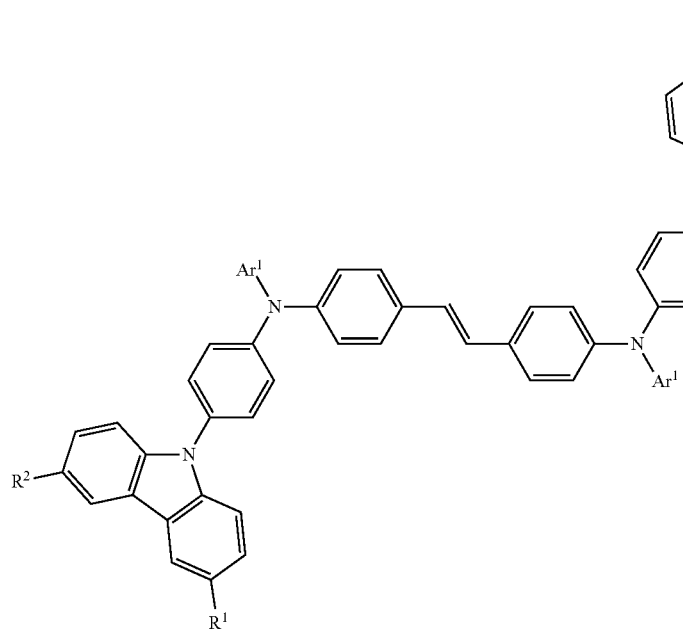

wherein each of $R^1$ and $R^2$ is hydrogen, an alkyl group having 1 to 4 carbon atoms, or an aryl group having 6 to 25 carbon atoms; and wherein $Ar^1$ is an aryl group having 6 to 25 carbon atoms.

8. The light-emitting device according to claim 7, wherein the layer including a stilbene derivative represented by a general formula (8),

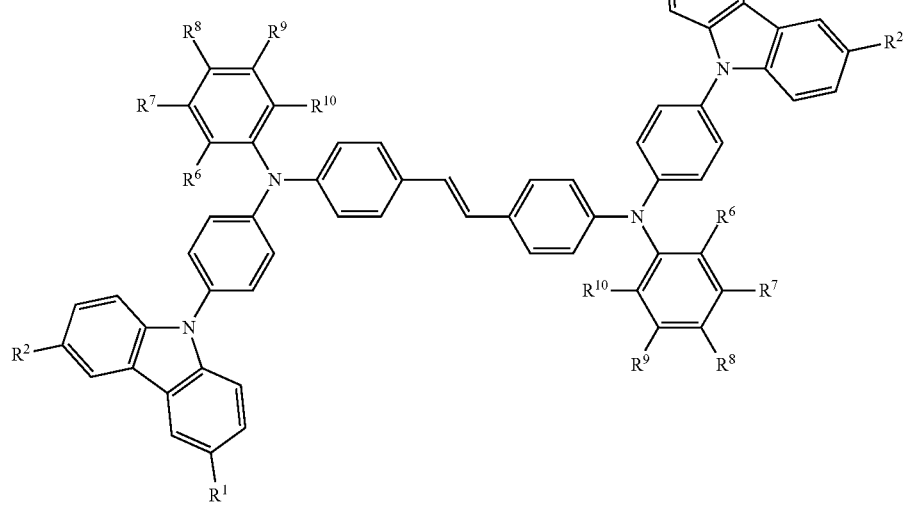

wherein each of $R^1$ and $R^2$ is hydrogen, an alkyl group having 1 to 4 carbon atoms, or an aryl group having 6 to 25 carbon atoms; and wherein each of $R^6$ to $R^{10}$ is hydrogen, an alkyl group having 1 to 4 carbon atoms, or an aryl group having 6 to 25 carbon atoms.

9. The light-emitting device according to claim 1, wherein the substrate is made of transparent plastic.

10. The light-emitting device according to claim 1, wherein the light-emitting device is a lighting or a light-source of a traffic signal machine.

11. The light-emitting device according to claim 3, wherein the substrate is made of transparent plastic.

12. The light-emitting device according to claim 3, wherein the light-emitting device is a lighting or a light-source of a traffic signal machine.

13. The light-emitting device according to claim 5, wherein the substrate is made of transparent plastic.

14. The light-emitting device according to claim 5, wherein the light-emitting device is a lighting or a light-source of a traffic signal machine.

15. The light-emitting device according to claim 7, wherein the substrate is made of transparent plastic.

16. The light-emitting device according to claim 7, wherein the light-emitting device is a lighting or a light-source of a traffic signal machine.

* * * * *

UNITED STATES PATENT AND TRADEMARK OFFICE
CERTIFICATE OF CORRECTION

PATENT NO. : 8,193,701 B2
APPLICATION NO. : 13/036234
DATED : June 5, 2012
INVENTOR(S) : Masakazu Egawa et al.

Page 1 of 6

It is certified that error appears in the above-identified patent and that said Letters Patent is hereby corrected as shown below:

In the Specification:

Columns 45-46, Figure (83);

Change

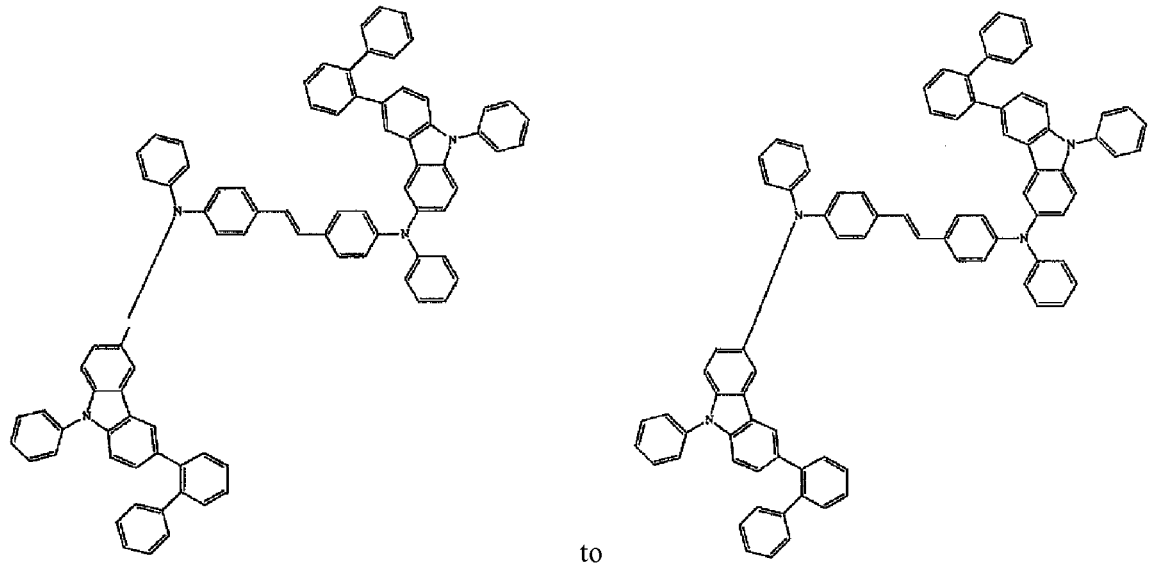

to

Columns 47-48, Figure (84);

Signed and Sealed this
Twentieth Day of November, 2012

David J. Kappos
*Director of the United States Patent and Trademark Office*

Change
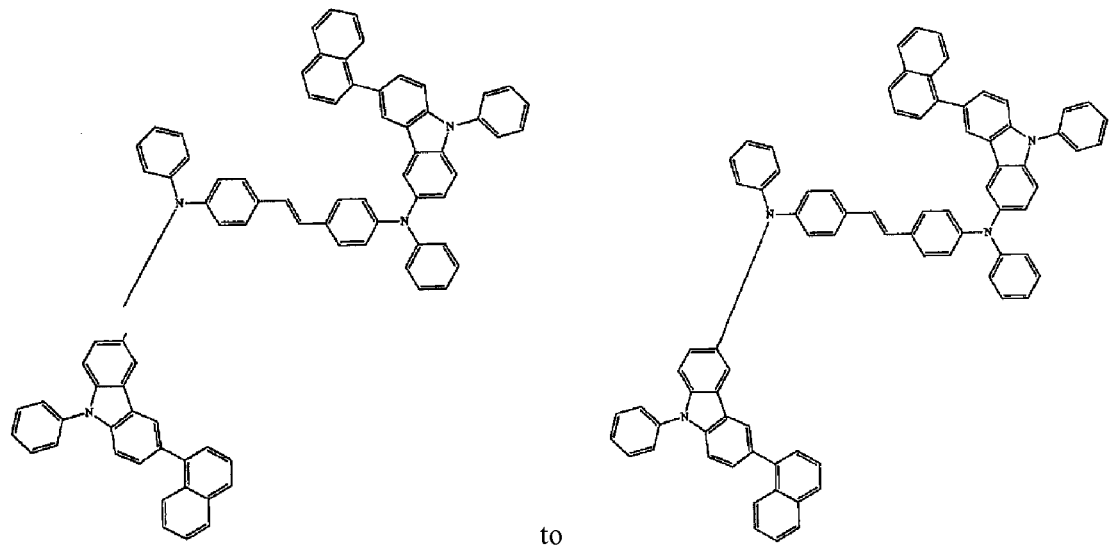
Columns 49-50, Figure (87);
Change
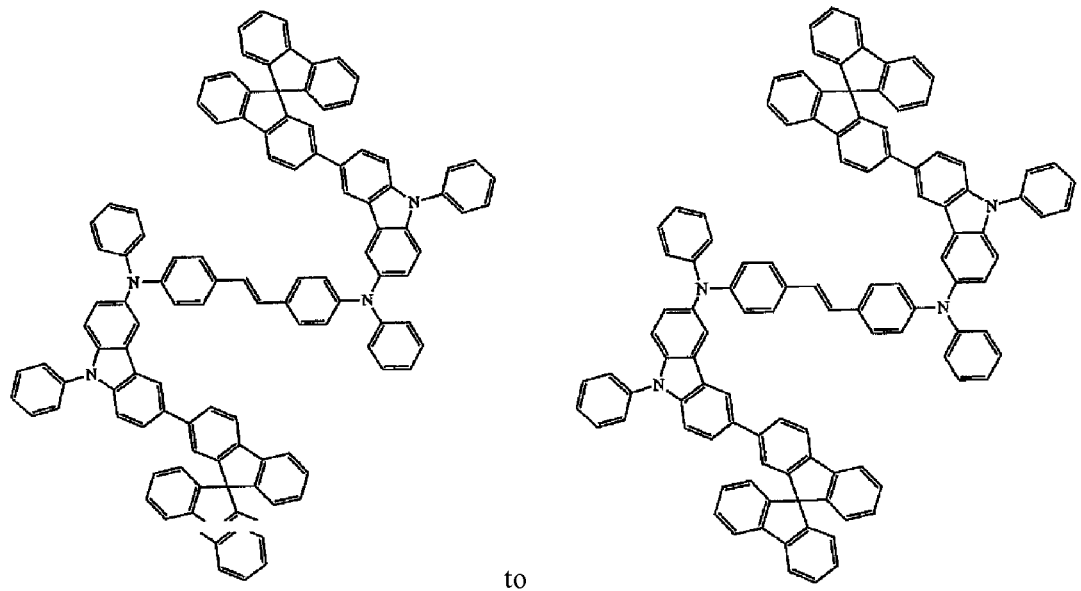
Columns 73-74, Figure (137);

Change
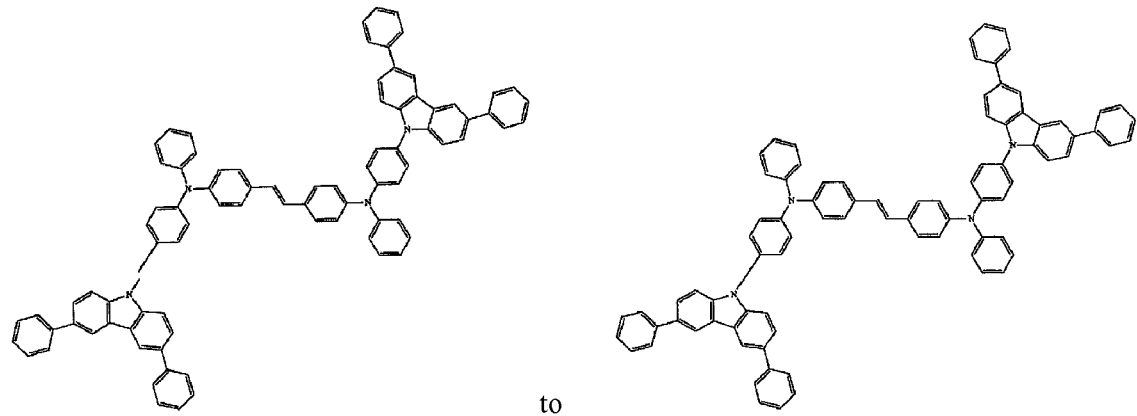
Columns 75-76, Figure (138);
Change
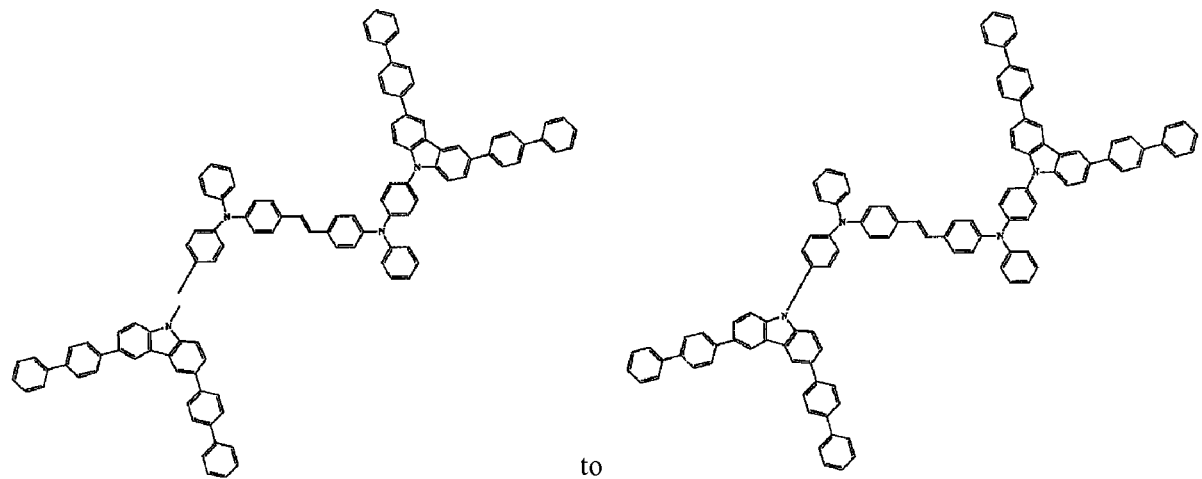
Columns 77-78, Figure (140);

Change
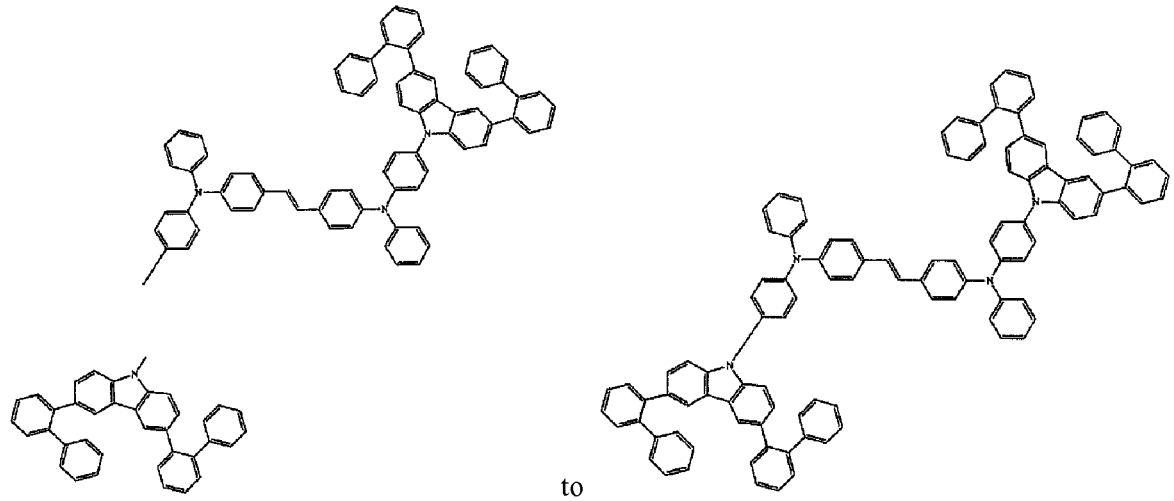
Columns 79-80, Figure (141);
Change
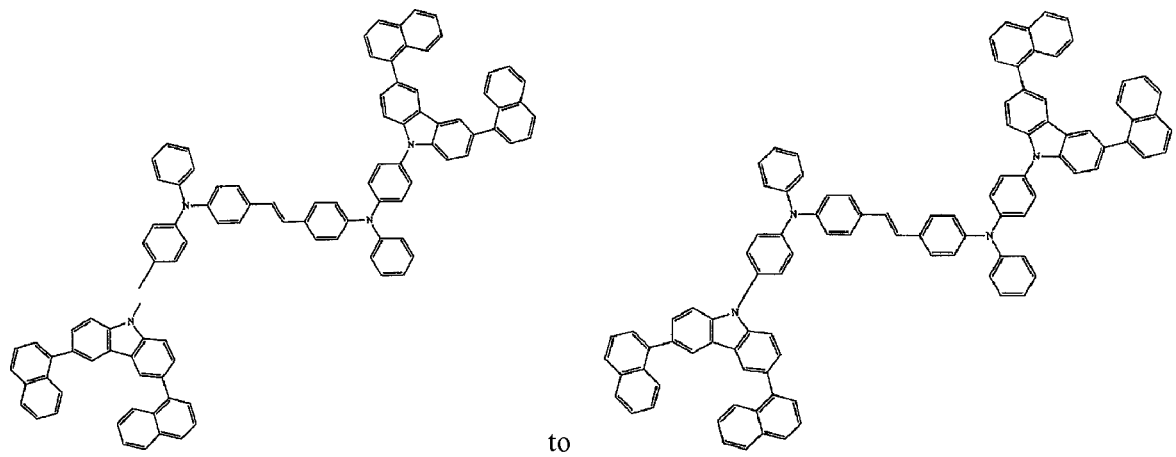
Columns 89-90, Figure (151);

Change
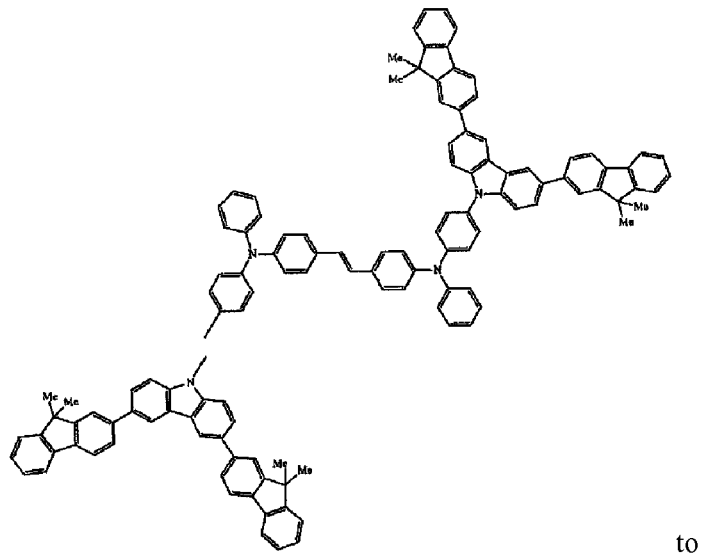
to
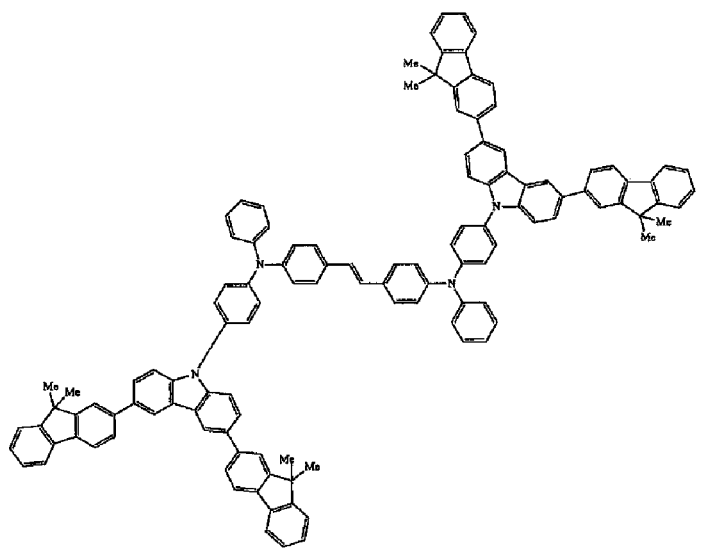

CERTIFICATE OF CORRECTION (continued)

U.S. Pat. No. 8,193,701 B2

Column 105, Line 45; Change "referred to as TED" to --referred to as TPD--.

Column 106, Lines 4-5; Change "sewing" to --serving--.

Column 108, Line 9; Change "titanium nitride (TN)" to --titanium nitride (TiN)--.

Column 108, Line 40; Change "iridium (It)" to --iridium (Ir)--.

Column 108, Line 50; Change "titanium nitride (TN)" to --titanium nitride (TiN)--.

Column 109, Line 3; Change "111" to --TFT--.

Column 111, Line 49; Change "n-channel ITT 423" to --n-channel TFT 423--.

Column 118, Line 10; Change "Therefore, the MT" to --Therefore, the DFT--.

Column 123, Line 56; Change "thereto-gravimetric" to --thermo-gravimetric--.

Column 132, Line 11; Change "0522 cd/A" to --0.522 cd/A--.